US012799151B2

(12) United States Patent
Banasik et al.

(10) Patent No.: US 12,799,151 B2
(45) Date of Patent: Nov. 17, 2026

(54) TRANSLOCATION CONTROL ELEMENTS, REPORTER CODES, AND FURTHER MEANS FOR TRANSLOCATION CONTROL FOR USE IN NANOPORE SEQUENCING

(71) Applicant: Roche Sequencing Solutions, Inc., Pleasanton, CA (US)

(72) Inventors: Brent Banasik, Seattle, WA (US); Cynthia Cech, Newcastle, WA (US); Jagadeeswaran Chandrasekar, Seattle, WA (US); Drew Goodman, Seattle, WA (US); Aaron Jacobs, Seattle, WA (US); Mark Stamatios Kokoris, Bothell, WA (US); Svetlana Kritzer, Seattle, WA (US); Matthew Lopez, Seattle, WA (US); Cara Machacek, Seattle, WA (US); Lacey Merrill, Seattle, WA (US); Melud Nabavi, Seattle, WA (US); Dylan O'Connell, Seattle, WA (US); John Tabone, Kirkland, WA (US); Jessica Vellucci, Bremerton, WA (US)

(73) Assignee: Roche Sequencing Solutions, Inc., Pleasanton, CA (US)

( * ) Notice: Subject to any disclaimer, the term of this patent is extended or adjusted under 35 U.S.C. 154(b) by 945 days.

(21) Appl. No.: 17/456,342

(22) Filed: Nov. 23, 2021

(65) Prior Publication Data

US 2022/0411458 A1 Dec. 29, 2022

Related U.S. Application Data

(63) Continuation of application No. PCT/US2020/032950, filed on May 14, 2020.

(60) Provisional application No. 62/885,746, filed on Aug. 12, 2019, provisional application No. 62/877,183, filed on Jul. 22, 2019, provisional application No. 62/852,262, filed on May 23, 2019.

(51) Int. Cl.

| | |
|---|---|
| ***C07H 19/10*** | (2006.01) |
| ***C07H 19/14*** | (2006.01) |
| ***C12Q 1/6869*** | (2018.01) |
| ***G01N 33/487*** | (2006.01) |

(52) U.S. Cl.

CPC ............. *C07H 19/10* (2013.01); *C07H 19/14* (2013.01); *C12Q 1/6869* (2013.01); *G01N 33/48721* (2013.01)

(58) Field of Classification Search

CPC ...... C07H 19/10; C07H 19/14; C07H 19/213; C07H 19/11; C12Q 1/6869; C12Q 2525/117; C12Q 2525/197; C12Q 2527/125; C12Q 2527/137; C12Q 2565/631; G01N 33/48721

See application file for complete search history.

(56) References Cited

U.S. PATENT DOCUMENTS

| | | | |
|---|---|---|---|
| 6,465,193 B2 | 10/2002 | Akeson et al. | |
| 7,939,259 B2 | 5/2011 | Kokoris et al. | |
| 10,457,979 B2 | 10/2019 | Mcruer et al. | |
| 2010/0297644 A1 | 11/2010 | Kokoris et al. | |
| 2012/0088235 A1 | 4/2012 | Kokoris et al. | |
| 2013/0186757 A1 | 7/2013 | Reinhart et al. | |
| 2015/0368710 A1 | 12/2015 | Fuller et al. | |
| 2016/0145292 A1* | 5/2016 | Kokoris ................ | C07H 23/00 558/73 |
| 2017/0073740 A1 | 3/2017 | McRuer et al. | |

FOREIGN PATENT DOCUMENTS

| | | |
|---|---|---|
| WO | 2008/157696 A2 | 12/2008 |
| WO | 2015110777 A1 | 7/2015 |
| WO | 2015/148402 A1 | 10/2015 |
| WO | 2015175789 A1 | 11/2015 |
| WO | 2016081871 A1 | 5/2016 |
| WO | 2017/014762 A1 | 1/2017 |
| WO | 2020172479 A1 | 8/2020 |

OTHER PUBLICATIONS

Kim, S. J. et al., Synthesis of Novel Phosphoramidite Building Blocks from Pentaerythritol, Synlett, vol. 12, No. 12, pp. 1838-1840, 2003.

Wang, Yue et al., The evolution of nanopore sequencing, Frontiers in Genetics, vol. 5, Art. 449, 20 pp., 2015.

Fuller, Carl W. et al., Real-time single-molecule electronic DNA sequencing by synthesis using polymer-tagged nucleotides on a nanopore array, PNAS, vol. 113, No. 19, pp. 5233-5238, 2016.

Wang, Rongliang et al., Research Progress in Nanopores-based Sensing Technology for Nucelic Acid Detection, Progress in Chinese Materials, vol. 37 , No. 1, pp. 59-67, with EN-Abstract, 2018.

(Continued)

*Primary Examiner* — Scarlett Y Goon
*Assistant Examiner* — Hoi Yan Lee
(74) *Attorney, Agent, or Firm* — Kristen K. Walker

(57) ABSTRACT

Phosphoramidate-based monomers are provided for use in the synthesis of expandable polymers for nanopore-based sensing. Such monomers comprising a reporter construct that contain a first reporter code, a symmetrical chemical brancher bearing a translocation control element, and a second reporter code, wherein the ends of the reporter construct are attached to phosphoramidate-nucleoside. Related methods and products are also provided.

14 Claims, 24 Drawing Sheets

Specification includes a Sequence Listing.

(56) References Cited

OTHER PUBLICATIONS

Cherf et al., Automated forward and reverse ratcheting of DNA in a nanopore at 5-A precision, Nat Biotechnol, Feb. 2012, pp. 344-348, 30 (4).
International Search Report and Written Opinion mailed Oct. 8, 2020 in PCT/US20/32950 filed May 14, 2020, 19 pages.
Kasianowicz et al., Characterization of individual polynucleotide molecules using a membrane channel, Proceedings of the National Academy of Sciences USA, Nov. 1996, pp. 13770-13773, vol. 93.

* cited by examiner

Key:

R=
Q=
D=
X=
L=
4=
Y=
5=

Exemplary
SSRT

5'-RQQDDDDDDDDLLLDX
5'-RQQDDDDDDDDLLLDX Y44444444444455-3'

5'-RQQDDDDDDDD44LXXX
5'-RQQDDDDDDDD44LXXX Y44444444444455-3'

5'-RQQDDDDDDDD444LLDX
5'-RQQDDDDDDDD444LLDX Y44444444444455-3'

5'-RQQDDDDDDXXL444444LLLLLL
5'-RQQDDDDDDXXL444444LLLLLL Y44444444444455-3'

DTB = Desthiobiotin

SEQUENCE LISTING

```
<160> NUMBER OF SEQ ID NOS: 10

<210> SEQ ID NO 1
<211> LENGTH: 14
<212> TYPE: DNA
<213> ORGANISM: Artificial Sequence
<220> FEATURE:
<223> OTHER INFORMATION: synthetic construct

<400> SEQUENCE: 1

ccgatcgaag gcct                                                    14


<210> SEQ ID NO 2
<211> LENGTH: 99
<212> TYPE: DNA
<213> ORGANISM: Artificial Sequence
<220> FEATURE:
<223> OTHER INFORMATION: synthetic construct

<400> SEQUENCE: 2

taccccagac ctgaagctct cttctggtgg ggctgttggc tctggtctgc tctgaagaaa      60

attccctggc cttcccttgt aggaaggcca gatcttccc                             99


<210> SEQ ID NO 3
<211> LENGTH: 60
<212> TYPE: DNA
<213> ORGANISM: Artificial Sequence
<220> FEATURE:
<223> OTHER INFORMATION: synthetic construct
```

<400> SEQUENCE: 3
acacacacac acacacacac acacacacac acacacacac acacacacac acacacacac 60

<210> SEQ ID NO 4
<211> LENGTH: 60
<212> TYPE: DNA
<213> ORGANISM: Artificial Sequence
<220> FEATURE:
<223> OTHER INFORMATION: synthetic construct

<400> SEQUENCE: 4
cagtcagtca gtcagtcagt cagtcagtca gtcagtcagt cagtcagtca gtcagtcagt 60

<210> SEQ ID NO 5
<211> LENGTH: 90
<212> TYPE: DNA
<213> ORGANISM: Artificial Sequence
<220> FEATURE:
<223> OTHER INFORMATION: synthetic construct

<400> SEQUENCE: 5
ccgaagatct ggccttccta caagggaagg ggagggaatt ttcttcagag ccaacagccc 60
caccagaaga gagcttcagg tctggggtag 90

<210> SEQ ID NO 6
<211> LENGTH: 222
<212> TYPE: DNA
<213> ORGANISM: Streptococcus pneumoniae

<400> SEQUENCE: 6
ggtagtgatg caagtgcacc ttttaagcaa atgtcatgca acatctactc ttatgcggta 60
ttagctatcg tttccaatag ttatccccg ctaccaggca ggttacctac gcgtatctca 120
cccgttcgca actcatccag agaagcaagc tcctccttca gcgtcctact tgcatgtatt 180
aggcacgccg ccagcgttcg tcctcagcca ggatcaaact ct 222

<210> SEQ ID NO 7
<211> LENGTH: 6
<212> TYPE: DNA
<213> ORGANISM: Artificial Sequence
<220> FEATURE:
<223> OTHER INFORMATION: synthetic construct

<400> SEQUENCE: 7 ccaagg 6

<210> SEQ ID NO 8
<211> LENGTH: 8
<212> TYPE: DNA
<213> ORGANISM: Artificial Sequence
<220> FEATURE:
<223> OTHER INFORMATION: synthetic construct

<400> SEQUENCE: 8 ccacaagg 8

<210> SEQ ID NO 9
<211> LENGTH: 4
<212> TYPE: DNA
<213> ORGANISM: Artificial Sequence
<220> FEATURE:
<223> OTHER INFORMATION: synthetic construct -continued

```
<400> SEQUENCE: 9

cagg                                                                 4


<210> SEQ ID NO 10
<211> LENGTH: 61
<212> TYPE: DNA
<213> ORGANISM: Artificial Sequence
<220> FEATURE:
<223> OTHER INFORMATION: synthetic construct

<400> SEQUENCE: 10

gaggtaggat gttgcatgac atttgcttaa aagggggtgc cccacttgcc atcccactac    60

c                                                                   61
```

TRANSLOCATION CONTROL ELEMENTS, REPORTER CODES, AND FURTHER MEANS FOR TRANSLOCATION CONTROL FOR USE IN NANOPORE SEQUENCING

CROSS REFERENCE TO RELATED APPLICATIONS

This patent application is a continuation of International Patent Application No. PCT/US2020/032950, filed May 14, 2020, which claims priority to and the benefit of United States Provisional Application No. U.S. 62/852,262, filed May 23, 2019, United States Provisional Application No. U.S. 62/877,183, filed Jul. 22, 2019 and U.S. Provisional Application No. 62/885,746 filed Aug. 12, 2019. Each of the above patent applications is incorporated herein by reference as if set forth in its entirety.

STATEMENT REGARDING SEQUENCE LISTING

The Sequence Listing associated with this application is provided in text format in lieu of a paper copy, and is hereby incorporated by reference into the specification. The name of the text file containing the Sequence Listing is P36231-US-3_SEQ_LIST_ST25. The text file is 3 KB, was created on Aug. 4, 2022, and is being submitted electronically via EFS-Web.

BACKGROUND

Technical Field

The present invention relates generally to new synthetic reporter constructs, more specifically to new nucleotide-free, phosphoramidite-based translocation control elements, reporter codes and other features that generate unique signals when passed through a nanopore, and methods for the manufacture and utilization thereof, particularly in nanopore-based polymer sequencing methods.

Description of the Related Art

Measurement of biomolecules is a foundation of modem medicine and is broadly used in medical research, and more specifically in diagnostics and therapy, as well in drug development. Nucleic acids encode the necessary information for living things to function and reproduce, and are essentially a blueprint for life. Determining such blueprints is useful in pure research as well as in applied sciences. In medicine, sequencing can be used for diagnosis and to develop treatments for a variety of pathologies, including cancer, heart disease, autoimmune disorders, multiple sclerosis, and obesity. In industry, sequencing can be used to design improved enzymatic processes or synthetic organisms. In biology, this tool can be used to study the health of ecosystems, for example, and thus have a broad range of utility. Similarly, measurement of proteins and other biomolecules has provided markers and understanding of disease and pathogenic propagation.

An individual's unique DNA sequence provides valuable information concerning their susceptibility to certain diseases. It also provides patients with the opportunity to screen for early detection and/or to receive preventative treatment. Furthermore, given a patient's individual blueprint, clinicians will be able to administer personalized therapy to maximize drug efficacy and/or to minimize the risk of an adverse drug response. Similarly, determining the blueprint of pathogenic organisms can lead to new treatments for infectious diseases and more robust pathogen surveillance. Low cost, whole genome DNA sequencing will provide the foundation for modern medicine. To achieve this goal, sequencing technologies must continue to advance with respect to throughput, accuracy, and read length.

Over the last decade, a multitude of next generation DNA sequencing technologies have become commercially available and have dramatically reduced the cost of sequencing whole genomes. These include sequencing by synthesis ("SBS") platforms (Illumina, Inc., 454 Life Sciences, Ion Torrent, Pacific Biosciences) and analogous ligation based platforms (Complete Genomics, Life Technologies Corporation). A number of other technologies are being developed that utilize a wide variety of sample processing and detection methods. For example, GnuBio, Inc. (Cambridge, Mass.) uses picoliter reaction vessels to control millions of discreet probe sequencing reactions, whereas Halcyon Molecular (Redwood City, Calif.) was attempting to develop technology for direct DNA measurement using a transmission electron microscope.

Nanopore based nucleic acid sequencing is a compelling approach that has been widely studied. Kasianowicz et al. (Proc. Natl. Acad. Sci. USA 93: 13770-13773, 1996) characterized single-stranded polynucleotides as they were electrically translocated through an alpha hemolysin nanopore embedded in a lipid bilayer. It was demonstrated that during polynucleotide translocation partial blockage of the nanopore aperture could be measured as a decrease in ionic current. Polynucleotide sequencing in nanopores, however, is burdened by having to resolve tightly spaced bases (0.34 nm) with small signal differences immersed in significant background noise. The measurement challenge of single base resolution in a nanopore is made more demanding due to the rapid translocation rates observed for polynucleotides, which are typically on the order of 1 base per microsecond. Translocation speed can be reduced by adjusting run parameters such as voltage, salt composition, pH, temperature, and viscosity, to name a few. However, such adjustments have been unable to reduce translocation speed to a level that allows for single base resolution.

Stratos Genomics has developed a method called Sequencing by Expansion ("SBX") that uses a biochemical process to transcribe the sequence of DNA onto a measurable polymer called an "Xpandomer" (Kokoris et al., U.S. Pat. No. 7,939,259, "High Throughput Nucleic Acid Sequencing by Expansion"). The transcribed sequence is encoded along the Xpandomer backbone in high signal-to-noise reporters that are separated by ~10 nm and are designed for high-signal-to-noise, well-differentiated responses. These differences provide significant performance enhancements in sequence read efficiency and accuracy of Xpandomers relative to native DNA. Xpandomers can enable several next generation DNA sequencing detection technologies and are well suited to nanopore sequencing.

Nanopores have proven to be powerful amplifiers, much like their highly-exploited predecessors, Coulter Counters. However, the current generation of organic nanopores (such as Hemolysin and MspA), that have been tasked with base recognition of DNA, are transmembrane proteins that do not interact with DNA in nature. They do not have natural functions for controlling DNA translocation. This is a recognized shortcoming that some have attempted to correct by adding functionality with protein motors adjacent to the nanopores. For example, Akeson's group added phi 29 polymerase adjacent to the alpha-hemolysin nanopore so that ss-DNA could be fed into the pore at a controlled rate (see G. M. Cherf et al. "Automated forward and reverse ratcheting of DNA in a nanopore at 5-A precision," Nat Biotech, vol. advance online publication, February 2012). This approach complicates the assay and imposes a separation of the measurement region in the alpha hemolysin from the position control in the polymerase that can introduce additional noise and sequence dependent variation to the measurement.

In another approach, referred to as translocation control by hybridization (TCH), a nanopore translocation event is paused by using a structure created by hybridization, which disassociates for translocation to proceed (see, e.g. U.S. Pat. No. 10,457,979 to McRuer and Kokoris). Akeson et al. (U.S. Pat. No. 6,465,193) first demonstrated this by pausing DNA translocation with sequential hairpin duplexed regions. Translocation stopped at the duplex because it was larger than the alpha-hemolysin nanopore aperture. When the duplex released due to stochastic thermal fluctuation, translocation proceeded to the next duplex. During each pause, the region of DNA located in the nanopore (adjacent to the duplex) could be measured and identified. When applied to nanopore sequencing, this duplexing approach to translocation control suffers from limitations, including incomplete duplex formation, or hybridization fill rate, and the stochastics of duplex dissociation, which can lead to deletions or insertions events. Insertion and deletions that cannot be localized can seriously degrade the data quality.

While significant advances have been made in this field, commercially viable implementation of translocation control with, for example, Xpandomers, would benefit from improvements that overcome limitations caused by duplexing. The present invention fulfills these needs and provides further related advantages as discussed below.

All of the subject matter discussed in the Background section is not necessarily prior art and should not be assumed to be prior art merely as a result of its discussion in the Background section. Along these lines, any recognition of problems in the prior art discussed in the Background section or associated with such subject matter should not be treated as prior art unless expressly stated to be prior art. Instead, the discussion of any subject matter in the Background section should be treated as part of the inventor's approach to the particular problem, which in and of itself may also be inventive.

BRIEF SUMMARY OF THE INVENTION

In brief, compounds (e.g., XNTPs) including polymeric reporter and linker constructs synthesized from a collection of novel phosphoramidite monomeric units and methods are disclosed for improved nanopore sequencing (for example, generating sequences of higher read length, accuracy, and/or throughput) of polymeric analytes (e.g., Xpandomers).

In some embodiments, the polymeric constructs may be designed to completely lack nucleotides.

In one aspect, the present disclosure provides a compound (i.e., an XNTP) having the following structure: Reporter Construct

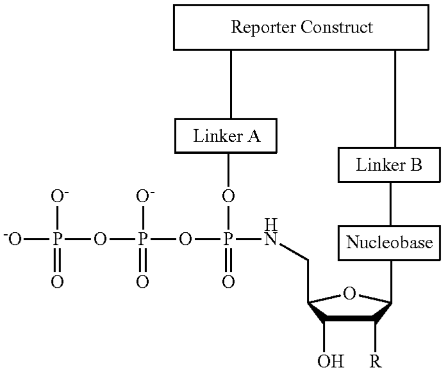

wherein R is OH or H; nucleobase is adenine, cytosine, guanine, thymine, uracil or a nucleobase analog; reporter construct is a polymer having a first end and a second end, and includes, in series from the first end to the second end, a first reporter code, a symmetrical chemical brancher bearing a translocation control element, and a second reporter code; linker A joins the oxygen atom of the alpha phosphoramidate to the first end of the reporter construct; linker B joins the nucleobase to the second end of the reporter construct; and in which the translocation control element is a polymer as described below.

In one embodiment, the translocation control element is a polymer comprising two or more repeat units selected from: 1,3-O-bis(phosphodiester)-2S-O-mPEG4-propane (compound 12b), 1,3-O-bis(phosphodiester)-2-(4-Me-O-PEG3)-1-(Et-O-Ac)-1,2,3-triazole)-propane (compound 35b), 1,3-O-bis(phosphodiester)-2s-O-mPEG6-propane (compound 12c), 1,2-O-bis(phosphodiester)-3-O-mPEG2-propane (compound 16), 2,3-O-bis(phosphodiester)-1-(5-benzofuran)-propane (compound 20i), 1,2-O-bis(phosphodiester)-3-(4-methylpiperazine-1-yl)-propane (compound 20j), 2,3-O-bis(phosphodiester)-1-(N1-(2-Me-5-nitroindole)-propane (compound 20g), 1,8-O-bis(phosphodiester)-N,N-Diethylpiperazine (compound 26h), 1,2-O-bis(phosphodiester)-3-(4-(Me-O-PEG3-O-Bz)-1-(1,2,3-triazole))-propane (compound 31d), 1,3-O-bis(phosphodiester)-2s-O-(4-(Me-O-PEG2)-1-(Et-OBz)-1,2,3-triazole)-propane (compound 35a), 1,3-O-bis(phosphodiester-2-(4-(Me-O-PEG5)-1-(Et-O-Ac)-1,2,3-triazole)-propane (compound 35c), 1,3-O-bis (phosphodiester-2s-O-(4-(Me-O-PEG7)-1-(Et-OBz)-1,2,3-triazole)-propane (compound 35d), 1,3-O-bis (phosphodiester-2s-O-(4-(Me-O-PEG3)-1-(Me-acetate)-1,2,3-triazole)-propane (compound 35e), 1,3-O-bis (phosphodiester-2s-O-(4-(Me-O-PEG3)-1-(Et-2,2,2-Tris-(Me-O-Bz))-1,2,3-triazole)-propane (compound 37a), 1,3-O-bis(phosphodiester-2-(4-(Me-O-PEG5)-1-(Et-2,2,2-Tris-(Me-O-Ac))-1,2,3-triazole)-propane (compound 37b), 1,3-O-bis(phosphodiester-2S-O-(PEG4-O-Bz)-propane (compound 38b), 1,3-O-bis(phosphodiester-2,2-bis(Me-O-mPEG2)-propane (compound 45b), 1,3-O-bis(phosphodiester-2,2-bis(4-(Me-O-PEG2-O-Me)-1-(Et-O-Bz)-1,2,3-triazole)-propane (compound 47f), 1,3-O-bis(phosphodiester-2,2-bis(4-(Me-O-PEG3-O-Me)-1-(Et-O-Bz)-1,2,3-triazole)-propane (compound 47Gg, 1,3-O-bis(phosphodiester-2,2-bis(4-(Me-O-PEG3-O-Me)-1-(Et-2,2,2-Tris-(Me-O-Bz))-1,2,3-triazole)-propane (compound 47i), or 1,3-O-bis (phosphodiester-2,2-bis(1-Me-4-(Me-O-PEG2-O-Bz)-1,2,3-triazole)-propane (compound 52).

In some embodiments, R is OH.

In some embodiments, R is H.

In other embodiments, nucleobase is adenine, cytosine, guanine, thymine, or uracil.

In other embodiments, nucleobase is a nucleobase analog.

In other embodiments, the symmetrical chemical brancher is 1,2,3-O-tris-(phosphosphodiester)-propane, 1,3-bis-(5-O-phosphodiester-pentylamido)-2-O-phosphodiester-propane, or 1,4,7-O-tris-(phosphodiester)-heptane.

In other embodiments, the symmetrical chemical brancher is 1,2,3-O-tris-(phosphosphodiester)-propane.

In other embodiments, the translocation control element is a polymer comprising two or more repeat units selected from Table 1A.

In other embodiments, the translocation control element is a polymer comprising two or more repeat units selected from 1,3-O-bis(phosphodiester)-2S-O-mPEG4-propane (compound 12b) and 1,3-O-bis(phosphodiester)-2-(4-Me-O-PEG3)-1-(Et-O-Ac)-1,2,3-triazole)-propane (compound 35b).

In yet other embodiments, the translocation control element is a polymer comprising the following sequence: [(1,3-O-bis(phosphodiester)-2S-O-mPEG4-propane (compound 12b))]n1[(1,3-O-bis(phosphodiester)-2-(4-Me-O-PEG3)-1-(Et-O-Ac)-1,2,3-triazole)-propane (compound 35b))]n2, wherein n1 is from 0 to 6 and n2 is from 6 to 10.

In other embodiments, the first and second reporter codes are identical.

In further embodiments, the first and second reporter codes are polymers comprising two or more repeat units selected from: hexaethylene glycol (D), ethane (L), triaethylene glycol (X), 1,3-O-bis(phosphodiester)-2S-O-mPEG4-propane (compound 12b), 1,3-O-bis(phosphodiester)-2-(4-Me-O-PEG3)-1-(Et-O-Ac)-1,2,3-triazole)-propane (compound 35b), 1,3-O-bis(phosphodiester-2,2-bis(Me-O-mPEG2)-propane (compound 45b), 1,3-O-bis(phosphodiester-2S-O-(PEG4-O-Bz)-propane (compound 38b), 1,3-O-bis (phosphodiester)-2s-O-mPEG6-propane (compound 12c), 1,3-O-bis(phosphodiester-2s-O-(4-(Me-O-PEG3)-1-(Et-2,2,2-Tris-(Me-O-Bz))-1,2,3-triazole)-propane (compound 37a), 1,3-O-bis(phosphodiester-2s-O-(4-(Me-O-PEG3)-1-(Me-acetate)-1,2,3-triazole)-propane (compound 35e), 1,3-O-bis(phosphodiester)-2s-O-(4-(Me-O-PEG2)-1-(Et-OBz)-1,2,3-triazole)-propane (compound 35a), 1,3-O-bis (phosphodiester)-2-(4-Et-1-(Et-O-mPEG1)-1,2,3-triazole)-propane (compound 31a), 2,3-O-bis(phosphodiester)-1-(1 dimethoxyquinazolinedione)-propane (compound 20c), 2,3-O-bis(phosphodiester)-1-(N9-(3,6-dimethoxycarbazole)-propane (compound 20e), 1,1'-O-bis(phosphodiester)-2,2'-(sulfonylbis(benz-4-yl))-diethanol (compound 26d), 1,1'-O-bis(phosphodiester)-2,2'-bipyridin-4,4'-yl)-dimethanol (compound 26a), 2,3-O-bis(phosphodiester)-1-(N1-(4,6-dimethoxy-3-Me-indole)-propane (compound 20b), 3-(1,2-O-bis(phosphodiester)-propyl)-8,8-dimethylhexahydro-3H-3a, 6-methanobenzo[c]isothiazole 2,2-dioxide (compound 20d), 2,3-O-bis(phosphodiester)-1-(N1-(6-Azathymine))-propane (compound 20f), 1,5-O-bis(phosphodiester)-hexahydrofuro [2,6]furan (compound 23), 1,1'-O-bis(phosphodiester)-octahydro-2,6-dimethyl-3,8:4,7-dimethano-2,6-naphthyridin-4, 8-diyl)-dimethanol (compound 26e), 2,3-O-bis (phosphodiester)-1-(N1-(2-Me-5-nitroindole)-propane (compound 20h), 2,3-O-bis(phosphodiester)-1-(N1-(2-Me-5-nitroindole)-propane (compound 20g), 2,3-O-bis(phosphodiester)-1-(5-benzofuran)-propane (compound 20i), 1,2-O-bis(phosphodiester)-3-0-mPEG2-propane (compound 5b), 1,3-O-bis(phosphodiester)-2-(4-Et-1-(Et-O-mPEG3)-1, 2,3-triazole)-propane (compound 31b), and 1,3-O-bis(phosphodiester)-3-O-mPEG4-propane (compound 5a).

In other embodiments, the first and second reporter codes are polymers comprising two or more repeat units selected from hexaethylene glycol, ethane, triaethylene glycol, and any of the compounds set forth in Table 1A.

In further embodiments, the first and second reporter codes are polymers comprising two or more repeat units selected from hexaethylene glycol, ethane, triaethylene glycol, and 1,3-O-bis(phosphodiester)-2S-O-mPEG4-propane (compound 12b).

In more specific embodiments, the first and second reporter codes are polymers comprising a sequence selected from: (i) [(hexaethylene glycol)2(ethane)3(hexaethylene glycol)(triaethylene glycol)], (ii) [(hexaethyleneglycol)2(1, 3-O-bis(phosphodiester)-2S-O-mPEG4-propane (compound 12b))2(ethane)(triaethylene glycol)3], (iii) [(hexaethylene glycol)2(1,3-O-bis(phosphodiester)-2S-O-mPEG4-propane (compound 12b))3(ethane)2(hexaethylene glycol) (triaethylene glycol)], and (iv) [(triaethylene glycol)2 (ethane)(1,3-O-bis(phosphodiester)-2S-O-mPEG4-propane (compound 12b))6(ethane)7].

In other embodiments, Linker A and Linker B are polymers comprising two or more repeat units selected from: spermine (Q), hexaethylene glycol (D), 2-((4-((3-(benzoyloxy)-2-(((1-(3-(benzoyloxy)-2-((benzoyloxy)methyl)-2-((phosphodiester-oxy)methyl)propyl)-1H-1,2,3-triazol-4-yl) methoxy)methyl)-2-((benzoyloxy)methyl)propoxy)methyl)-1H-1,2,3-triazol-1-yl)methyl)-2-O-phosphodiester-propane-1,3-diyl dibenzoate (compound 62), 1,3-O-bis (phosphodiester-2,2-bis(1-Me-4-(Me-O-PEG2-O-Bz)-1,2, 3-triazole)-propane (compound 52), 1,3-O-bis (phosphodiester-2-(4-(Me-O-PEG5)-1-(Et-O-Ac)-1,2,3-triazole)-propane (compound 35c), 1,3-O-bis (phosphodiester-2s-O-(4-(Me-O-PEG7)-1-(Et-OBz)-1,2,3-triazole)-propane (compound 35d), 1,3-O-bis (phosphodiester-2s-O-(4-(Me-O-PEG3)-1-(Et-2,2,2-Tris-(Me-O-Bz))-1,2,3-triazole)-propane (compound 37a), 1,3-O-bis(phosphodiester-2-(4-(Me-O-PEG5)-1-(Et-2,2,2-Tris-(Me-O-Ac))-1,2,3-triazole)-propane (compound 37b), 1,2-O-bis(phosphodiester)-3-(4-(Me-O-PEG3-O-Bz)-1-(1,2,3-triazole))-propane (compound 31d), 1,3-O-bis (phosphodiester-2,2-bis(4-(Me-O-PEG2-O-Me)-1-(Et-O-Bz)-1,2,3-triazole)-propane (compound 47f), 1,3-O-bis (phosphodiester-2,2-bis(4-(Me-O-PEG3-O-Me)-1-(Et-2,2, 2-Tris-(Me-O-Bz))-1,2,3-triazole)-propane (compound 47i), 1,2-O-bis(phosphodiester)-3-(4-methylpiperazine-1-yl)-propane (compound 20j), 1,3-O-bis(phosphodiester-2,2-bis (4-(Me-O-PEG3-O-Me)-1-(Et-O-Bz)-1,2,3-triazole)-propane (compound 47g), and 1,1'-O-bis(phosphodiester)-N(p-tolyl)-diethanolamine (compound 26b).

In other embodiments, Linker A and Linker B are polymers comprising two or more repeat units selected from spermine and any of the compounds set forth in Table 1A.

In yet other embodiments, Linker A and Linker B comprise a polymerase enhancement region comprising two repeat units of spermine.

In further embodiments, Linker A and Linker B comprise a translocation deceleration region comprising two or more repeat units selected from: 1,3-O-bis(phosphodiester-2-(4-(Me-O-PEG5)-1-(Et-O-Ac)-1,2,3-triazole)-propane (compound 35c), 1,3-O-bis(phosphodiester-2s-O-(4-(Me-O-PEG7)-1-(Et-OBz)-1,2,3-triazole)-propane (compound 35d), 1,3-O-bis(phosphodiester-2s-O-(4-(Me-O-PEG3)-1-(Et-2,2,2-Tris-(Me-O-Bz))-1,2,3-triazole)-propane (compound 37a), and 1,3-O-bis(phosphodiester-2-(4-(Me-O-PEG5)-1-(Et-2,2,2-Tris-(Me-O-Ac))-1,2,3-triazole)-propane (compound 37b).

In more specific embodiments, Linker A and Linker B comprise a translocation deceleration region comprising a polymer selected from: (i) [((hexaethylene glycol) (1,3-O-bis(phosphodiester-2-(4-(Me-O-PEG5)-1-(Et-O-Ac)-1,2,3-triazole)-propane (compound 35c))3(hexaethylene glycol) 2], (ii) [((hexathylene glycol)(1,3-O-bis(phosphodiester-2-(4-(Me-O-PEG5)-1-(Et-O-Ac)-1,2,3-triazole)-propane (compound 35c))4(hexaethylene glycol)2], (iii) [((hexathylene glycol)(1,3-O-bis(phosphodiester-2s-O-(4-(Me-O-PEG7)-1-(Et-OBz)-1,2,3-triazole)-propane (compound 35d))4(hexaethylene glycol)2], and (iv) [((hexathylene glycol)(1,3-O-bis(phosphodiester-2-(4-(Me-O-PEG5)-1-(Et-2,2,2-Tris-(Me-O-Ac))-1,2,3-triazole)-propane (compound 37b))4(hexaethylene glycol)2].

In other embodiments, Liker A is joined to the oxygen atom of the alpha phosphoramidate by a linkage comprising a triazole and Liker B is joined to the nucleobase by a linkage comprising a triazole.

In another aspect, the present invention provides a reporter construct comprising a polymer having a first end and a second end, and including in series from the first end to the second end a first reporter code, a symmetrical chemical brancher bearing a translocation control element, and a second reporter code; and in which the translocation control element is a polymer comprising two or more repeat units selected from: 1,3-O-bis(phosphodiester)-2S-O-mPEG4-propane (compound 12b), 1,3-O-bis(phosphodiester)-2-(4-Me-O-PEG3)-1-(Et-O-Ac)-1,2,3-triazole)-propane (compound 35b), 1,3-O-bis(phosphodiester)-2s-O-mPEG6-propane (compound 12c), 1,2-O-bis(phosphodiester)-3-O-mPEG2-propane (compound 16), 2,3-O-bis(phosphodiester)-1-(5-benzofuran)-propane (compound 20i), 1,2-O-bis (phosphodiester)-3-(4-methylpiperazine-1-yl)-propane (compound 20j), 2,3-O-bis(phosphodiester)-1-(N1-(2-Me-5-nitroindole)-propane (compound 20g), 1,8-O-bis(phosphodiester)-N,N-Diethylpiperazine (compound 26h), 1,2-O-bis(phosphodiester)-3-(4-(Me-O-PEG3-O-Bz)-1-(1,2,3-triazole))-propane (compound 31d), 1,3-O-bis (phosphodiester)-2s-O-(4-(Me-O-PEG2)-1-(Et-OBz)-1,2,3-triazole)-propane (compound 35a), 1,3-O-bis (phosphodiester-2-(4-(Me-O-PEG5)-1-(Et-O-Ac)-1,2,3-triazole)-propane (compound 35c), 1,3-O-bis (phosphodiester-2s-O-(4-(Me-O-PEG7)-1-(Et-OBz)-1,2,3-triazole)-propane (compound 35d), 1,3-O-bis (phosphodiester-2s-O-(4-(Me-O-PEG3)-1-(Me-acetate)-1,2,3-triazole)-propane (compound 35e), 1,3-O-bis (phosphodiester-2s-O-(4-(Me-O-PEG3)-1-(Et-2,2,2-Tris-(Me-O-Bz))-1,2,3-triazole)-propane (compound 37a), 1,3-O-bis(phosphodiester-2-(4-(Me-O-PEG5)-1-(Et-2,2,2-Tris-(Me-O-Ac))-1,2,3-triazole)-propane (compound 37b), 1,3-O-bis(phosphodiester-2S-O-(PEG4-O-Bz)-propane (compound 38b), 1,3-O-bis(phosphodiester-2,2-bis(Me-O-mPEG2)-propane (compound 45b), 1,3-O-bis(phosphodiester-2,2-bis(4-(Me-O-PEG2-O-Me)-1-(Et-O-Bz)-1,2,3-triazole)-propane (compound 47f), 1,3-O-bis(phosphodiester-2,2-bis(4-(Me-O-PEG3-O-Me)-1-(Et-O-Bz)-1,2,3-triazole)-propane (compound 47Gg, 1,3-O-bis(phosphodiester-2,2-bis(4-(Me-O-PEG3-O-Me)-1-(Et-2,2,2-Tris-(Me-O-Bz))-1,2,3-triazole)-propane (compound 47i), or 1,3-O-bis (phosphodiester-2,2-bis(1-Me-4-(Me-O-PEG2-O-Bz)-1,2,3-triazole)-propane (compound 52).

In some embodiments, the symmetrical chemical brancher is 1,2,3-O-tris-(phosphosphodiester)-propane, 1,3-bis-(5-O-phosphodiester-pentylamido)-2-O-phosphodiester-propane, or 1,4,7-O-tris-(phosphodiester)-heptane.

In another embodiment, the symmetrical chemical brancher is 1,2,3-O-tris-(phosphosphodiester)-propane.

In other embodiments, the translocation control element is a polymer comprising two or more repeat units selected from Table 1A.

In yet other embodiments, the translocation control element is a polymer comprising two or more repeat units selected from 1,3-O-bis(phosphodiester)-2S-O-mPEG4-propane (compound 12b) and 1,3-O-bis(phosphodiester)-2-(4-Me-O-PEG3)-1-(Et-O-Ac)-1,2,3-triazole)-propane (compound 35b).

In further embodiments, the translocation control element is a polymer comprising the following sequence: [(1,3-O-bis(phosphodiester)-2S-O-mPEG4-propane (compound 12b))]n1[(1,3-O-bis(phosphodiester)-2-(4-Me-O-PEG3)-1-(Et-O-Ac)-1,2,3-triazole)-propane (compound 35b))]n2, wherein n1 is from 0 to 6 and n2 is from 6 to 10.

In other embodiments, the first and second reporter codes are identical.

In some embodiments, the first and second reporter codes are polymers comprising two or more repeat units selected from: hexaethylene glycol (D), ethane (L), triaethylene glycol (X), 1,3-O-bis(phosphodiester)-2S-O-mPEG4-propane (compound 12b), 1,3-O-bis(phosphodiester)-2-(4-Me-O-PEG3)-1-(Et-O-Ac)-1,2,3-triazole)-propane (compound 35b), 1,3-O-bis(phosphodiester-2,2-bis(Me-O-mPEG2)-propane (compound 45b), 1,3-O-bis(phosphodiester-2S-O-(PEG4-O-Bz)-propane (compound 38b), 1,3-O-bis(phosphodiester)-2s-O-mPEG6-propane (compound 12c), 1,3-O-bis(phosphodiester-2s-O-(4-(Me-O-PEG3)-1-(Et-2,2,2-Tris-(Me-O-Bz))-1,2,3-triazole)-propane (compound 37a), 1,3-O-bis(phosphodiester-2s-O-(4-(Me-O-PEG3)-1-(Me-acetate)-1,2,3-triazole)-propane (compound 35e), 1,3-O-bis (phosphodiester)-2s-O-(4-(Me-O-PEG2)-1-(Et-OBz)-1,2,3-triazole)-propane (compound 35a), 1,3-O-bis (phosphodiester)-2-(4-Et-1-(Et-O-mPEG1)-1,2,3-triazole)-propane (compound 31a), 2,3-O-bis(phosphodiester)-1-(1 dimethoxyquinazolinedione)-propane (compound 20c), 2,3-O-bis(phosphodiester)-1-(N9-(3,6-dimethoxycarbazole)-propane (compound 20e), 1,1'-O-bis(phosphodiester)-2,2'-(sulfonylbis(benz-4-yl))-diethanol (compound 26d), 1,1'-O-bis(phosphodiester)-2,2'-bipyridin-4,4'-yl)-dimethanol (compound 26a), 2,3-O-bis(phosphodiester)-1-(N1-(4,6-dimethoxy-3-Me-indole)-propane (compound 20b), 3-(1,2-O-bis(phosphodiester)-propyl)-8,8-dimethylhexahydro-3H-3a,6-methanobenzo[c]isothiazole 2,2-dioxide (compound 20d), 2,3-O-bis(phosphodiester)-1-(N1-(6-Azathymine))-propane (compound 20f), 1,5-O-bis(phosphodiester)-hexahydrofuro [2,6]furan (compound 23), 1,1'-O-bis(phosphodiester)-octahydro-2,6-dimethyl-3,8:4,7-dimethano-2,6-naphthyridin-4,8-diyl)-dimethanol (compound 26e), 2,3-O-bis (phosphodiester)-1-(N1-(2-Me-5-nitroindole)-propane (compound 20h), 2,3-O-bis(phosphodiester)-1-(N1-(2-Me-5-nitroindole)-propane (compound 20g), 2,3-O-bis(phosphodiester)-1-(5-benzofuran)-propane (compound 20i), 1,2-O-bis(phosphodiester)-3-O-mPEG2-propane (compound 5b), 1,3-O-bis(phosphodiester)-2-(4-Et-1-(Et-O-mPEG3)-1,2,3-triazole)-propane (compound 31b), and 1,3-O-bis(phosphodiester)-3-O-mPEG4-propane (compound 5a).

In other embodiments, the first and second reporter codes are polymers comprising two or more repeat units selected from hexaethylene glycol, ethane, triaethylene glycol, and any of the compounds set forth in Table 1A.

In further embodiments, the first and second reporter codes are polymers comprising two or more repeat units selected from hexaethylene glycol, ethane, triaethylene glycol, and 1,3-O-bis(phosphodiester)-2S-O-mPEG4-propane (compound 12b).

In further embodiments, the first and second reporter codes are polymers comprising a sequence selected from: (i) [(hexaethylene glycol)2(ethane)3(hexaethylene glycol)(triaethylene glycol)], (ii) [(hexaethyleneglycol)2(1,3-O-bis(phosphodiester)-2S-O-mPEG4-propane (compound 12b))2(ethane)(triaethylene glycol)3], (iii) [(hexaethylene glycol)2(1,3-O-bis(phosphodiester)-2S-O-mPEG4-propane (compound 12b))3(ethane)2(hexaethylene glycol)(triaethylene glycol)], and (iv) [(triaethylene glycol)2(ethane)(1,3-O-bis(phosphodiester)-2S-O-mPEG4-propane (compound 12b))6(ethane)7].

In another aspect, the present invention provides a symmetrically synthesized report tether (SSRT), in which the symmetrically synthesized reporter tether is a polymer having a first end and a second end, and includes in series from the first end to the second end a first linker, a reporter construct according to any one of the above reporter constructs, and a second linker, in which the first and second linkers are identical and are polymers comprising two or more repeat units selected from: spermine (Q), hexaethylene glycol (D), 2-((4-((3-(benzoyloxy)-2-(((1-(3-(benzoyloxy)-2-((benzoyloxy)methyl)-2-((phosphodiester-oxy)methyl)propyl)-1H-1,2,3-triazol-4-yl)methoxy)methyl)-2-((benzoyloxy)methyl)propoxy)methyl)-1H-1,2,3-triazol-1-yl)methyl)-2-O-phosphodiester-propane-1,3-diyl dibenzoate (compound 62), 1,3-O-bis(phosphodiester-2,2-bis(1-Me-4-(Me-O-PEG2-O-Bz)-1,2,3-triazole)-propane (compound 52), 1,3-O-bis(phosphodiester-2-(4-(Me-O-PEG5)-1-(Et-O-Ac)-1,2,3-triazole)-propane (compound 35c), 1,3-O-bis(phosphodiester-2s-O-(4-(Me-O-PEG7)-1-(Et-OBz)-1,2,3-triazole)-propane (compound 35d), 1,3-O-bis(phosphodiester-2s-O-(4-(Me-O-PEG3)-1-(Et-2,2,2-Tris-(Me-O-Bz))-1,2,3-triazole)-propane (compound 37a), 1,3-O-bis(phosphodiester-2-(4-(Me-O-PEG5)-1-(Et-2,2,2-Tris-(Me-O-Ac))-1,2,3-triazole)-propane (compound 37b), 1,2-O-bis(phosphodiester)-3-(4-(Me-O-PEG3-O-Bz)-1-(1,2,3-triazole))-propane (compound 31d), 1,3-O-bis(phosphodiester-2,2-bis(4-(Me-O-PEG2-O-Me)-1-(Et-O-Bz)-1,2,3-triazole)-propane (compound 47f), 1,3-O-bis(phosphodiester-2,2-bis(4-(Me-O-PEG3-O-Me)-1-(Et-2,2,2-Tris-(Me-O-Bz))-1,2,3-triazole)-propane (compound 47i), 1,2-O-bis(phosphodiester)-3-(4-methylpiperazine-1-yl)-propane (compound 20j), 1,3-O-bis(phosphodiester-2,2-bis(4-(Me-O-PEG3-O-Me)-1-(Et-O-Bz)-1,2,3-triazole)-propane (compound 47g), and 1,1'-O-bis(phosphodiester)-N(p-tolyl)-diethanolamine (compound 26b).

In some embodiments, the symmetrically synthesized reporter tether (SSRT) includes a polymerase enhancement region comprising two repeat units of spermine.

In other embodiments, the symmetrically synthesized reporter tether (SSRT) includes a translocation deceleration region comprising two or more repeat units selected from: 1,3-O-bis(phosphodiester-2-(4-(Me-O-PEG5)-1-(Et-O-Ac)-1,2,3-triazole)-propane (compound 35c), 1,3-O-bis(phosphodiester-2s-O-(4-(Me-O-PEG7)-1-(Et-OBz)-1,2,3-triazole)-propane (compound 35d), 1,3-O-bis(phosphodiester-2s-O-(4-(Me-O-PEG3)-1-(Et-2,2,2-Tris-(Me-O-Bz))-1,2,3-triazole)-propane (compound 37a), and 1,3-O-bis(phosphodiester-2-(4-(Me-O-PEG5)-1-(Et-2,2,2-Tris-(Me-O-Ac))-1,2,3-triazole)-propane (compound 37b).

In other embodiments, the symmetrically synthesized reporter tether (SSRT) includes a translocation deceleration region comprising a polymer selected from: (i) [((hexaethylene glycol) (1,3-O-bis(phosphodiester-2-(4-(Me-O-PEG5)-1-(Et-O-Ac)-1,2,3-triazole)-propane (compound 35c))3(hexaethylene glycol)2], (ii) [((hexathylene glycol)(1,3-O-bis(phosphodiester-2-(4-(Me-O-PEG5)-1-(Et-O-Ac)-1,2,3-triazole)-propane (compound 35c))4(hexaethylene glycol)2], (iii) [((hexathylene glycol)(1,3-O-bis(phosphodiester-2s-O-(4-(Me-O-PEG7)-1-(Et-OBz)-1,2,3-triazole)-propane (compound 35d))4(hexaethylene glycol)2], and (iv) [((hexathylene glycol)(1,3-O-bis(phosphodiester-2-(4-(Me-O-PEG5)-1-(Et-2,2,2-Tris-(Me-O-Ac))-1,2,3-triazole)-propane (compound 37b))4(hexaethylene glycol)2].

In yet other embodiments, the first end and the second end of the symmetrically synthesized reporter tether (SSRT) include a linkage moiety and, in certain embodiments, the linkage moiety is an azido ($-N_3$) group.

In another aspect, the present invention provides a method for sequencing a target nucleic acid, comprising the steps of: a) providing a daughter strand produced by a template-directed synthesis, the daughter strand comprising a plurality of XNTP subunits coupled in a sequence corresponding to a contiguous nucleotide sequence of all or a portion of the target nucleic acid, wherein the individual XNTP subunits of the daughter strand comprise a reporter construct, a nucleobase residue, and a selectively cleavable bond, and wherein the reporter construct, upon cleavage of the selectively cleavable bond, permits lengthening of the subunits of the daughter strand; b) cleaving the selectively cleavable bonds to yield an Xpandomer of a length longer than the plurality of the subunits of daughter strand, the Xpandomer comprising the reporter constructs for parsing genetic information in a sequence corresponding to the contiguous nucleotide sequence of all or a portion of the target nucleic acid; and c) detecting the reporter constructs of the Xpandomer.

In some aspects, the reporter constructs for parsing the genetic information comprise a reporter code and a translocation control element, wherein the translocation control element provides translocation control by steric hindrance and pauses translocation of the Xpandomer when passed through a nanopore subjected to a baseline voltage, wherein the translocation control element engages the reporter code within the aperture of the nanopore, wherein the reporter code is sensed by the nanopore.

In some embodiments, the Xpandomer resumes translocation through the nanopore by application of a pulse voltage, in which the pulse voltage is sufficient to allow translocation of the translocation control element, while leaving the next reporter construct of the Xpandomer free to engage with the nanopore.

In other embodiments, the translocation control element of the reporter construct engaged with the nanopore by steric hindrance translocates upon each pulse of the pulsed voltage.

In some embodiments, the target construct is sensed by the nanopore during the time period between pulses of the pulsed voltage.

In certain embodiments, the baseline voltage is from about 55 mV to about 75 mV and the pulse voltage is from about 550 mV to about 700 mV.

In some embodiments, the pulse voltage has a duration from about 5 μs to about 10 μs and a periodicity from about 0.5 ms to 1.5 ms.

In other embodiments, the nanopore is subjected to an alternating current (AC).

In further embodiments, one or more of the XNTP subunits includes a 2' Fluoroarabinosyl epimer.

In another aspect, the present disclosure provides a buffer for controlling the rate of translocation of a polymer through a nanopore comprising at least one salt selected from the group consisting of $NH_4Cl$, $MgCl_2$, LiCl, KCl, CsCl, NaCl, and $CaCl_2$.

In some embodiments, the buffer further comprises at least one solvent selected from the group consisting of 3-methyl-2-oxazolidinone (MOA), DMF, ACN, DMSO, and NMP, wherein the solvent is present in the range from about 1% vol/vol to about 35% vol/vol.

In other embodiments, the buffer further comprises at least one additive selected from the group consisting of sodium hexanoate (NaHex), EDTA, redox reagents, PEG, glycerol, ficoll, and the like.

In another aspect, the present disclosure provides a buffer system for controlling the rate of translocation of a polymer through a nanopore detector comprising a cis buffer and a trans buffer, wherein the cis buffer has a first salt concentration and the trans buffer has a second salt concentration, wherein the first salt concentration is lower than the second salt concentration.

DETAILED DESCRIPTION OF THE INVENTION

Figure 1A:
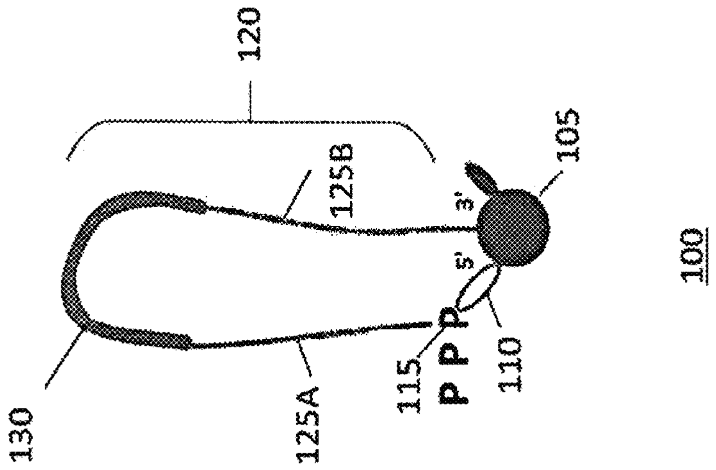
FIGS. 1A, 1B, 1C and 1D are condensed schematics illustrating the main features of a generalized XNTP and their functions in Sequencing by Expansion (SBX).

The present invention may be understood more readily by reference to the following detailed description of preferred embodiments of the invention and the Examples included herein. Unless otherwise explained, all technical and scientific terms used herein have the same meaning as commonly understood by one of ordinary skill in the art to which this disclosure belongs.

Reference throughout this specification to "one embodiment" or "an embodiment" and variations thereof means that a particular feature, structure, or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

As used in this specification and the appended claims, the singular forms "a," "an," and "the" include plural referents, i.e., one or more, unless the content and context clearly dictates otherwise. It should also be noted that the conjunctive terms, "and" and "or" are generally employed in the broadest sense to include "and/or" unless the content and context clearly dictates inclusivity or exclusivity as the case may be. Thus, the use of the alternative (e.g., "or") should be understood to mean either one, both, or any combination thereof of the alternatives. In addition, the composition of "and" and "or" when recited herein as "and/or" is intended to encompass an embodiment that includes all of the associated items or ideas and one or more other alternative embodiments that include fewer than all of the associated items or ideas.

Unless the context requires otherwise, throughout the specification and claims that follow, the word "comprise" and synonyms and variants thereof such as "have" and "include", as well as variations thereof such as "comprises" and "comprising" are to be construed in an open, inclusive sense, e.g., "including, but not limited to." The term "consisting essentially of" limits the scope of a claim to the specified materials or steps, or to those that do not materially affect the basic and novel characteristics of the claimed invention.

The abbreviation, "e.g." is derived from the Latin exempli gratia, and is used herein to indicate a non-limiting example. Thus, the abbreviation "e.g." is synonymous with the term "for example." It is also to be understood that as used herein and in the appended claims, the singular forms "a," "an," and "the" include plural reference unless the context clearly dictates otherwise, the term "X and/or Y" means "X" or "Y" or both "X" and "Y", and the letter "s" following a noun designates both the plural and singular forms of that noun. In addition, where features or aspects of the invention are described in terms of Markush groups, it is intended, and those skilled in the art will recognize, that the invention embraces and is also thereby described in terms of any individual member and any subgroup of members of the Markush group, and Applicants reserve the right to revise the application or claims to refer specifically to any individual member or any subgroup of members of the Markush group.

Any headings used within this document are only being utilized to expedite its review by the reader, and should not be construed as limiting the invention or claims in any manner. Thus, the headings and Abstract of the Disclosure provided herein are for convenience only and do not interpret the scope or meaning of the embodiments.

Where a range of values is provided herein, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either or both of those included limits are also included in the invention.

For example, any concentration range, percentage range, ratio range, or integer range provided herein is to be understood to include the value of any integer within the recited range and, when appropriate, fractions thereof (such as one tenth and one hundredth of an integer), unless otherwise indicated. Also, any number range recited herein relating to any physical feature, such as polymer subunits, size or thickness, are to be understood to include any integer within the recited range, unless otherwise indicated. As used herein, the term "about" means±20% of the indicated range, value, or structure, unless otherwise indicated.

Sequencing by Expansion

The "Sequencing by Expansion" (SBX) protocol, developed by Stratos Genomics (see, e.g., Kokoris et al., U.S. Pat. No. 7,939,259, "High Throughput Nucleic Acid Sequencing by Expansion") is based on the polymerization of highly modified, non-natural nucleotide analogs referred to as "XNTPs". In general terms, SBX uses biochemical polymerization to transcribe the sequence of a DNA template onto a measurable polymer called an "Xpandomer". The transcribed sequence is encoded along the Xpandomer backbone in high signal-to-noise reporters that are separated by −10 nm and are designed for high-signal-to-noise, well-differentiated responses. These differences provide significant performance enhancements in sequence read efficiency and accuracy of Xpandomers relative to natural DNA. A generalized overview of the SBX process is depicted in FIGS. 1A, 1B, 1C and 1D.

XNTPs are expandable, 5' triphosphate modified non-natural nucleotide analogs compatible with template dependent enzymatic polymerization. A highly simplified XNTP is illustrated in FIG. 1A, which emphasizes the unique features of these non-natural substrates: XNTP 100 has two distinct functional regions; namely, a selectively cleavable phosphoramidate bond 110, linking the 5' a-phosphate 115 to the nucleobase 105, and a symmetrically synthesized reporter tether (SSRT) 120 that is attached within the nucleoside triphosphoramidate at positions that allow for controlled expansion by cleavage of the phosphoramidate bond. The SSRT includes linkers 125A and 125B separated by the selectively cleavable phosphoramidate bond. Each linker attaches to one end of a reporter code 130. XNTP 100 is illustrated in the "constrained configuration", characteristic of the XNTP substrates and the daughter strand products of template-dependent polymerization. The constrained configuration of polymerized XNTPs is the precursor to the expanded configuration, as found in Xpandomer products. The transition from the constrained configuration to the expanded configuration occurs upon scission of the P--N bond of the phosphoramidate within the primary backbone of the daughter strand.

Figure 1B:
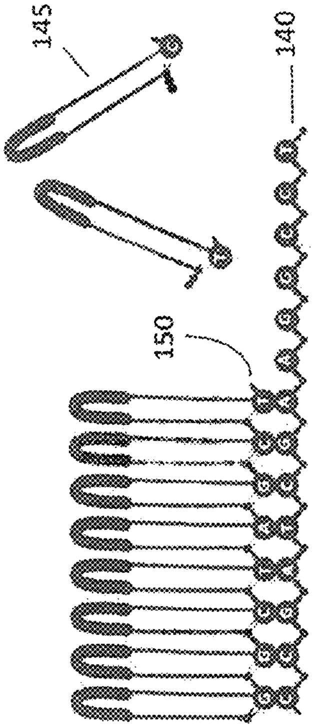
Figure 1C:
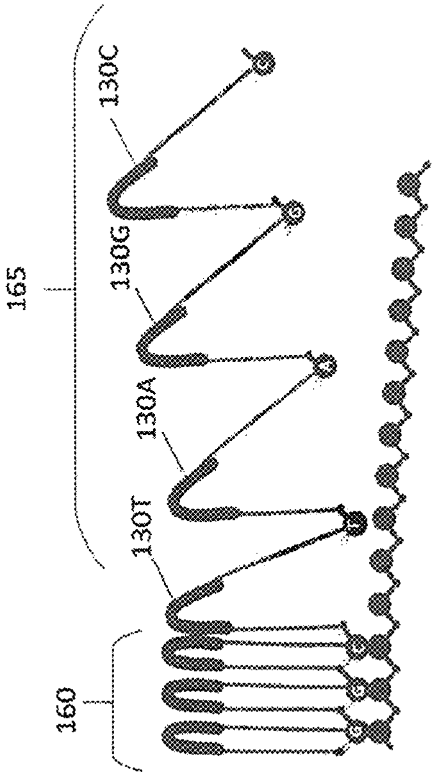

Synthesis of an Xpandomer polymer is summarized in FIGS. 1B and 1C. During assembly, the monomeric XNTP substrates 145 (XATP, XCTP, XGTP and XTTP) are polymerized on the extendable terminus of a nascent daughter strand 150 by a process of template-directed polymerization using single-stranded template 140 (SEQ ID NO:1) as a guide. Generally, this process is initiated from a primer and proceeds in the 5' to 3' direction. Generally, a DNA polymerase or other polymerase is used to form the daughter strand, and conditions are selected so that a complimentary copy of the template strand is obtained. After the daughter strand is synthesized, the coupled SSRTs form the constrained Xpandomer that further forms the daughter strand. SSRTs in the daughter strand have the "constrained configuration" of the XNTP substrates. The constrained configuration of the SSRT is the precursor to the expanded configuration, as found the Xpandomer product.

As shown in FIG. 1C, the transition from the constrained configuration 160 to the expanded configuration 165 results from cleavage of the selectively cleavable phosphoramidate bonds (illustrated for simplicity by the unshaded ovals) within the primary backbone of the daughter strand. In this embodiment, the SSRTs include one or more reporters or reporter codes, 130A, 130C, 130G, or 130T, specific for the nucleobase to which they are linked, thereby encoding the sequence information of the template. In this manner, the SSRTs provide a means to expand the length of the Xpandomer and lower the linear density of the sequence information of the parent strand.

Figure 1D:
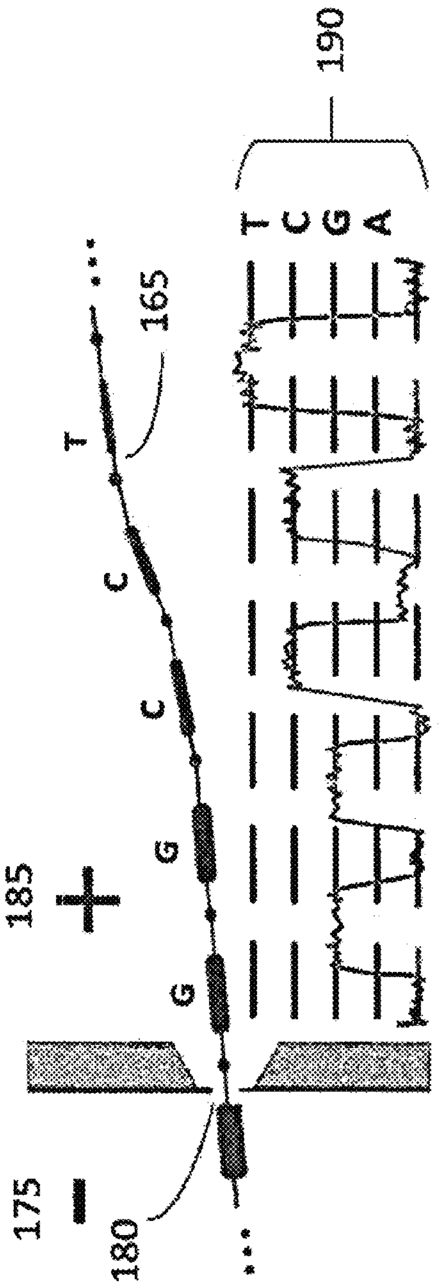

FIG. 1D illustrates an Xpandomer 165 translocating through a nanopore 180, from the cis reservoir 175 to the trans reservoir 185. Upon passage through the nanopore, each of the reporter codes of the linearized Xpandomer (in this illustration, labeled "G", "C" and "T") generates a distinct and reproducible electronic signal (illustrated by superimposed trace 190), specific for the nucleobase to which it is linked.

Figure 2:
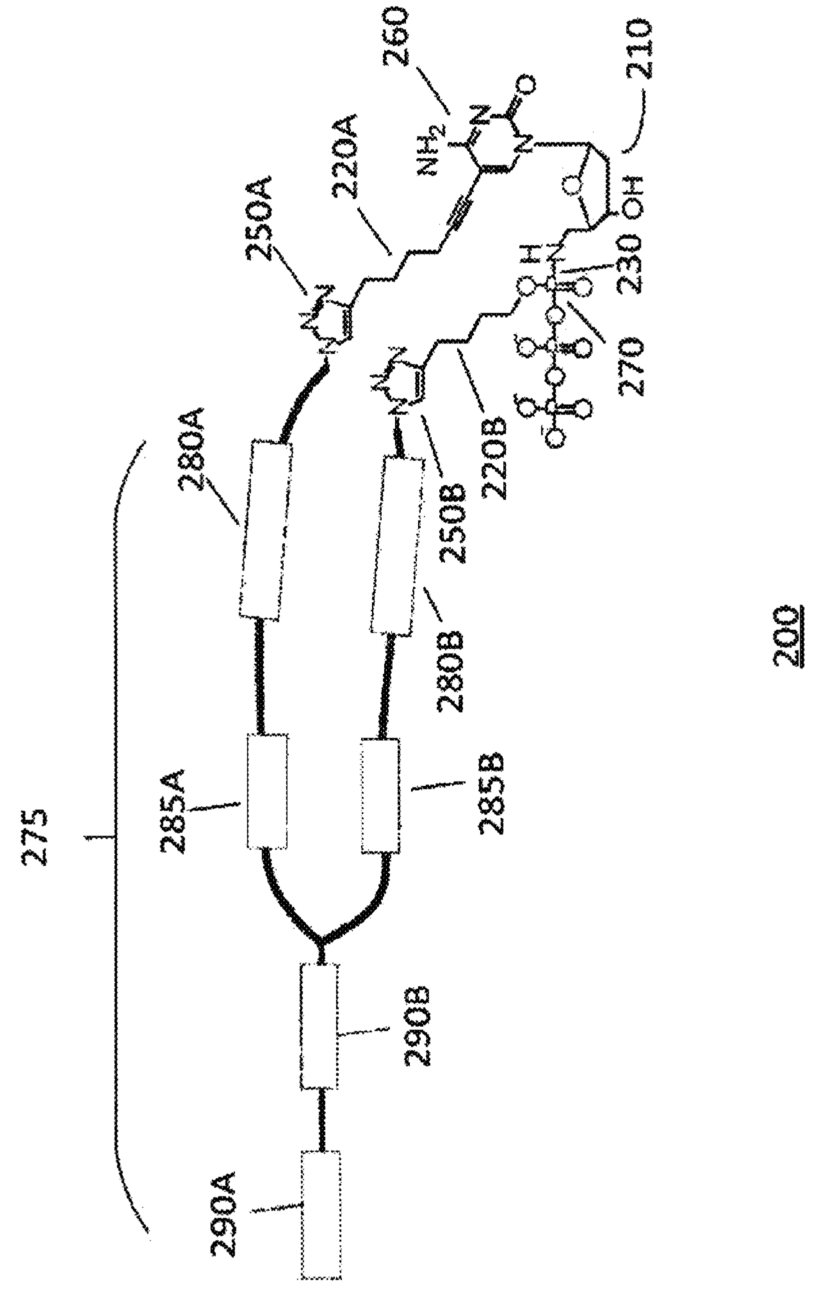
FIG. 2 is a schematic illustrating more details of one embodiment of an XNTP.

FIG. 2 depicts the generalized structure of one embodiment of an XNTP in more detail. XNTP 200 includes nucleoside triphosphoramidate 210 with linker arm moieties 220A and 220B separated by selectively cleavable phosphoramidate bond 230. SSRTs are joined to the nucleoside triphosphoramidate at linkage groups 250A and 250B, in which a first SSRT end is joined to the heterocycle 260 (represented here by cytosine, though the heterocycle may be any one of the four standard nucleobases, A, C, G, or T) and a second SSRT end is joined to the alpha phosphate 270 of the nucleobase backbone. The skilled artisan will appreciate that many suitable coupling chemistries known in the art may be used to form the final XNTP substrate product, for example, SSRT conjugation may be accomplished through formation of a triazole linkage group.

In this embodiment, SSRT 275 includes several functional elements, or "features" such as polymerase enhancement regions 280A and 280B, reporter codes 285A and 285B, and translation control element (TCEs) 290A and 290B. In other embodiments, the SSRT includes a single TCE. Each of these features performs a unique function during translocation of the Xpandomer through a nanopore to produce a series of unique and reproducible electronic signal. SSRT 275 is designed for controlling the rate of Xpandomer translocation by the TCE through a combination of sterics and/or electrorepulsion, as discussed further herein. Different reporter codes are sized to block ion flow through a nanopore at different measureable levels. Specific SSRT polymeric sequences can be efficiently synthesized using phosphoramidite chemistry typically used for oligonucleotide synthesis. Reporter codes and other features can be designed by selecting a sequence of specific phosphoramidites from commercially available and/or proprietary libraries. Such libraries include, but are not limited to, polyethylene glycol with lengths of 1 to 12 or more ethylene glycol units and aliphatic polymers with lengths of 1 to 12 or more carbon units. In certain embodiments, the SSRTs include features referred to as "polymerase enhancement regions" at the ends of the SSRTs proximal to the nucleotide triphosphoramidate diester. Polymerase enhancement regions may include positively charged polyamine spacers (e.g., primary, secondary, tertiary, or quarternary amines) or triamine spacers (three secondary amines each separated by three carbons) that facilitate incorporation of XNTP structures by a nucleic acid polymerase. In certain embodiments, the polymerase enhancement region includes two repeat units of spermine, in which the spermine moiety is provided by a phosphoramidite monomer having the following structure (as one of skill in the art will recognize, the trifluoroacetamide protecting groups are removed at the end of SSRT synthesis to expose the amine groups on spermine):

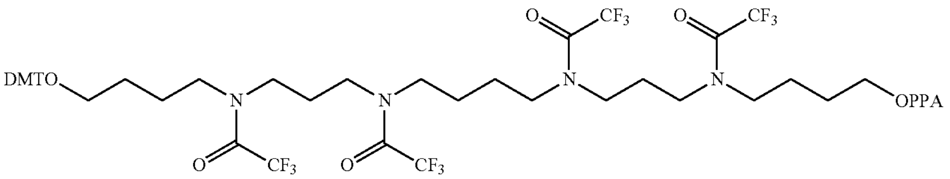

As used throughout the present disclosure, the term "reporter construct" refers to the element of the SSRT that includes the reporter codes, a symmetrical chemical brancher, and a translocation control element. In certain embodiments, the reporter construct is a polymer that includes, in series, from a first end to a second end, a first reporter code, a symmetrical chemical brancher bearing a translocation control element, and a second reporter code. The term "bearing" refers to a covalent linkage between the symmetrical brancher and the translocation control element, which produces an advantageous orientation of the translocation control element with respect to the two reporter codes. As discussed further herein and with reference to FIGS. 6-8, the symmetrical chemical brancher can be represented by the letter "Y", in which the two reporter codes are joined to the arms of the Y, while the translocation control element is joined to the stem of the Y. Thus, the two reporter codes are joined in-line by the brancher, while the brancher bears the translocation control element in a perpendicular orientation with respect to the linear, in-line, SSRT.

As used throughout the present disclosure, the terms "linker A" and "linker B" refer to the regions of the SSRT that each include a polymerase enhancing region and one or more translocation deceleration features or regions, and, in certain embodiments, a spacer region that includes a polymer of, e.g., PEG6, which can be customized to modulate the length of the SSRT traversed in a nanopore.

In certain embodiments, an XNTP may be a compound having the following generalized structure:

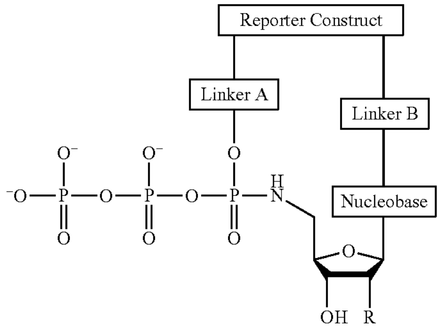

In one embodiment, R may be H, for example, when the compounds are used to sequence a DNA template. In another embodiment, R may be OH, for example, when the compounds are used to sequence an RNA template.

In certain embodiments, nucleobase is adenine, cytosine, guanine, thymine, uracil or a nucleobase analog. As one of skill in the art will appreciate, adenine, cytosine, guanine, thymine, and uracil are naturally occurring nucleobases. As used herein, the term "nucleobase analog" refers to non-naturally occurring nucleobases that are capable of forming Watson and Crick base pair with a complementary nucleobase on an adjacent single-stranded nucleic acid template. Exemplary nucleobase analogs include, but are not limited to, 5-fluorouracil; 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, 2,6-diaminopurine, 3-nitropyrrole, 8-aza-7-deazaguanine, 8-aza-7-deazainosine, and 8-aza-7-deazaadenine.

As discussed herein, the reporter construct is a polymer having a first end and a second end, and includes, in series from the first end to the second end, the first reporter code, the symmetrical chemical brancher bearing the translocation control element, and the second reporter code. This series of features reflects the symmetrical structure of the reporter construct (and the entire SSRT, which includes the symmetrical linkers, linker A and linker B), in which the sequences of the two reporter codes are identical and joined, in-line in reverse orientation by the symmetrical chemical brancher. Synthesis of the entire SSRT, including the reporter construct, is discussed further herein with reference to FIGS. 6-8). Briefly, synthesis proceeds in the 3' to 5' direction, initiating at the 3' end of the TCE. Addition of the symmetrical brancher to the 5' end of the TCE enables simultaneous polymerization of the first and second reporter codes off each arm of the brancher, followed by simultaneous synthesis of linker A and linker B, terminating at the 5' end of the first end and the second end of the SSRT. It has been found that the in-line redundancy provided by two identical reporter codes separated by the symmetrical brancher bearing the translocation control element offers several advantages during nanopore sequencing. For example, Xpandomers can potentially be read by the nanopore when translocated in either direction, i.e., the Xpandomer can be read either "forwards" or "backwards". This flexibility enables the "ratcheting" method of sequencing, which is discussed further herein, and other methods, such as "flossing" that are based on an AC pattern of voltage application.

Figure 3:
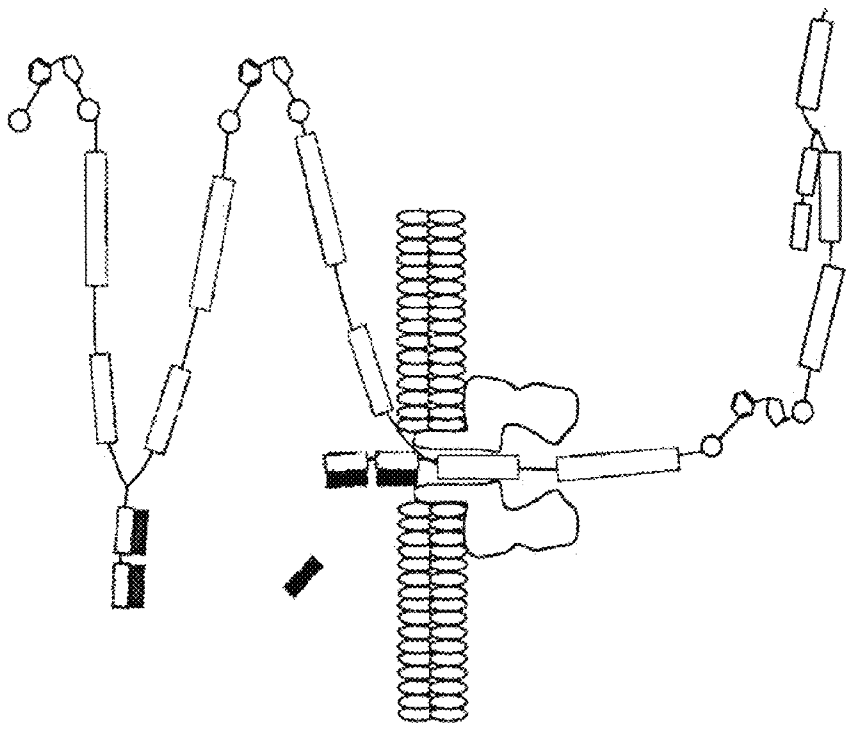
FIG. 3 is a schematic illustrating one embodiment of an Xpandomer passing through a biological nanopore.

FIG. 3 shows one embodiment of a cleaved Xpandomer in the process of translocating an a-hemolysin nanopore. This biological nanopore is embedded into a lipid bilayer membrane which separates and electrically isolates two reservoirs of electrolytes. A typical electrolyte has 1 molar KCl buffered to a pH of 7.0. When a small voltage, typically 100 mV, is applied across the bilayer, the nanopore constricts the flow of ion current and is the primary resistance in the circuit. Xpandomer reporter codes are designed to give specific ion current blockage levels and sequence information can be read by measuring the sequence of ion current levels as the sequence of reporter codes translocate the nanopore.

The α-hemolysin nanopore is typically oriented so translocation occurs by entering the vestibule side and exiting the stem side. As shown in FIG. 3, the nanopore is oriented to capture the Xpandomer from the stem side first. In some circumstances, this orientation may cause fewer blockage artifacts than occur when entering vestibule first. However, according to the present invention, the a-hemolysin nanopore may be oriented in either direction. As the Xpandomer translocates, a reporter enters the stem until its translocation control element stops at the stem entrance. The reporter is held in the stem until the TCE is enabled to pass into and through the stem, whereupon translocation proceeds to the next reporter. In this embodiment, TCE passage into the stem is enabled by dissociation of a translocation control moiety from the TCE. Advantageously, the inventors have discovered that TCEs constructed from a novel class of pendant-PEG phorphoramidites provide significantly improved translocation control based on intrinsic physicochemical and steric properties and thus obviate reliance on association and dissociation of translocation control moieties that act in trans.

Novel Compounds for SSRT Feature Design

Phosphoramidite chemistry, typically used for automated oligonucleotide synthesis, provides an efficient and convenient means to synthesize polymeric SSRTs. However, the ultimate potential of SSRT feature design is significantly limited by the repertoire of phosphoramidite monomers (PPAs) available in commercial libraries. Commercial PPAs are largely based on nucleosidic core structures and therefore do not offer the range of physicochemical properties necessary for the design of a broader array of features that improve the efficiency and accuracy of nanopore reads. To address this shortcoming in the art, the inventors have designed and synthesized a large collection of new PPA monomeric compounds. Significantly, these compounds are not based on nucleosidic core structures, which are well known in the art and, as mentioned, constrain feature design.

As used herein, the abbreviation "PPA" refers to phosphoramidites that are 0-(2-cyanoethyl)-(N,N-diisopropyl)-phosphoramidites. It is readily understood by one of skill in the art, that the term "phosphoramidite" refers to the structure of the monomeric precursor; following in-line polymerization of PPAs into an SSRT, the monomers are converted into phosphodiester linked oligomeric products.

Other methods used to make phosphodiester backbones polymers can be used to synthesize SSRTs. Accordingly, the monomers used with these chemistries can also produce SSRTs with non-nucleosidic elements. Additional methods of assembly may involve use of automated or manual assembly strategies done in solution phase or on a solid support. H-phosphonate synthesis and phosphotriester synthesis are examples known in the art. In addition, methods using enzymatic synthesis may be adapted to synthesize SSRTs (e.g., those employed in enzymatic oligonucleotide synthesis). In some embodiments, synthesis of an SSRT may be based on a combination of any of the above synthesis methods.

What follows is a brief, non-limiting summary of certain principles used to guide PPA monomer design. 1) Phosphate spacing. Compounds were designed that maintained a C3 (3 atom) spacing, which mimics the spacing of a natural nucleotide backbone. Other suitable spacings include, in certain embodiments, from 2 to 20 atom spacing. Unexpectedly, atom spacing was found to influence the rate of nanopore translocation, allowing for fine-tuning of translocation control. 2) Hydrophilicity. Compounds were designed to optimize the hydrophilic properties of SSRT features, as desired for particular functionalities. Several monomer designs were based on PEG, due to its ability to increase water solubility, which is an important property of, e.g., reporter codes. The inventors were able to fine-tune the hydrophilicity of PPA monomers by adjusting the length of the PEG polymer, as well as by terminating the PEG polymer with methyl ether or introducing 1,2,3-triazoles into the polymer, which had the unanticipated effect of further improving water solubility. 3) Steric volume. Several alternative configurations of linear, branched, cyclic, and dendrimeric PPA structures were designed and tested to evaluate the effect of steric volume on current flow through the nanopore. 4) Chirality in the backbone. The nanopore is a chiral environment. Enantiomeric compounds were designed to determine whether key nanopore signal properties were affected in any way. 5) Charge. In addition to back phosphate charge, certain compounds carry either a positive charge, e.g., teritiary amines or a negative charge, e.g., carboxylic acid. 6) Aromaticity. Compounds composed of a wide variety of aromatic hydrocarbons and heteroaromatic structures were incorporated into the backbone to determine if interactions with the nanopore produced desirable signal properties.

PPA monomeric compounds, in addition to attenuating nanopore signal properties, such as translocation rate control or current level control, also influence physicochemical properties of the Xpandomer. The Xpandomer, as a semi-synthetic polymer, exhibits properties associated with both natural polymers, e.g., DNA, and synthetic polymers. In some embodiments, certain PPA monomers may enable attenuation of undesirable inter-Xpandomer interactions or interaction between the Xpanodmer and certain process elements of the SBX work-flow. For example, it may be possible to reduce Xpandomer self-aggregation, formation of higher order glasses or gelatin, isolation, passive adsorption to, or interaction with, surfaces of containers, walls of nanochannels or fabrication devices containing the membrane and nanopore.

One class of compounds that has proven to provide outstanding functionality when incorporated into SSRT features is referred to herein as "pendant PEG". These structures are based on a molecular core that enables linkage of one or more PEG-containing polymers in a pendant configuration relative to the core. A structural analogy can be drawn between polymers of pendant PEG compounds and a comb, in which the phosphodiester bonds between individual compounds form the base of the comb and the PEG-based polymers form the teeth. Advantageously, several properties of the pendant PEG "teeth" can be customized for particular SSRT features, e.g., one or more of the spacing, length, and composition of the polymeric teeth. Structures 1a, 2a, 3a, and 4a below illustrate four exemplary embodiments of pendant PEG core structures.

1a

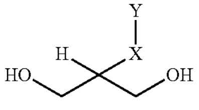

2a

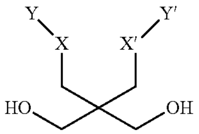

3a

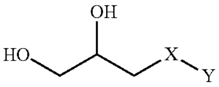

-continued

4a

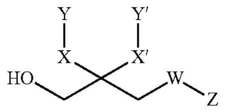

In certain non-limiting embodiments, X or X' may represent $—CH_2O—[CH_2CH_2O—]_mO—$ in which m is 1-10 and Y or Y' may represent —H, $—CH_3$,

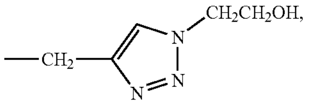

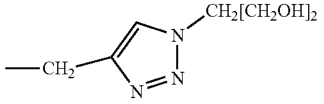

or

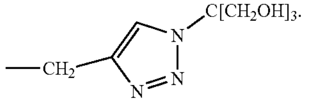

Tables 1A-C set forth non-limiting collections of novel phosphoramidite monomeric compounds for use in, e.g., SSRT feature design. Synthetic schemes for each compound are referred to with reference to the relevant Example and specific precursors are included for each. Analytic data characterizing the purified synthesized compounds are also set forth in Table 1A. These compounds may be used to synthesize any suitable polymeric feature, e.g., SSRT reporter codes, translocation control elements and translocation deceleration features, as described in further detail herein. Table LA also provides the names of the compounds with reference to the in-line structures they assume following incorporation into synthetic polymers.

TABLE 1A

| Exemplary Novel Phosphoramidite (PPA) Monomers-Group A | |
|---|---|
| Chemical Structure<br>A. Chemical Name of Monomeric PPA Compound<br>B. Chemical Name of Compound in Polymer<br>C. Code Identifier | 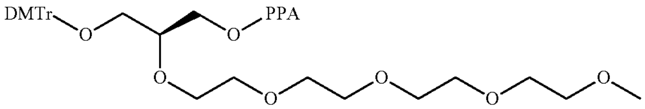<br>A. 1-O-DMT-2-O-PPA-3-O-mPEG4-propane<br>B. 1,3-O-bis(phosphodiester)-3-O-mPEG4-propane<br>C. code: PPA023 |
| Cmpd # Method | 5a<br>Ex. 1 |
| Key intermediate | 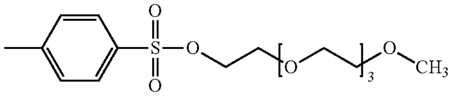 |
| Analytic data | 1H NMR (300 MHz, ACN-d3) d ppm 1.07-1.23 (m, 12 H, N(iPr)2) 2.54-2.65 (m, 2 H, —CH2-CN) 3.08-3.22 (m, 2 H, N(iPr)2) 3.30 (s, 3 H, —OCH3 (mPEG)) 3.45-3.76 (m, 15 H, —CH2O (glycerol, PEG, CNEt)) 3.79 (s, 6 H, Ph-OCH3) 6.89 (d, J = 8.96 Hz, 4 H, Ph-H) 7.22-7.39 (m, 7 H, Ph-H) 7.49 (d, J = 8.19 Hz, 2 H, Ph-H) |
| $^{31}P$ | 147.98 |

TABLE 1A-continued

| Exemplary Novel Phosphoramidite (PPA) Monomers-Group A | |
|---|---|
| Chemical Structure<br>A. Chemical Name of Monomeric PPA Compound<br>B. Chemical Name of Compound in Polymer<br>C. Code Identifier | 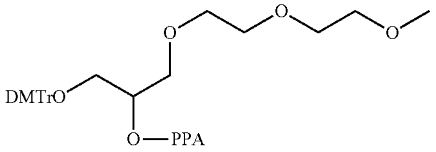<br>A. 1-O-DMT-2-O-PPA-3-O-mPEG2-propane<br>B. 1,2-O-bis(phosphodiester)-3-O-mPEG2-propane<br>code: PPA022 |
| Cmpd # Method | 5b<br>Ex. 1 |
| Key intermediate | 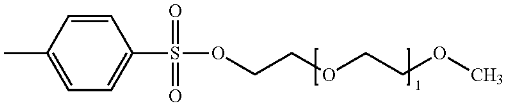 |
| Analytic data | 1H NMR (300 MHz, ACN-d3) d ppm 0.93-1.22 (m, 12 H, N(iPr)2) 2.57 (q, J = 6.32 Hz, 2 H, CH2-CN) 2.91-3.23 (m, 2 H, N(iPr)2) 3.28 (s, 3 H, —OCH3 (PEG)) 3.43-3.76 (m, 23 H, —CH2O (glycerol, PEG, CNEt)) 3.79 (s, 6 H, Ph-OCH3) 6.86 (d, J = 8.96 Hz, 4 H, Ph-H) 7.19-7.38 (m, 7 H, Ph-H) 7.46 (d, J = 7.42 Hz, 2 H, Ph-H) |
| $^{31}$p | 147.98 |
| Chemical Structure<br>A. Chemical Name of Monomeric PPA Compound<br>B. Chemical Name of Compound in Polymer<br>C. Code Identifier | 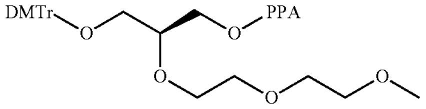<br>A. 1-O-DMT-3-O-PPA-2S-O-mPEG2-propane<br>B. 1,3-O-bis(phosphodiester)-2S-O-mPEG2-propane<br>C. code: PPA037 |
| Cmpd # Method | 12a<br>Ex. 2 |
| Key intermediate | 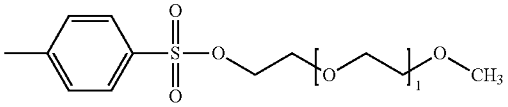 |
| Analytic data | 1H NMR (300 MHz, ACN-d3) d ppm 1.06-1.23 (m, 12 H, N(iPr)2) 2.52-2.69 (m, 2 H, —CH2-CN) 3.08-3.23 (m, 2 H, N(iPr)2) 3.30 (s, 3 H, —OCH3 (PEG)) 3.45-3.80 (m, 15 H, —CH2O (glycerol, PEG, CNEt)) 3.79 (s, 6 H, Ph-OCH3) 6.79-6.96 (m, 4 H, Ph-H) 7.22-7.28 (m, 1 H, Ph-H) 7.29-7.39 (m, 6 H, Ph-H) 7.43-7.57 (m, 2 H, Ph-H) |
| $^{31}$p | 147.99 |
| Chemical Structure<br>A. Chemical Name of Monomeric PPA Compound<br>B. Chemical Name of Compound in Polymer<br>C. Code Identifier | 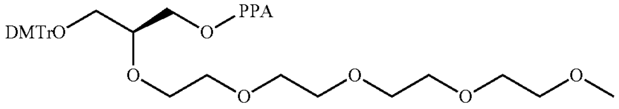<br>A. 1-O-DMT-3-O-PPA-2S-O-mPEG4-propane<br>B. 1,3-O-bis(phosphodiester)-2S-O-mPEG4-propane<br>C. code: PPA032 |
| Cmpd # Method | 12b<br>Ex. 2 |

TABLE 1A-continued

| Exemplary Novel Phosphoramidite (PPA) Monomers-Group A | |
|---|---|
| Key intermediate | 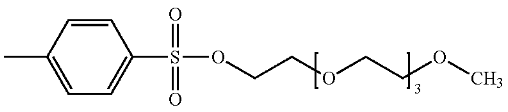 |
| Analytic data | 1H NMR (300 MHz, ACN-d3) d ppm 1.04-1.21 (m, 12 H, N(iPr)2), 2.57 (m, 2 H, —CH2-CN) 3.07-3.22 (m, 2 H, NH(iPr)) 3.30 (s, 3 H, —OCH3 (PEG)) 3.44-3.76 (m, 23 H, —CH2O (PEG, CNEt and glycerol)) 3.79 (s, 6 H, Ph-OCH3) 6.89 (d, J = 8.71 Hz, 4 H, Ph-H) 7.20-7.53 (m, 9 H, Ph-H) |
| $^{31}P$ | 147.95 |
| Chemical Structure<br>A. Chemical Name of Monomeric PPA Compound<br>B. Chemical Name of Compound in Polymer<br>C. Code Identifier | 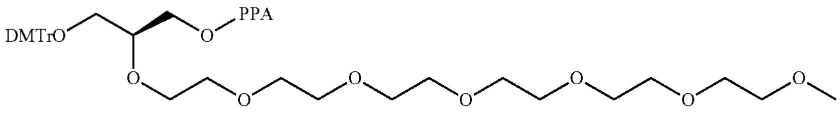<br>A. 1-O-DMT-3-O-PPA-2s-O-mPEG6-propane<br>B. 1,3-O-bis(phosphodiester)-2s-O-mPEG6-propane<br>C. code: PPA031 |
| Cmpd # Method | 12c<br>Ex. 2 |
| Key intermediate | 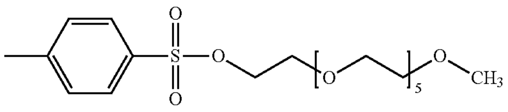 |
| Analytic data | 1H NMR (300 MHz, ACN-d3) d ppm 1.06-1.23 (m, 12 H, N(iPr)2) 2.52-2.65 (m, 2 H, —CH2-CN) 3.07-3.22 (m, 2 H, N(iPr)2) 3.31 (s, 3 H, —OCH3 (PEG)) 3.47-3.74 (m, 31 H, —CH2O (PEG, glycerol, CNEt)) 3.79 (s, 6 H, Ph-OCH3) 6.80-6.94 (m, 4 H, Ph-H) 7.22-7.39 (m, 7 H, Ph-H) 7.42-7.52 (m, 2 H, Ph-H) |
| $^{31}P$ | 147.98 |
| Chemical Structure<br>A. Chemical Name of Monomeric PPA Compound<br>B. Chemical Name of Compound in Polymer<br>C. Code Identifier | 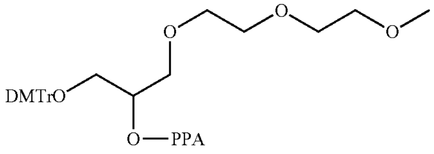<br>A. 1-O-DMT-2-O-PPA-3-O-mPEG2-propane<br>B. 1,2-O-bis(phosphodiester)-3-O-mPEG2-propane<br>C. code: PPA029 |
| Cmpd # Method | 16<br>Ex. 3 |
| Key intermediate | 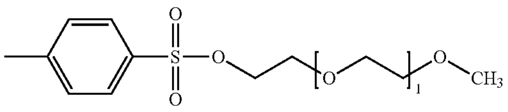 |
| Analytic data | 1H NMR (300 MHz, ACN-d3) d ppm 1.06-1.26 (m, 12 H, N(iPr)2) 2.55-2.76 (m, 2 H, —CH2-CN) 3.15-3.23 (m, 2 H, N(iPr)2) 3.29 (s, 3 H, —OCH3 (PEG)) 3.41-3.82 (m, 14 H, —CH2O (glycerol, PEG, CNEt)) 3.79 (s, 6 H, Ph-OCH3) 4.01-4.16 (m, 1 H, CHO (glycerol)) 6.83-6.99 (m, 4 H, Ph-H) 7.23-7.39 (m, 7 H, Ph-H) 7.45-7.54 (m, 2 H, Ph-H) |
| $^{31}P$ | 148.77, 149.26 |

TABLE 1A-continued

| Exemplary Novel Phosphoramidite (PPA) Monomers-Group A | |
|---|---|
| Chemical Structure<br>A. Chemical Name of Monomeric PPA Compound<br>B. Chemical Name of Compound in Polymer<br>C. Code Identifier | 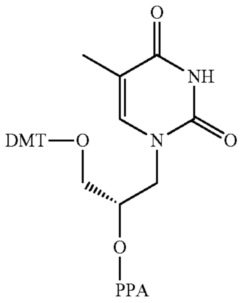<br>A. 3-O-DMT-2S-O-PPA-1-(N3-Thymine)-propane<br>B. 2,3-O-bis(phosphodiester)-1-(N3-Thymine)-propane<br>C. code: PPA002 |
| Cmpd # Method | 20a<br>Ex. 4 |
| Key intermediate | 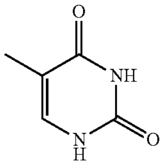 |
| Analytic data | Expected 1H NMR d ppm 1.06 (d, 12 H, N(iPr)2) 2.34 (s, 3 H, C5—CH3) 2.60 (m, 2 H, —CH2CN) 2.83 (m, 2 H, N(iPr)2) 3.17-3.63 (m, 4 H, —CH2O (glycerol), —CH2N) 3.81 (s, 6 H, Ph-OCH3) 3.90 (m, 2H, CNEt) 4.42 (m, 1 H, CHO) 6.89 (m, 4 H, Ph-H) 7.19 (s, 1 H, C6—H) 7.26-7.28 (m, 9 H, Ph-H) |
| $^{31}P$ | 149.79, 149.64 |
| Chemical Structure<br>A. Chemical Name of Monomeric PPA Compound<br>B. Chemical Name of Compound in Polymer<br>C. Code Identifier | 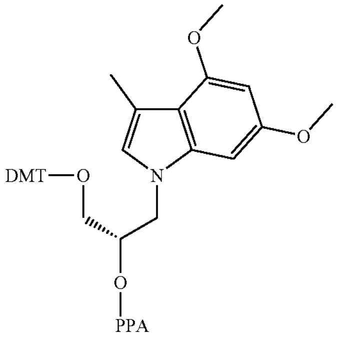<br>A. 3-O-DMT-2S-O-PPA-1-(N1-(4,6-dimethoxy-3-Me-indole)-propane<br>B. 2,3-O-bis(phosphodiester)-1-(N1-(4,6-dimethoxy-3-Me-indole)-propane<br>C. code: PPA006 |
| Cmpd # Method | 20b<br>Ex. 4 |
| Key intermediate | 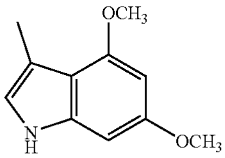 |
| Analytic data | 1H NMR (300 MHz, ACN-d 3 ) d ppm 1.02-1.17 (m, 12 H, N(iPr)2) 2.26 (d, J = 3.84 Hz, 3 H, indole-CH3) 2.43-2.54 (m, 2 H, —CH2CN) 2.89-3.14 (m, 2 H, N(iPr)2) 3.02 (dd, J-8.45, 4.86 Hz, 1 H, CH) 3.52-3.71 (m, 4 H, —CH2O (DMT, CNEt)) 3.75 (s, 3 H, indole-OCH3) 3.76 (s, 3 H, indole-OCH3) 3.82 (s, 3 H, Ph-OCH3) 4.11-4.36 (m, 2 H, —CH2-indole) 6.11 (d, J = 1.54 Hz, 1 H, indole-H) 6.40 (d, J = 1.54 Hz, 1 H, indole-H) 6.57 (d, J = 9.47 Hz, 1 H, indole-H) 6.82 (td, J = 5.76, 2.56 Hz, 4 H, Ph-H) 7.19-7.33 (m, 7 H, Ph-H) 7.43-7.49 (m, 2 H, Ph-H) |
| $^{31}P$ | 149.91, 148.47 |

TABLE 1A-continued

| Exemplary Novel Phosphoramidite (PPA) Monomers-Group A | |
|---|---|
| Chemical Structure<br>A. Chemical Name of Monomeric PPA Compound<br>B. Chemical Name of Compound in Polymer<br>C. Code Identifier | 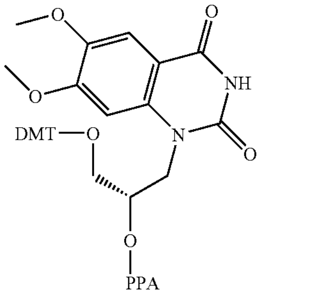<br>A. 3-O-DMT-2S-O-PPA-1-(1 dimethoxyquinazolinedione)-propane<br>B. 2,3-O-bis(phosphodiester)-1-(1 dimethoxyquinazolinedione)-propane<br>C. code: PPA007 |
| Cmpd # Method | 20c<br>Ex. 4 |
| Key intermediate | 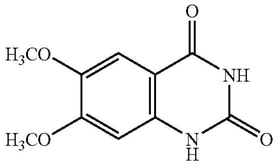 |
| Analytic data | 1H NMR (300 MHz, ACN-d3) d ppm 0.88-1.17 (m, 12 H, N(iPr)2) 2.43-2.53 (m, 2 H, —CH2CN) 3.25-3.39 (m, 2 H, N(iPr)2) 3.43-3.79 (m, 10 H, —CH2O (DMT, CNEt), Ph-OCH3) 3.85-3.94 (m, 3 H, Ph-OCH3) 3.99-4.16 (m, 1 H, —CH) 4.30-4.47 (m, 2 H, —CH2N) 6.75-6.92 (m, 4 H, Ph-H) 7.21-7.38 (m, 7 H, Ph-H) 7.40-7.54 (m, 4 H, Ph-H) |
| $^{31}P$ | 149.19, 148.83 |
| Chemical Structure<br>A. Chemical Name of Monomeric PPA Compound<br>B. Chemical Name of Compound in Polymer<br>C. Code Identifier | 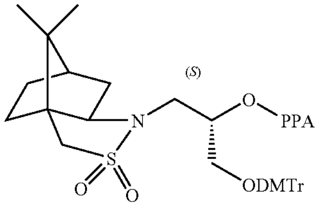<br>A. 3-(1-O-DMT-2S-O-PPA-propyl)-8,8-dimethylhexahydro-3H-3a,6-methanobenzo[c]isothiazole 2,2-dioxide<br>B. 3-(1,2-O-bis(phosphodiester)-propyl)-8,8-dimethylhexahydro-3H-3a,6-methanobenzo[c]isothiazole 2,2-dioxide<br>C. code: PPA009 |
| Cmpd # Method | 20d<br>Ex. 4 |
| Key intermediate | 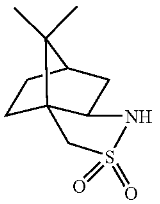 |
| Analytic data | 1H NMR (300 MHz, ACN-d3) d ppm 0.80-0.97 (m, 6 H, camphor-CH3) 1.14-1.29 (m, 16 H, N(iPr)2, camphor) 1.58-2.01 (m, 6 H, camphor) 2.53 (t, J = 6.02 Hz, 2 H, —CH2N) 2.67-2.82 (m, 2 H, —CH2CN) 2.89-3.21 (m, 4 H, CH2O (DMT, CNEt)) 3.25-3.42 (m, 2 H, —CH2S) 3.72-3.82 (m, 6 H, Ph-OCH3) 4.15-4.31 (m, 1 H, CH) 6.78-6.95 (m, 4 H, Ph-H) 7.23-7.40 (m, 7 H, Ph-H) 7.44-7.58 (m, 2 H, Ph-H) |
| $^{31}P$ | 148.79, 148.37 |

TABLE 1A-continued

| Exemplary Novel Phosphoramidite (PPA) Monomers-Group A | |
|---|---|
| Chemical Structure<br>A. Chemical Name of Monomeric PPA Compound<br>B. Chemical Name of Compound in Polymer<br>C. Code Identifier | 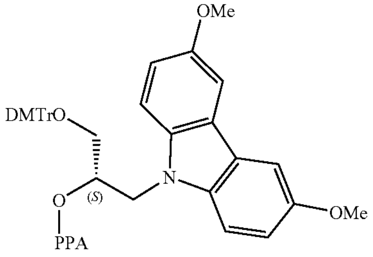<br>A. 3-O-DMT-2S-O-PPA-1-(N9-(3,6-dimethoxycarbazole)-propane<br>B. 2,3-O-bis(phosphodiester)-1-(N9-(3,6-dimethoxycarbazole)-propane<br>C. code: PPA010 |
| Cmpd # Method | 20e<br>Ex. 4 |
| Key intermediate | 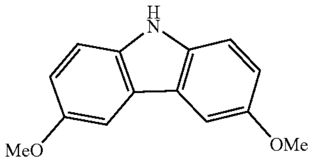 [SMILES: COc1ccc2[nH]c3ccc(OC)cc3c2c1] |
| Analytic data | 1H NMR (300 MHz, ACN-d3) d ppm 0.84-1.04 (m, 12 H, N(iPr)2) 2.30-2.41 (m, 2 H, —CH2CN) 3.00-3.23 (m, 2 H, N(iPr)2) 3.14 (d, J = 4.15 Hz, 1 H, CH) 3.30-3.62 (m, 4 H, CH2O (glycerol, CNEt)) 3.75 (d, J = 3.32 Hz, 6 H, carbazole-OCH3) 3.86 (d, J = 1.45 Hz, 6 H, Ph-OCH3) 4.34-4.52 (m, 2 H, CH2-carbazole) 6.80 (ddd, J = 8.81, 5.70, 3.11 Hz, 4 H, Ph-H) 6.99 (dt, J = 8.76, 3.08 Hz, 2 H, carbazole) 7.19-7.36 (m, 9 H, Ph-H, carbazole) 7.46 (d, J = 7.67 Hz, 2 H, Ph-H) 7.57 (s, 2 H, carbazole) |
| $^{31}P$ | 148.67, 148.98 |
| Chemical Structure<br>A. Chemical Name of Monomeric PPA Compound<br>B. Chemical Name of Compound in Polymer<br>C. Code Identifier | 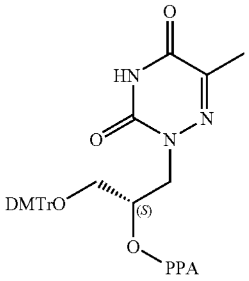<br>A. 3-O-DMT-2S-O-PPA-1-(N1-(6-Azathymine))-propane<br>B. 2,3-O-bis(phosphodiester)-1-(N1-(6-Azathymine))-propane<br>C. code: PPA012 |
| Cmpd # Method | 20f<br>Ex. 4 |
| Key intermediate | 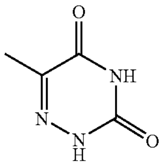 |
| Analytic data | 1H NMR (300 MHz, ACN-d3) d ppm 1.03-1.19 (m, 12 H) 2.03-2.20 (m, 2 H, glycerol) 2.47-2.65 (m, 2 H, CH2CN) 3.18-3.81 (m, 5 H, CH2O (glycerol, CNEt)) 3.78 (s, 6 H, Ph-OCH3) 4.05-4.17 (m, 1 H, CH2O (glycerol)) 4.23-4.36 (m, 1 H, CHO (glycerol)) 6.86-6.87 (m, 4 H, Ph-H) 7.22-7.38 (m, 7 H, Ph-H) 7.40-7.56 (m, 2 H, Ph-H) |
| $^{31}P$ | 148.83, 149.06 |

TABLE 1A-continued

Exemplary Novel Phosphoramidite (PPA) Monomers-Group A

| | |
|---|---|
| Chemical Structure<br>A. Chemical Name of Monomeric PPA Compound<br>B. Chemical Name of Compound in Polymer<br>C. Code Identifier | 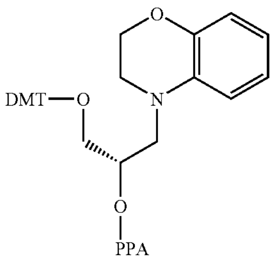<br>A. 3-O-DMT-2S-O-PPA-1-(N1-(2-Me-5-nitroindole)-propane<br>B. 2,3-O-bis(phosphodiester)-1-(N1-(2-Me-5-nitroindole)-propane<br>C. code: PPA013 |
| Cmpd # Method | 20g<br>Ex. 4 |
| Key intermediate | 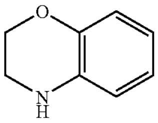 |
| Analytic data | Expected 1H NMR d ppm 1.06 (d, 12 H, N(iPr)2) 2.60 (m, 2 H, —CH2CN) 2.83 (m, 2 H, N(iPr)2) 3.35-3.63 (m, 5 H, —CH2O, —CHO (glycerol), —CH2N) 3.77 (m, 2 H, —CH2N) 3.81 (s, 6 H, Ph-OCH3) 3.90 (m, 2H, CNEt) 4.17 (m, 2 H, CH2O) 6.70-6.89 (m, 8 H, Ph-H) 7.26-7.28 (m, 9 H, Ph-H) |
| $^{31}P$ | 148.93, 148.69 |
| Chemical Structure<br>A. Chemical Name of Monomeric PPA Compound<br>B. Chemical Name of Compound in Polymer<br>C. Code Identifier | 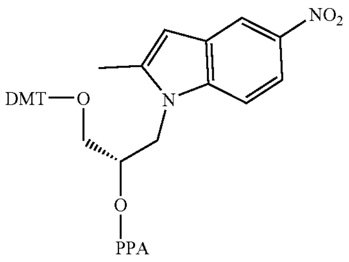<br>A. 3-O-DMT-2S-O-PPA-1-(N1-(2-Me-5-nitroindole)-propane<br>B. 2,3-O-bis(phosphodiester)-1-(N1-(2-Me-5-nitroindole)-propane<br>C. code: PPA015 |
| Cmpd # Method | 20h<br>Ex. 4 |
| Key intermediate | 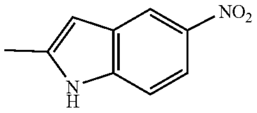 |
| Analytic data | 1H NMR (300 MHz, ACN-d3) d ppm 0.94-1.35 (m, 12 H, N(iPr)2) 2.39 (ddd, J = 17.03, 6.02, 5.89 Hz, 2 H, —CH2CN) 2.50 (d, J-6.14 Hz, 3 H, indole-CH3) 3.30-3.38 (m, 2 H, N(iPr)2) 3.44-3.62 (m, 4 H, CH2O (glycerol, CNEt)) 3.79 (d, J = 4.61 Hz, 6 H, Ph-OCH3) 4.25-4.47 (m, 3 H, —CH2-indole, —CH) 6.39-6.52 (m, 1 H, indole) 6.80-6.96 (m, 4 H, Ph-H) 7.30-7.43 (m, 7 H, Ph-H) 7.48-7.56 (m, 2 H, Ph-H) 7.97 (dt, J = 9.15, 1.70 Hz, 1 H, indole) 8.41 (t, J = 2.56 Hz, 1 H, indole) |
| $^{31}P$ | 149.01, 149.28 |

TABLE 1A-continued

| Exemplary Novel Phosphoramidite (PPA) Monomers-Group A | |
|---|---|
| Chemical Structure<br>A. Chemical Name of Monomeric PPA Compound<br>B. Chemical Name of Compound in Polymer<br>C. Code Identifier | 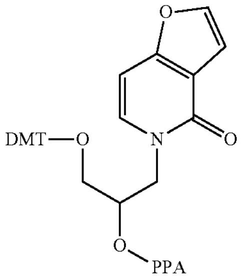<br>A. 3-O-DMT-2S-O-PPA-1-(5-benzofuran)-propane<br>B. 2,3-O-bis(phosphodiester)-1-(5-benzofuran)-propane<br>C. code: PPA018 |
| Cmpd # Method | 20i<br>Ex. 4 |
| Key intermediate | 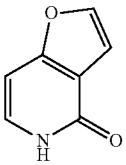 |
| Analytic data | 1H NMR (300 MHz, ACN-d3) d ppm 1.09 (dd, J = 19.97, 6.91 Hz, 12 H, N(iPr)2) 2.51 (dt, J = 17.92, 6.02 Hz, 2 H, —CH2CN) 3.10-3.73 (m, 6 H, —CH2 (DMT, CNEt, -NAr)) 3.76 (s, 6 H, Ph-OCH3) 3.98-4.15 (m, 1 H, CHO-PPA) 4.30-4.46 (m, 2 H, pyr) 6.50-6.86 (m, 1 H, furan) 6.86-6.96 (m, 4 H, Ph-H) 7.24-7.40 (m, 7 H, Ph-H) 7.44-7.57 (m, 2 H, Ph-H) 7.57-7.67 (m, 1 H, furan) |
| $^{31}P$ | 149.08 |
| Chemical Structure<br>A. Chemical Name of Monomeric PPA Compound<br>B. Chemical Name of Compound in Polymer<br>C. Code Identifier | 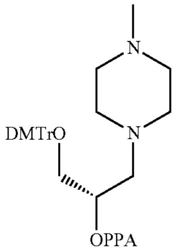<br>A. 1-O-DMT-2S-O-PPA-3-(4-methylpiperazine-1-yl)-propane<br>B. 1,2-O-bis(phosphodiester)-3-(4-methylpiperazine-1-yl)-propane<br>C. code: PPA043 |
| Cmpd # Method | 20j<br>Ex 4 |
| Key intermediate | 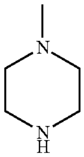 |
| Analytic data | 1H NMR (300 MHz, ACN-d3) d ppm 0.98-1.26 (m, 12 H, N(iPr)2) 2.17 (d, J = 4.10 Hz, 3 H, NCH3) 2.22-2.47 (m, 6 H, CH2N) 2.50-2.60 (m, 4 H, CH2N) 2.64-2.71 (m, 2 H, CH2CN) 3.09-3.23 (m, 2 H, N(iPr)2) 3.60-3.82 (m, 10 H, |

TABLE 1A-continued

| Exemplary Novel Phosphoramidite (PPA) Monomers-Group A | |
|---|---|
| | HC2O, Ph-OCH3) 3.98-4.14 (m, 1 H, CH) 6.79-6.95 (m, 4 H, Ph-H) 7.23-7.40 (m, 7 H, Ph-H) 7.43-7.57 (m, 2 H, Ph-H) |
| $^{31}P$ | 148.49, 148.02 |
| Chemical Structure | |
| Chemical Structure<br>A. Chemical Name of Monomeric PPA Compound<br>B. Chemical Name of Compound in Polymer<br>C. Code Identifier | 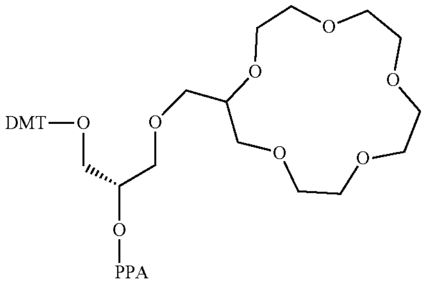<br>A. 1-O-DMT-2S-O-PPA-3-O-(2-Me-(10-crown-5))-propane<br>B. 1,2-O-bis(phosphodiester)-3-O-(2-Me-(10-crown-5))-propane<br>C. code: PPA021 |
| Cmpd # Method | 20k<br>Ex. 4 |
| Key intermediate | 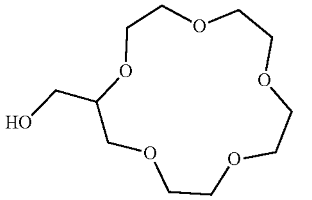 [SMILES: OCC1COCCOCCOCCOCCO1] |
| Analytic data | 1H NMR (300 MHz, CDCl3) d ppm 0.82-0.94 (m, 1 H) 1.05 (d, J = 6.66 Hz, 2 H) 1.13-1.30 (m, 15 H, N(iPr)2) 2.65 (t, J = 6.53 Hz, 2 H, CH2CN) 3.60-3.76 (m, 24 H-CH2O, Ph-OCH3 (glycerol, crown-ether)) 3.79-3.85 (m, 4 H-CH2O (CNEt, glycerol)) 6.73-6.88 (m, 1 H Ph-H) 7.20-7.36 (m, 2 H, Ph-H) |
| $^{31}P$ | 148.59 |
| Chemical Structure<br>A. Chemical Name of Monomeric PPA Compound<br>B. Chemical Name of Compound in Polymer<br>C. Code Identifier | 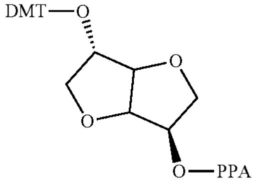<br>A. 1-O-DMT-5-O-PPA-hexahydrofuro[2,6]furan<br>B. 1,5-O-bis(phosphodiester)-hexahydrofuro[2,6]furan<br>C. code: PPA014 |
| Cmpd # Method | 23<br>Ex. 5 |
| Key intermediate | 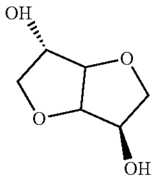 |
| Analytic data | 1H NMR (300 MHz, ACN-d3) d ppm 1.09-1.25 (m, 12 H) 2.57-2.71 (m, 2 H, -CH2CN) 2.98-3.14 (m, 2 H, N(iPr)2) 3.53-3.67 (m, 2 H, CNEt) 3.70-4.08 (m, 6 H, isosorbide) 3.79 (s, 6 H, Ph-OCH3) 4.16-4.32 (m, 2 H, —CHO (isosorbide)) 6.77-6.89 (m, 4H, Ph-H) 7.27 (d, J = 7.17 Hz, 1 H, Ph-H) 7.31-7.44 (m, 6 H, Ph-H) 7.47-7.62 (m, 2 H, Ph-H) |
| $^{31}P$ | 148.30, 147.73 |

TABLE 1A-continued

| Exemplary Novel Phosphoramidite (PPA) Monomers-Group A | |
|---|---|
| Chemical Structure<br>A. Chemical Name of Monomeric PPA Compound<br>B. Chemical Name of Compound in Polymer<br>C. Code Identifier | 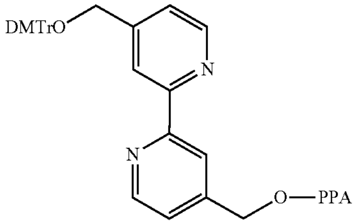<br>A. 1-O-DMT-1'-O-PPA-(2,2'-bipyridin-4,4'-yl)-dimethanol<br>B. 1,1'-O-bis(phosphodiester)-2,2'-bipyridin-4,4'-yl)-dimethanol<br>C. code: PPA005 |
| Cmpd # Method | 26a<br>Ex. 6 |
| Key intermediate | 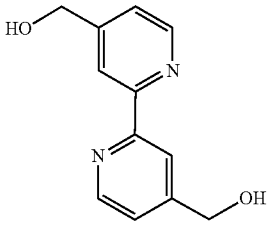 [SMILES: OCc1ccnc(-c2cc(CO)ccn2)c1] |
| Analytic data | 1H NMR (300 MHz, ACN-d3) d ppm 1.24 (d, J = 7.17 Hz, 12 H, N(iPr)2) 2.71 (t, J = 6.02 Hz, 2 H, —CH2CN) 3.68-3.81 (m, 2 H, N(iPr)2) 3.79 (s, 6 H, Ph-OCH3) 3.84-3.93 (m, 2 H, CNEt) 4.34 (s, 2 H, CH2O-DMT) 4.79-4.95 (m, 2 H, CH2O-PPA) 6.91 (d, J = 8.96 Hz, 4 H, Ph-H) 7.29 (d, J = 7.42 Hz, 1 H, Ph-H) 7.33-7.45 (m, 8 H, Ph-H) 7.48-7.63 (m, 2 H, pyr) 8.37 (s, 1 H, pyr) 8.45 (s, 1 H, pyr) 8.55-8.67 (m, 2 H, pyr) |
| $^{31}P$ | 148.96 |
| Chemical Structure<br>A. Chemical Name of Monomeric PPA Compound<br>B. Chemical Name of Compound in Polymer<br>C. Code Identifier | 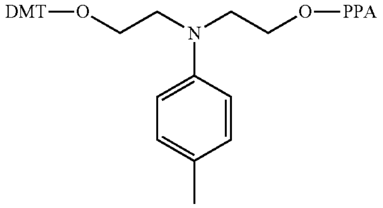<br>A. 1-O-DMT-1'-O-PPA-N(p-tolyl)-diethanolamine<br>B. 1,1'-O-bis(phosphodiester)-2N(p-tolyl)-diethanolamine<br>C. code: PPA001 |
| Cmpd # Method | 26b<br>Ex. 6 |
| Key intermediate | 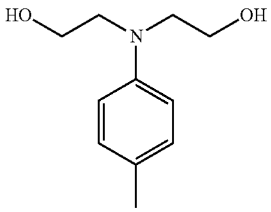 |
| Analytic data | 1H NMR (300 MHz, CDCl3-d) d ppm 1.19 (dd, J = 10.88, 6.78 Hz, 12 H, N(iPr)2) 2.24 (s, 3 H, Ph-CH3) 2.57 (t, J = 6.53 Hz, 2 H, —CH2CN) 3.22-3.35 (m, 2 H, N(iPr)2) 3.52-3.68 (m, 6 H, —CH2O (DMT, PPA, CNEt)) 3.70-3.83 (m, 4 H, —CH2N) 3.80 (s, 6 H, Ph-OCH3) 6.57 (m, J-8.70 Hz, 2 H, toluyl-H) 6.80 (d, J = 8.96 Hz, 4 H, Ph-H) 6.99 (m, J = 8.45 Hz, 2 H, toluyl-H) 7.18-7.35 (m, 7 H, Ph-H) 7.41-7.48 (m, 2 H, Ph-H) |
| $^{31}P$ | 148.04 |

TABLE 1A-continued

| Exemplary Novel Phosphoramidite (PPA) Monomers-Group A | |
|---|---|
| Chemical Structure<br>A. Chemical Name of Monomeric PPA Compound<br>B. Chemical Name of Compound in Polymer<br>C. Code Identifier | 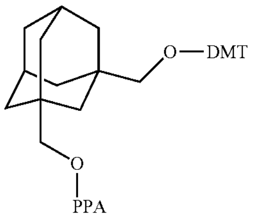<br>A. 1-O-DMT-1'-O-PPA-(adamantan-1,3-yl)-dimethanol<br>B. 1,1'-O-bis(phosphodiester)-adamantan-1,3-yl)-dimethanol<br>C. code: PPA003 |
| Cmpd # Method | 26c<br>Ex. 6 |
| Key intermediate | 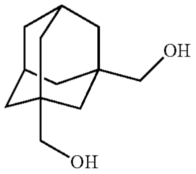 [SMILES: OCC12CC3CC(C1)CC(CO)(C3)C2] |
| Analytic data | Expected 1H NMR d ppm 0.82-1.66 (m, 26 H, adamantine, N(iPr)2) 2.60 (m, 2 H, —CH2CN) 3.27-3.52 (m, 4 H, CH2O) 3.81 (s, 6 H, Ph-OCH3) 3.90 (m, 2 H, CNEt), 6.89 (m, 4 H, Ph-H) 7.26-7.28 (m, 9 H, Ph-H) |
| $^{31}P$ | Expected 148 |
| Chemical Structure<br>A. Chemical Name of Monomeric PPA Compound<br>B. Chemical Name of Compound in Polymer<br>C. Code Identifier | 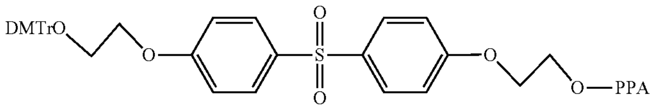<br>A. 1-O-DMT-1'-O-PPA-2,2'-(sulfonylbis(benz-4-yl))-diethanol<br>B. 1,1'-O-bis(phosphodiester)-2,2'-(sulfonylbis(benz-4-yl))-diethanol<br>C. code: PPA004 |
| Cmpd # Method | 26d<br>Ex. 6 |
| Key intermediate | 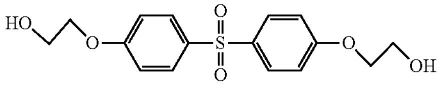 [SMILES: O=S(=O)(c1ccc(OCCO)cc1)c1ccc(OCCO)cc1] |
| Analytic data | 1H NMR (300 MHz, ACN-d3) d ppm 1.16 (dd, J = 10.37, 6.84 Hz, 12 H, N(iPr)2) 2.62 (t, J = 6.01 Hz, 2 H, —CH2CN) 3.32-3.40 (m, 2 H, N(iPr)2) 3.62 (m, 2 H, —CH2O (CNEt)) 3.78 (s, 6 H, Ph-OCH3), 3.70-3.99 (m, 4 H, —CH2O (DMT, PPA)) 4.17-4.30 (m, 4 H, —CH2O-sultone) 6.81-6.93 (m, 4 H, Ph-H) 7.04-7.18 (m, 4 H, sultone) 7.19-7.35 (m, 7 H, Ph-H) 7.37-7.48 (m, 2 H, Ph-H) 7.82-7.88 (m, 4 H, sultone) |
| $^{31}P$ | 148.83 |
| Chemical Structure<br>A. Chemical Name of Monomeric PPA Compound<br>B. Chemical Name of Compound in Polymer<br>C. Code Identifier | 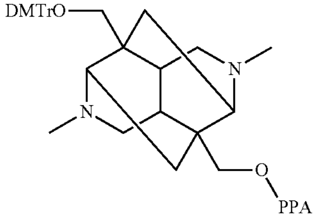<br>A. 1-O-DMT-1'-O-PPA-(octahydro-2,6-dimethyl-3,8:4,7-dimethano-2,6-naphthyridin-4,8-diyl)-dimethanol<br>B. 1,1'-O-bis(phosphodiester)-octahydro-2,6-dimethyl-3,8:4,7-dimethano-2,6-naphthyridin-4,8-diyl)-dimethanol<br>C. code: PPA008 |

TABLE 1A-continued

Exemplary Novel Phosphoramidite (PPA) Monomers-Group A

| | |
|---|---|
| Cmpd # Method | 26e<br>Ex. 6 |
| Key intermediate | 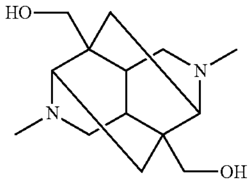 |
| Analytic data | 1H NMR (300 MHz, ACN-d3) d ppm 1.10-1.27 (m, 12 H, N(iPr)2) 1.31-2.76 (m, 10 H, —CH, —CH2, —CH2CN) 2.95-3.88 (m, 10 H, N-CH3, CNEt, N(iPr)2) 3.79 (s, 6 H, Ph-OCH3) 6.89 (d, J = 8.96 Hz, 4 H, Ph-H) 7.21-7.38 (m, 7 H, Ph-H) 7.40-7.54 (m, 2 H, Ph-H) |
| $^{31}P$ | 147.76 |
| Chemical Structure<br>A. Chemical Name of Monomeric PPA Compound<br>B. Chemical Name of Compound in Polymer<br>C. Code Identifier | 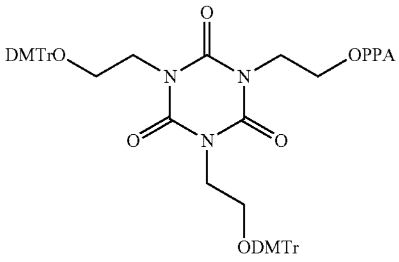<br>A. 3,5-bis(DMT-O-ethoxy)- 1-(PPA-O-ethoxy)-1,3,5-triazene-2,4,6-trione<br>B. 3,5-bis(phosphodiester-O-ethoxy)- 1-(phosphodiester-O-ethoxy)-1,3,5-triazene-2,4,6-trione<br>C. code: PPA038 |
| Cmpd # Method | 26f<br>Ex. 6 |
| Key intermediate | 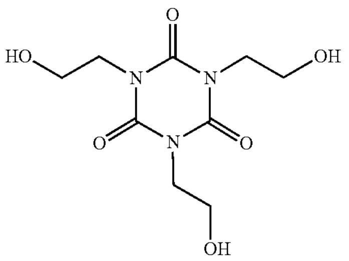 [SMILES: O=c1n(CCO)c(=O)n(CCO)c(=O)n1CCO] |
| Analytic data | 1H NMR (300 MHz, ACN-d 3 ) d ppm 0.88-1.14 (m, 12 H, N(iPr)2) 2.56 (t, J = 6.14 Hz, 2 H, —CH2CN) 3.25-4.02 (m, 14 H, Et and N(iPr)2) 6.73-6.81 (m, 8 H, Ph-H) 7.14-7.27 (m, 14 H, Ph-H) 7.32-7.38 (m, 4 H, Ph-H) |
| $^{31}P$ | 148.13 |
| Chemical Structure<br>D. Chemical Name of Monomeric PPA Compound<br>E. Chemical Name of Compound in Polymer<br>Code Identifier | 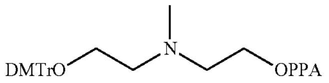<br>A. 1-O-DMT-1'-O-PPA-N-methyl-N,N-diethanolamine<br>B. 1,1'-O-bis(phosphodiester)-N-methyl-N,N-diethanolamine<br>C. code: PPA041 |
| Cmpd # Method | 26g<br>Ex. 6 |
| Key intermediate | 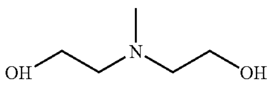 |

TABLE 1A-continued

| Exemplary Novel Phosphoramidite (PPA) Monomers-Group A | |
|---|---|
| Analytic data | 1H NMR (300 MHz, ACN-d3) d ppm 1.07-1.21 (m, 12 H, N(iPr)2) 2.21 (s, 3 H, —NCH3) 2.52-2.67 (m, 6 H, —CH2CN, —CH2N) 3.04-3.11 (m, 2 H, N(iPr)2) 3.52-3.77 (m, 6 H, —CH2O (CNEt, DMT, PPA)) 3.75 (s, 6 H, Ph-OCH3) 6.82-6.88 (m, 4 H, Ph-H) 7.19-7.34 (m, 7 H, Ph-H) 7.41-7.46 (m, 2 H, Ph-H) |
| $^{31}P$ | 147.49 |
| Chemical Structure<br>A. Chemical Name of Monomeric PPA Compound<br>B. Chemical Name of Compound in Polymer<br>C. Code Identifier | 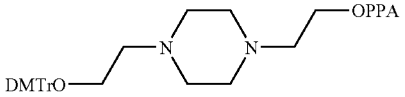<br>A. 1-O-DMT-8-O-PPA-N,N-Diethylpiperazine<br>B. 1,8-O-bis(phosphodiester)-N,N-Diethylpiperazine<br>C. code: PPA044 |
| Cmpd # Method | 26h<br>Ex. 6 |
| Key intermediate | 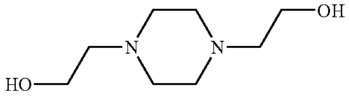 [SMILES: OCCN1CCN(CCO)CC1] |
| Analytic data | 1H NMR (300 MHz, ACN-d3) d ppm 1.19 (d, J = 6.91 Hz, 12 H) 2.41-2.57 (m, 12 H, CH2N) 2.64-2.71 (m, 2 H, CH2CN) 3.10 (t, J = 5.76 Hz, 2 H, N(iPr)2) 3.60-3.69 (m, 2 H, CH2O (CNEt)) 3.71-3.84 (m, 4 H, CH2O (DMT, PPA)) 3.79 (s, 6 H, Ph-OCH3) 6.81-6.98 (m, 4 H, Ph-H) 7.21-7.38 (m, 7 H, Ph-H) 7.42-7.57 (m, 2 H, Ph-H) |
| $^{31}P$ | 147.79 |
| Chemical Structure<br>A. Chemical Name of Monomeric PPA Compound<br>B. Chemical Name of Compound in Polymer<br>C. Code Identifier | 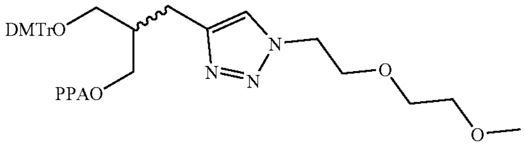<br>A. 1-O-DMT-3-O-PPA-2-(4-Et-1-(Et-O-mPEG1)-1,2,3-triazole)-propane<br>B. 1,3-O-bis(phosphodiester)-2-(4-Et-1-(Et-O-mPEG1)-1,2,3-triazole)-propane<br>C. code: PPA026 |
| Cmpd # Method | 31a<br>Ex. 7 |
| Key intermediate | 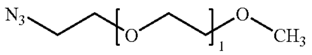 |
| Analytic data | 1H NMR (300 MHz, ACN-d3) d ppm 0.93-1.17 (m, 12 H, N(iPr)2) 2.13 (m, 1 H, CH) 2.57 (q, J = 5.63 Hz, 2 H, —CH2CN) 2.69-2.83 (m, 2 H, —CH2-triazole) 3.09 (d, J = 5.63 Hz, 2 H, N(iPr)2) 3.24 (s, 3 H, OCH2 (PEG)) 3.35-3.70 (m, 10, CH2O (PEG, glycerol)) 3.79 (s, 6 H, Ph-OCH3) 4.37-4.42 (m, 2 H, —CH2-triazole) 6.82-6.87 (m, 4 H, Ph-H) 7.19-7.32 (m, 7 H, Ph-H) 7.38-7.44 (m, 3 H, Ph-H and triazole) |
| $^{31}P$ | 147.16 |
| Chemical Structure<br>A. Chemical Name of Monomeric PPA Compound<br>B. Chemical Name of Compound in Polymer<br>C. Code Identifier | 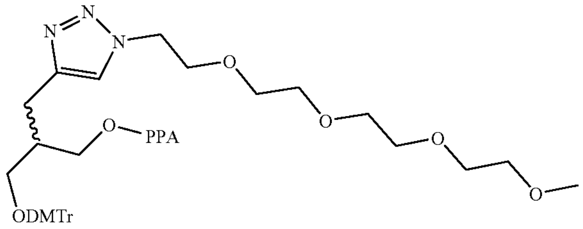<br>A. 1-O-DMT-3-O-PPA-2-(4-Et-1-(Et-O-mPEG3)-1,2,3-triazole)-propane<br>B. 1,3-O-bis(phosphodiester)-2-(4-Et-1-(Et-O-mPEG3)-1,2,3-triazole)-propane<br>C. code: PPA027 |

TABLE 1A-continued

| Exemplary Novel Phosphoramidite (PPA) Monomers-Group A | |
|---|---|
| Cmpd # Method | 31b<br>Ex. 7 |
| Key intermediate | 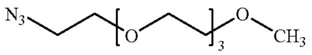 |
| Analytic data | 1H NMR (300 MHz, ACN-d3) d ppm 0.90-1.17 (m, 12 H, N(iPr)2) 2.57 (q, J = 5.72 Hz, 2 H, —CH2-CN) 2.67-2.84 (m, 2 H, NH(iPr)2) 2.96-3.18 (m, 2 H, O-CH2 (glycerol)) 3.27 (s, 3 H, —OCH3 (PEG)) 3.41-3.61 (m, 14 H, —CH2O (PEG, glycerol)) 3.64-3.80 (m, 12 H, Ph-OCH3, —CH2O (glycerol, PEG) 4.40 (t, J = 4.74 Hz, 2 H, CH2-triazole (glycerol)) 6.81-6.88 (m, 4 H, Ph-H) 7.18-7.33(m, 7 H, Ph-H) 7.37-7.53 (m, 3 H, Ph-H, C-CH (triazole)) |
| $^{31}P$ | 147.03 |
| Chemical Structure<br>A. Chemical Name of Monomeric PPA Compound<br>B. Chemical Name of Compound in Polymer<br>C. Code Identifier | 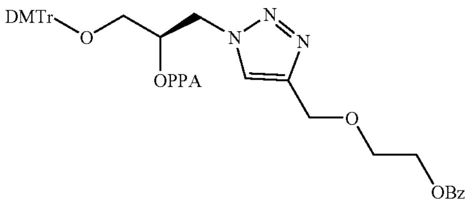<br>A. 1-O-DMT-2-O-PPA-3-(4-(Me-O-PEG1-O-Bz)-1-(1,2,3-triazole))-propane<br>B. 1,2-O-bis(phosphodiester)-3-(4-(Me-O-PEG1-O-Bz)-1-(1,2,3-triazole))-propane<br>C. code: PPA054 |
| Cmpd # Method | 31c<br>Ex. 7 |
| Key intermediate | 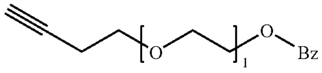 |
| Analytic data | 1H NMR (300 MHz, ACN-d3) d ppm 1.05-1.11 (m ,12 H, N(iPr)2) 2.61 (t, J = 6.02 Hz, 2 H, —CH2CN) 3.10-3.25 (m, 2 H, N(iPr)2) 3.49-3.87 (m, 12 H, -CH2O (DMT, CNEt, PEG), Ph-OCH3) 4.40-4.47 (m, 1 H, CH) 4.52-4.67 (m, 4 H, —CH2OBz, —CH2-triazole) 6.82-6.95 (m, 4 H, Ph-H) 7.23-7.39 (m, 9 H, Ph-H and OBz) 7.42-7.57 (m, 3 H, Ph-H and triazole) 7.59-8.06 (m, 3 H, OBz) |
| $^{31}P$ | 149.08, 149.67 |
| Chemical Structure<br>A. Chemical Name of Monomeric PPA Compound<br>B. Chemical Name of Compound in Polymer<br>C. Code Identifier | 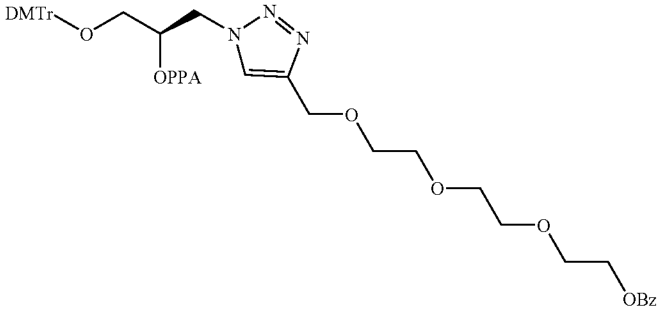<br>A. 1-O-DMT-2-O-PPA-3-(4-(Me-O-PEG3-O-Bz)-1-(1,2,3-triazole))-propane<br>B. 1,2-O-bis(phosphodiester)-3-(4-(Me-O-PEG3-O-Bz)-1-(1,2,3-triazole))-propane<br>C. Code: PPA060 |
| Cmpd # Method | 31d<br>Ex. 7 |
| Key intermediate | 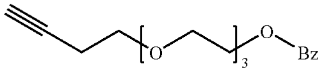 |
| Analytic data | 1H NMR (300 MHz, ACN-d3) d ppm 1.08 (d, J = 6.66 Hz, 3 H, N(iPr)2) 1.02 (d, J = 6.91 Hz, 4 H, N(iPr)2) 1.13 (d, J = 6.66 Hz, 7 H, N(iPr)2) 1.91-2.02 (m, 2 H, CH3CN) 2.48 (t, J = 6.02 Hz, 1 H, CH2-CN) 2.62 (t, J = 5.89 Hz, 1 H, CH2-CN) 3.11-3.25 (m, 2 H, NH(iPr)2) 3.52-3.67 (m, 7 H, CH2O (PEG, glycerol)) 3.57 (s, 5 H, CH2-O, (PEG)) 3.74-3.80 (m, 8 H, O-CH2 (CNEt, Ph-OCH3) 3.81 (br. s., 1 H) 4.30-4.45 (m, 3 H, CH-CH2-triazole (glycerol)) 4.49-4.63 (m, 4 H, triazole-CH2-PEG, PEG-CH2-Bz) 6.81-6.96 (m, 4 H, Ph-H) 7.23-7.39 (m, 8 |

TABLE 1A-continued

| Exemplary Novel Phosphoramidite (PPA) Monomers-Group A | |
|---|---|
| | H, Ph-H) 7.42-7.58 (m, 3 H, Ph-H) 7.58-7.71 (m, 1 H, Ph-H) 7.98-8.07 (m, 1 H, C-CH (triazole)) |
| $^{31}P$ | 149.06, 149.76 |
| Chemical Structure<br>A. Chemical Name of Monomeric PPA Compound<br>B. Chemical Name of Compound in Polymer<br>C. Code Identifier | 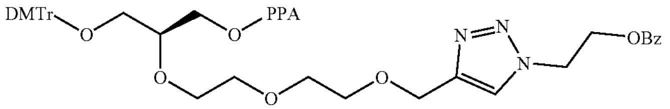<br>A. 1-O-DMT-3-O-PPA-2s-O-(4-(Me-O-PEG2)-1-(Et-OBz)-1,2,3-triazole)-propane<br>B. 1,3-O-bis(phosphodiester)-2s-O-(4-(Me-O-PEG2)-1-(Et-OBz)-1,2,3-triazole)-propane<br>C. code: PPA062 |
| Cmpd # Method | 35a<br>Ex. 8 |
| Key intermediate | 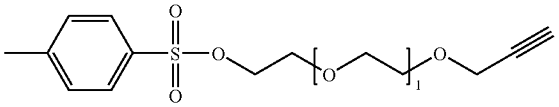 |
| Analytic data | 1H NMR (300 MHz, ACN-d3) d ppm 1.06-1.19 (m, 12 H, N(iPr)2) 2.51-2.64 (m, 2 H, —CH2CN) 3.05-3.22 (m, 2 H, N(iPr)2) 3.50-3.73 (m, 13 H, —CH2O (PEG)) 3.78 (s, 6 H, Ph-OCH3) 4.56 (s, 2 H, —OCH2-triazole) 4.61-4.77 (m, 4 H, Et-Bz) 6.88 (d, J-8.96 Hz, 4 H, Ph-H) 7.22-7.38 (m, 7 H, Ph-H) 7.48 (d, J = 7.68 Hz, 3 H, Ph-H) 7.88-8.01 (m, 3 H, Ph-H, triazole) |
| 31 p | 147.98 |
| Chemical Structure<br>A. Chemical Name of Monomeric PPA Compound<br>B. Chemical Name of Compound in Polymer<br>C. Code Identifier | 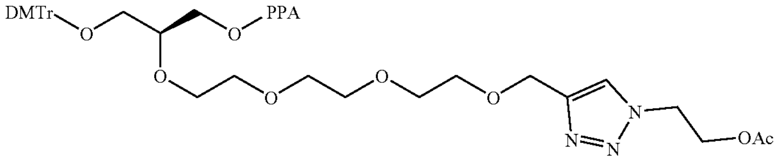<br>A. 1-O-DMT-3-O-PPA-2-(4-Me-O-PEG3)-1-(Et-O-Ac)-1,2,3-triazole)-propane<br>B. 1,3-O-bis(phosphodiester)-2-(4-Me-O-PEG3)-1-(Et-O-Ac)-1,2,3-triazole)-propane<br>C. code: PPA061/081 |
| Cmpd # Method | 35b<br>Ex. 8 |
| Key intermediate | 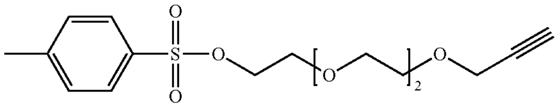 |
| Analytic data | 1H NMR (300 MHz, ACN-d3) d ppm 1.08-1.24 (m, 12 H, N(iPr)2) 1.99 (s, 3 H, OAc) 2.55-2.70 (m, 2 H, —CH2CN) 3.08-3.21 (m, 2 H, N(iPr)2) 3.54-3.74 (m, 19 H, CH2O (glycerol, PEG, CNEt) 3.79 (s, 6 H, Ph-OCH3) 4.43 (d, J = 5.60 Hz, 2 H, —OCH2-triazole) 4.55-4.71 (m, 4 H, EtOAc) 6.85-6.99 (m, 4 H, Ph-H) 7.29-7.42 (m, 7 H, Ph-H) 7.45-7.60 (m, 3 H, Ph-H and triazole) |
| $^{31}P$ | 147.95 |
| Chemical Structure<br>A. Chemical Name of Monomeric PPA Compound<br>B. Chemical Name of Compound in Polymer<br>C. Code Identifier | 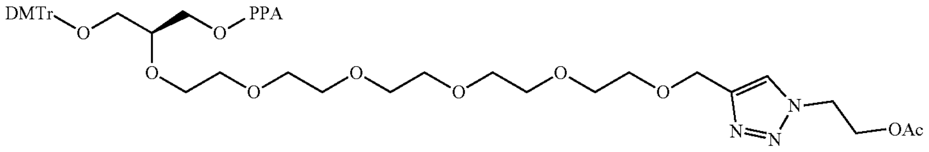<br>A. 1-O-DMT-3-O-PPA-2-(4-(Me-O-PEG5)-1-(Et-O-Ac)-1,2,3-triazole)-propane<br>B. 1,3-O-bis(phosphodiester-2-(4-(Me-O-PEG5)-1-(Et-O-Ac)-1,2,3-triazole)-propane<br>C. code: PPA083/PPA063 |
| Cmpd # Method | 35c<br>Ex. 8 |

TABLE 1A-continued

| Exemplary Novel Phosphoramidite (PPA) Monomers-Group A | |
|---|---|
| Key intermediate | 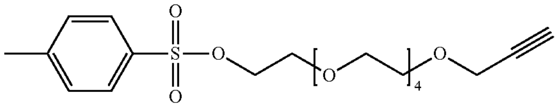 |
| Analytic data | 1H NMR (300 MHz, ACN-d3) d ppm 1.05-1.20 (m, 12 H, N(iPr)2) 1.90-2.06 (m, 1 H) 1.90-2.06 (m, 5 H, OAc) 2.60 (dt, J = 8.45, 5.89 Hz, 2 H, CH2-CN) 3.04-3.21 (m, 2 H, NH(iPr)2) 3.51-3.63 (m, 21 H, —OCH2 (PEG, —CH (glycerol)) 3.65-3.74 (m, 5 H, —OCH3 (Gylcerol, CNEt)) 3.78 (s, 6 H, Ph-OCH3) 4.33-4.47 (m, 2 H, PEG-OCH2-Triazole) 4.51-4.66 (m, 4 H, triazole-CH2-CH2-Ac) 6.88 (d, J = 8.70 Hz, 4 H, Ph-H) 7.22-7.38 (m, 7 H, PH-H) 7.47 (s, 1 H, Ph-H) 7.48-7.54 (m, 1 H, C = CH (Triazole)) |
| $^{31}$P | 147.95 |
| Chemical Structure<br>A. Chemical Name of Monomeric PPA Compound<br>B. Chemical Name of Compound in Polymer<br>C. Code Identifier | 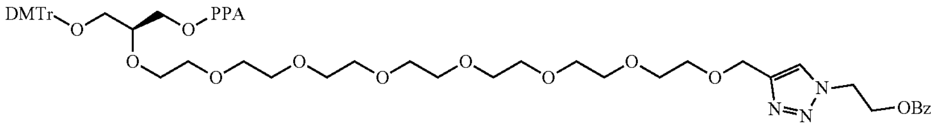<br>A. 1-O-DMT-3-O-PPA-2s-O-(4-(Me-O-PEG7)-1-(Et-OBz)-1,2,3-triazole)-propane<br>B. 1,3-O-bis(phosphodiester-2s-O-(4-(Me-O-PEG7)-1-(Et-OBz)-1,2,3-triazole)-propane<br>C. code: PPA064 |
| Cmpd # Method | 35d<br>Ex. 8 |
| Key intermediate | 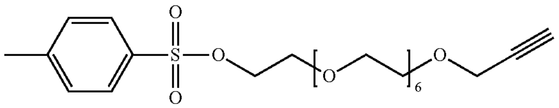 |
| Analytic data | 1H NMR (300 MHz, ACN-d3) d ppm 1.08-1.19 (m, 12 H, N(iPr)2) 2.51-2.65 (m, 2 H, CH2-CN) 3.06-3.22 (m, 2 H, NH(iPr)2) 3.49-3.72 (m, 36 H, —CH2O (PEG, glycerol)) 3.79 (s, 7 H, Ph-OCH3) 4.58 (s, 2 H, PEG-CH2-triazole) 4.66-4.81 (m, 4 H, triazole-CH2-CH2-Bz) 6.89 (d, J = 8.70 Hz, 4 H, Ph-H) 7.19-7.69 (m, 12 H, Ph-H) 7.83-8.01 (m, 2 H, Ph-H, C-CH (triazole)) |
| $^{31}$P | 148 |
| Chemical Structure<br>A. Chemical Name of Monomeric PPA Compound<br>B. Chemical Name of Compound in Polymer<br>C. Code Identifier | 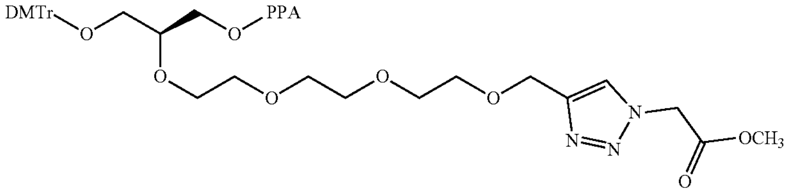<br>A. 1-O-DMT-3-O-PPA-2s-O-(4-(Me-O-PEG3)-1-(Me-acetate)-1,2,3-triazole)-propane<br>B. 1,3-O-bis(phosphodiester-2s-O-(4-(Me-O-PEG3)-1-(Me-acetate)-1,2,3-triazole)-propane<br>C. code: PPA065 |
| Cmpd # Method | 35e<br>Ex. 8 |
| Key intermediate | 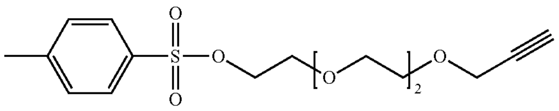 |
| Analytic data | 1H NMR (300 MHz, ACN-d3) d ppm 1.07-1.20 (m, 12 H, N(iPr)2)) 2.52-2.67 (m, 2 H, CH2CN) 3.07-3.23 (m,2 H, N(iPr)2) 3.54-3.80 (m, 22 H, —CH2O (PEG, Glycerol, CNEt), —OCH3) 4.60 (s, 2 H, O-CH2-Triazole) 5.21 (s, 2 H, CH2-(N)Triazole)) 6.89 (d, J = 8.96 Hz, 4 H, Ph-H) 7.23-7.55 (m, 9 H, Ph-H) |
| $^{31}$P | 147.93 |

TABLE 1A-continued

| Exemplary Novel Phosphoramidite (PPA) Monomers-Group A | |
|---|---|
| Chemical Structure<br>A. Chemical Name of Monomeric PPA Compound<br>B. Chemical Name of Compound in Polymer<br>C. Code Identifier | 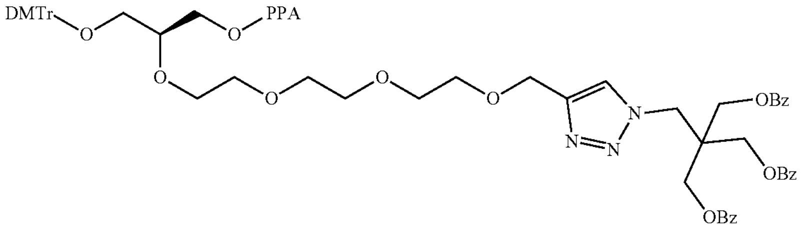<br>A. 1-O-DMT-3-O-PPA-2s-O-(4-(Me-O-PEG3)-1-(Et-2,2,2-Tris-(Me-O-Bz))-1,2,3-triazole)-propane<br>B. 1,3-O-bis(phosphodiester-2s-O-(4-(Me-O-PEG3)-1-(Et-2,2,2-Tris-(Me-O-Bz))-1,2,3-triazole)-propane<br>C. code: PPA068 |
| Cmpd # Method | 37a<br>Ex. 9 |
| Key intermediate | 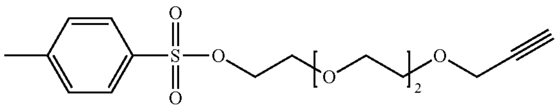 |
| Analytic data<br><br><br><br><br><br><br><br>$^{31}P$ | 1H NMR (300 MHz, DMSO-d6) d ppm 0.98-1.13 (m, 12 H, N(iPr)2) 2.71 (t, J = 6.02 Hz, 2 H, —CH2CN) 3.26 (br. s., 2H, NH(iPr)2) 3.49 (br. s., 2 H, —CH2O (glycerol)) 3.52 (d, J = 8.70 Hz, 5 H-CH2O (glycerol, PEG)) 3.62 (s, 7 H, Ph-OCH3) 3.67-3.83 (m, 4 H, —CH2O (glycerol, PEG)) 4.23 (s, 3 H, PEG-CH2-triazole) 4.29-4.42 (m, 11 H, CH2-Bz) 4.52 (br. s., 2 H) 4.60 (s, 2 H, triazole-CH2-C) 6.71 (d, J = 8.96 Hz, 4 H, Ph-H) 7.11-7.25 (m, 7 H, Ph-H) 7.30-7.36 (m, 2 H, Ph-H) 7.39-7.54 (m, 13 H, Ph-H) 7.60-7.67 (m, 4 H, Ph-H) 7.78-7.86 (m, 7 H, Ph-H) 7.90 (s, 1 H, C-CH, triazole) 7.91 (d, J = 6.91 Hz, 3 H, Ph-H)<br>147.93 |
| Chemical Structure<br>A. Chemical Name of Monomeric PPA Compound<br>B. Chemical Name of Compound in Polymer<br>C. Code Identifier | 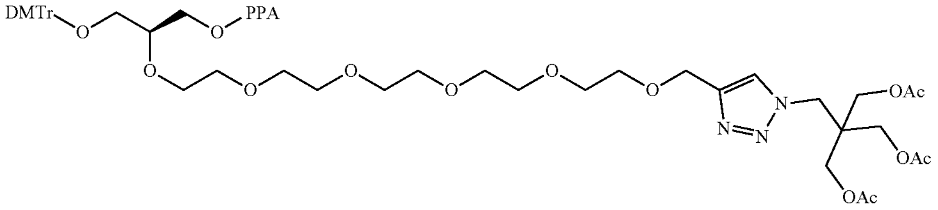<br>A. 1-O-DMT-3-O-PPA-2-(4-(Me-O-PEG5)-1-(Et-2,2,2-Tris-(Me-O-Ac))-1,2,3-triazole)-propane<br>B. 1,3-O-bis(phosphodiester-2-(4-(Me-O-PEG5)-1-(Et-2,2,2-Tris-(Me-O-Ac))-1,2,3-triazole)-propane<br>C. code: PPA093 |
| Cmpd # Method | 37b<br>Ex. 9 |
| Key intermediate | 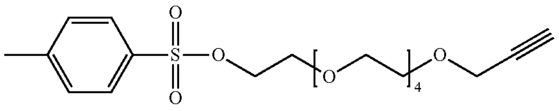 |
| Analytic data<br><br><br><br><br><br>$^{31}P$ | 1H NMR (300 MHz, ACN-d3) d ppm 0.99-1.14 (m, 12 H, N(iPr)2) 2.03 (s, 9 H, -OAc) 2.45-2.61 (m, 2 H, —CH2CN) 3.00-3.17 (m, 2 H, N(iPr)2) 3.41-3.70 (m, 27 H, —CH2O (PEG, CNEt), —CH (glycerol), -NCH2 (Erythritol)) 3.73 (s, 6 H, Ph-OCH3) 4.00 (s, 6 H, —OCH2 (Erythritol)) 4.51 (d, J = 8.71 Hz, 4 H, P-OCH2 (Glycerol), —OCH2-Triazole) 6.78-6.89 (m, 4 H, Ph-H) 7.12-7.47 (m, 9 H, Ph-H) 7.70 (s, 1 H, —CH (Triazole))<br>147.96 |
| Chemical Structure<br>A. Chemical Name of Monomeric PPA Compound<br>B. Chemical Name of Compound in Polymer<br>C. Code Identifier | 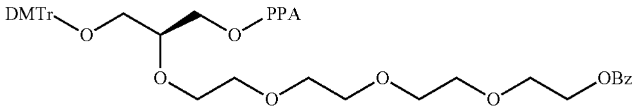<br>A. 1-O-DMT-3-O-PPA-2S-O-(PEG4-O-Bz)-propane<br>B. 1,3-O-bis(phosphodiester-2S-O-(PEG4-O-Bz)-propane<br>C. code: PPA050 |

TABLE 1A-continued

Exemplary Novel Phosphoramidite (PPA) Monomers-Group A

| | |
|---|---|
| Cmpd # Method | 38b<br>Ex. 10 |
| Key intermediate | 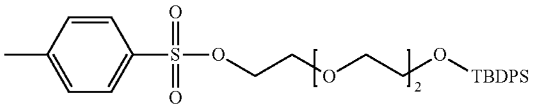 |
| Analytic data | 1H NMR (300 MHz, ACN-d3) d ppm 1.05-1.22 (m, 12 H, N(iPr)2) 2.52-2.68 (m, 2 H, —CH2-CN) 3.06-3.22 (m, 2 H, N(iPr)2) 3.53-3.77 (m, 21 H, —CH2O (glycerol, PEG, CNEt)) 3.79 (s, 6 H, Ph-OCH3) 4.42 (dd, J-5.63, 3.84 Hz, 2 H, —CH2-OBz) 6.88 (d, J = 8.70 Hz, 4 H, Ph-H) 7.23-7.38 (m, 10 H, Ph-H) 7.42-7.57 (m, 3 H, Ph-H) 7.99-8.07 (m, 1 H, Ph-H) |
| $^{31}P$ | 147.98 |
| Chemical Structure<br>A. Chemical Name of Monomeric PPA Compound<br>B. Chemical Name of Compound in Polymer<br>C. Code Identifier | 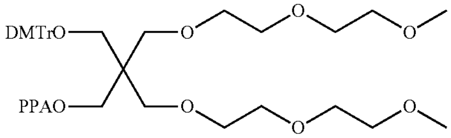<br>A. 1-O-DMT-3-O-PPA-2,2-bis(Me-O-mPEG2)-propane<br>B. 1,3-O-bis(phosphodiester-2,2-bis(Me-O-mPEG2)-propane<br>C. code: PPA040 |
| Cmpd # Method | 45b<br>Ex. 11 |
| Key intermediate | 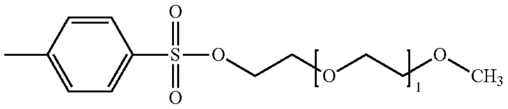 |
| Analytic data | 1H NMR (300 MHz, ACN-d3) d ppm 1.07-1.23 (m, 12 H, N(iPr)2) 2.59 (t, J = 6.02 Hz, 2 H, —CH2CN) 3.10 (m, 2 H N(iPr)2) 3.30 (s, 6 H, —OCH3 (PEG)) 3.43-3.59 (m, 20 H, —CH2O (PEG)) 3.65-3.81 (m, 4 H, —CH2O (DMT, PPA)) 3.79 (s, 6 H, Ph-OCH3) 6.88 (d, J = 8.96 Hz, 4 H, Ph-H) 7.21-7.37 (m, 7 H, Ph-H) 7.40-7.55 (m, 2 H, Ph-H) |
| $^{31}P$ | 147.1 |
| Chemical Structure<br>A. Chemical Name of Monomeric PPA Compound<br>B. Chemical Name of Compound in Polymer<br>C. Code Identifier | 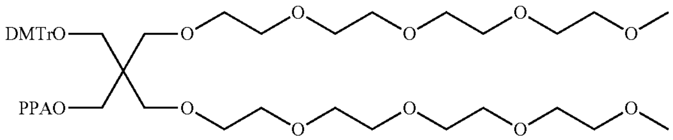<br>A. 1-O-DMT-3-O-PPA-2,2-bis(Me-O-mPEG4)-propane<br>B. 1,3-O-bis(phosphodiester-2,2-bis(Me-O-mPEG4)-propane<br>C. code: PPA035 |
| Cmpd # Method | 45c<br>Ex. 11 |
| Key intermediate | 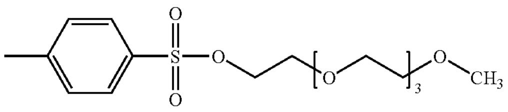 |
| Analytic data | 1H NMR (300 MHz, ACN-d 3 ) d ppm 1.06-1.20 (m, 12 H, N(iPr)2) 2.57 (t, J = 5.89 Hz, 2 H, —CH2CN) 3.07 (s, 2 H, N(iPr)2) 3.26-3.30 (m, 6 H, OCH3 (PEG)) 3.44-3.59 (m, 36 H, —CH2O (PEG, Erythritol)) 3.77 (s, 6 H, Ph-OCH3) 6.85 (d, J = 8.96 Hz, 4 H, Ph-H) 7.22-7.33 (m, 7 H, Ph-H) 7.42-7.46 (m, 2 H, Ph-H) |
| $^{31}P$ | 147.1 |

TABLE 1A-continued

| Exemplary Novel Phosphoramidite (PPA) Monomers-Group A | |
|---|---|
| Chemical Structure<br>A. Chemical Name of Monomeric PPA Compound<br>B. Chemical Name of Compound in Polymer<br>C. Code Identifier | 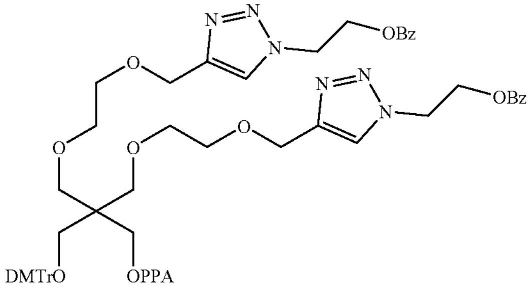<br>A. 1-O-DMT-3-O-PPA-2,2-bis(4-(Me-O-PEG1-O-Me)-1-(Et-O-Bz)-1,2,3-triazole)-propane<br>B. 1,3-O-bis(phosphodiester-2,2-bis(4-(Me-O-PEG1-O-Me)-1-(Et-O-Bz)-1,2,3-triazole)-propane<br>C. code: PPA070 |
| Cmpd # Method | 46e<br>Ex. 11 |
| Key intermediate | 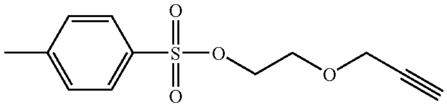 [SMILES: C#CCOCCOS(=O)(=O)c1ccc(C)cc1] |
| Analytic data | 1H NMR (300 MHz, ACN-d3) d ppm 1.02-1.19 (m, 12 H, N(iPr)2) 2.56 (t, J = 5.89 Hz, 2 H, —CH2CN) 3.07 (s, 2 H, N(iPr)2) 3.42-3.59 (m, 16 H, —CH2O (PEG)) 3.61-3.78 (m, 6 H, —CH2O (DMT, CNEt, PPA)) 3.76 (s, 6 H, Ph-OCH3) 4.46-4.59 (m, 4 H, —OCH2-triazole) 4.60-4.76 (m, 8 H, Et-OBz) 6.84 (d, J = 8.70 Hz, 4 H, Ph-H) 7.17-7.34 (m, 7 H, Ph-H) 7.37-7.49 (m, 4 H, Ph-H) 7.54-7.95 (m, 10 H, Ph-H and triazole) |
| $^{31}P$ | 147.03 |
| Chemical Structure<br>A. Chemical Name of Monomeric PPA Compound<br>B. Chemical Name of Compound in Polymer<br>C. Code Identifier | 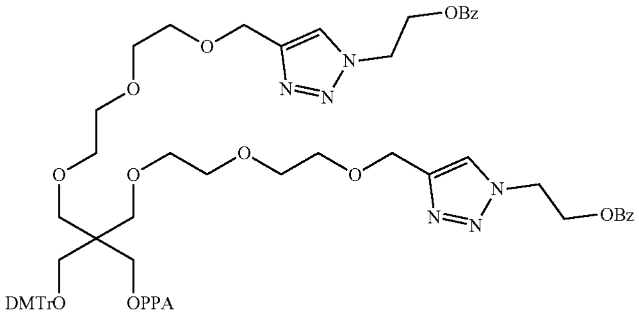<br>A. 1-O-DMT-3-O-PPA-2,2-bis(4-(Me-O-PEG2-O-Me)-1-(Et-O-Bz)-1,2,3-triazole)-propane<br>B. 1,3-O-bis(phosphodiester-2,2-bis(4-(Me-O-PEG2-O-Me)-1-(Et-O-Bz)-1,2,3-triazole)-propane<br>C. code: PPA069 |
| Cmpd # Method | 47f<br>Ex. 11 |
| Key intermediate | 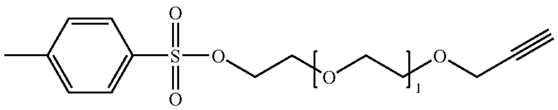 |
| Analytic data | 1H NMR (300 MHz, ACN-d3) d ppm 1.12 (dd, J = 18.31, 6.78 Hz, 12 H, N(iPr)2) 2.57 (t, J = 6.02 Hz, 2 H, —CH2CN) 3.07 (s, 2 H, N(iPr)2) 3.43-3.59 (m, 24 H, —CH2O (PEG, Erythritol) 3.62-3.73 (m, 2 H, CH2O (CNEt)) 3.77 (s, 6 H, Ph-OCH3) 4.55 (s, 4 H, —OCH2-triazole) 4.63-4.80 (m, 8 H, Et-OBz) 6.86 (d, J = 8.96 Hz, 4 H, Ph-H) 7.19-7.35 (m, 7 H, Ph-H) 7.50 (d, J = 7.94 Hz, 2 H, Ph-H) 7.45-7.70 (m, 6 H, Ph-H) 7.83 (s, 2 H, triazole) 7.96 (dd, J = 8.32, 1.15 Hz, 4 H, Ph-H) |
| 31 P | 147.12 |

TABLE 1A-continued

| Exemplary Novel Phosphoramidite (PPA) Monomers-Group A | |
|---|---|
| Chemical Structure<br>A. Chemical Name of Monomeric PPA Compound<br>B. Chemical Name of Compound in Polymer<br>C. Code Identifier | 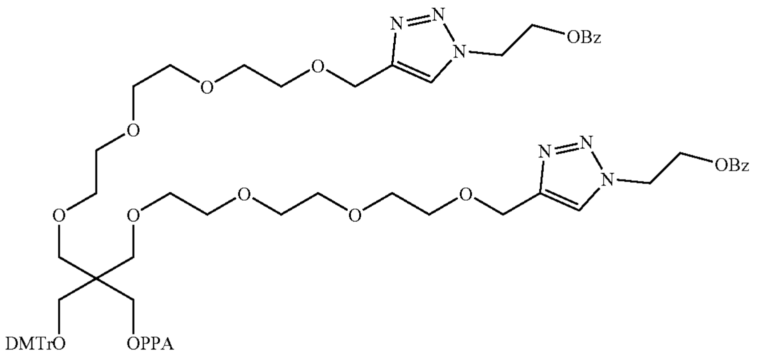<br>A. 1-O-DMT-3-O-PPA-2,2-bis(4-(Me-O-PEG3-O-Me)-1-(Et-O-Bz)-1,2,3-triazole)-propane<br>B. 1,3-O-bis(phosphodiester-2,2-bis(4-(Me-O-PEG3-O-Me)-1-(Et-O-Bz)-1,2,3-triazole)-propane<br>C. code: PPA075 |
| Cmpd # Method | 47g<br>Ex. 11 |
| Key intermediate | 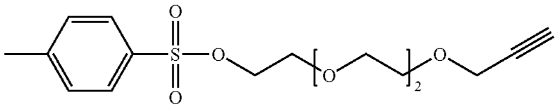 |
| Analytic data | 1H NMR (300 MHz, ACN-d3) d ppm 1.16 (d, J-6.91 Hz, 6 H, N(iPr)) 1.10 (d, J = 6.91 Hz, 6 H, N(iPr)) 2.58 (t, J = 6.02 Hz, 2 H, —CH2CN) 3.08 (s, 2 H, N(iPr)2) 3.43-3.80 (m, 34 H, CH2O (Erythritol, PEG, CNEt) 3.77 (s, 6 H, Ph-OCH3) 4.57 (s, 4 H, —CH2-triazole) 4.62-4.79 (m, 8 H, EtOBz) 6.87 (d, J-8.96 Hz, 4 H, Ph-H) 7.19-7.36 (m, 9 H, Ph-H) 7.39-7.80 (m, 10 H, Ph-H) 7.90-8.00 (m, 2 H, triazole) |
| $^{31}$p | 147.05 |
| Chemical Structure<br>A. Chemical Name of Monomeric PPA Compound<br>B. Chemical Name of Compound in Polymer<br>C. Code Identifier | 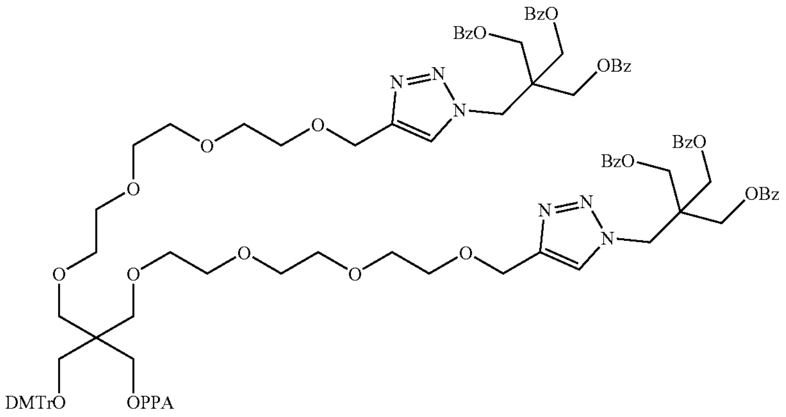<br>A. 1-O-DMT-3-O-PPA-2,2-bis(4-(Me-O-PEG3-O-Me)-1-(Et-2,2,2-Tris-(Me-O-Bz))-1,2,3-triazole)-propane<br>B. 1,3-O-bis(phosphodiester-2,2-bis(4-(Me-O-PEG3-O-Me)-1-(Et-2,2,2-Tris-(Me-O-Bz))-1,2,3-triazole)-propane<br>C. code: PPA078 |
| Cmpd # Method | 47i<br>Ex. 11 |
| Key intermediate | 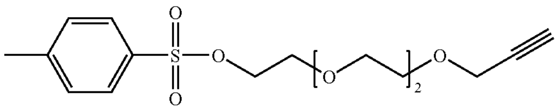 |
| Analytic data | 1H NMR (300 MHz, ACN-d3) d ppm 1.11 (dd, J = 16.90, 6.91 Hz, 12 H, N(iPr)2)) 2.57 (t, J = 6.02 Hz, 2 H, CH2CN) 3.07 (m, 2 H, NH(iPr)2) 3.42-3.79 (m, 37 H, —CH2 (PEG, glycerol, CNEt), OCH3) 3.77 (s, 4 H, —CH2(N)triazole)) 4.47 (s, 4 H, —CH2-triazole) 4.56 (s, 12 H, —CH2OBz) 4.88 (s, 4 H) 6.79-6.92(m, 4 H, Ph-H) 7.18-7.43 (m, 9 H, Ph-H) 7.48-7.69 (m, 18 H, OBz-H) 7.84 (s, 2 H, triazole) 7.99-8.01 (m, 12 H, OBz-H) |

TABLE 1A-continued

| Exemplary Novel Phosphoramidite (PPA) Monomers-Group A | |
|---|---|
| $^{31}P$ | 147.17 |
| Chemical Structure<br>A. Chemical Name of Monomeric PPA Compound<br>B. Chemical Name of Compound in Polymer<br>C. Code Identifier | 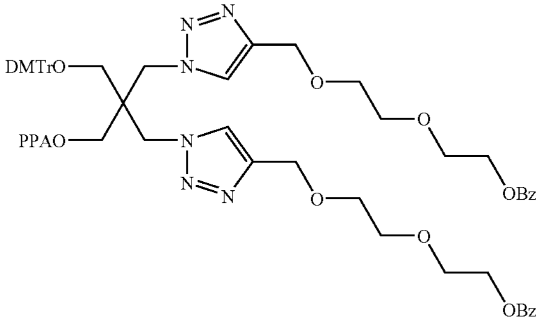<br>A. 1-O-DMT-3-O-PPA-2,2-bis(1-Me-4-(Me-O-PEG2-O-Bz)-1,2,3-triazole)-propane<br>B. 1,3-O-bis(phosphodiester-2,2-bis(1-Me-4-(Me-O-PEG2-O-Bz)-1,2,3-triazole)-propane<br>C. code: PPA056 |
| Cmpd # Method | 52<br>Ex. 12 |
| Key intermediate | 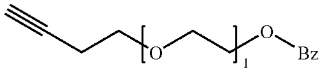 |
| Analytic data | 1H NMR (300 MHz, ACN-d3) d ppm 1.09 (d, J = 6.66 Hz, 6 H, N(iPr)) 1.18 (d, J = 6.66 Hz, 6 H, N(iPr)) 2.64 (t, J = 6.02 Hz, 2 H, —CH2CN) 2.96-3.13 (m, 2 H, N(iPr)2) 3.40-3.69 (m, 12 H, —CH2O (PEG)) 3.72-3.88 (m, 6 H, —CH2O (Erythritol, CNEt)) 3.79 (s, 6 H, Ph-OCH3) 4.39-4.45 (m, 4 H, —OCH2-tiazole) 4.47-4.56 (m, 8 H, —CH2-OBz, —CH2-triazole) 6.87 (d, J-8.96 Hz, 4 H, Ph-H) 7.22-7.36 (m, 7 H, Ph-H) 7.37-7.42 (m, 2 H, Ph-H) 7.45-7.61 (m, 10 H, Ph-H) 8.02 (d, J = 7.42 Hz, 2 H, triazole) |
| $^{31}P$ | 148.11 |
| Chemical Structure<br>A. Chemical Name of Monomeric PPA Compound<br>B. Chemical Name of Compound in Polymer<br>C. Code Identifier | 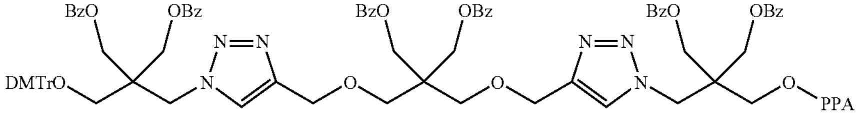<br>A. 2-((4-((3-(benzoyloxy)-2-(((1-(3-(benzoyloxy)-2-((benzoyloxy)methyl)-2-((PPA-oxy)methyl)propyl)-1H-1,2,3-triazol-4-yl)methoxy)methyl)-2-((benzoyloxy)methyl)propoxy)methyl)-1H-1,2,3-triazol-1-yl)methyl)-2-O-DMT-propane-1,3-diyl dibenzoate<br>B. 2-((4-((3-(benzoyloxy)-2-(((1-(3-(benzoyloxy)-2-((benzoyloxy)methyl)-2-((phosphodiester-oxy)methyl) propyl)-1H-1,2,3-triazol-4-yl)methoxy)methyl)-2-((benzoyloxy)methyl)propoxy)methyl)-1H-1,2,3-triazol-1-yl)methyl)-2-O-phosphodiester-propane-1,3-diyl dibenzoate<br>C. code: PPA058 |
| Cmpd # Method | 62<br>Ex. 13 |
| Key intermediate | 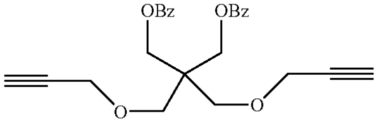 |
| Analytic data | 1H NMR (300 MHz, DMSO-d6) d ppm 0.98-1.13 (m, 12 H, N(iPr)2) 2.71 (t, J = 6.02 Hz, 2 H, —CH2CN) 3.52 (d, J = 8.70 Hz, 4 H, —CH2 (Erythritol)) 3.62 (s, 6 H, Ph-OCH3) 3.67-3.83 (m, 4 H, —CH2 (Erythritol)) 4.23-4.42 (m, 12 H, CH2OBz) 4.52 (br. s., 2 H, —CH2-triazole) 4.60 (s, 2 H, —CH2-triazole) 6.71 (d, J = 8.96 Hz, 4 H, Ph-H) 7.11-7.25 (m, 7 H, Ph-H) 7.30-7.36 (m, 2 H, Ph-H) 7.39-7.91 (m, 32 H, Ph-H and triazole). |
| 31P | 147.76 |

TABLE 1A-continued

Exemplary Novel Phosphoramidite (PPA) Monomers-Group A

| | |
|---|---|
| Chemical Structure<br>A. Chemical Name of Monomeric PPA Compound<br>B. Chemical Name of Compound in Polymer<br>C. Code Identifier | 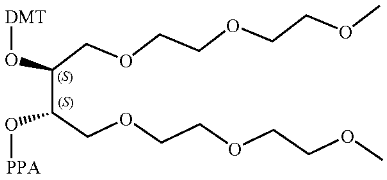<br>A. 2-O-DMT-3-O-PPA-1S,4S-bis(O-mPEG2)-butane<br>B. 2,3-O-bis(phosphodiester-1S,4S-bis(O-mPEG2)-butane<br>C. code: PPA016 |
| Cmpd # Method | 67<br>Ex. 14 |
| Key intermediate | 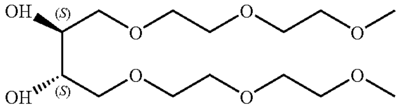 |
| Analytic data | 1H NMR (300 MHz, ACN-d3) d ppm 1.07-1.21 (m, 12 H, N(iPr)2) 2.50 (td, J = 5.89, 3.33 Hz, 1 H, —CH2CN) 2.62 (t, J = 6.14 Hz, 1H, CH2CN) 3.17-3.83 (m, 36 H, —CH2O (PEG, CNEt), —OCH3, —CHO) 6.80-6.92 (m, 4 H, Ph-H) 7.12-7.44 (m, 7 H, Ph-H) 7.52 (d, J = 8.19 Hz, 2 H, Ph-H) |
| $^{31}P$ | 147.61, 147.66 |
| Chemical Structure<br>A. Chemical Name of Monomeric PPA Compound<br>B. Chemical Name of Compound in Polymer<br>C. Code Identifier | 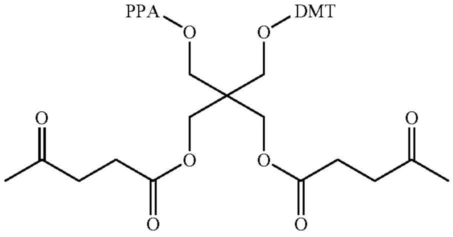<br>A. 1-O-DMT-3-O-PPA-2,2-bis(Me-O-levulinate)-propane<br>B. 1,3-O-bis(phosphodiester 2,2-bis(Me-O-levulinate)-propane<br>C. code: PPA036 |
| Cmpd # Method | 72<br>Ex. 15 |
| Key intermediate | 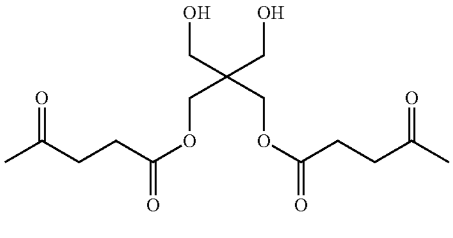 [SMILES: CC(=O)CCC(=O)OCC(CO)(CO)COC(=O)CCC(C)=O] |
| Analytic data | 1H NMR (300 MHz, ACN-d3) d ppm 1.07-1.24 (m, 12 H, N(iPr)2) 2.05-2.22 (m, 6 H, OAc) 2.43 (td, J = 6.66, 3.33 Hz, 4 H, levulinyl) 2.52-2.65 (m, 2 H, N(iPr)2) 2.65-2.77 (m, 4 H, levulinyl) 3.07-3.23 (m, 2 H, N(iPr)2) 3.50-3.82 (m, 6 H, —CH2O (erythritol-PPA, erythritol-DMT, CNEt)) 3.79 (s, 6 H, Ph-OCH3) 4.02-4.18 (m, 4 H, —CH2O (erythritol-levulinyl) 6.90 (d, J = 8.70 Hz, 4 H, Ph-H) 7.21-7.38 (m, 7 H, Ph-H) 7.40-7.52 (m, 2 H, Ph-H) |
| $^{31}P$ | 147.71 |

TABLE 1B

Exemplary Novel Phosphoramidite (PPA) Monomers-Group B

| Chemical name (code identifier) | Chemical Structure |
|---|---|
| 1-O-DMT-3-O-PPA-2R-mPEG4-propane (PPA106) | 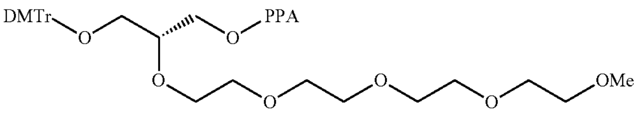 |
| 1-O-DMT-3-O-PPA-2S-O-mPEG8-propane (PPA033) | 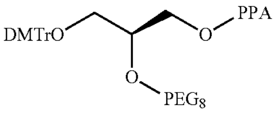 |
| 1-O-DMT-3-O-PPA-2S-O-mPEG10-propane (PPA034) | 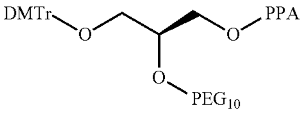 |
| 1-O-DMT-3-O-PPA-2-(4-(Me-O-PEG3)-1-(Et-2,2,2-Tris-(Me-O-Ac))-1,2,3-triazole)-propane (PPA079) | 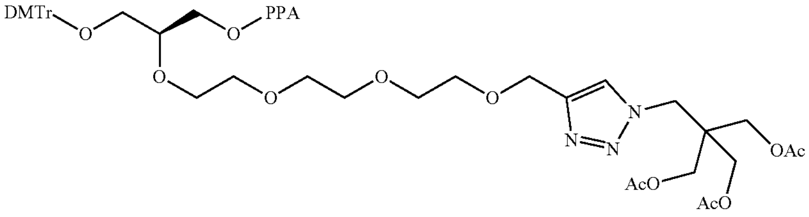 |
| 1-O-DMT-3-O-PPA-2-(4-(Me-O-PEG7)-1-(Et-O-Ac)-1,2,3-triazole)-propane (PPA084) | 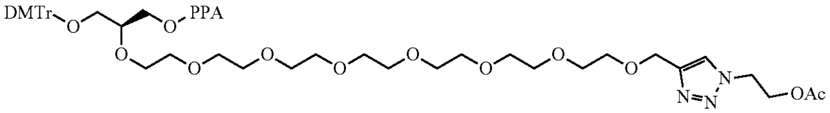 |
| 1-O-DMT-3-O-PPA-2-(4-(Me-O-PEG7)-1-(Et-2,2,2-Tris-(Me-O-Ac))-1,2,3-triazole)-propane (PPA094) | 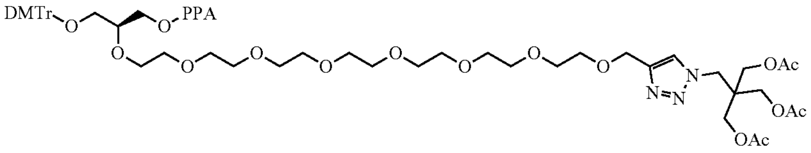 PP094 |
| 1-O-DMT-3-O-PPA-2,2-bis(4-(Me-O-PEG2-O-Me)-1-(Et-2,2,2-Tris-(Me-O-Bz))-1,2,3-triazole)-propane (PPA077) | 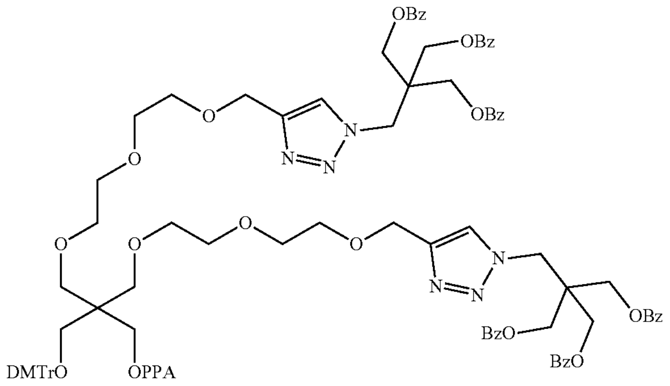 |

TABLE 1B-continued

| Exemplary Novel Phosphoramidite (PPA) Monomers-Group B | |
|---|---|
| Chemical name (code identifier) | Chemical Structure |
| 2-(16-(2-DMT-methoxy)ethyl)-1,4,10,13-tetraoxa-7,16-diazacyclooctadecan-7-yl)ethyl PPA (PPA087) | 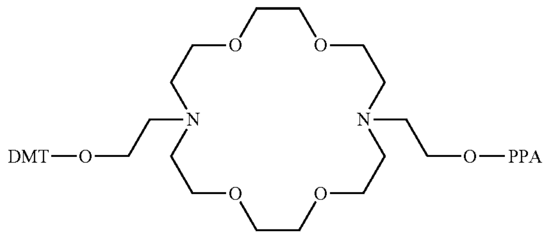 |
| 1-O-DMT-1'-O-PPA-(N,N)-(4,7,13,16-tetraoxa-1,10-diazacyclooctadecane-1,10-diyl)-bisethylurea (PPA047) | 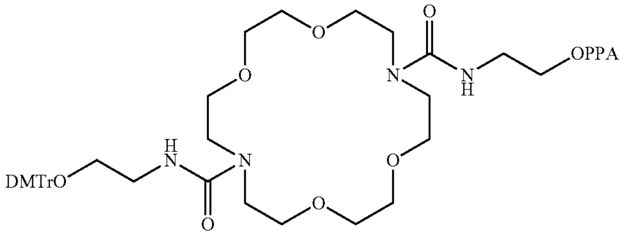 |
| 3-O-DMT-10-O-PPA-3,4,6,7,10,11-hexahydro-2H,9H-benzo[b][1,4,8,11]tetraoxacyclotetra decine (PPA049) | 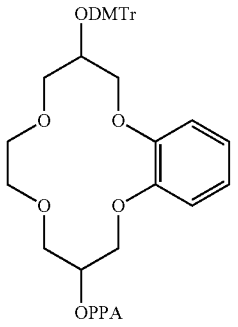 |
| 2-((4-((2-DMT)ethoxy)methyl-1,2,3-triazol-1-yl)methyl)-2-((4-((PPA)ethoxy)methyl)-1,2,3-triazol-1-yl)methyl)propane-1,3-diyl dibenzoate (PPA057) | 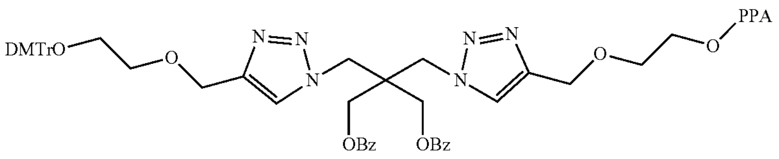 |
| 1-O-DMT-3-O-PPA-2-(4-methyl-1-(p-methoxy)-1,2,3-triazole)-propane (PPA019) | 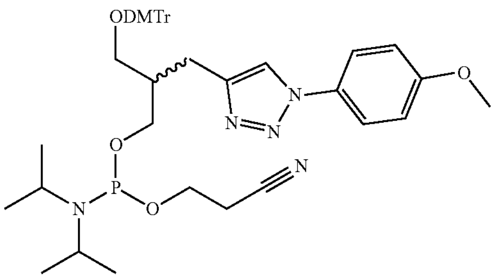 |

TABLE 1B-continued

Exemplary Novel Phosphoramidite (PPA) Monomers-Group B

| Chemical name (code identifier) | Chemical Structure |
| --- | --- |
| 1-O-DMT-2S-O-PPA-3-(N-(1-aza-15-crown-5)-propane (PPA048) | 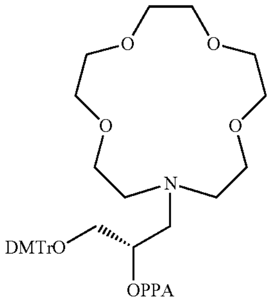 |
| 1-O-DMT-2S-O-PPA-3-(3-methoxy-pyridin-2-one-1-yl)-propane (PPA051) | 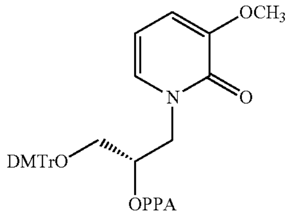 |
| 1-O-DMT-2-O-PPA-3-((N,N-dipyridin-2-yl)amino)-propane (PPA052) | 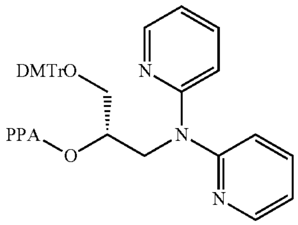 |
| 1-O-DMT-2-O-PPA-3-(pyridazin-3-on-2-yl)-propane (PPA053) | 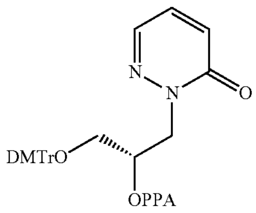 |
| 1-O-DMT-1'-O-PPA-N(butyl) Diethanolamine (PPA045) | 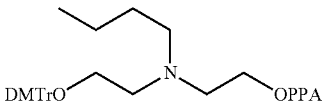 |
| 1-O-DMT-3-O-PPA-2,2-bis(4-(Me-O-PEG2-O-Me)-1-(Et-O-Bz)-1,2,3-triazole)-propane (PPA069) | 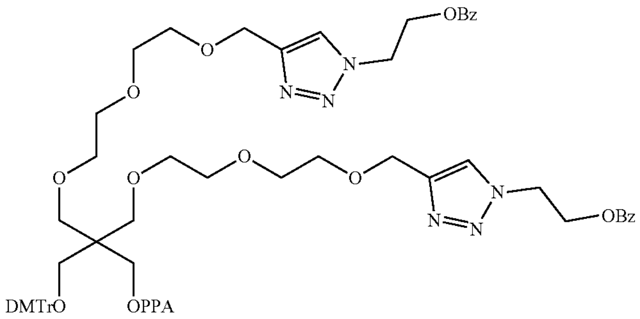 |
| (PPA046) | 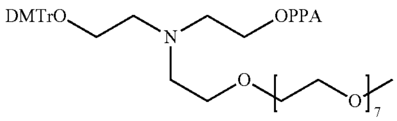 |

TABLE 1B-continued
| Exemplary Novel Phosphoramidite (PPA) Monomers-Group B | |
|---|---|
| Chemical name (code identifier) | Chemical Structure |
| (PPA070) | 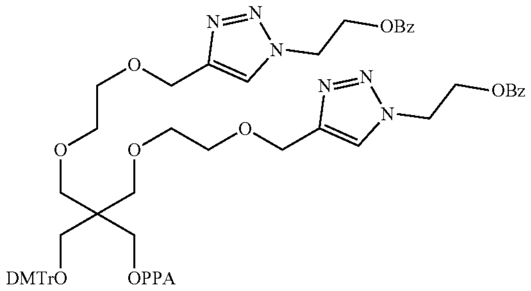 |
TABLE 1C
| Exemplary Novel Phosphoramidite (PPA) Monomers-Group C | |
|---|---|
| Chemical name (code identifier) | Chemical Structure |
| 3-O-DMT-4-O-PPA-1,2,5,6-tetrakis-(O-mPEG2)-hexane (PPA085) | 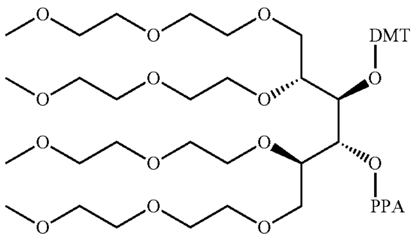 |
| 1-O-DMT-2S-O-PPA-3-O-(acetoxamido-15-crown-6)-propane (PPA024) | 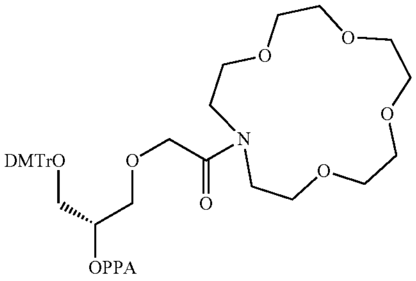 |

TABLE 1C-continued

| Exemplary Novel Phosphoramidite (PPA) Monomers-Group C | |
|---|---|
| Chemical name (code identifier) | Chemical Structure |
| 1-O-DMT-2S-O-PPA-3-O-(2,2-bis(Me-O-mPEG2)-3-O-mPEG2-propane) propane (PPA020) | 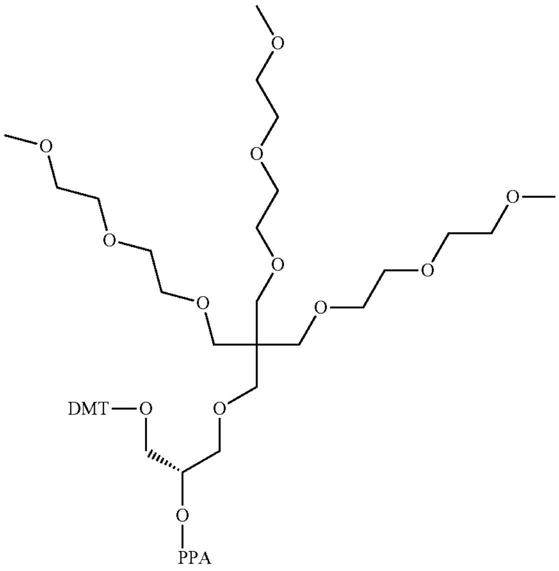 |
| 1-O-DMT-3-O-PPA-2S-(4-(Me-O-PEG2)-1-(Et-O-Ac)-1,2,3-triazole)-propane (PPA092) | 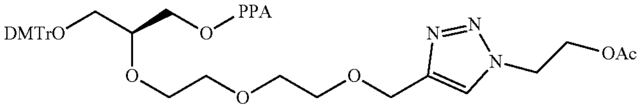 |
| 1-O-DMT-3-O-PPA-2S-(4-(Me-O-PEG5)-1-(Et-2,2,2-Tris-(Me-O-Bz))-1,2,3-triazole)-propane (PPA103) | 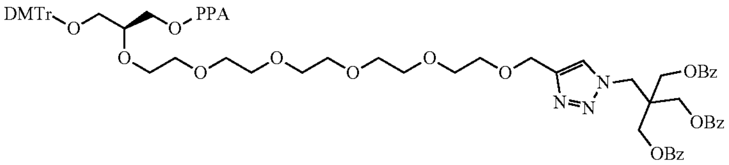 |
| 1-O-DMT-3-O-PPA-2S-(4-(Me-O-PEG7)-1-(Et-2,2,2-Tris-(Me-O-Bz))-1,2,3-triazole)-propane (PPA104) | 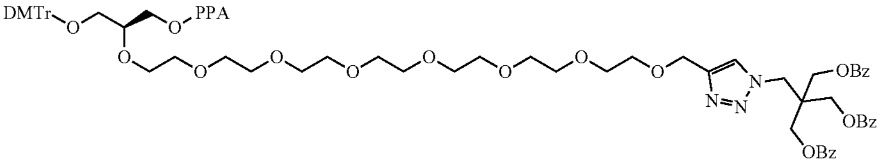 |
| 1-O-DMT-3-O-PPA-2,2-bis(4-(Me-O-PEG2-O-Me)-1-(Et-2,2,2-Tris-(Me-O-Ac))-1,2,3-triazole)-propane (PPA080) | 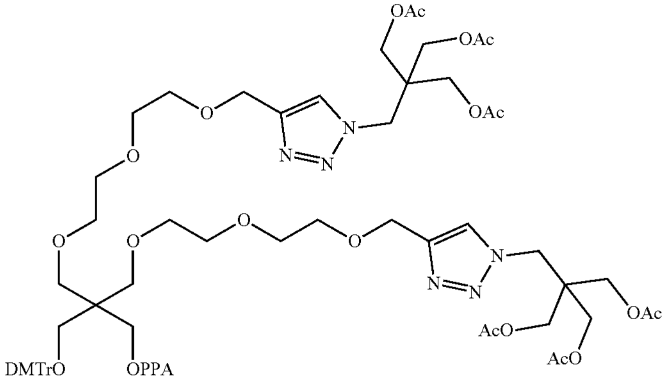 |

TABLE 1C-continued
| Exemplary Novel Phosphoramidite (PPA) Monomers-Group C | |
|---|---|
| Chemical name (code identifier) | Chemical Structure |
| 1-O-DMT-3-O-PPA-2,2-bis(4-(Me-O-PEG2-O-Me)-1-(Et-2,2,2-Tris-(Me-O-Ac))-1,2,3-triazole)-propane (PPA082) | 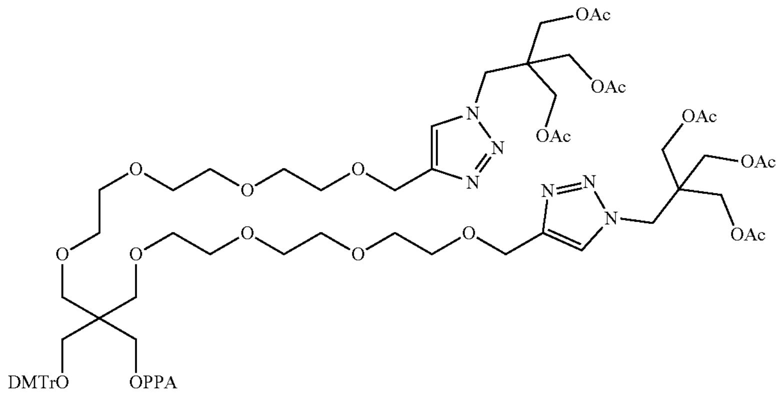 |
| 1-O-DMT-3-O-PPA-2S-O-(bis(Et-O-PEG2-(Et-2,2,2-Tris-(Me-O-Bz))-1,2,3-triazole))-3-O--(Et-2,2,2-Tris-(Me-O-Bz))-1,2,3-triazole))-propane (PPA076) | 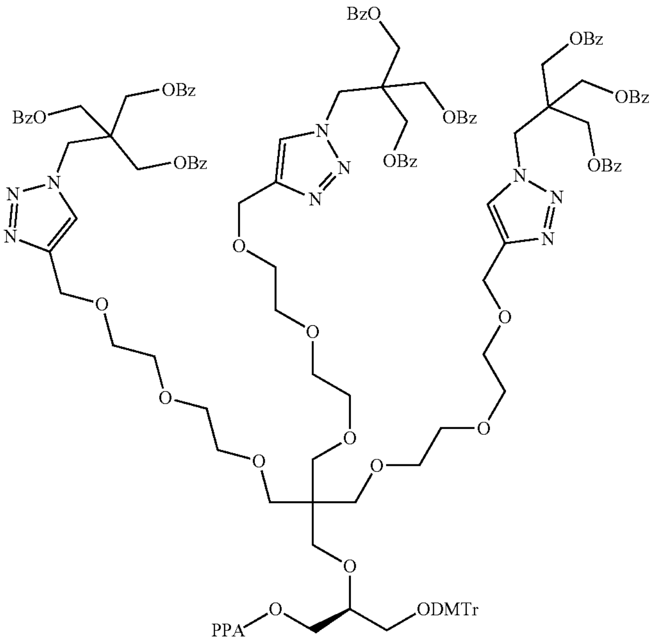 |
| 2,2-bis(DMT-O-Me)-1-O-PPA-butane (PPA039) | 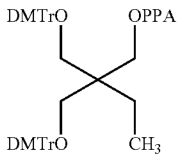 |
| N4-(2-O-DMT-Et)-N10-(2-O-PPA-ethyl)-1,7-dioxa-4,10-diazacyclododecane-4,10-dicarboxamide (PPA086) | 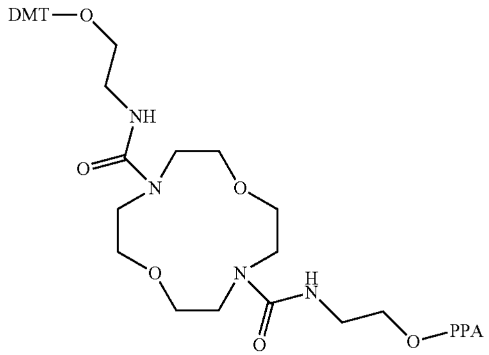 |

TABLE 1C-continued

| Exemplary Novel Phosphoramidite (PPA) Monomers-Group C | |
|---|---|
| Chemical name (code identifier) | Chemical Structure |
| 19-DMT-1,4,7,11,14,17-hexaoxacycloicosan-9-yl PPA (PPA028) | 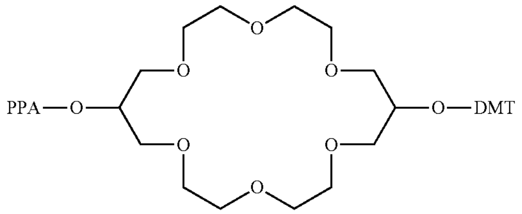 |
| 2-(3-(10-(3-(2-DMT-methoxy)ethoxy)propanoyl)-1,7-dioxa-4,10-diazacyclododecan-4-yl)-3-oxopropoxy)ethyl PPA (PPA088) | 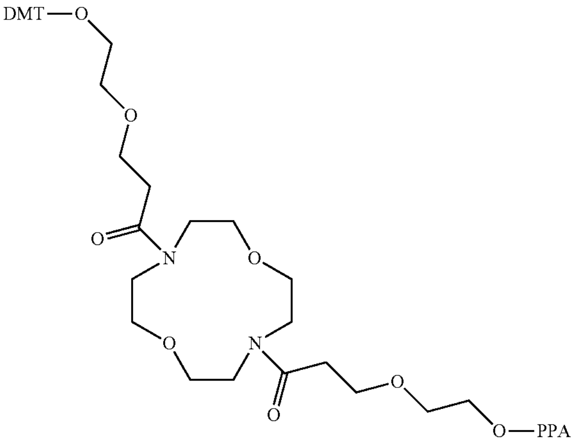 |
| 3-O-DMT-10-O-PPA-5,8,15,18,23,26-hexaoxa-1,12-diazabicyclo[10.8.8]octacosane-13,20-dione (PPA090) | 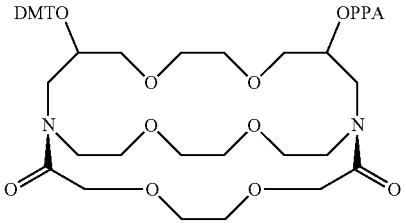 |
| 1-O-DMT-1'-O-PPA-2-(4,7,13,16-tetraoxa-1,10-diazacyclododecane-1,10-diyl)-diethylamide (PPA017) | 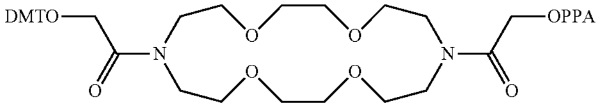 |
| 1-O-DMT-1'-O-PPA-(4,7,13,16-tetraoxa-1,10-diazacyclododecane-1,10-diyl)-di-PEG1-amide (PPA030) | 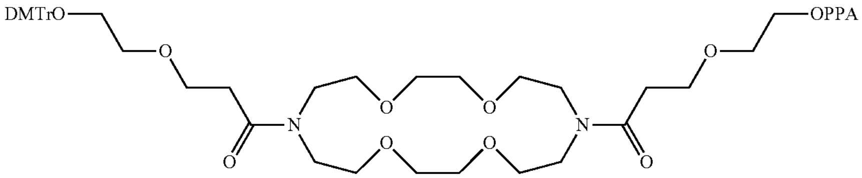 |
| 1-O-DMT-22-O-PPA-11,11-bis(Me-O-Bz)-3,6,9,13,16,19-hexaoxadocosane (PPA059) | 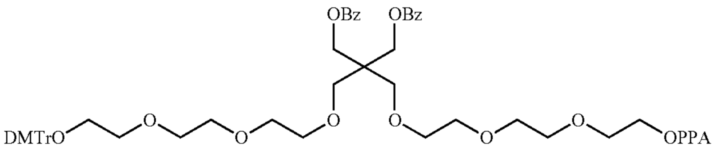 |
| 1-0-DMT-23-O-PPA-5,5,12,12,19,19-hexakis(Me-O-Bz)hexaoxatricosane (PPA066) | 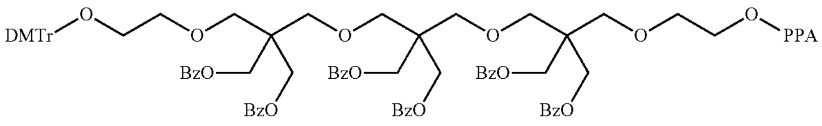 |

TABLE 1C-continued
| Exemplary Novel Phosphoramidite (PPA) Monomers-Group C | |
|---|---|
| Chemical name (code identifier) | Chemical Structure |
| 1-(DMT-O-Me)-4-(PPA-2-O-Et)-1,2,3-triazole (PPA067) | 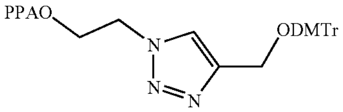 |
| 3-O-DMT-2S-O-PPA-1-(7-dioxaneindole)-propane (PPA011) | 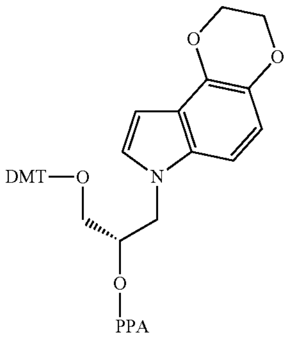 |
| 1-O-DMT-2S-O-PPA-3-O-((N,N-bis-mPEG2)acetamide)-propane (PPA025) | 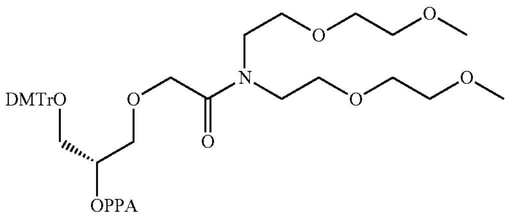 |
| 1-O-DMT-2-O-PPA-3-(4-methylpiperazine-1-yl)acetamide (PPA095) | 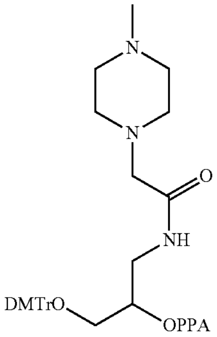 |
| 1-O-DMT-2-O-PPA-3-((4-methylpiperazine-1-yl)-Et-(1,2,3-triazole)-propane) (PPA096) | 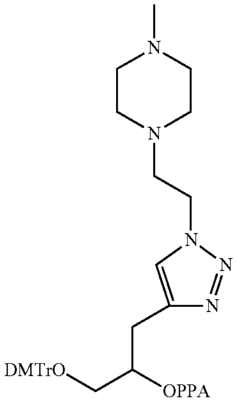 |

TABLE 1C-continued

| Exemplary Novel Phosphoramidite (PPA) Monomers-Group C | |
|---|---|
| Chemical name (code identifier) | Chemical Structure |
| 1-O-DMT-2-O-PPA-3-((trimethylamino)acetamide)-propane (PPA097) | 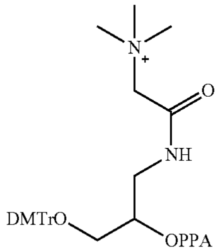 |
| 1-O-DMT-1'-O-PPA-N,N(dimethyl)Diethanolamine (PPA098) | 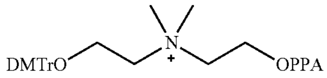 |
| 1-O-DMT-1'-O-PPA-N(PEG4-OMe)Diethanolamine (PPA099) | 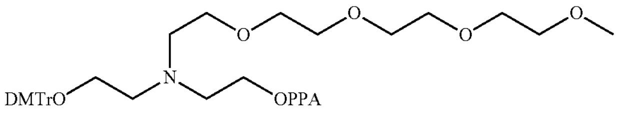 |
| 1-O-DMT-2-(S)-O-PPA-3-(N,N-di(PEG4-OMe)amine) (PPA100) | 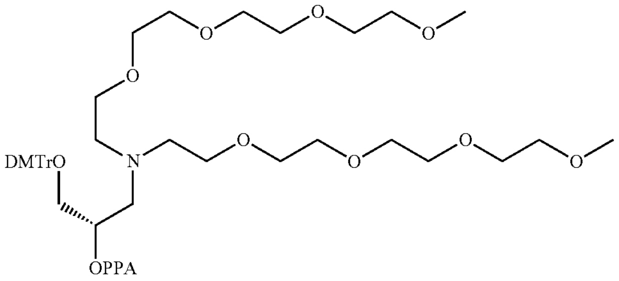 |
| 1-O-DMT-2(S)-O-PPA-3-(1-H-3-imidazole)-propane (PPA101) | 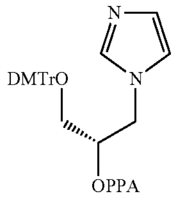 |
| 1-O-DMT-2-O-PPA-3-((1H-imidazol-4-yl)acetamide)-propane (PPA102) | 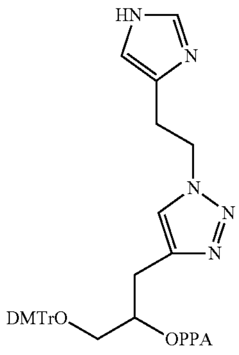 |

TABLE 1C-continued

| Exemplary Novel Phosphoramidite (PPA) Monomers-Group C | |
|---|---|
| Chemical name (code identifier) | Chemical Structure |
| 1-O-DMT-2-O-PPA-3-((1H-imidazol-4-yl)acetamide)-propane (PPA107) | 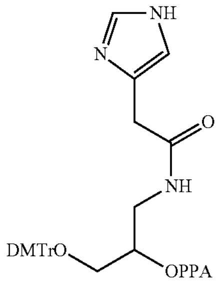 |
| 1-O-DMT-2-O-PPA-3-((1-Me-imidazol-4-yl)acetamide)-propane (PPA108) | 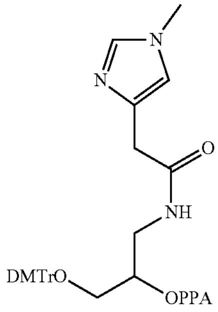 |

Translocation Control Elements (TCEs) Based on Novel Phosphoramidite Monomers.

As discussed herein, the TCE feature of an SSRT is designed to stall Xpandomer translocation so as to position the reporter code within the nanopore aperture for measurement. The availability of the new phosphoramidite monomeric compounds of the present invention has enabled design of next-generation TCE structures, which control translocation rate through one or more of steric hindrance, electro-repulsion, and preferential interaction with the nanopore. The resistance of the TCE to the driving force of the ion current when positioned at the pore aperture and the consequent increase in applied voltage (i.e., the voltage pulse) necessary to overcome the arrest and resume translocation, can be customized by modulating various properties of the TCE, (and in some embodiments, the reporter codes and other elements of the SSRT) e.g., the bulk, length, and/or charge density. Importantly, because translocation rate is controlled by properties intrinsic to the TCE, translocation control is relieved of the burden of relying on prior art strategies, which employ, e.g., nucleotide hybridization strategies based on reversible interaction with soluble oligonucleotides.

In certain embodiments, TCEs are polymers produced by solid-phase synthesis using the phosphoramidite method with suitable monomeric building blocks that terminate with a branched structure (i.e., the "brancher"). Branched phosphoramidites are known in the art and include both symmetrical and asymmetrical branchers, commercially available from, e.g., Glen Research and ChemGenes. In one embodiment, the TCE brancher is a symmetrical branching CED phosphoramidite, wherein each arm of the brancher is linked to a reporter code. Exemplary symmetrical chemical branchers include 1,2,3-O-tris-(phosphosphodiester)-propane, 1,3-bis-(5-O-phosphodiester-pentylamido)-2-O-phosphodiester-propane, and 1,4,7-O-tris-(phosphodiester)-heptane.

Figure 4:
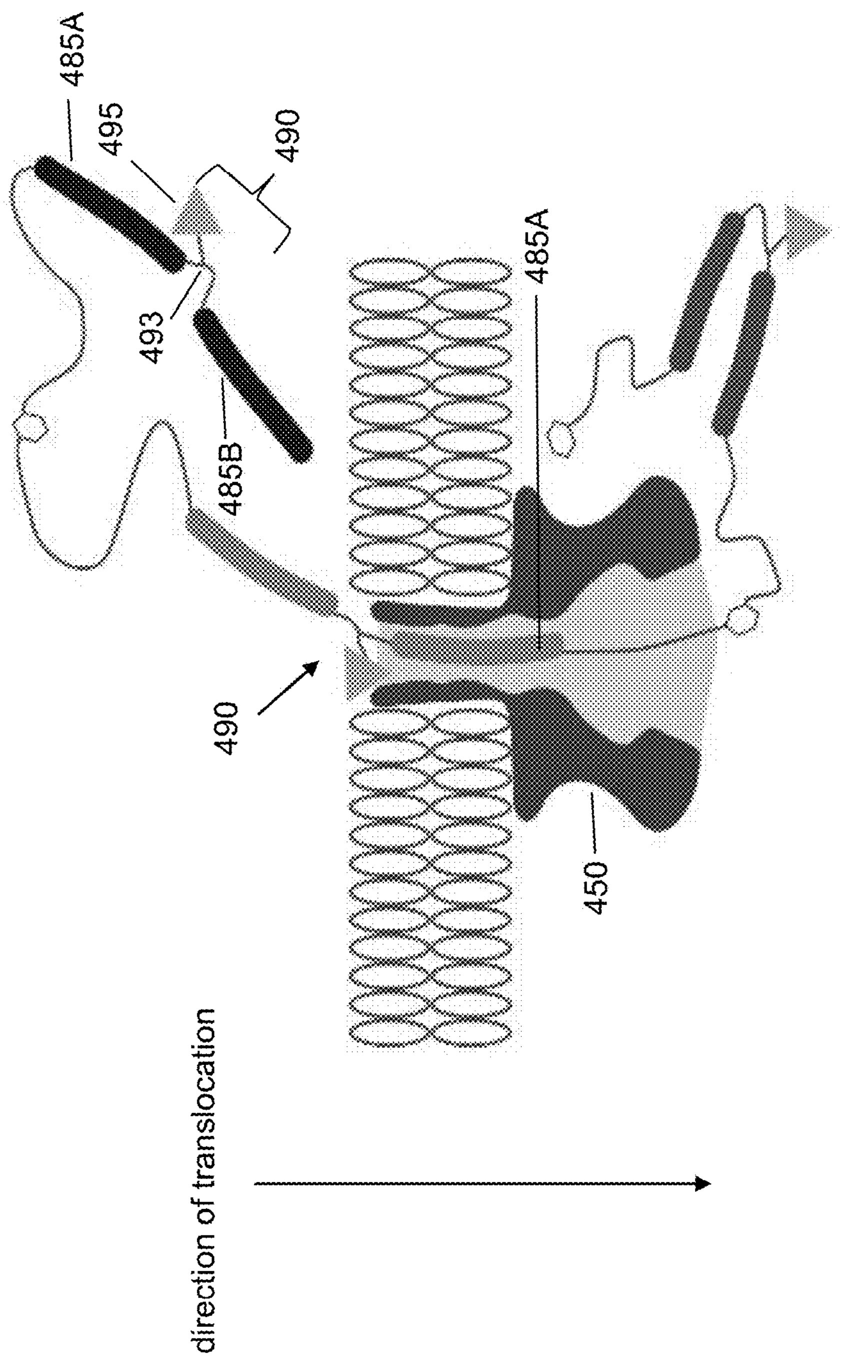
FIG. 4 is a schematic illustrating another embodiment of an Xpandomer passing through a biological nanopore.

FIG. 4 illustrates, in simplified form, how a TCE arrests Xpandomer translocation through a nanopore. Here, each SSRT of the Xpandomer includes reporter codes 485A and 485B that are linked to TCE 490 at the ends of the arms of brancher structure 493 of the TCE. In this embodiment, TCE 490 includes a structure 495 with a larger physical bulk relative to that of the reporter codes. Xpandomer translocation through the barrel of nanopore 450 is arrested when TCE 490, encounters the pore aperture. In certain embodiments, both the bulk of the TCE and the charge densities of the reporter codes (i.e., the local electric field at the arrest site) contribute to translocation arrest. During the pause, reporter code 495A is held in the barrel of the nanopore and blocks the flow of current through the pore in a characteristic and detectable manner. To overcome the arrest, a voltage pulse is applied to the system, which forces the TCE to enter and pass through the pore. Translocation then resumes until the next TCE encounters the pore aperture.

To customize translocation control, several structural properties of the TCE (and in certain embodiments, other features of the SSRT) can be adapted. For example, one or more of the length, bulk, and charge density of the TCE and the spatial positioning of charged elements within the barrel of the nanopore can be modified. In some embodiments, the bulk of the TCE is increased by incorporating one or more pendant PEG phosphoramidites into the polymeric structure. For example, the TCE may incorporate from 2 to 30, from 2 to 20, from 3 to 15, or from 4 to 14 pendant PEG phosphoramidite compounds. In other embodiments, TCEs may include any suitable number and combination of phosphoramidite compounds set forth in Tables 1A-C. For example, a TCE may include from 1 to 10, 2 to 8, or 2 or 3 different phosphoramidite compounds, in any order; in certain embodiments, at least one of the phosphoramidite compounds is a pendant PEG phosphoramidite. In certain embodiments, the length of the entire TCE may include from 2 to 30, from 2 to 20, from 3 to 15, or from 4 to 14 phosphoramidite compounds. In some embodiments, the formula of the TCE may be represented by $(PPA1)_{n1}(PPA2)_{n2}$ wherein PPA1 and/or PPA2 represent a pendant PEG phosphoramidite compound and n1=1 to 12 and n2=0 to 10. The inventors have discovered that TCE based on this formula significantly reduce sequencing errors (e.g., insertion or deletion events) and enable single-pulse transitions between sequential SSRTs. In certain embodiments, the TCE includes a polymer synthesized from phosphoramidite compounds with the following sequence: $[(1\text{-O-DMT-3-O-PPA-2S-O-mPEG4-propane (compound 12b))}]_{n1}$[(1-O-DMT-3-O-PPA-2-(4-Me-O-PEG3)-1-(Et-O-Ac)-1,2,3-triazole)-propane (compound 35b)]n2, in which n1 is from 0 to 6 and n2 is from 6 to 10. In other embodiments, the TCE includes one or more phosphoramidite chromophores that can be detected by UV radiation, e.g., benzofuran or triazole-containing PPAs.

In other embodiments, TCEs may include a brancher structure with more than two arms. In one embodiment, the phosphoramidite brancher may have a terminally branched structure. In this embodiment, the brancher has four arms, two of which are linked to the reporter codes, and two of which contribute to translocation control. In other embodiments. The brancher may be customized to optimize features such as size, polarity, and stability. In one embodiment, the brancher includes an isocyanuate trimer.

In further embodiments, the TCEs of the present invention may include two branchers (i.e., "double brancher" TCEs), in which the branchers are separated by a plurality of unbranched phosphoramidites. The branchers may be symmetrical or asymmetrical structures. The asymmetric structure may be a single enantiomer or racemic. Moreover, a combination of the racemate and/or both enantiomers can be used at different positions in the TCE. In this embodiment, each brancher contributes to a distinct translocation pause event, the first of which may be referred to as a "code pause" that maintains a reporter code in the nanopore, and the second of which may be referred to as a "clock pause" that produces a unique signal indicating that the preceding reporter codes has been "read" by the detection system.

Table 2 sets forth several exemplary TCE sequences. It is to be emphasized that the present invention is not intended to be limited to these particular embodiments, as the skilled artisan will appreciate that, based on the present disclosure, an extensive library of diverse TCEs can be designed to suit a wide range of experimental requirements. In certain embodiments, any of the TCE sequences set forth below could terminate at the end distal to the brancher with one or more spacer compounds, including C3, benzofuran, or PEG3. The key in Table 2 identifies the compounds in their form as phosphoramidite monomers. It will be readily apparent to one of ordinary skill in the art that the descriptor "phosphoramidite" only applies to the compounds in monomeric form; descriptors that apply to the compounds in multimeric, "in-line", form are set forth in Table 1A.

TABLE 2

Exemplary Translocation Control Elements (TCEs)

| TCE sequence | Key |
|---|---|
| $Y(PPA032)_6(PPA061)_6$<br>$Y(PPA032)_2(PPA061)_{10}$<br>$Y(PPA032)_2(PPA061)_8$<br>$Y(PPA032)_2(PPA061)_6$<br>$Y(PPA032)_5(PPA061)_6$ | Y: symmetrical brancher (e.g., Chemgenese Cat. No. CLP-5215)<br>PPA032: 1-O-DMT-3-O-PPA-2S—O-mPEG4-propane<br>PPA061: 1-O-DMT-3-O-PPA-2-(4-Me—O-PEG3)-1-(Et—O—Ac)-1,2,3-triazole)-propane |
| $Y(PPA061)_8$ | Y: symmetrical brancher<br>PPA061: 1-O-DMT-3-O-PPA-2-(4-Me—O-PEG3)-1-(Et—O—Ac)-1,2,3-triazole)-propane |
| $Y(PPA032)_{12}$ | Y: symmetrical brancher<br>PPA032: 1-O-DMT-3-O-PPA-2S—O-mPEG4-propane<br>PPA061: 1-O-DMT-3-O-PPA-2-(4-Me—O-PEG3)-1-(Et—O—Ac)-1,2,3-triazole)-propane |
| $Y(PPA031)_2(PPA032)_{10}$ | Y: symmetrical brancher<br>PPA031: 1-O-DMT-3-O-PPA-2s-O-mPEG6-propane<br>PPA032: 1-O-DMT-3-O-PPA-2S—O-mPEG4-propane |
| $Y(PPA040)_{12}$ | Y: symmetrical brancher<br>PPA040: 1-O-DMT-3-O-PPA-2,2-bis(Me—O-mPEG2)-propane |
| $Y(PPA032)_4(PPA064)_3$ | Y: symmetrical brancher<br>PPA032: 1-O-DMT-3-O-PPA-2S—O-mPEG4-propane<br>PPA064: 1-O-DMT-3-O-PPA-2S—O-(4-(Me—O-PEG7)-1-(Et—OBz)-1,2,3-triazole)-propane |
| $Y(PPA032)_4(PPA068)_5$ | Y: symmetrical brancher<br>PPA032: 1-O-DMT-3-O-PPA-2S—O-mPEG4-propane<br>PPA068: 1-O-DMT-3-O-PPA-2S—O-(4-(Me—O-PEG3)-1-(Et-2,2,2-Tris-(Me—O-Bz))-1,2,3-triazole)-propane |
| $Y(PPA032)_4(PPA094)_3$ | Y: symmetrical brancher<br>PPA032: 1-O-DMT-3-O-PPA-2S—O-mPEG4-propane<br>PPA094: 1-O-DMT-3-O-PPA-2-(4-(Me—O-PEG7)-1-(Et-2,2,2-Tris-(Me—O—Ac))-1,2,3-triazole)-propane |

TABLE 2-continued

| Exemplary Translocation Control Elements (TCEs) | |
|---|---|
| TCE sequence | Key |
| Y[(PPA032)(PPA062)]$_6$ | Y: symmetrical brancher<br>PPA032: 1-O-DMT-3-O-PPA-2S—O-mPEG4-propane<br>PPA062: 1-O-DMT-3-O-PPA-2S—O-(4-(Me—O-PEG2)-1-(Et—OBz)-1,2,3-triazole)-propane |
| Y(PPA044)$_8$ | Y: symmetrical brancher<br>PPA044: 1-O-DMT-8-O-PPA-N,N-Diethylpiperazine |
| Y(PPA062)$_{12}$ | Y: symmetrical brancher<br>PPA062: 1-O-DMT-3-O-PPA-2S—O-(4-(Me—O-PEG2)-1-(Et—OBz)-1,2,3-triazole)-propane |
| Y(PPA063)$_6$ | Y: symmetrical brancher<br>PPA063: 1-O-DMT-3-O-PPA-2-(4-(Me—O-PEG5)-1-(Et—O—Ac)-1,2,3-triazole)-propane |
| Y(PPA065)$_8$ | Y: symmetrical brancher<br>PPA065: 1-O-DMT-3-O-PPA-2S—O-(4-(Me—O-PEG3)-1-(Me-acetate)-1,2,3-triazole)-propane |
| Y(PPA068)$_6$ | Y: symmetrical brancher<br>PPA068: 1-O-DMT-3-O-PPA-2S—O-(4-(Me—O-PEG3)-1-(Et-2,2,2-Tris-(Me—O-Bz))-1,2,3-triazole)-propane |
| Y(PPA069)$_4$ | Y: symmetrical brancher<br>PPA069: 1-O-DMT-3-O-PPA-2,2-bis(4-(Me—O-PEG2-O—Me)-1-(Et—O-Bz)-1,2,3-triazole)-propane |
| Y(PPA075)$_2$ | Y: symmetrical brancher<br>PPA075: 1-O-DMT-3-O-PPA-2,2-bis(4-(Me—O-PEG3-O—Me)-1-(Et—O-Bz)-1,2,3-triazole)-propane |
| Y(PPA078)<br>Y(PPA078)$_3$ | Y: symmetrical brancher<br>PPA078: 1-O-DMT-3-O-PPA-2,2-bis(4-(Me—O-PEG3-O—Me)-1-(Et-2,2,2-Tris-(Me—O-Bz))-1,2,3-triazole)-propane |
| Y(PPA093)$_5$ | Y: symmetrical brancher<br>PPA093: 1-O-DMT-3-O-PPA-2-(4-(Me—O-PEG5)-1-(Et-2,2,2-Tris-(Me—O—Ac))-1,2,3-triazole)-propane |
| Y(PPA094)$_4$ | Y: symmetrical brancher<br>PPA094: 1-O-DMT-3-O-PPA-2-(4-(Me—O-PEG7)-1-(Et-2,2,2-Tris-(Me—O—Ac))-1,2,3-triazole)-propane |
| Y(PPA032)$_6$(PPA060)$_6$ | Y: symmetrical brancher<br>PPA032: 1-O-DMT-3-O-PPA-2S—O-mPEG4-propane<br>PPA060: 1-O-DMT-2-O-PPA-3-(4-(Me—O-PEG3-O-Bz)-1-(1,2,3-triazole))-propane |
| Y(PPA032)$_8$(PPA056)$_3$ | Y: symmetrical brancher<br>PPA032: 1-O-DMT-3-O-PPA-2S—O-mPEG4-propane<br>PPA056: 1-O-DMT-3-O-PPA-2,2-bis(1-Me-4-(Me—O-PEG2-O-Bz)-1,2,3-triazole)-propane |
| Y(PPA032)$_6$(PPA043)(PPA032)$_6$(PPA043)$_2$ | Y: symmetrical brancher<br>PPA032: 1-O-DMT-3-O-PPA-2S—O-mPEG4-propane<br>PPA043: 1-O-DMT-2S—O-PPA-3-(4-methylpiperazine-1-yl)-propane |
| Y(PPA050)$_{12}$ | Y: symmetrical brancher<br>PPA50: 1-O-DMT-3-O-PPA-2S—O-(PEG4-O-Bz)-propane |
| Y(PPA031)$_{12}$(PPA018)$_2$<br>Y(PPA031)$_6$(PPA018)$_2$ | Y: symmetrical brancher<br>PPA031: 1-O-DMT-3-O-PPA-2S—O-mPEG6-propane<br>PPA018: 3-O-DMT-2S—O-PPA-1-(5-benzofuran)-propane |
| Y(PPA033)$_{12}$(PPA018)$_2$ | Y: symmetrical brancher<br>PPA033: 1-O-DMT-3-O-PPA-2S—O-mPEG8-propane<br>PPA018: 3-O-DMT-2S—O-PPA-1-(5-benzofuran)-propane |
| Y(PPA033)$_7$ | Y: symmetrical brancher<br>PPA033: 1-O-DMT-3-O-PPA-2S—O-mPEG8-propane |

TABLE 2-continued

Exemplary Translocation Control Elements (TCEs)

| TCE sequence | Key |
|---|---|
| Y(DTB)X(PPA018)$_4$XD(DTB) | Y: symmetrical brancher |
| | DTB: desthiobiotin |
| Y(DTB)X(PPA018)$_4$XD(DTB) | X: PEG3 |
| | D: PEG6 |
| | PPA018: PPA018: 3-O-DMT-2S—O-PPA-1-(5-benzofuran) -propane |
| Y(DTB)X(PPA032)$_4$XD(DTB)(PPA018)$_2$ | Y: symmetrical brancher |
| | DTB: desthiobiotin |
| | X: PEG3 |
| | D: PEG6 |
| | PPA032: PPA032: 1-O-DMT-3-O-PPA-2S—O-mPEG4-propane |
| | PPA018: PPA018: 3-O-DMT-2S—O-PPA-1-(5-benzofuran)-propane |
| Y(PPA032)$_{12}$(PPA018)$_2$ | Y: symmetrical brancher |
| Y(PPA029)$_{12}$(PPA018)$_2$ | PPA032: 1-O-DMT-3-O-PPA-2S—O-mPEG4-propane |
| | PPA029: 1-O-DMT-2-O-PPA-3-O-mPEG2-propane |
| | PPA018: PPA018: 3-O-DMT-2S—O-PPA-1-(5-benzofuran)-propane |
| Y(PPA032)$_4$(PPA018)$_2$W | Y: symmetrical brancher |
| Y(PPA018)$_2$W | PPA032: 1-O-DMT-3-O-PPA-2S—O-mPEG4-propane |
| | PPA018: PPA018: 3-O-DMT-2S—O-PPA-1-(5-benzofuran) -propane |
| | W: SIMA-HEX fluorophore |
| YL(Fluor)(PPA018)$_2$ | Y: symmetrical brancher |
| | L: C2 spacer |
| | Fluor: Fluorescien PPA |
| | PPA018: PPA018: 3-O-DMT-2S—O-PPA-1-(5-benzofuran)-propane |
| Y(PPA032)$_6$(Lev)(PPA032)$_4$X | Y: symmetrical brancher |
| (PPA032) | Lev: asymmetrical branching CED |
| (PPA032) | phosphoramidite |
| (PPA032) | (Chemgenes CLP-7169) |
| (PPA032) | X: PEG3 |
| (PPA018) | D: PEG6 |
| (PPA018) | PPA032: PPA032: 1-O-DMT-3-O-PPA-2S—O- |
| N | mPEG4-propane |
| Y(PPA032)$_6$(Lev)DDDX | PPA018: PPA018: 3-O-DMT-2S—O-PPA-1- |
| D | (5-benzofuran) -propane |
| D | |
| D | |
| (PPA018) | |
| (PPA018) | |
| N | |
| Y(PPA032)$_8$DD(Lev)(PPA032)$_4$X | |
| (PPA032) | |
| (PPA032) | |
| (PPA032) | |
| (PPA032) | |
| (PPA018) | |
| (PPA018) | |
| N | |
| Y(PPA032)$_8$DD(Lev)DDDX | |
| D | |
| D | |
| D | |
| (PPA018) | |
| (PPA018) | |
| N | |
| Y(PPA032)$_6$(Lev)DDD(PPA018)$_2$X | |
| D | |
| D | |
| D | |
| N | |
| Y(DTB) | Y: symmetrical brancher |
| | DTB: desthiobiotin |

Methods and Constructs to Reduce the Rate of Insertion and Deletion Events During Xpandomer Translocation In other aspects, the present invention provides means of translocation control through Xpandomer modification in combination with discrete translocation deceleration features (referred to herein also as "D-cells") designed into the SSRT. As disclosed herein, Xpandomers are subjected to several processing steps following synthesis, including an amine modification step. During amine modification, Xpandomers are treated with succinic anhydride, which reacts with the secondary amine groups (and, in certain circumstances, the primary amine group introduced by the acid cleavage step) on the spermine constituents of the polymerase enhancement regions of the SSRT. Succinylation of an amine group results in the introduction of a negatively charged hemi-succinate group. By increasing the degree of succinylation, the degree of negative charge on the spermine-based enhancers is likewise increased. Each spermine phosphoramidite constituent has a net charge of (+3); in a standard modification reaction, the charge of each individual amine moiety is changed from (+1) to (−1). The inventors have discovered conditions that give varying degrees of spermine succinylation such that the net charge of a spermine constituent can be changed from between (+3) to (−5). Under certain conditions, increasing the negative charge of the enhancer regions may be desirable so as to increase the rate of Xpandomer translocation upon application of a voltage pulse (referred to herein as an enhancer electromobility. Notably, this electromobility has been found to reduce the percentage of insertion errors during the sequence read as well as to increase overall sequencing throughput.

Thus, in certain embodiments, Xpandomer processing includes an amine modification step. Amine (e.g., spermine) modification may be achieved through altering one or more of the succinylation reaction conditions, e.g., the reaction time, temperature, pH, and/or the concentration of succinic anhydride used in the reaction. In other embodiments, Xpandomer processing further includes one or more of a HEPES wash step following the amine modification step in order to achieve more complete amine succinlyation.

In another aspect, the present disclosure provides one or more translocation deceleration features or regions (the terms "features" and "regions" are used interchangeably in this context), which are permanently charged, e.g., tertiary or quarternary amines and/or bulky compounds. Translocation deceleration features may be introduced into the SSRT at a position within or adjacent to the polymerase enhancers. The deceleration features are selected so as not to be altered during the Xpandomer modification (e.g., succinylation) reaction. Inclusion of one or more deceleration features into a suitable location in the SSRT has been found to reduce the percentage of deletion errors, which arise due to the increased translocation rate resulting from over-modification of the enhancer. Without being bound by theory, it is speculated that the bulk of the deceleration feature creates a "friction"-type of force that reduces the rate of Xpandomer translocation upon encountering the nanopore aperture. Typically, the deceleration features are introduced into the SSRT at a position between the polymerase enhancer and the reporter code (i.e., adjacent to the enhancer).

The translocation deceleration features of the present invention may incorporate any suitable number and combination of the phosphoramidite compounds set forth in Tables 1A-1C or commercially available phosphoramidites. In some embodiments, the deceleration features include a combination of from 1 to 4 different monomeric units. In other embodiments, the deceleration features may include 1 or 2 different monomeric units. The entire length of a deceleration feature may be from 1 to 15 monomeric units or, in other embodiments, from 4 to 12 or from 6 to 10 monomeric units. Table 3 sets forth non-limiting examples of alternative translocation deceleration features. The key in Table 3 identifies the compounds in their form as phosphoramidite monomers. It will be readily apparent to one of ordinary skill in the art that the descriptor "phosphoramidite" only applies to the compounds in monomeric form; descriptors that apply to the compounds in multimeric, "in-line", form are set forth in Table 1A.

TABLE 3

Exemplary Translocation Deceleration Features

| D-cell sequence | Key |
|---|---|
| $(PPA058)_6$ | PPA058: 2-((4-((3-(benzoyloxy)-2-(((1-(3-(benzoyloxy)-2-((benzoyloxy)methyl)-2-((PPA-oxy)methyl)propyl)-1H-1,2,3-triazol-4-yl)methoxy)methyl)-2-((benzoyloxy)methyl)propoxy)methyl)-1H-1,2,3-triazol-1-yl)methyl)-2-O-DMT-propane-1,3-diyl dibenzoate |
| $[D(PPA056)]_3DD$ | D: PEG6<br>PPA056: 1-O-DMT-3-O-PPA-2,2-bis(1-Me-4-(Me—O-PEG2-O-Bz)-1,2,3-triazole)-propane |
| D(PPA060)D(PPA060)DDDD | D: PEG6<br>PPA060: 1-O-DMT-2-O-PPA-3-(4-(Me—O-PEG3-O-Bz)-1-(1,2,3-triazole))-propane |
| $[D(PPA063)]_3DD$<br>$[D(PPA063)]_4DD$ | D: PEG6<br>PPA063: 1-O-DMT-3-O-PPA-2-(4-(Me—O-PEG5)-1-(Et—O—Ac)-1,2,3-triazole)-propane |
| $[D(PPA064)]_3DD$<br>$[D(PPA064)]_4DD$ | D: PEG6<br>PPA064: 1-O-DMT-3-O-PPA-2S—O-(4-(Me—O-PEG7)-1-(Et—OBz)-1,2,3-triazole)-propane |
| $[D(PPA068)]_4DD$ | D: PEG6<br>PPA068: 1-O-DMT-3-O-PPA-2S—O-(4-(Me—O-PEG3)-1-(Et-2,2,2-Tris-(Me—O-Bz))-1,2,3-triazole)-propane |
| $[D(PPA069)]_3DD$ | D: PEG6<br>PPA069: 1-O-DMT-3-O-PPA-2,2-bis(4-(Me—O-PEG2-O—Me)-1-(Et—O-Bz)-1,2,3-triazole)-propane |

TABLE 3-continued

Exemplary Translocation Deceleration Features

| D-cell sequence | Key |
|---|---|
| $[D(PPA078)]_3DD$ | D: PEG6<br>PPA078: 1-O-DMT-3-O-PPA-2,2-bis(4-(Me—O-PEG3-O—Me)-1-(Et-2,2,2-Tris-(Me-O-Bz))-1,2,3-triazole)-propane |
| $[D(PPA63)]_3DD$ | D: PEG6<br>PPA063: 1-O-DMT-3-O-PPA-2-(4-(Me—O-PEG5)-1-(Et—O—Ac)-1,2,3-triazole)-propane |
| $[D(PPA093)]_4DD$ | D: PEG6<br>PPA093: 1-O-DMT-3-O-PPA-2-(4-(Me—O-PEG5)-1-(Et-2,2,2-Tris-(Me—O—Ac))-1,2,3-triazole)-propane |
| $[D(PPA094)]_3DD$ | D: PEG6<br>PPA094: 1-O-DMT-3-O-PPA-2-(4-(Me—O-PEG7)-1-(Et-2,2,2-Tris-(Me—O—Ac))-1,2,3-triazole)-propane |
| $DDD(PPA063)_3DD$ | D: PEG6<br>PPA063: 1-O-DMT-3-O-PPA-2-(4-(Me—O-PEG5)-1-(Et—O—Ac)-1,2,3-triazole)-propane |
| D(PPA043)(PPA043)DDDDDD<br>$D(PPA043)_2D(PPA043)_2DDDDD$ | D: PEG6<br>PPA043: 1-O-DMT-2S—O-PPA-3-(4-methylpiperazine-1-yl)-propane |
| $(PPA109)(PPA043)_2W(PPA043)_2WDD$ | D: PEG6<br>PPA043: 1-O-DMT-2S—O-PPA-3-(4-methylpiperazine-1-yl)-propane<br>PPA109:in-line PEG12 |
| DD(PPA033)D(PPA033)D(PPA033)DD<br>$DD(PPA033)_2D(PPA033)_2D(PPA033)_2DD$ | D: PEG6<br>PPA033: 1-O-DMT-3-O-PPA-2S—O-mPEG8-propane |
| $[D(PPA075)]_3DD$ | D: PEG6<br>PPA075: 1-O-DMT-3-O-PPA-2,2-bis(4-(Me—O-PEG3-O—Me)-1-(Et—O-Bz)-1,2,3-triazole)-propane |
| DD(PPA001)D(PPA001)DDD | D: PEG6<br>PPA001: 1 -O-DMT-1'-O-PPA-N(p-tolyl)-diethanolamine |

Reporter Codes

Each SSRT uses the TCE to position the reporter code within a zone of the nanopore that has high ion current resistance. In alpha hemolysin, this zone is the stem. In this zone, different reporters are sized to block ion flow at different measurable levels. Reporters can be designed by selecting a sequence of specific phosphoramidites from the collection of phosphoramidite monomeric compounds set for in Tables 1A-1C and/or commercially available libraries. Suitable monomeric compounds are also disclosed in Applicants' U.S. Pat. No. 10,457,979, which is herein incorporated by reference in its entirety, including PEG3, PEG6, and C2.

Each constituent monomeric compound contributes to the net current resistance according to its position in the nanopore, its displacement, its charge, its interaction with the nanopore, its chemical and thermal environment and other factors.

Reporter code design is guided by balancing measurement characteristics including: (i) normalized ion current ($I/I_o$): where I is ion current and $I_o$ is the open channel current; (ii) ion current noise: includes multi-state responses, blockages, random spiking, and the like; and/or (iii) release time of the control moiety or the time during which the TCE is otherwise is stalled at the stem entrance.

Figures 5A, 5B, 5C, 5D:
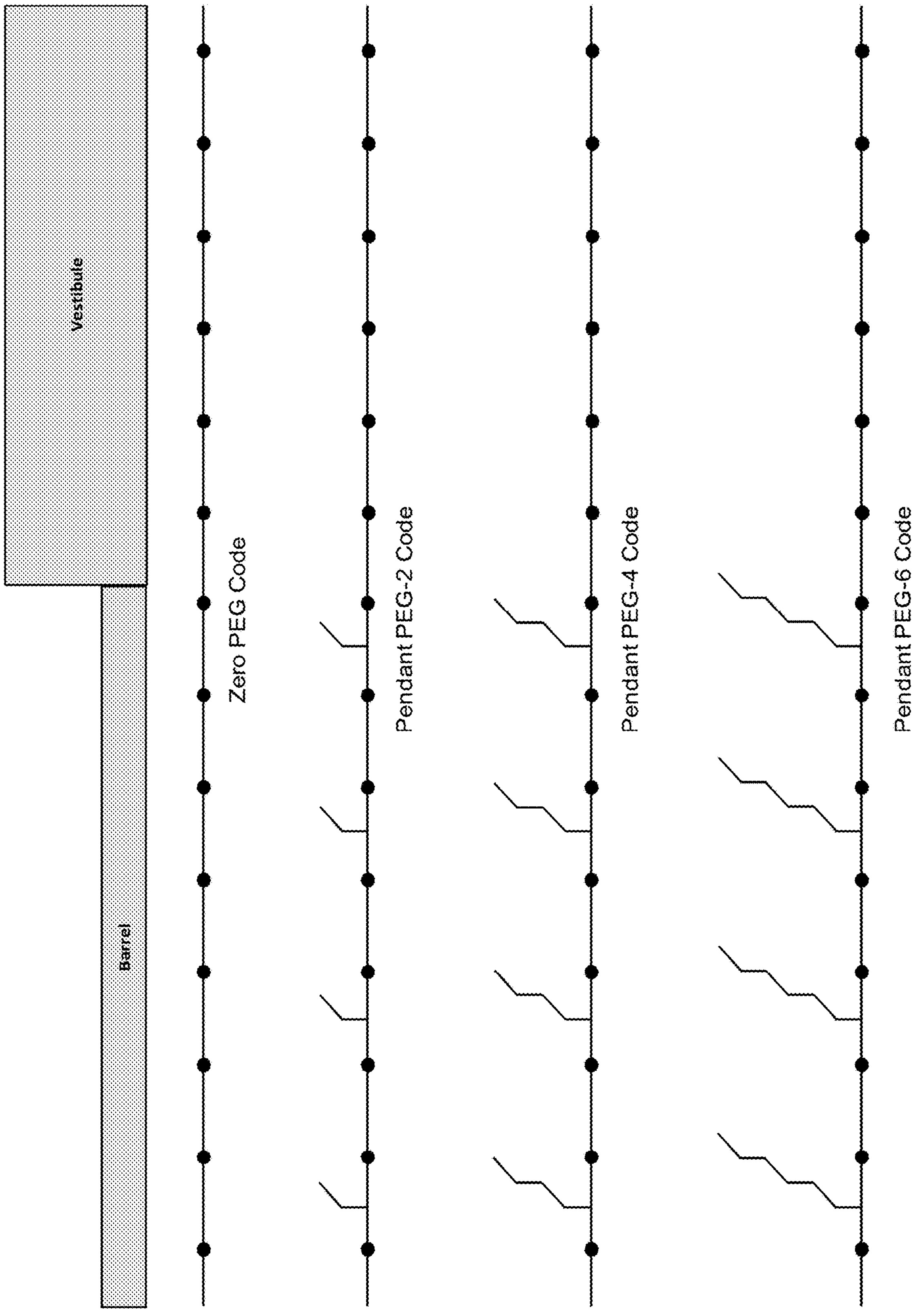
FIGS. 5A-5D are schematics illustrating alternative embodiments of reporter codes.

FIGS. 5A-5D illustrate how different reporter codes can be designed to maintain similar charge densities along the backbone, while providing signature levels of pore blockage due to differential volumes occupied by each unique monomeric constituent. In these illustrations, a nanopore is depicted in cross-section with the barrel and vestibule portions indicated. The reporter codes are depicted in simplified form with the black circles representing the charged phosphodiester moieties introduced by the phosphoramidite constituents of the codes. FIG. 5A illustrates a linear code, in this embodiment identified a "zero PEG code", although the invention is not intended to be so limited, e.g., in certain embodiments linear codes may include PEG moieties. FIGS. 5B, 5C, and 5D illustrate how unique codes can be constructed from repeating units of a single branched monomeric compound showing exemplary PEG-based structures, e.g., a pendant PEG compound. In these embodiments, the branched-moieties of the three different codes occupy different volumes in the pore channel and thus generate unique signals that can be differentiated from each other. In these embodiments, the charge density along the backbone is the same for each reporter code. However, as discussed further herein, in other embodiments, reporter codes can be designed with a gradient of charge density along the backbone.

Reporter ion current blockage and its duplex release time is also modulated by measurement conditions such as: (i) voltage; (ii) electrolyte; (iii) temperature; (iv) pressure; and/or (v) pH, as described further herein.

In some embodiments, the TCE associated with the reporter also contributes to the ion current blockage.

For a given set of measurement conditions reporters can be designed for a minimum and maximum I/Io levels that define the measurement dynamic range. Other reporters can be designed with different I/Io levels within the dynamic range. As each reporter is paused in the nanopore, the measured I/Io level must remain stationary long enough and have low enough noise that the reporter type can be uniquely distinguished. Dynamic range is maximized by selecting a backbone of low impedance molecules (reporter code polymers), typically those with small physical cross-sections and low linear mass densities.

Table 4 sets forth exemplary reporter codes, though It is to be understood that the present invention contemplates reporter codes incorporating any suitable combination and number of phosphoramidite compounds disclosed herein. The key in Table 4 identifies the compounds in their form as phosphoramidite monomers. It will be readily apparent to one of ordinary skill in the art that the descriptor "phosphoramidite" only applies to the compounds in monomeric form; descriptors that apply to the compounds in multimeric, "in-line", form are set forth in Table 1A.

TABLE 4

| Exemplary Reporter Codes | |
|---|---|
| Code Sequence | Key |
| XXXXXX | X: Triethyleneglycol (PEG3) |
| DDDD | D: Hexaethyleneglycol (PEG6) |
| LLLLLLLLLLLL | L: ethane (C2) |
| WW | W: Dodecaethyleneglycol (PEG12) |
| DDDDDLLLL | D: PEG6<br>L: C2 |
| XXXXLLLL | X: PEG3<br>L: C2 |
| DDLLLDX | D: PEG6<br>X: PEG3<br>L: C2 |
| DDLLLLLXX | D: PEG6<br>L: C2 |
| DDLLLLLLLDX | D: PEG6<br>X: PEG3<br>L: C2 |
| DD(PPA032)(PPA032)LDX | D: PEG6<br>X: PEG3<br>L: C2<br>PPA032: 1-O-DMT-3-O-PPA-2S—O-mPEG4-propane |
| DD(PPA032)LL(PPA032) DX | D: PEG6<br>X: PEG3<br>L: C2<br>PPA032: 1-O-DMT-3-O-PPA-2S—O-mPEG4-propane |
| DD(PPA032)(PPA032)LXXX | D: PEG6<br>X: PEG3<br>L: C2<br>PPA032: 1-O-DMT-3-O-PPA-2S—O-mPEG4-propane |
| DXLLL(PPA032)(PPA032)LXXX | D: PEG6<br>X: PEG3<br>L: C2<br>PPA032: 1-O-DMT-3-O-PPA-2S—O-mPEG4-propane |
| DD((PPA040)(PPA040)LXXX | D: PEG6<br>X: PEG3<br>L: C2<br>PPA040: 1-O-DMT-3-O-PPA-2,2-bis(Me—O-mPEG2)-propane |
| DD(PPA050)(PPA050)LXXX | D: PEG6<br>X: PEG3<br>L: C2<br>PPA050: 1-O-DMT-3-O-PPA-2S—O-(PEG4-O-Bz)-propane |
| DD(PPA061)(PPA061)LXXX | D: PEG6<br>X: PEG3<br>L: C2<br>PPA061: 1-O-DMT-3-O-PPA-2-(4-Me—O-PEG3)-1-(Et—O—Ac)-1,2,3-triazole)-propane |
| DD(PPA032)$_3$LLDX | D: PEG6<br>X: PEG3<br>L: C2<br>PPA032: 1-O-DMT-3-O-PPA-2S—O-mPEG4-propane |
| DD(PPA040)$_3$LLDX | D: PEG6<br>X: PEG3<br>L: C2<br>PPA040: 1-O-DMT-3-O-PPA-2,2-bis(Me—O-mPEG2)-propane |

TABLE 4-continued

| Exemplary Reporter Codes | |
|---|---|
| Code Sequence | Key |
| DD(PPA032)$_3$XXLLLL | D: PEG6<br>X: PEG3<br>L: C2<br>PPA032: 1-O-DMT-3-O-PPA-2S—O-mPEG4-propane |
| DD(PPA032)$_3$LLLLLLLL | D: PEG6<br>L: C2<br>PPA032: 1-O-DMT-3-O-PPA-2S—O-mPEG4-propane |
| DD(PPA050)$_3$LLDX | D: PEG6<br>X: PEG3<br>L: C2<br>PPA050: 1-O-DMT-3-O-PPA-2S—O-(PEG4-O-Bz)-propane |
| DD(PPA061)$_3$LLDX | D: PEG6<br>X: PEG3<br>L: C2<br>PPA061: 1-O-DMT-3-O-PPA-2-(4-Me—O-PEG3)-1-(Et—O—Ac)-1,2,3-triazole)-propane |
| [X(PPA032)]$_4$X | X: PEG3<br>PPA032: 1-O-DMT-3-O-PPA-2S—O-mPEG4-propane |
| DDLL(PPA031)X(PPA031)X(PPA031)L | D: PEG6<br>X: PEG3<br>L: C2<br>PPA031: 1-O-DMT-3-O-PPA-2S—O-mPEG6-propane |
| DDLL(PPA033)X(PPA033)X(PPA033)L | D: PEG6<br>X: PEG3<br>L: C2<br>PPA033: 1-O-DMT-3-O-PPA-2S—O-mPEG8-propane |
| XXL(PPA032)$_6$LLLLLLL | X: PEG3<br>L: C2<br>PPA032: 1-O-DMT-3-O-PPA-2S—O-mPEG4-propane |
| XXL(PPA032)$_6$XXL | X: PEG3<br>L: C2<br>PPA032: 1-O-DMT-3-O-PPA-2S—O-mPEG4-propane |
| XXL(PPA050)$_6$LLLLLLL | X: PEG3<br>L: C2<br>PPA050: 1-O-DMT-3-O-PPA-2S—O-(PEG4-O-Bz)-propane |
| XXL(PPA061)$_6$LLLLLLL | X: PEG3<br>L: C2<br>PPA061: 1-O-DMT-3-O-PPA-2-(4-Me—O-PEG3)-1-(Et—O—Ac)-1,2,3-triazole)-propane |
| XXL(PPA040)$_6$XLLLL | X: PEG3<br>L: C2<br>PPA040: 1-O-DMT-3-O-PPA-2,2-bis(Me—O-mPEG2)-propane |
| XXL(PPA068)$_6$LLLLLLL | X: PEG3<br>L: C2<br>PPA068: 1-O-DMT-3-O-PPA-2S—O-(4-(Me—O-PEG3)-1-(Et-2,2,2-Tris-(Me—O-Bz))-1,2,3-triazole)-propane |
| XXL(PPA065)$_6$LLLLLLL | X: PEG3<br>L: C2<br>PA065: 1-O-DMT-3-O-PPA-2S—O-(4-(Me—O-PEG3)-1-(Me-acetate)-1,2,3-triazole)-propane |
| XXL[(PPA050)(PPA061)]$_3$LLLLLLL | X: PEG3<br>L: C2<br>50: hydroxyl (Bz) pendant PEG4 (PPA050)<br>PPA061: 1-O-DMT-3-O-PPA-2-(4-Me—O-PEG3)-1-(Et—O—Ac)-1,2,3-triazole)-propane |
| XXL(PPA062)$_6$LLLLLLL | X: PEG3<br>L: C2<br>PPA062: 1-O-DMT-3-O-PPA-2S—O-(4-(Me—O-PEG2)-1-(Et—OBz)-1,2,3-triazole)-propane |

TABLE 4-continued

| Exemplary Reporter Codes | |
|---|---|
| Code Sequence | Key |
| XX(PPA061)$_5$xllllll | X: PEG3<br>L: C2<br>PPA061: 1-O-DMT-3-O-PPA-2-(4-Me—O-PEG3)-1-(Et—O—Ac)-1,2,3-triazole)-propane |
| XXX(PPA026)LL(PPA026)XXLL | D: PEG6<br>X: PEG3<br>L: C2<br>PPA026: 1-O-DMT-3-O-PPA-2-(4-Et-1-(Et—O-mPEGl)-1,2,3-triazole)-propane |
| XXL(PPA007)$_4$LLXXLL | X: PEG3<br>L: C2<br>PPA007: 3-O-DMT-2S—O-PPA-1-(1 dimethoxyquinazolinedione)- propane |
| XXL(PPA010)$_4$LLXXLL | X: PEG3<br>L: C2<br>PPA010: 3-O-DMT-2S—O-PPA-1-(N9-(3,6-dimethoxycarbazole)-propane |
| (PPA004)$_4$LLLL | L: C2<br>PPA004: 1-O-DMT-1'-O-PPA-2,2'-(sulfonylbis(benz-4-yl))-diethanol |
| XXL(PPA005)$_4$LLXXLL | X: PEG3<br>L: C2<br>PPA005: 1-O-DMT-1'-O-PPA-(2,2'-bipyridin-4,4'-yl)-dimethanol |
| XXL(PPA006)$_4$LLXXLL | X: PEG3<br>L: C2<br>PPA006: 3-O-DMT-2S—O-PPA-1-(N1-(4,6-dimethoxy-3-Me-indole)-propane |
| XXL(PPA009)$_4$LLXXLL | X: PEG3<br>L: C2<br>PPA009: 3-(1-O-DMT-2S—O-PPA-propyl)-8,8-dimethylhexahydro-3 H-3a,6-methanobenzo[c]isothiazole 2,2-dioxide |
| XXL(PPA012)$_4$LLXXLL | X: PEG3<br>L: C2<br>PPA012: 3-O-DMT-2S—O-PPA-1-(N1-(6-Azathymine))-propane |
| XXL(PPA014)$_4$LLXXLL | X: PEG3<br>L: C2<br>PPA014: 1-O-DMT-5-O-PPA-hexahydrofuro[2,6]furan |
| XXL(PPA008)$_4$LLXXLL | X: PEG3<br>L: C2<br>PPA008: 1-O-DMT-1'-O-PPA-(octahydro-2,6-dimethyl-3,8:4,7-dimethano-2,6-naphthyridin-4,8 -diyl)-dimethanol |
| XXL(PPA015)$_4$LLXXLL | X: PEG3<br>L: C2<br>PPA015: 3-O-DMT-2S—O-PPA-1-(N1-(2-Me-5-nitroindole)-propane |
| XXL(PPA013)$_4$LLXXLL | X: PEG3<br>L: C2<br>PPA013: 3-O-DMT-2S—O-PPA-1-(N1-(2-Me-5-nitroindole)-propane |
| XXL(PPA018)$_4$LLXXLL | X: PEG3<br>L: C2<br>PPA018: 3-O-DMT-2S—O-PPA-1-(5-benzofuran)-propane |
| XXL(PPA023)$_4$LLXXLL | X: PEG3<br>L: C2<br>PPA023: 1-O-DMT-2-O-PPA-3-O-mPEG4-propane |
| XXL(PPA026)$_4$LLXXLL | X: PEG3<br>L: C2<br>PPA026: 1-O-DMT-3-O-PPA-2-(4-Et-1-(Et—O-mPEG1)-1,2,3-triazole)-propane |
| XXL(PPA024)$_4$LLXXLL | X: PEG3<br>L: C2<br>PPA024: 1-O-DMT-2S—O-PPA-3-O-(acetoxamido-15-crown-6)-propane |
| XLL(PPA040)$_2$XXXLLLL | X: PEG3<br>L: C2<br>PPA040: 1-O-DMT-3-O-PPA-2,2-bis(Me—O-mPEG2)-propane |

TABLE 4-continued

| Exemplary Reporter Codes | |
|---|---|
| Code Sequence | Key |
| XLL(PPA027)$_2$XXXLLLL | X: PEG3<br>L: C2<br>PPA027: 1-O-DMT-3-O-PPA-2-(4-Et-1-(Et—O-mPEG3)-1,2,3-triazole)-propane |
| XLL(PPA022)$_2$XXXLLLL | X: PEG3<br>L: C2<br>PPA022: 1-O-DMT-2-O-PPA-3-O-mPEG2-propane |
| XX(PPA022)X(PPA022)X(PPA022)X | X: PEG3<br>L: C2<br>PPA022: 1-O-DMT-2-O-PPA-3-O-mPEG2-propane |

Synthesis of SSRTs and XNTPs

Figure 6:
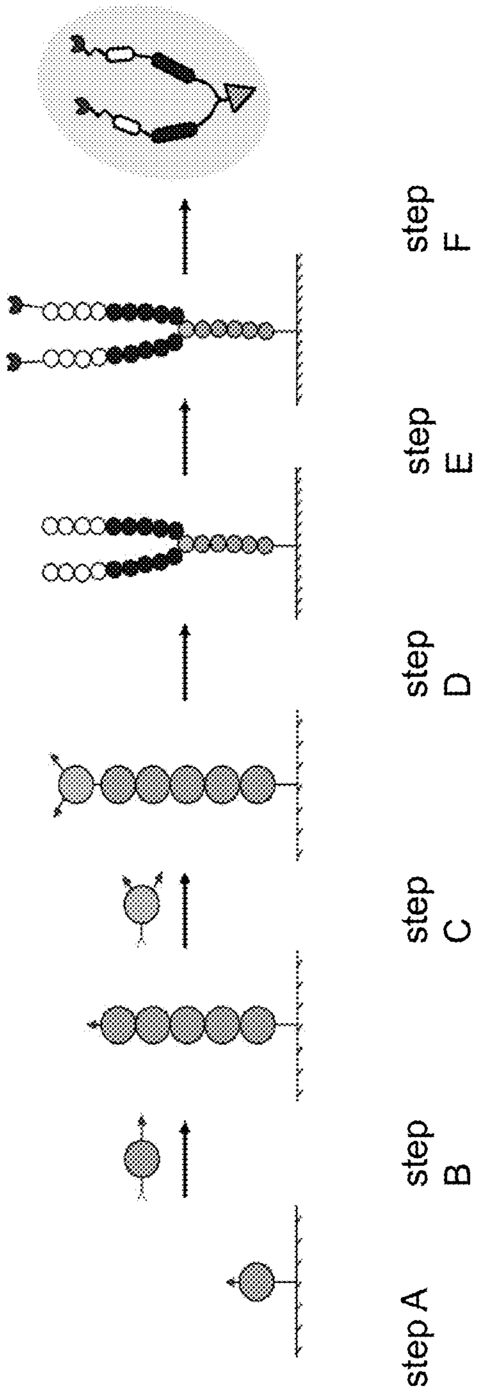
FIG. 6 is a schematic illustrating one embodiment of solid state synthesis of a SSRT reporter construct.

As disclosed herein, symmetrically synthesized reporter tethers (SSRTs) are synthesized using standard automated oligonucleotide synthesis protocols. FIG. 6 illustrates SSRT synthesis in simplified form. In step A, a phosphoramidite is immobilized on a solid support; in step B, phosphoramidite coupling is used to polymerize phosphoramidite monomers on the support; in step C, a symmetric brancher is adding to the growing SSRT structure; in step D, symmetric phosphoramidite branches are polymerized off each arm of the symmetric brancher; in step E, a terminal azido group is added that enables conjugation of the SSRT to a dNTP-2c via a click reaction; in step F, the SSRT is released from the substrate in its final form.

In one embodiment, SSRT synthesis utilizes a four-step iterative process that includes 1) synthesis of SSRT polymers on solid support controlled pore glass beads (reflected in the cartoons of steps A-D). In this step, SSRTs are synthesized one reporter construct at a time at a 1 μM scale using a MerMade™ 12 Synthesizer (commercially available from BioAutomation). The MerMade™ sequence manager is first prepared followed by preparation of the phosphoramidites (e.g., preparation of 0.067M solution of each phosphoramidite). Suitable coupling times for each phosphoramidite are programmed into the synthesizer. The SSRT synthesis cycle is based on a conventional four step process: detritylation (using a solvent of, e.g., 3% DCA in dichloromethane), monomer coupling (using a solvent of, e.g., 0.25M ETT in acetonitrile), capping (using solvents of, e.g., THF/lutidine/Ac2O (CAP A) and 16% methylimidazole in THF (CAP B)), and oxidation (using a solvent of, e.g., 0.02M I2 in THF/pyridine/$H_2O$). Step 2) functionalization of the 5' end with a manual conversion that displaces the Br with azide (reflected in the cartoon of step E), i.e. "azido modification". In this step, the synthesis column is washed with 1 mL DCM and transferred to a 2 mL tube; an azide conversion solution is prepared (100 mM sodium iodide and 100 mM sodium azide in DMF) and 1.6 mL is added to the tube and incubated for 2 hrs. at RT; the support is then rinsed with 1 mL DMF and transferred to the column; the column is rinsed with 2 mL DMF followed by 3 mL ACN and 1 mL DCM. Step 3) removal of cyanoethyl protection groups. In this step, a 10% DEA solution is prepared in ACN that may include 0.1M nitromethanse; with vacuum, a steady stream of this solution is passed through the column for at least 10'; the column is then rinsed with 2 mL ACN followed by 1 mL DCM. Step 4) cleavage complete deprotection of the SSRT from the solid support (reflected in the cartoon of step F). In this step, the support is transferred to a 2 ml tube and 500 μL of 30% $NH_4OH$ that may include 100 mM nitromethane is added to the tube and incubated for 30' at 55° C.; the tube is then chilled for 5' in a freezer; 500 μL of 40% methylamine is added to the tube and incubated for 1 hr at 65° C. The sample is then chilled for 5' in a freezer; the sample is then desalted by draining the column and rinsing with 15 mL $H_2O$; the SSRT is then eluted from the column with 100 mM TEAA and quantitated.

Figure 7:
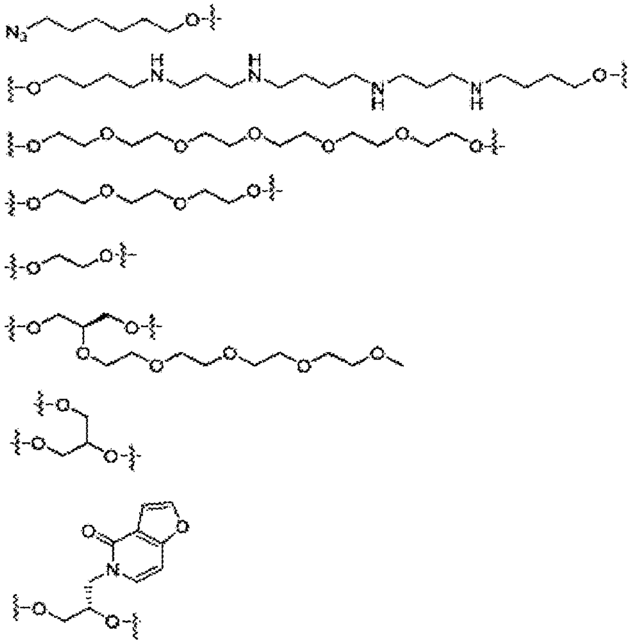
FIG. 7 illustrates alternative structural embodiments of SSRT reporter constructs.

FIG. 7 illustrates four exemplary SSRT products that can be used as reporter constructs for the formation of XATP, XCTP, XGTP, and XTTP, each of which is designed to generate a unique electronic signal when passed through a nanopore. The key illustrates the chemical structures of these particular phosphoramidite as they exist in the final SSRT reporter construct. As used throughout the present disclosure, R represents azido hex, Q represents spermine, D represents PEG6, X represents PEG3, L represents C2 spacer, 4 represents pendant PEG 4, Y represents the symmetric chemical brancher, and 5 represents benzofuran. In this embodiment, R provides the azide conjugation feature, the QQ polymer provides the enhancer feature, the Y444444444444 polymer provides the TCE feature, and the DDLLLDX, DDD44LXXX, DDD4444LLDX, and XXL444444LLLLLLL polymers provide the four unique reporter code features.

Figure 8A:
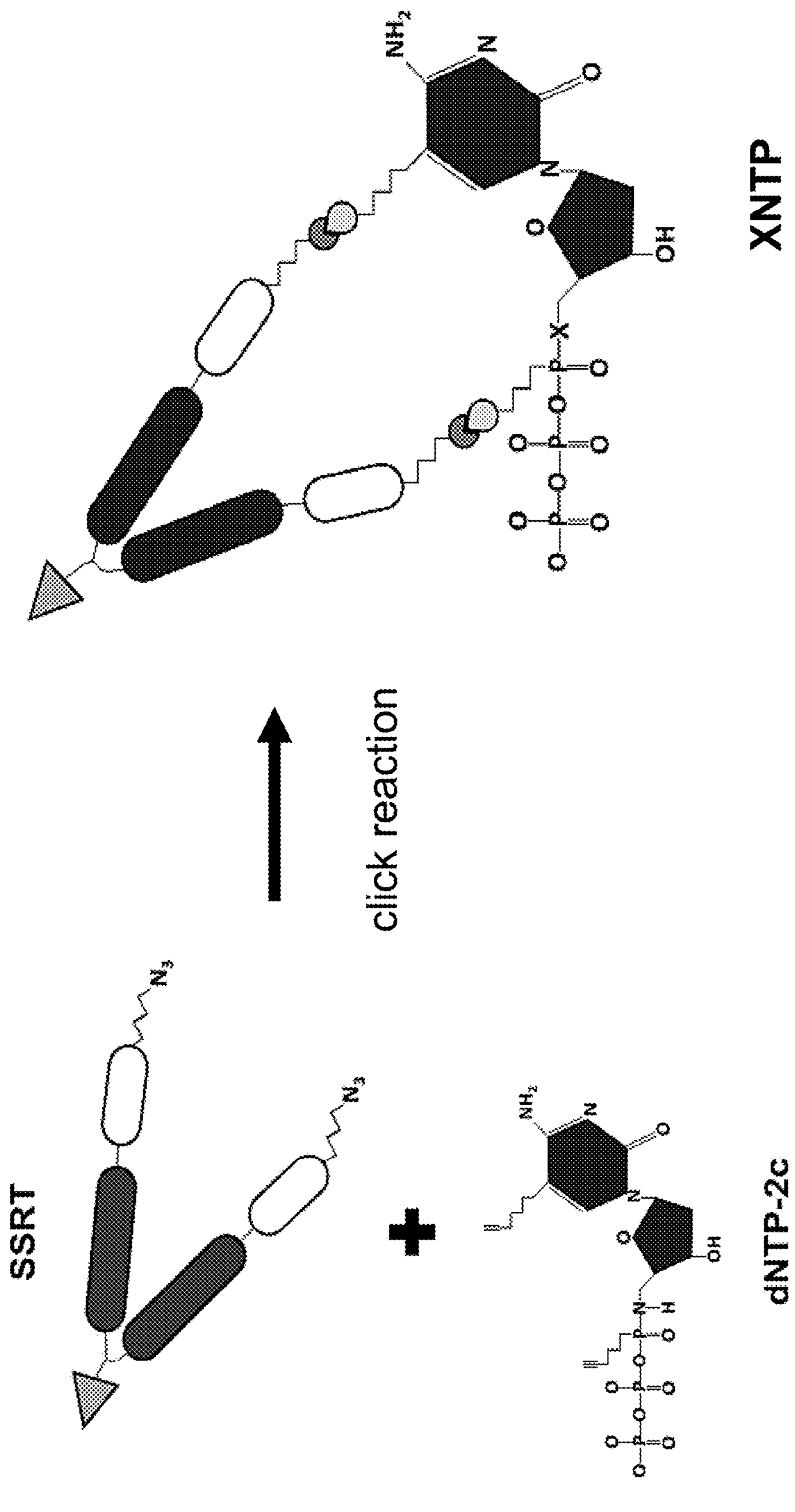
FIGS. 8A and 8B are schematics illustrating one embodiment of the cyclization of an SSRT and a dNTP-2*c* to form an XNTP.
Figure 8B:
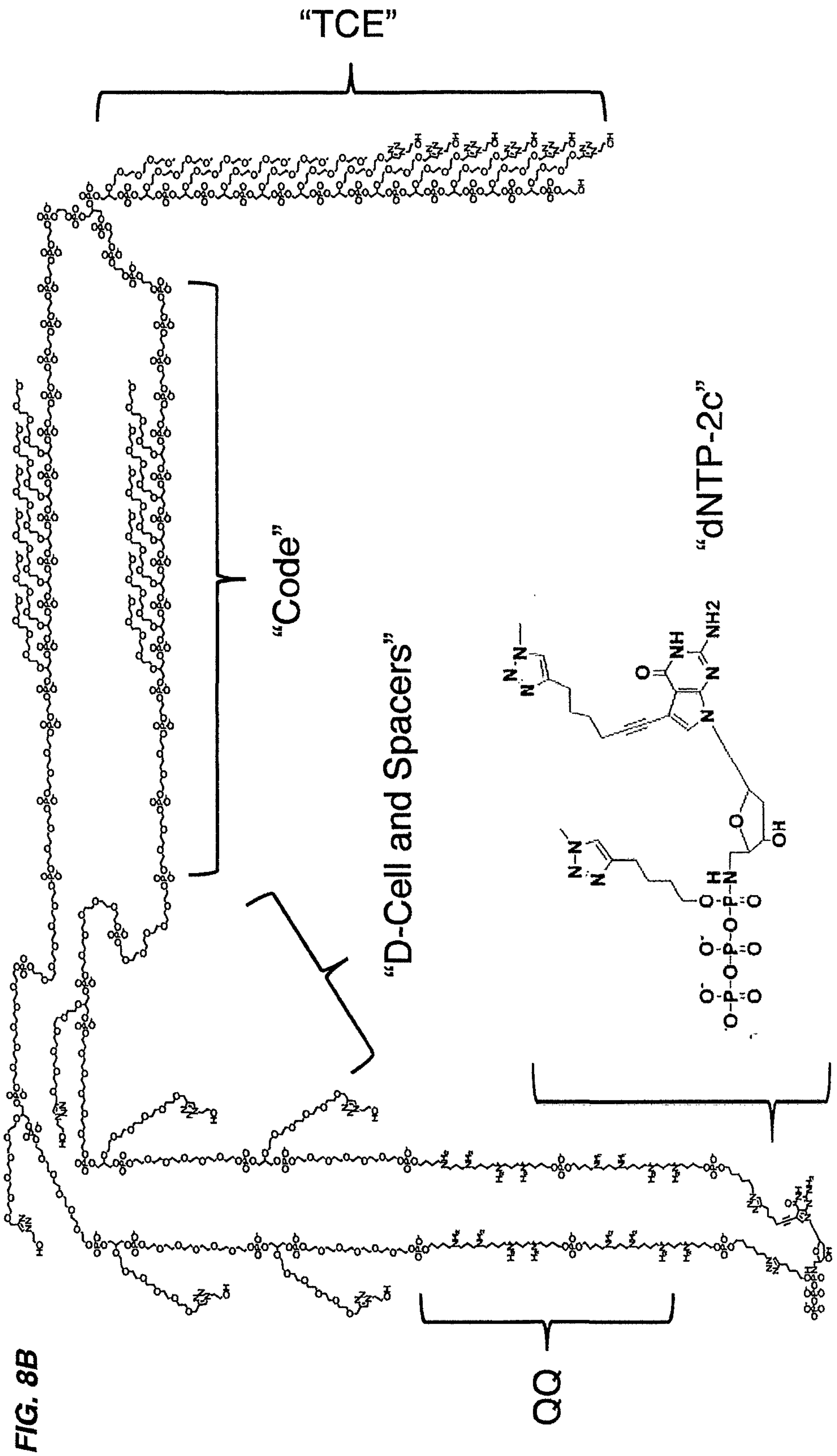

FIG. 8A summarizes formation of an exemplary XNTP via the cyclization of an SSRT and a dNTP-2c, via a copper catalyzed click reaction. As used throughout the present disclosure, a "dNTP-2c" refers to a cleavable nucleoside triphosphoramidate analog that includes an 1,7-octadiynyl linker conjugated to the heterocycle moiety of the nucleoside and a 5-hexynyl linker conjugated to the alpha phosphoramidate moiety of the triphosphoramidate. This is a three-step process that includes: 1) the click reaction; in one embodiment, the SSRT and dNTP-2c are added to a click reaction solution composed of 0.2 mM $CuSO_4$/0.6 mM THPTA/1.2 mM NaAsc and incubated for 30'; 2) standard HPLC purification; and 3) desalting using art-recognized methodologies. Further details of the structure and synthesis of the dNTP-2c compounds is disclosed in Applicants' issued U.S. Pat. No. 10,301,345, which is herein incorporated by reference in its entirety. FIG. 8B illustrates an exemplary XNTP in a detailed chemical structure.

In certain embodiments, the nucleobase of the XNTP may be a non-natural analog, e.g., 7-deazaadenine, 7-deazaguanine, and the like.

Additional Means of Translocation Control

Figures 9A, 9B:
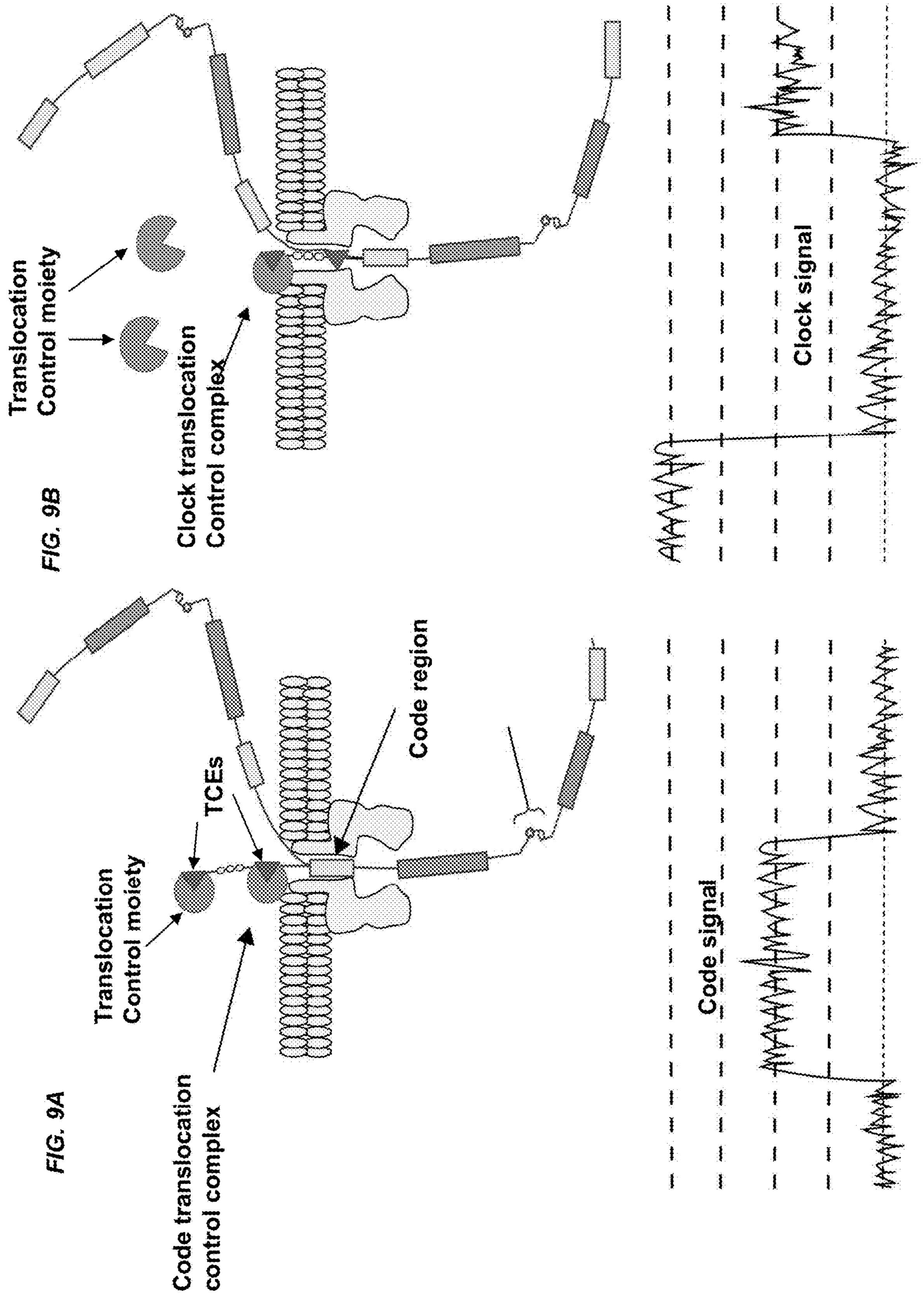
FIGS. 9A and 9B are schematics illustrating one embodiment of translocation control of an Xpandomer through a nanopore.

I. Translocation Control by Reversible Binding of Translocation Control Moieties This embodiment of translocation control is illustrated in simplified form in FIGS. 9A and 9B. In this embodiment, the rate of translocation is controlled by the binding and dissociation of soluble translocation binding moieties to the TCEs of the Xpandomer. As shown in FIG. 9A, binding of a first soluble translocation binding moiety to the first TCE element, proximal to a first reporter code of the Xpandomer, forms a "code translocation control complex". This reversible interaction stalls, pauses, or arrests (for simplicity, these terms are used interchangeably herein) the first reporter code in the nanopore and generates a change in current that is unique to the first code. These code signals are used to identify each monomeric unit of the Xpandomer. Subsequently, as depicted in FIG. 9B, the first translocation binding moiety dissociates from the first TCE, allowing the first reporter code to pass through, i.e. exit, the nanopore on the opposite side from which it entered the pore. This translocation event is then stalled by the binding of a second translocation binding moiety to the second TCE in the Xpandomer, distal to the first reporter code. This second translocation control complex is referred to herein as the "clock translocation control complex". This interruption of translocation generates a change in current (i.e. a "clock signal") signaling complete translocation of the first code region through the nanopore. In certain embodiments, the clock signals of each unit of the Xpandomer may be identical, or nearly indistinguishable, from each other. One of skill in the art will appreciate that the code signals are sufficient in themselves to determine sequence information of the Xpandomer.

Figure 10:
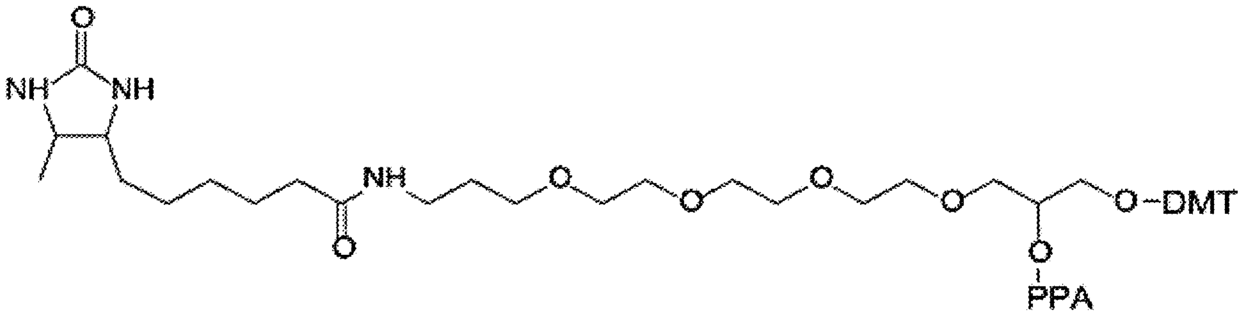
FIG. 10 is a schematic illustrating one embodiment of a biotin derivative.

Any suitable set of reversible binding partners may be used for translocation control according to the present invention. In one embodiment, the TCEs include a derivative of biotin, while the translocation control moiety is provided by streptavidin. In this embodiment, the biotin derivative may be engineered to bind streptavidin with lower affinity than natural biotin. One example of a suitable biotin derivative is desthiobiotin (DTB), which is depicted in FIG. 10. In other embodiments, the biotin-SA TCE system can be controlled by, e.g., using other biotin analogs that form weaker biotin-SA complexes, and/or using SA mutants that form weaker complexes.

II. Translocation Control Through Tuning of Run Conditions

It has been found that fine tuning of various conditions used in the nanopore-based detection system improves Xpandomer translocation control and the accuracy of code reads. Thus, in other aspects, the present disclosure provides means to improve the rate of polymer translocation through a nanopore by modification of one or more of the following run conditions:

A. Voltage Parameters

The flow of ions from the cis chamber to the trans chamber of the nanopore-based detection systems described herein results from the application of a voltage potential across the membrane that is referred to interchangeably as the "read voltage" or "baseline voltage". In one embodiment of the present invention, Xpandomer translocation rate is modulated by altering the baseline voltage. In some embodiments, the baseline voltage may be in the range of from about 40 mV to about 150 mV. In other embodiments, the baseline voltage may be in the range of from about 90 mV to about 110 mV. In yet other embodiments, the baseline voltage may be in the range of from about 55 mV to about 75 mV. In some embodiments, a higher baseline voltage may be desired to capture reporter code reads at a higher rate.

As discussed herein, Xpandomer translocation is arrested when the TCE proximal to a reporter code encounters the aperture of the pore. The reporter code is maintained in the pore until a voltage pulse is applied that is sufficiently strong to overcome the resistance provided by TCE structure held at the pore. Thus, in another embodiment, Xpandomer translocation rate is modulated by altering the strength of the pulse voltage. In some embodiments, the pulse voltage is in the range of from about 250 mV to about 2000 mV. In other embodiments, the pulse voltage is in the range of from about 550 mV to about 700 mV. Likewise, the duration of the voltage pulse can influence the rate of Xpandomer translocation. In some embodiments, the duration of the voltage pulse is in the range of from about 1p s to about 50 μs. In other embodiments, the duration of the voltage pulse is in the range of from about 5 μs to about 10 μs. In another embodiment, the periodicity of the pulse voltages may be optimized. In some embodiments, the periodicity is in the range of from about 0.5 ms to about 20 ms. In yet other embodiments, the periodicity of the pulse voltages is from about 0.5 ms to about 1.5 ms. The skilled artisan will appreciate that the strength, duration, and periodicity of the optimal voltage pulses will depend upon many factors, e.g., the force of TCE.

B. Salts

The rate of current flow through the nanopore-based detection systems described herein can be influenced by the salt composition of the buffers that fill the cis and trans chambers of the system. Thus, in certain embodiments, the rate of Xpandomer translocation through the pore can be modulated by salt composition. In these embodiments, salts comprising any suitable mono- or di-valent cation may be utilized. In some embodiments, suitable salts include, but are not limited, to $NH_4Cl$, $MgCl_2$, LiCl, KCl, CsCl, NaCl, and $CaCl_2$. In other embodiments, suitable salts include those in which the anion is acetate. In conditions where a slower current is desired, salts with a lower ionic mobility, e.g., LiCl may be advantageous. In some embodiments, the trans chamber comprises 2M $NH_4Cl$ and a second optional salt with a suitable molarity around 0.2M and the cis chamber comprises $NH_4Cl$ with a suitable molarity in the range from about 0.4M to about 1M and a second optional salt with a suitable molarity in the range from about 0.2M to about 0.8M. In other embodiments, other molarities lying outside of these ranges and/or other combinations of salts may be desirable.

C. Chaotropic Agents

In certain other aspects, the cis chamber of the nanopore-based detection systems of the present invention may include one or more chaotropic agents to improve translocation of individual polymeric analytes, e.g., linearized Xpandomers. Any suitable chaotropic agent may be employed, e.g., urea and/or guanidine hydrochloride (GuCl). In some embodiments, the buffer compositions of the cis chamber include GuCl and/or urea in the range from about 200 mM to about 2M.

D. Osmotic Gradients

In other aspects, present invention provides nanopore-based detection systems in which an osmotic gradient is established across the membrane to influence that rate of Xpandomer translocation through the pore. Without being bound by theory, it is hypothesized that a gradient, wherein the concentration of salts and/or other additives is higher in the trans chamber relative to the cis chamber, generates a flow of water towards the nanopore, thereby drawing Xpandomers towards the pore. Under these conditions, an increase in the rate of event frequencies (e.g., code reads) may be observed at a lower run voltage. Thus, in some embodiments, the run conditions include establishment of an osmotic gradient of around 50% across the membrane; e.g., a salt (and/or other additive) concentration of around 1M in the cis chamber and a salt (and/or other additive) concentration of around 2M in the trans chamber. In further embodiments, any other suitable osmotic gradient may be employed.

E. Solvents

It has been found that certain solvents can enhance Xpandomer solubility and improve the rate translocation through a nanopore. Thus, in certain embodiments, the sample buffers of the present invention include one or more organic solvents. Suitable solvents include, but are not limited to, 3-methyl-2-oxazolidinone (MOA), DMF, ACN, DMSO, and NMP used in the range of from about 1% to about 25%.

F. Buffers, additives, and other run conditions

Suitable buffers for use in the present invention include, but are not limited to, 20 mM-100 mM HEPES with a pH of about 7.4 and bis-tris-propane buffers with a molarity in the range of from about 25 mM to about 250 mM and with a pH in the range of from about 6 to about 10. In other aspects, the buffers of the present invention may include certain detergent additives, such as sodium hexanoate (NaHex), to enhance the rate of Xpandomer translocation. In certain embodiments, the sample buffers of the present invention include around 20 mM NaHex. Other suitable additives include, but are not limited to, stabilizers such as EDTA and redox reagents. The viscosity of any of the buffers may also be altered by additives such as PEG, glycerol, ficoll and the like.

In other aspects, translocation rate of Xpandomers may be modulated by temperature. In some embodiments, the run temperature may be in the range from about 4° C. to about 40° C. In other embodiments, the run temperature may be in the range from about 16° C. to about 22° C.

Cleavable Extension Oligonucleotides

In another aspect, the present disclosure provides cleavable extension oligonucleotides (EO) for Xpandomer synthesis. The cleavable design feature enables the EO to be removed, i.e., cleaved from, the Xpandomer following synthesis and prior to nanopore analysis. This functionality provides advantages when it is undesirable to translocate a polynucleotide sequence through a nanopore. Xpandomer synthesis, processing, and nanopore sequence analysis are carried out as has been described, e.g., in Applicants' PCT patent application no. PCT/US18/67763, which is herein incorporated by reference in its entirety.

Figure 11:
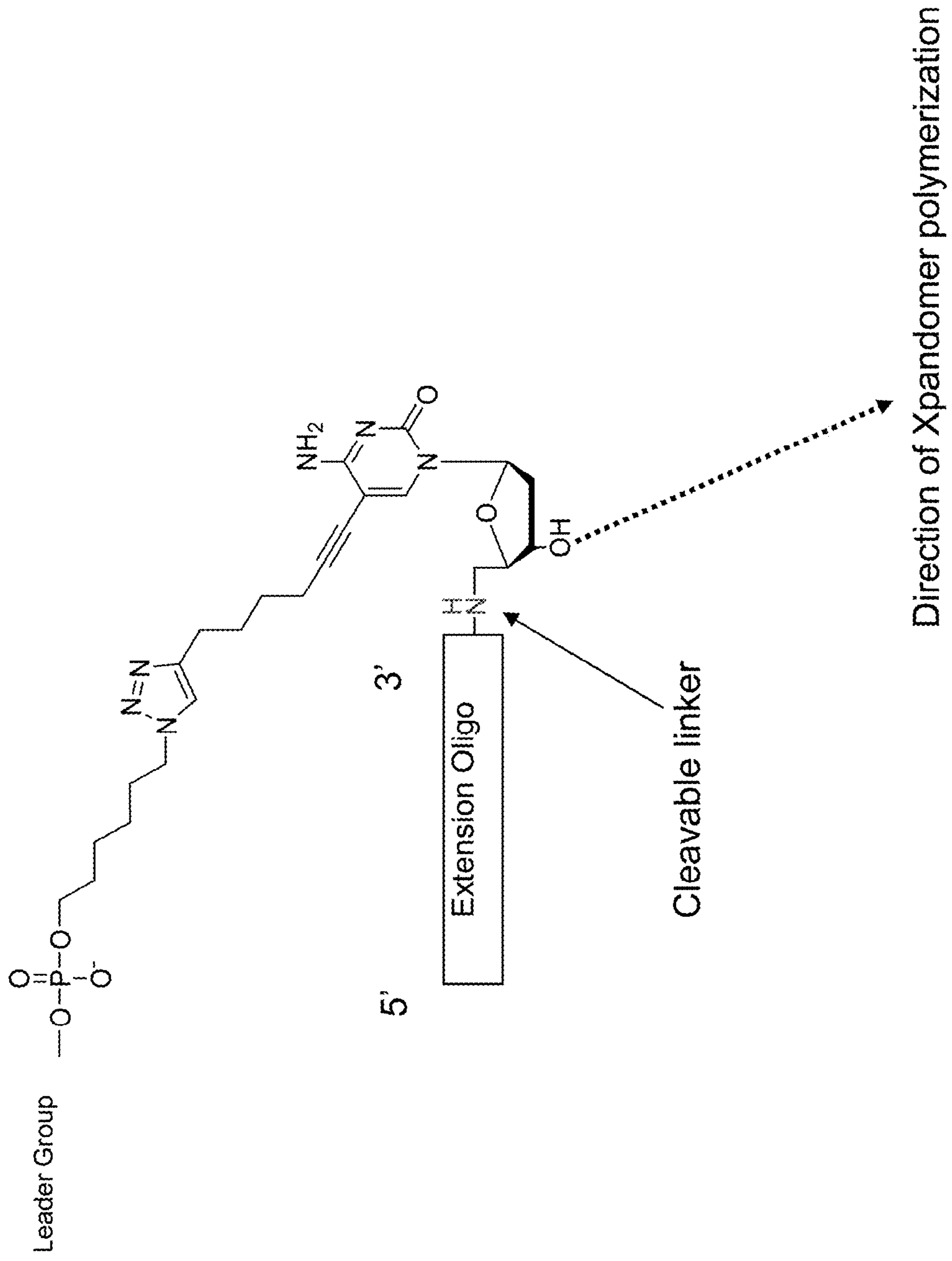
FIG. 11 is a schematic illustrating one embodiment of a cleavable extension oligonucleotide.

One embodiment of a cleavable extension oligonucleotide is illustrated in simplified form in FIG. 11. The 3' end of the EO is modified to include a cleavable bond, e.g., an acid cleavable phosphoramidate bond, represented here by "P-NH". The nucleobase attached to the EO by the cleavable linker provides a free 3' hydroxyl group for Xpandomer synthesis, the directionality of which is indicated by the dashed arrow. The base moiety of the same nucleobase is modified to provide other features necessary for nanopore translocation, e.g., a leader group also referred to herein as a "pendant leader sequence". Thus, following extension of the EO to form the Xpandomer, acid treatment releases the oligonucleotide primer, while the leader group and other joined features, remain associated with the Xpandomer. Advantageously, the inventors have found that Xpandomer synthesis is unaffected by the addition of a pendant leader sequence on the cleavable extension oligo.

Ratcheting

Figure 12:
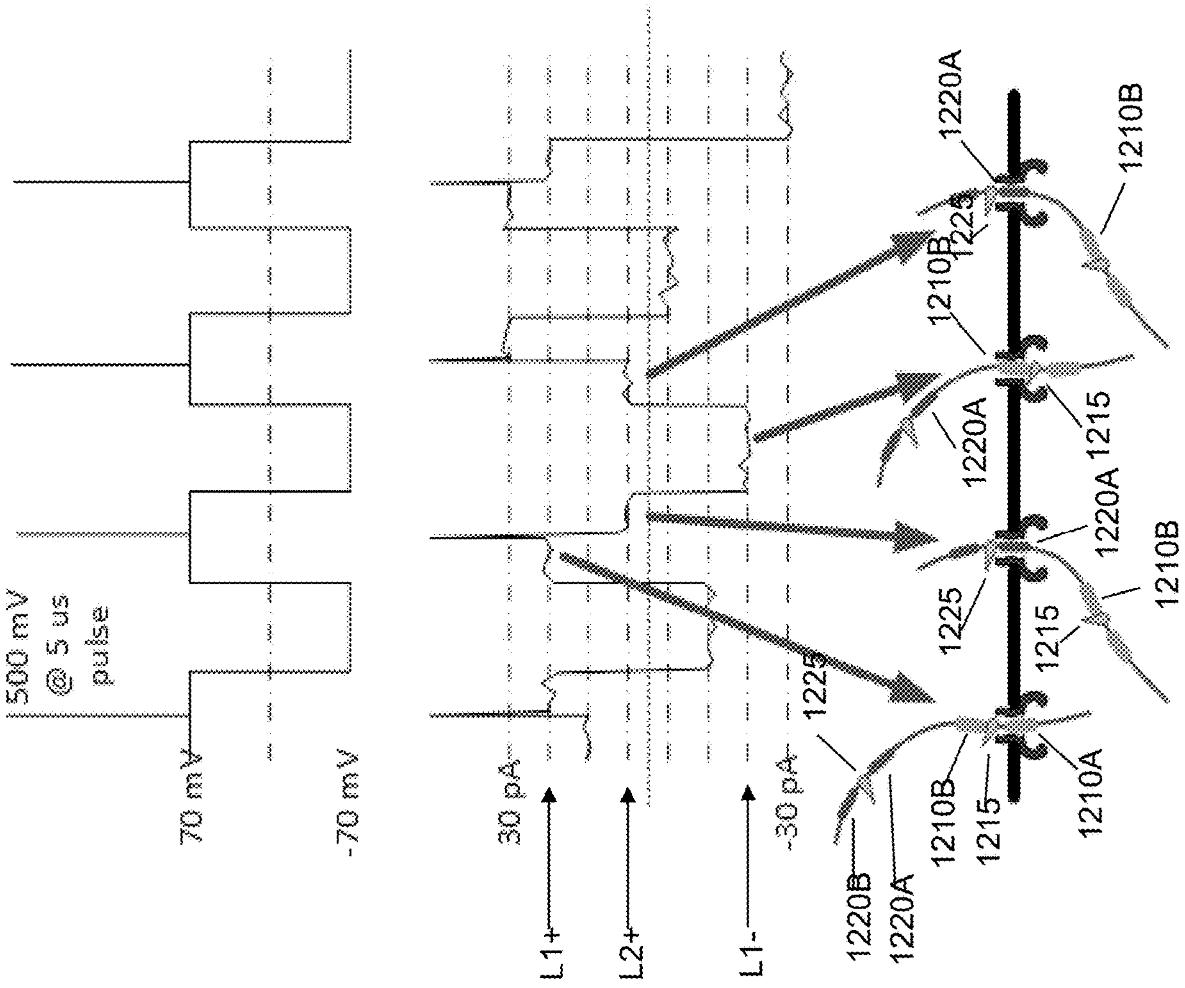
FIG. 12 is a schematic illustrating one embodiment of a polymer subjected to ratcheting through a nanopore.

One drawback of nanopore-based detection systems practiced in the art is the depletion of current over time resulting from electrolyte exhaustion that occurs during continuous application of DC voltage. For example, where an electrolyte circuit is based on a ferrocyanide-ferricyanide redox couple, each well in a nanopore array has a limited volume and thus contains a limited number of these redox ion species. Under DC voltage, one species converts to the other and will cause a drop in current. To overcome this problem of current depletion and maintain a more balanced current over time, the present disclosure provides means for detecting polymeric analytes with a nanopore-based detection system that relies, instead, on an alternating current (AC) pattern of voltage application. This pattern is referred to herein as "ratcheting". A generalized overview of ratcheting is presented in FIG. 12. The top panel of FIG. 12 illustrates an exemplary pattern of voltage application; in this embodiment, a "forward" read voltage of +70 mV is applied, in the middle of which the system is subjected to a brief (5 μs) pulse voltage of +500 mV. The "forward" read voltage is then followed by a "reverse" read voltage of −70 mV, and this cycle of +70 mV forward read/500 mV pulse/+70 mV forward read /−70 mV reverse read is repeated until the entire polymeric analyte has passed through the nanopore. One significant advantage of the ratchet protocol is that the electrolyte distribution is replenished during each forward read-reverse read cycle.

The bottom panel of FIG. 12 illustrates how the directionality of polymer translocation changes during ratcheting. In this embodiment, each unit of the polymeric analyte includes two identical reporter codes (e.g., 1210A and 1210B) separated by a translocation control element, e.g., TCE 1215. As illustrated in FIG. 12, application of the +70 mM forward run voltage results in polymer movement through the pore from the cis side of the membrane to the trans side until reporter code 1210A is arrested in the pore by the pause in translocation induced by TCE 1215. The change in current through the pore due to arrested reporter code 1210A is read as signal "L1+". Application of the 500 mV pulse forces TCE 1215 and reporter code 1210B through the pore. Following the 5 s pulse, the read voltage returns to +70 mV, whereupon the next reporter code in series, 1220A, is arrested in the pore by its corresponding TCE 1225. The change in current flow through the pore due to reporter code 1220A is read as signal "L2+". Next, the voltage is reversed by application of the reverse read voltage of −70 mM to the system, resulting in reversal of the direction of polymer translocation. During this period, reporter code 1220A is pushed back through the pore to the cis side of the membrane. Translocation proceeds until TCE 1215 encounters the pore, whereupon translocation arrested, positioning reporter code 1210B in the pore to generate a change in current measured as level "L 1-". Next, the voltage is returned to the +70 mM forward run voltage, whereupon the direction of polymer translocation is reversed back to the cis-to-trans direction, until an arrest occurs due to the ITC effect of TCE 1225, which positions reporter code 1220A in the pore. The resulting change in current is read as level "L2+". During this ratcheting protocol, the reporter code characterizing each unit in the polymer is read three times (reporter code "A" gets read twice and reporter code "B" gets read once). This redundancy provides a means of quality control for the sequence reads and improves the accuracy of the resulting sequence data. Insertion and deletion errors can readily be identified as deviations from the expected pattern, e.g., L1+/L2+/L1−/L2+.

Although the ratcheting pattern depicted in FIG. 12 shows the pulse voltage being applied during the "middle" of the forward read voltage, other patterns of pulsing are contemplated by the present invention. For example, in some embodiments, the pulse may be applied prior to application of the forward read voltage, while in other embodiments, the pulse may be applied at the end of the forward read voltage, just prior to application of the reverse read voltage.

In other embodiments, ratcheting provides means for compensating, or correcting, for one or both of current depletion due to pulsing and asymmetry in the resistance of the different reporter codes. For example, in some embodiments, the reverse read voltage can be increased to compensate for the current loss due to the pulses applied during the forward read voltage. The percent increase in the reverse read voltage can also be adjusted to balance the current when the different reporter codes have different intrinsic resistances.

In other variations of the ratcheting scheme, the sequence of forward, pulse, and reverse voltages can be altered. For example, in one embodiment, a ratcheting cycle could be run as follows: (forward read voltage), (forward read voltage), (reverse read voltage). In another embodiment, a ratcheting cycle could be run as follows: (forward read)n(reverse read)$_n$ in which "n" represents the total number of monomeric units in the polymer being measured by the nanopore.

In a related idea, "flossing" was proposed whereby DNA may be read in a nanopore along its full length, stopped and then upon reversing the voltage polarity could be read in the other direction (see, e.g., Kasianowicz, John J. "Nanopores: Flossing with DNA." Nature Materials 3, no. 6 (2004): 355-56. This is a less efficient method in an array because the DNA polymers are not captured or stopped synchronously whereas ratcheting is a continuous forward process on these time scales.

SBX-Based Diagnostic Methods and Kits

In another aspect, the present invention discloses methods and kits for the detection and diagnostics of genetic alterations/mutations in a target sample, which may be a solid tissue or a bodily fluid. The genetic alterations may be either germline or somatic mutations. The invention may be used for detection and diagnostics related to cancer, autoimmune disease, organ transplant rejection, genetic fetal abnormalities, pathogens, and other suitable conditions.

EXAMPLES

Material and Methods

The following materials, having the abbreviations as indicated, were obtained from the mentioned sources in the United States, unless otherwise indicated. 2-Phenyl-1,3-dioxan-5-ol, TBDPS-Cl (t-butyldiphenylchlorosilane), DMAP (4-dimethylaminopyridine), (R)-(+)-glycidol, (+)-2,3-O-Isopropylidene-L-threitol, isosorbide, 4,4'-Bis(hydroxymethyl)-2,2'-bipyridine, TBTA (Tris[(1-benzyl-1H-1,2,3-triazol-4-yl)methyl]amine) from TCI America (Portland, OR). NaH (sodium hydride), MeOH (methanol), toluene, THF (tetrahydrofuran), TBAF (tetrabutylammonium fluoride), DCM (dichloromethane), HCl (concentrated hydrochloric acid), DMSO (dimethylsulfoxide), Na ascorbate (sodium ascorbate), sodium bicarbonate, copper sulfate, dimethyl propargylmalonate, lithium borohydride, and acetic acid were obtained from Sigma-Aldrich (St. Louis, MO). DMT-Cl (4,4'-dimethoxytrityl chloride) and PPA-Cl (N,N-diisopropylamino cyanoethyl phosphonamidic chloride) from ChemGenes Corporation (Wilmington, MA). TEA (triethylamine), hexanes, ethyl acetate, EDTA (ethylenediaminetetraacetic acid), diethyl ether from EMD Millipore (Billerica, MA). m-PEG4-Tos was made from m-PEG4-OH (Cat. No. BP-23742). Furo[3,2-c]pyridin-4(5h)-one (Combi-Blocks, San Diego, CA).

High performance liquid chromatography (HPLC) was performed on a ProStar Helix™ HPLC system from Agilent Technologies, Inc. (Santa Clara, CA) consisting of two pumps (ProStar 210 Solvent Delivery Modules) with 10 ml titanium pump heads, a column oven (ProStar 510 Air Oven), a UV detector (ProStar 320 UV/Vis Detector) set at 292 nm. The system is controlled by Star Chromatography Workstation Software (version 6.41). The column used was a Cadenza Guard Column System CD-C18 (2.0 mm×5 mm) both from Imtakt USA (Portland, OR). The buffers used are Buffer A (100 mM triethylammonium acetate, pH 7.0) and Buffer B (100 mM triethylammonium acetate, pH 7.0 with 95% by volume acetonitrile). Automated solid phase phosphoramidite synthesis was done on a MerMade™ 12 synthesizer (Bioautomation Corp, Plano, TX). Synthesis solutions for the MerMade™ were purchased from Glen Research (Sterling, VA).

Example 1

Synthesis of DMT Phosphoramidite of Racemic 2-(3,6-Dioxaheptyloxy)-1,3-propanediol Pendant Code 2-glyceryl PEG-2 Phosphoramidite [Racemate]

2-Phenyl-1,3-dioxan-5-ol (1, 2.7 g, 15 mmol) was dissolved in 30 mL anhydrous THF. Sodium hydride (1.08 g, 27 mmol) was added to generate alkoxide. When the bubbling ceased, mPEG4-Tos (4.94 g, 18 mmol) was dissolved in 10 mL THF and added portion-wise. The reaction was brought to 40° C. and incubated with stirring for 3 h, then allowed to come down to room temperature overnight. Excess NaH was quenched with 1 mL MeOH, then diluted with water and extracted with DCM. The combined organic layers were concentrated under reduced pressure. The residue was resuspended in toluene, separated from remaining salts, and purified by flash chromatography to afford 2 in 73% yield.

Benzylidine protected 2b (3.05 g, 10.8 mmol) was dissolved in 10 mL MeOH and HCl (0.2 mL, 2.3 mmol) was added. The solution was incubated for 20 minutes, then neutralized with sodium bicarbonate (200 mg) and dried under reduced pressure. The residue was resuspended in DCM and purified by flash chromatography to afford diol 3 in 72% yield.

Diol 3 (1.52 g, 7.8 mmol) was dissolved in 20 mL DCM and TEA (2.17 mL, 15.6 mmol). A solution of DMT-Cl (1.85 g, 5.46 mmol) in 10 mL DCM was added portion-wise over 90 minutes to maximize monotritylation. MeOH (1 mL) was added and the reaction was dried under reduced pressure. The residue was resuspended in toluene and separated from the salts, then purified by flash chromatography to afford the mono-trityl product 4 in 48% yield as well as recovered starting diol.

Monotrityl 4 (1.84 g, 3.7 mmol) was dissolved in 10 mL DCM and TEA (1.03 mL 7.4 mmol). PPA-Cl (1.05 g, 4.4 mmol) was added and the reaction was incubated 15 minutes. The reaction was dried down under reduced pressure and resuspended in toluene with 1% TEA, then purified by flash chromatography. Phosphoramidite 5 (2.03 g, 2.9 mmol) was afforded in 79% yield and confirmed by 1H and 31P NMR.

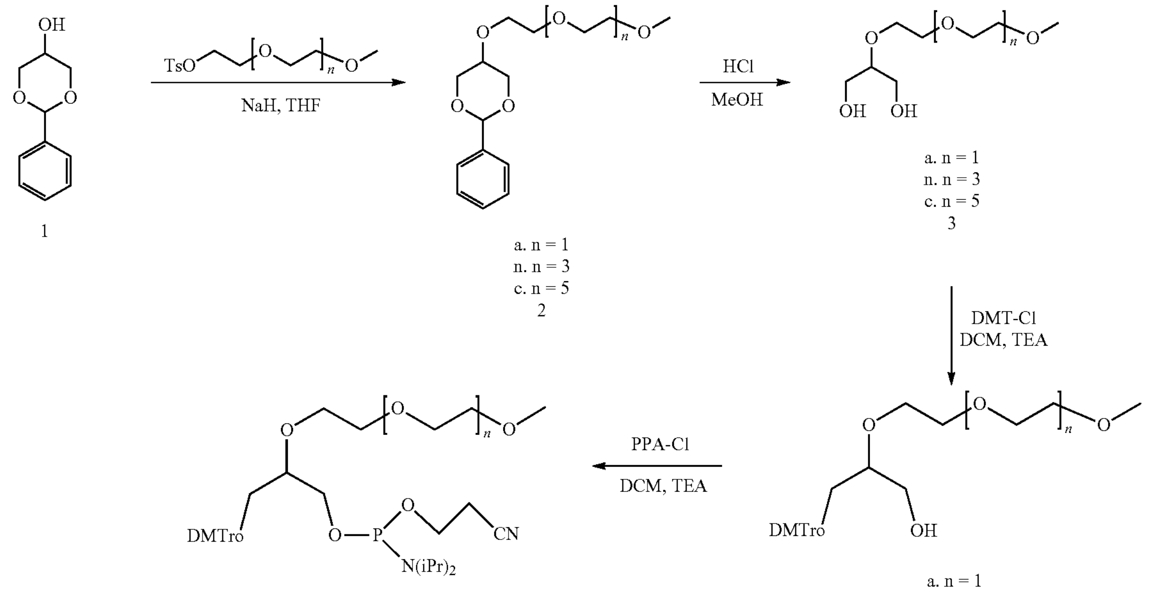

1 a. n = 1
n. n = 3
c. n = 5
2 a. n = 1
n. n = 3
c. n = 5
3 a. n = 1
n. n = 3
c. n = 5
4 a. n = 1
n. n = 3
c. n = 5
5

Example 2

Synthesis of DMT Phosphoramidite of Enantiomer 2-(3,6-Dioxaheptyloxy)-1,3-propanediol (12b) (Pendant Code 2-glyceryl PEG-2 Phosphoramidite [Enantiomer]

2,3-Isopropylidene-sn-glycerol 6 was dissolved in anhydrous DCM and TEA. DMAP and TBDPS-Cl were added. The reaction was extracted from water with DCM and purified by flash chromatography to afford product 7.

Silyl ether 7 was dissolved in MeOH and HCl was added. The solution was incubated 20 minutes, then neutralized with sodium bicarbonate and dried under reduced pressure. The residue was resuspended in DCM and purified by flash chromatography to afford diol 8.

Diol 8 was dissolved in DCM and TEA. A solution of DMT-Cl in DCM was added portion-wise. MeOH was added and the reaction was dried under reduced pressure. The residue was resuspended in toluene and separated from the salts, then purified by flash chromatography to afford the mono-trityl product 9.

Secondary alcohol 9 was dissolved in anhydrous THF. Sodium hydride was added to generate alkoxide. When the bubbling ceased, mPEG4-Tos was dissolved in THF and added portion-wise. The reaction was brought to 40° C. and incubated with stirring for 3 h, then allowed to come down to room temperature overnight. Excess NaH was quenched with 1 mL MeOH, then diluted with water and extracted with DCM. The combined organic layers were dried under reduced pressure. The residue was resuspended in toluene, separated from remaining salts, and purified by flash chromatography to afford 10.

mPEG4 ether 10b was resuspended in THF and TBAF was added. The reaction was concentrated under reduced pressure and purified by flash chromatography to afford 11.

DMT PEG4 alcohol 11b was dissolved in DCM and TEA. PPA-Cl was added and the reaction and incubated 15 minutes. The reaction was dried down under reduced pressure and resuspended in toluene with 1% TEA, then purified by flash chromatography. Phosphoramidite 12 was isolated and confirmed by 1H and 31P NMR.

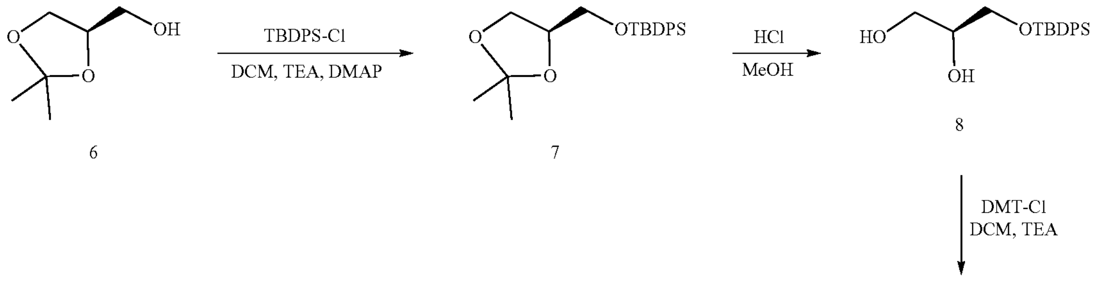

6

7

8

-continued

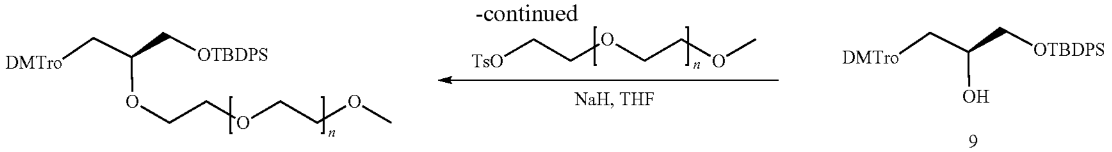

10
a. n = 1
b. n = 3
c. n = 5

9

TBAF
THF

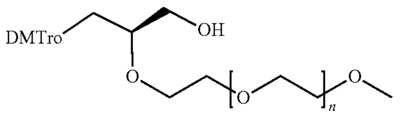

11
a. n = 1
b. n = 3
c. n = 5

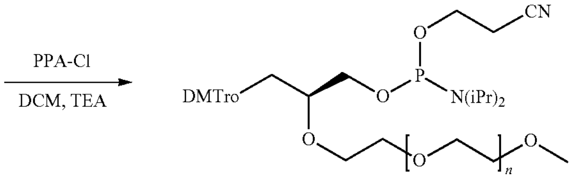

12
a. n = 1
b. n = 3
c. n = 5

Example 3

Synthesis of DMT Phosphoramidite of Enantiomer 1-(3,6-Dioxaheptyloxy)-2,3-propanediol

Pendant Code 1-Glyceryl PEG-2 Phosphoramidite 2,3-Isopropylidene-sn-glycerol 6 was dissolved in anhydrous THF. Sodium hydride was added to generate alkoxide. When the bubbling ceased, mPEG2-Tos (Broadpharm Cat. No. BP-2-982) was dissolved in THF and added portion-wise. The reaction was incubated for 24 hours. Excess NaH was quenched with MeOH, then diluted with water and extracted with DCM. The combined organic layers were concentrated under reduced pressure. The residue was resuspended in toluene, separated from remaining salts, and purified by flash chromatography to afford 13.

The PEG2 product 13 was dissolved in MeOH and HCl was added. The solution was incubated 20 minutes, then neutralized with sodium bicarbonate and dried under reduced pressure. The residue was resuspended in DCM and purified by flash chromatography to afford diol 14.

Diol 14 was dissolved in DCM and TEA. A solution of DMT-Cl in DCM was added portion-wise. MeOH was added and the reaction was dried under reduced pressure. The residue was resuspended in toluene and separated from the salts, then purified by flash chromatography to afford the mono-trityl product 15.

Mono DMT 15 was dissolved in DCM and TEA. PPA-Cl was added and the reaction was incubated 15 minutes. The reaction was dried down under reduced pressure and resuspended in toluene with 1% TEA, then purified by flash chromatography. Phosphoramidite 16 was isolated and confirmed by 1H and 31P NMR.

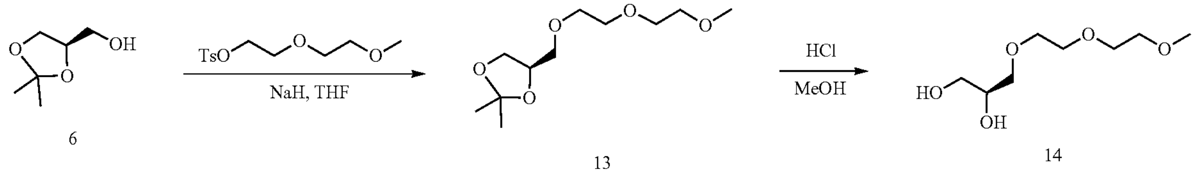

6

13

14

DMT-Cl
DCM, TEA

-continued

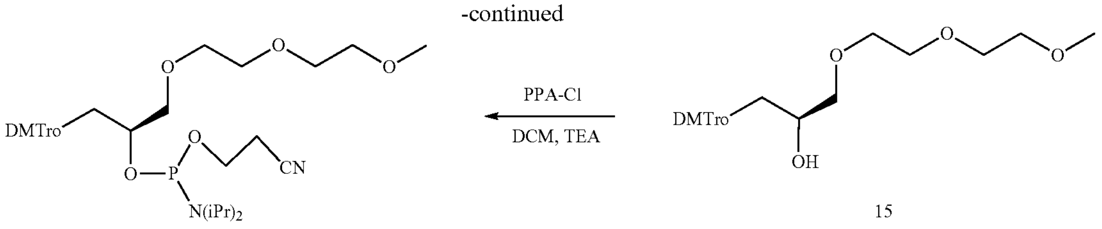

16 15

Example 4

Synthesis of DMT Phosphoramidite of 1-(5H-furo [3,2-c]pyridin-4-one)-2,3-propandiol (20) Pendant Code 1-Glyceryl Heterocycle Phosphoramidite (R)-(+)-glycidol 17 was dissolved in DCM and TEA. A solution of DMT-Cl in DCM was added portion-wise. MeOH was added and the reaction was dried under reduced pressure. The residue was resuspended in toluene and separated from the salts, then purified by flash chromatography to afford DMT ether 18.

DMT ether 18 was dissolved in anhydrous DMF. Sodium hydride was added to generate alkoxide. When the bubbling ceased, Furo[3,2-c]pyridin-4(5h)-one was dissolved in THE and added portion-wise. The reaction was brought to 100° C. and incubated with stirring for 12h. Excess NaH was quenched with MeOH, then diluted with water and extracted with DCM. The combined organic layers were concentrated under reduced pressure. The residue was resuspended in toluene, separated from remaining salts, and purified by flash chromatography to afford 19.

Secondary alcohol 19 was dissolved in DCM and TEA. PPA-Cl was added and the reaction and incubated 15 minutes. The reaction was dried down under reduced pressure and resuspended in toluene with 1% TEA, then purified by flash chromatography. Phosphoramidite 20 was isolated and confirmed by 1H and 31P NMR.

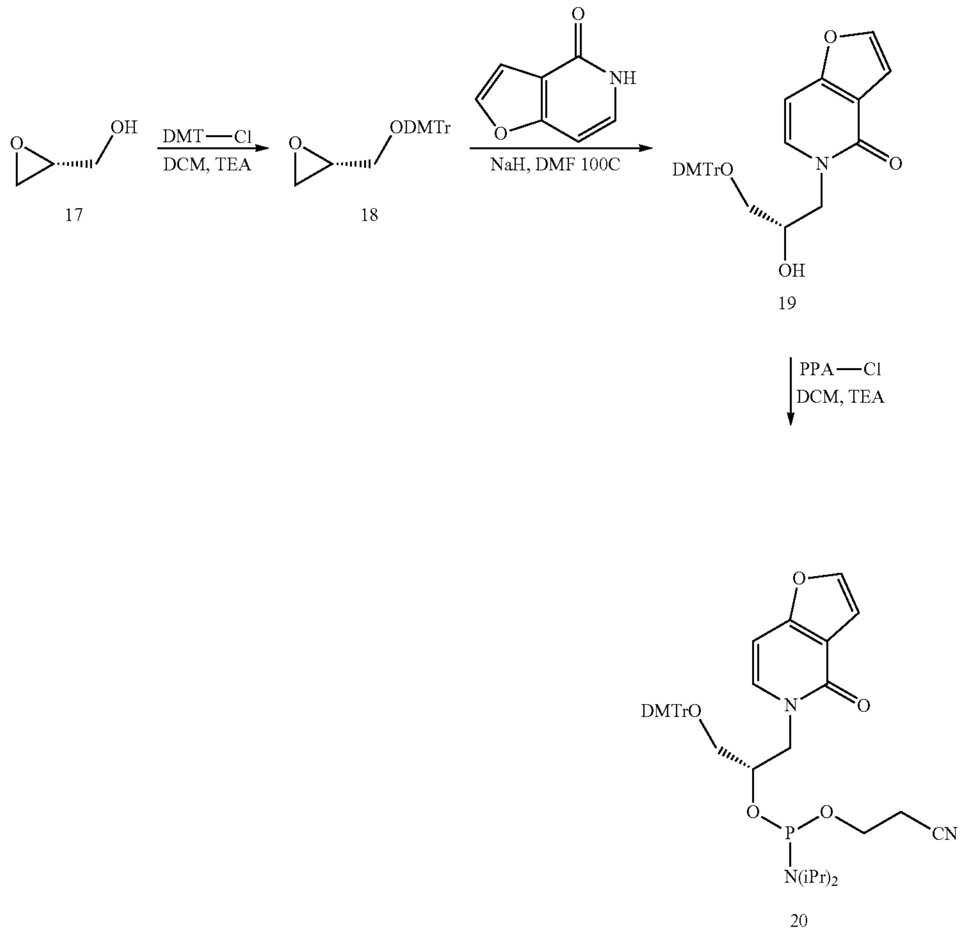

17 18 19 20

Example 5

Synthesis of in-Line Code DMT Phosphoramidite of Isosorbide (23) Bis-Secondary Alcohol Code Backbone Isosorbide 21 was dissolved in DCM and TEA. A solution of DMT-Cl in DCM was added portion-wise. MeOH was added and the reaction was dried under reduced pressure. The residue was resuspended in toluene and separated from the salts, then purified by flash chromatography to afford monotrityl 22.

Monotrityl 22 was dissolved in DCM and TEA. PPA-Cl was added and the reaction was incubated 15 minutes. The reaction was dried down under reduced pressure and resuspended in toluene with 1% TEA, then purified by flash chromatography. Phosphoramidite 23 was isolated and confirmed by 1H and 31P NMR.

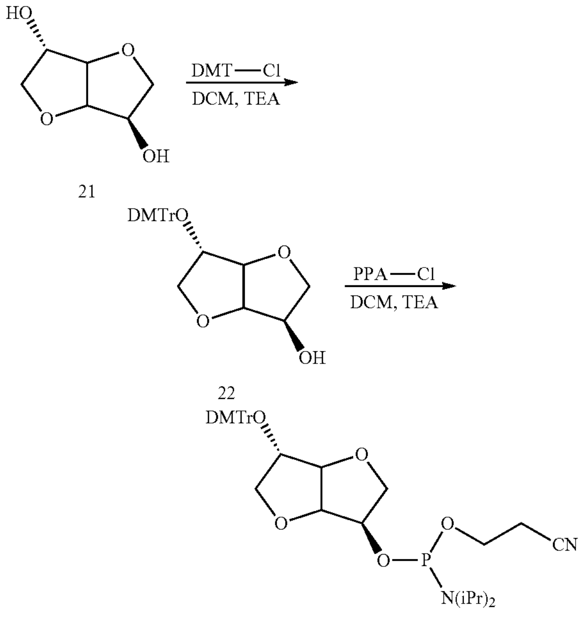

21

22

23

Example 6

Synthesis of in-Line Code DMT Phosphoramidite of Bipyridyl (26) Bis-Primary Alcohol Code Backbone 4,4'-Bis(hydroxymethyl)-2,2'-bipyridine 24 was dissolved in DCM and TEA. A solution of DMT-Cl in DCM was added portion-wise. MeOH was added and the reaction was dried under reduced pressure. The residue was resuspended in toluene and separated from the salts, then purified by flash chromatography to afford monotrityl 25.

Monotrityl 25 was dissolved in DCM and TEA. PPA-Cl was added and the reaction was incubated 15 minutes. The reaction was dried down under reduced pressure and resuspended in toluene with 1% TEA, then purified by flash chromatography. Phosphoramidite 26 was isolated and confirmed by 1H and 31P NMR.

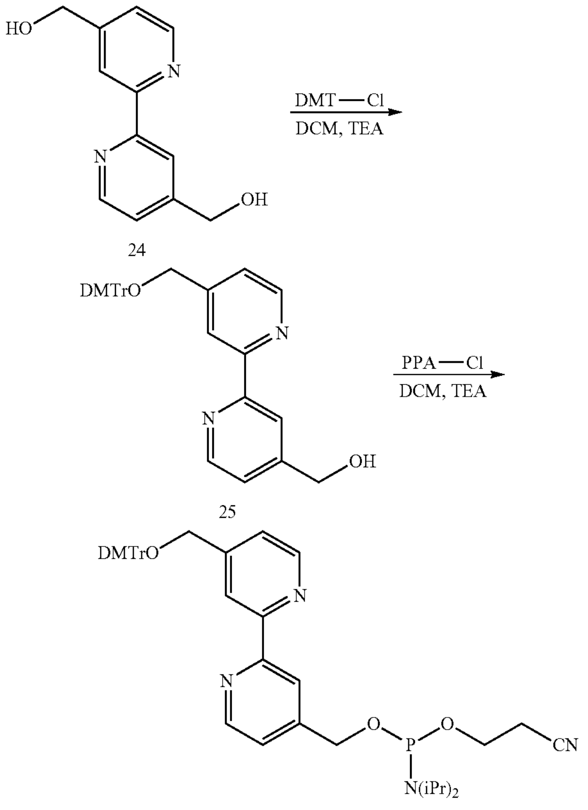

24

25

26

Example 7

Synthesis of Pendant Code DMT Phosphoramidite of 2-alkyl triazole PEG-2 1,3-propane diol (31a). Pendant Triazole PEG Code Dimethyl propargylmalonate 27 was added dropwise to a cold suspension of lithium borohydride in diethyl ether. The reaction was warmed to room temperature and incubated overnight. The reaction was quenched with methanol, then water, then acetic acid. The solution was extracted with ether and the combined organic layers were concentrated under reduced pressure. The crude material was purified by flash chromatography to afford diol 28.

Diol 28 was dissolved in DCM and TEA. A solution of DMT-Cl in DCM was added portion-wise. MeOH was added and the reaction was dried under reduced pressure. The residue was resuspended in toluene and separated from the salts, then purified by flash chromatography to afford DMT alcohol 29.

DMT alcohol 29 was dissolved in DMSO and azide (Cat. No. BP-20988 Broadpharm) was added. Separately, TBTA was dissolved in DMSO and sodium ascorbate and copper sulfate were combined. The TBTA solution was added to the alkyne/azide solution in portions with stirring. After 45 minutes of incubation, the reaction was quenched with EDTA. The solution was diluted with water and extracted with ethyl acetate, then the organic layers were concentrated under reduced pressure and purified by flash chromatography to afford 30.

1,2,3-Triazole 30a was dissolved in DCM and TEA. PPA-Cl was added and the reaction was incubated 15 minutes. The reaction was dried down under reduced pressure and resuspended in toluene with 1% TEA, then purified by flash chromatography. Phosphoramidite 31 was isolated and confirmed by 1H and 31P NMR.

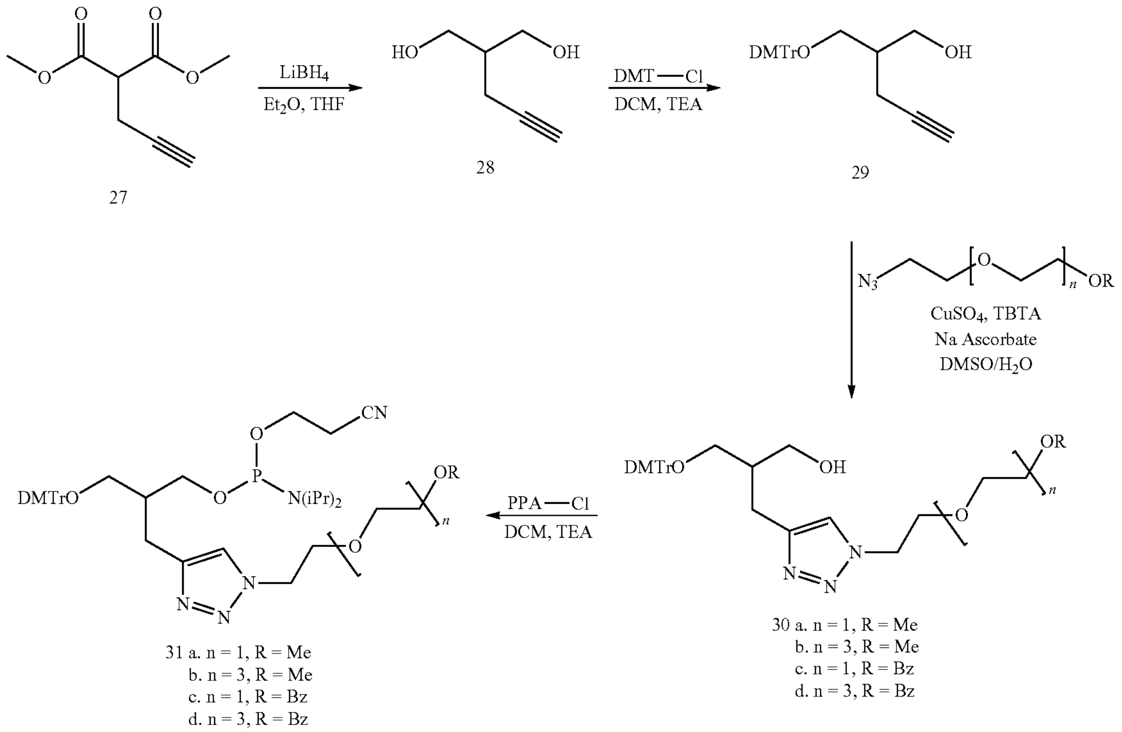

27 28 29

30 a. n = 1, R = Me
b. n = 3, R = Me
c. n = 1, R = Bz
d. n = 3, R = Bz 31 a. n = 1, R = Me
b. n = 3, R = Me
c. n = 1, R = Bz
d. n = 3, R = Bz

Example 8

Synthesis of Pendant PEG-2, PEG-4 and PEG-6 Phosphoramidites [Isomerically Pure] (35a)

1-U-TBDPS-3-U-DMTr-propane-1,2,3-triol 9 (from Example 2) was dissolved in anhydrous THF. Sodium hydride was added to generate alkoxide. When the bubbling ceased, tosylate (prepared via tosylation of Cat. No. BP-21657, Broadpharm) was added portion-wise. The reaction was incubated with stirring for 48h. Excess NaH was quenched with water, then the solution was transferred to a separatory funnel and extracted with ethyl acetate. The combined organic layers were washed with brine, dried with sodium sulfate, filtered and concentrated under reduced pressure. The residue was resuspended in toluene, separated from remaining salts, and purified by flash chromatography to afford 32.

Alkyne 32a was resuspended in THF and TBAF was added. The reaction was concentrated under reduced pressure and purified by flash chromatography to afford 33.

To a solution of alkyne 33a in DMSO was added 2-azidoethyl acetate. In a separate vial, dissolve sodium ascorbate in water and add DMSO followed by 1M $CuSO_4$, to prepare catalyst mixture. Add catalyst mixture to solution of alkyne/azide dropwise over 10 minutes. Upon completion, quench with 0.5M EDTA and stir for 15 minutes. Dilute with water and extract with ethyl acetate three times. Wash combined organic extractions with brine and dry over sodium sulfate. The residue was resuspended in toluene and purified by flash chromatography to afford 34a.

Triazole 34a was dissolved in DCM and TEA. PPA-Cl was added and the reaction was incubated 15 minutes. The reaction was dried down under reduced pressure and resuspended in toluene with 1% TEA, then purified by flash chromatography. Phosphoramidite 35 was isolated and confirmed by 1H and 31P NMR.

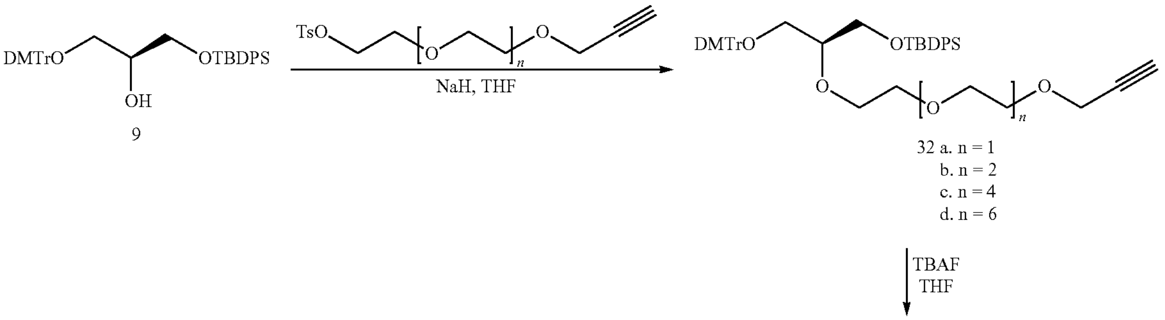

9

32 a. n = 1
b. n = 2
c. n = 4
d. n = 6

-continued

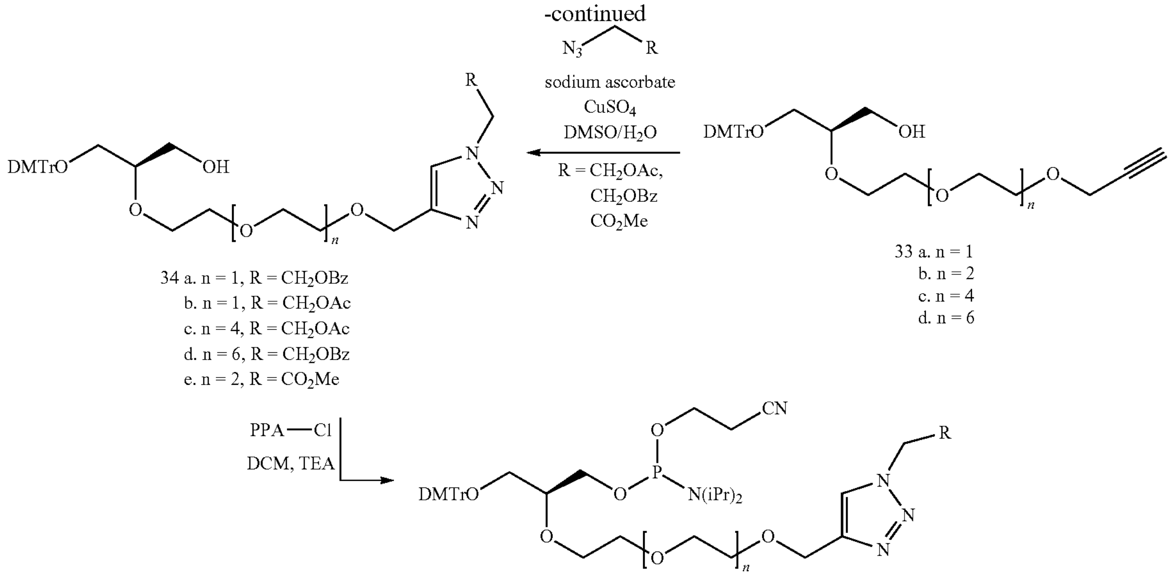

34 a. n = 1, R = $CH_2OBz$
b. n = 1, R = $CH_2OAc$
c. n = 4, R = $CH_2OAc$
d. n = 6, R = $CH_2OBz$
e. n = 2, R = $CO_2Me$ 33 a. n = 1
b. n = 2
c. n = 4
d. n = 6

35 a. n = 1, R = $CH_2OBz$
b. n = 1, R = $CH_2OAc$
c. n = 4, R = $CH_2OAc$
d. n = 6, R = $CH_2OBz$
e. n = 2, R = $CO_2Me$

Example 9

Synthesis of PEG-Based Reporter Codes (37b)

To a solution of product 33 in DMSO was added 2-(acetoxymethyl)-2-(azidomethyl)propane-1,3-diyl diacetate (prepared by dissolving 2-(Bromomethyl)-2-(hydroxymethyl)-1,3-propanediol in DMF and subsequent addition of NaN3. The reaction was incubated at 110° C., concentrated, and purified by flash chromatography. Upon isolation of the product, the residue was reacted with acetic anhydride and purified). In a separate vial, dissolve sodium ascorbate in water and add DMSO followed by 1M $CuSO_4$, to prepare catalyst mixture. Add catalyst mixture to solution of alkyne/azide dropwise over 10 minutes. Upon completion, quench with 0.5M EDTA and stir for 15 minutes. Dilute with water and extract with ethyl acetate three times. Wash combined organic extractions with brine and dry over sodium sulfate. The residue was resuspended in toluene and purified by flash chromatography to afford 36.

Primary alcohol 36b was dissolved in DCM and TEA. PPA-Cl was added and the reaction was incubated 15 minutes. The reaction was dried down under reduced pressure and resuspended in toluene with 1% TEA, then purified by flash chromatography. Phosphoramidite 37 was isolated and confirmed by 1H and 31P NMR.

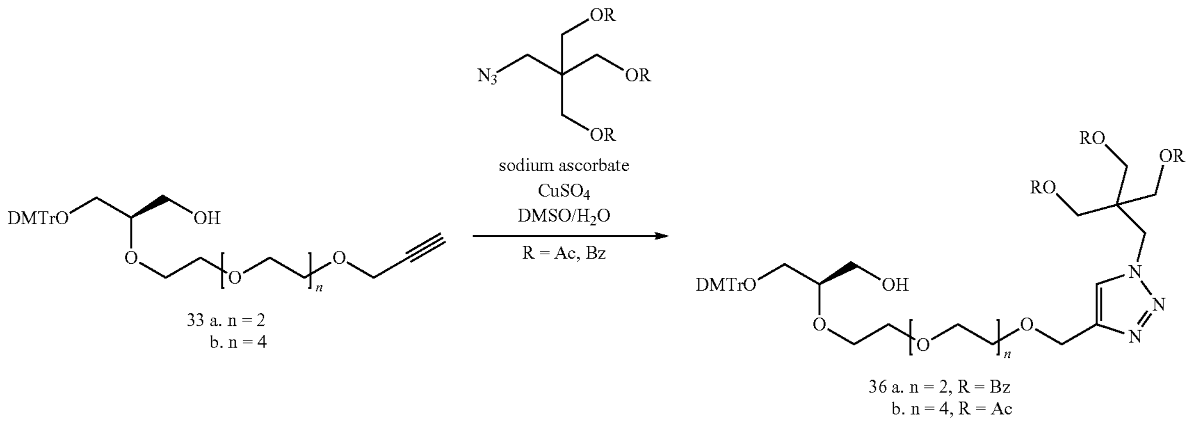

33 a. n = 2
b. n = 4

36 a. n = 2, R = Bz
b. n = 4, R = Ac

-continued

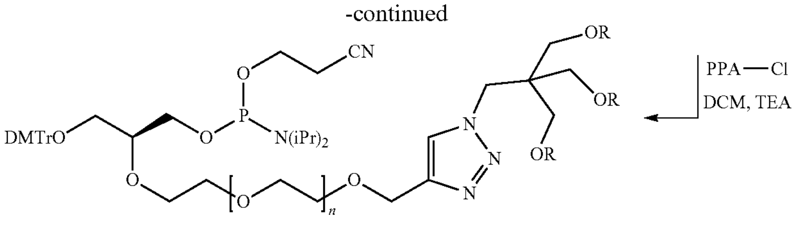

37 a. n = 2, R = Bz
b. n = 4, R = Ac

Example 10

Synthesis of PEG-Based Reporter Codes (40)

1-O-TBDPS-3-O-DMTr-propane-1,2,3-triol 9 (from Example 2) was dissolved in anhydrous THF. Sodium hydride was added to generate alkoxide. When the bubbling ceased, tosylate (prepared by sequential tosylation and silyl-protection of Cat. No. BP-21036, Broadpharm) was dissolved in THF and added portion-wise. The reaction was incubated with stirring overnight. Excess NaH was quenched with water and extracted with DCM. The combined organic layers were dried under reduced pressure. The residue was resuspended in toluene, separated from remaining salts, and purified by flash chromatography to afford 38.

Bis-silyl ether 38 was resuspended in THF and TBAF was added. The reaction was concentrated under reduced pressure and purified by flash chromatography. The purified material was resuspended in DCM and TEA was added. BzCl was added dropwise. The reaction was stirred at room temperature until complete. The reaction was concentrated under reduced pressure and purified by flash chromatography to afford alcohol 39.

Alcohol 39 was dissolved in DCM and TEA. PPA-Cl was added and the reaction and incubated 15 minutes. The reaction was dried down under reduced pressure and resuspended in toluene with 1% TEA, then purified by flash chromatography. Phosphoramidite 40 was isolated and confirmed by 1H and 31P NMR.

Example 11

Synthesis of bis-PEG-Based Reporter Codes (45a-d and 47e-i)

O,O'-Benzylidenepentaerythritol (41, Cat. No. B2682, TCI) was dissolved in anhydrous THF. Sodium hydride was added to generate alkoxide. When the bubbling ceased, tosylate (prepared via tosylation of Cat. No. BP-21397, Broadpharm or Cat. No. BP-21657, Broadpharm) was dissolved in THF and added portion-wise. The reaction was incubated with stirring overnight. Excess NaH was quenched with water and extracted with DCM. The combined organic layers were dried under reduced pressure. The residue was resuspended in toluene, separated from remaining salts, and purified by flash chromatography to afford 42a-h.

Products 42a-h were dissolved in MeOH and HCl was added. The reaction was incubated at room temperature overnight, then neutralized with sodium bicarbonate. It was concentrated under reduced pressure and purified by flash chromatography to afford 43a-h.

Products 43a-h were dissolved in DCM and TEA. A solution of DMT-Cl in DCM was added portion-wise. The reaction was dried under reduced pressure. The residue was resuspended in toluene and separated from the salts, then purified by flash chromatography to afford 44a-h.

Products 44a-d were dissolved in DCM and TEA. PPA-Cl was added and the reaction was incubated 15 minutes. The

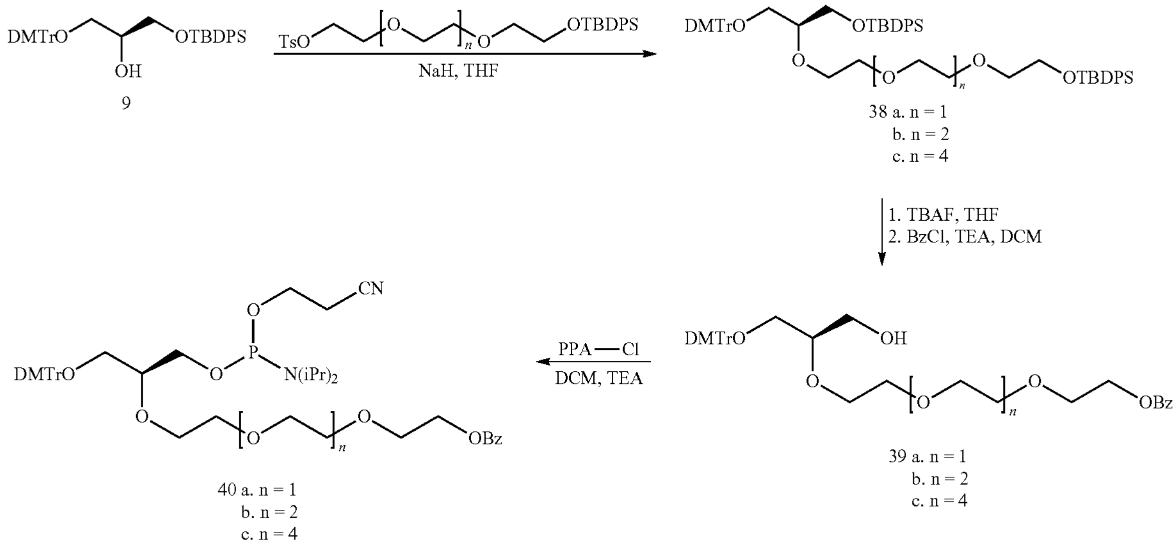

9

38 a. n = 1
b. n = 2
c. n = 4

39 a. n = 1
b. n = 2
c. n = 4

40 a. n = 1
b. n = 2
c. n = 4 reaction was dried down under reduced pressure and resuspended in toluene with 1% TEA, then purified by flash chromatography to afford phosphoramidites 45a-d.

To a solution of product 44 (e-h) in DMSO was added 2-azidoethyl acetate. In a separate vial, dissolve sodium ascorbate in water and add DMSO followed by 1M $CuSO_4$, to prepare catalyst mixture. Add catalyst mixture to solution of alkyne/azide dropwise over 10 minutes. Upon completion, quench with 0.5M EDTA and stir for 15 minutes. Dilute with water and extract with ethyl acetate three times. Wash combined organic extractions with brine and dry over sodium sulfate. The residue was resuspended in toluene and purified by flash chromatography to afford 46e-h.

Products 46e-h were dissolved in DCM and TEA. PPA-Cl was added and the reaction and incubated 15 minutes. The reaction was dried down under reduced pressure and resuspended in toluene with 1% TEA, then purified by flash chromatography to afford phosphoramidites 47e-h.

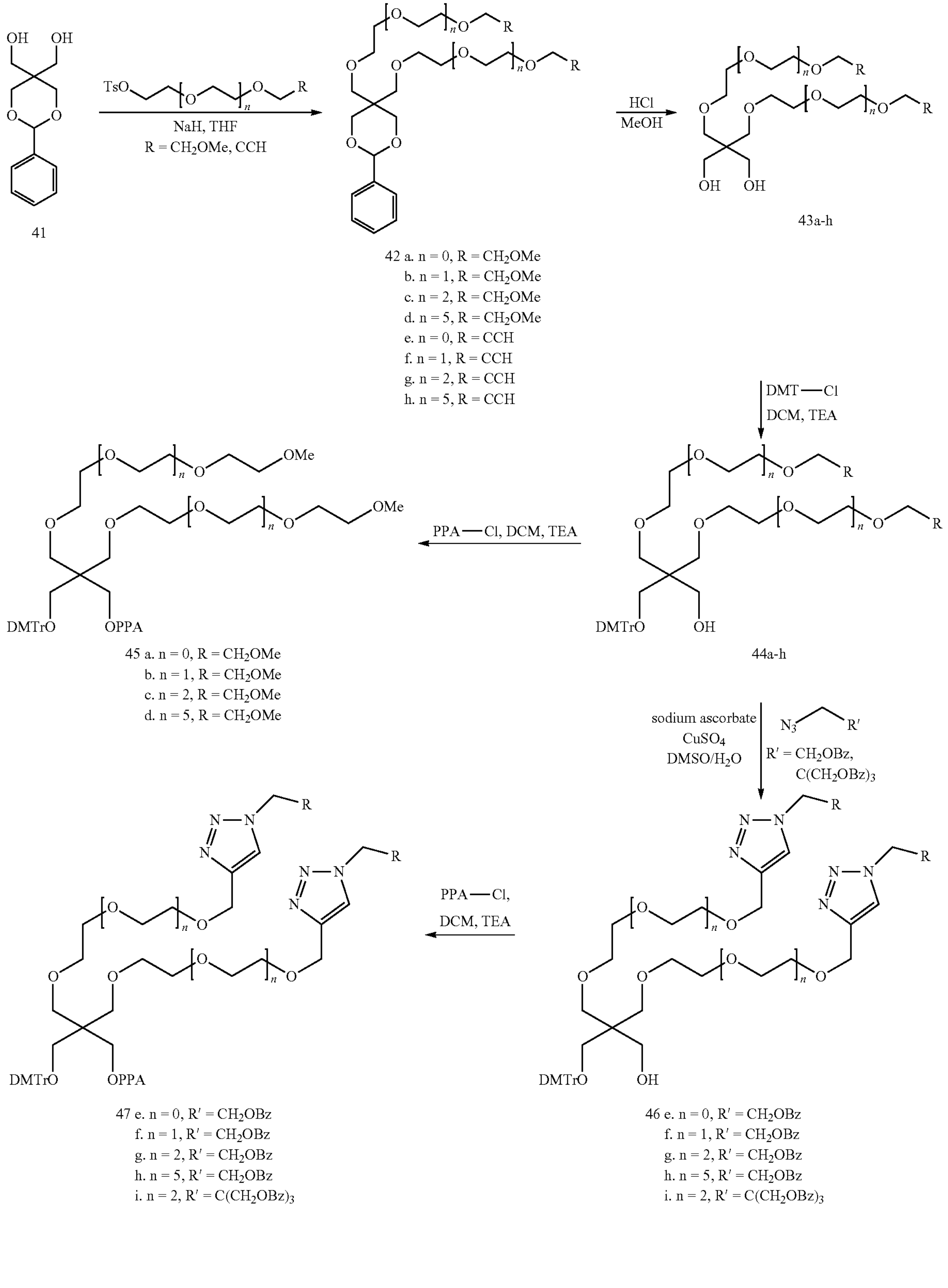

41

42 a. n = 0, R = $CH_2OMe$
b. n = 1, R = $CH_2OMe$
c. n = 2, R = $CH_2OMe$
d. n = 5, R = $CH_2OMe$
e. n = 0, R = CCH
f. n = 1, R = CCH
g. n = 2, R = CCH
h. n = 5, R = CCH 43a-h 44a-h 45 a. n = 0, R = $CH_2OMe$
b. n = 1, R = $CH_2OMe$
c. n = 2, R = $CH_2OMe$
d. n = 5, R = $CH_2OMe$ 46 e. n = 0, R′ = $CH_2OBz$
f. n = 1, R′ = $CH_2OBz$
g. n = 2, R′ = $CH_2OBz$
h. n = 5, R′ = $CH_2OBz$
i. n = 2, R′ = $C(CH_2OBz)_3$ 47 e. n = 0, R′ = $CH_2OBz$
f. n = 1, R′ = $CH_2OBz$
g. n = 2, R′ = $CH_2OBz$
h. n = 5, R′ = $CH_2OBz$
i. n = 2, R′ = $C(CH_2OBz)_3$

Example 12

Synthesis and Testing of PEG-Based Reporter Codes (52)

2,2-Bis(bromomethyl)-1,3-propanediol (48, Cat. No. D1808, TCI) was dissolved in DMF and NaN3 was added. The reaction was incubated at 110° C., concentrated, and purified by flash chromatography to afford product 49.

To a solution of 49 in DMSO was added 2-(2-(prop-2-yn-1-yloxy)ethoxy)ethyl benzoate (prepared by benzoylation of the commercial alcohol precursor). In a separate vial, dissolve sodium ascorbate in water and add DMSO followed by 1M $CuSO_4$, to prepare catalyst mixture. Add catalyst mixture to solution of alkyne/azide dropwise over 10 minutes. Upon completion, quench with 0.5M EDTA and stir for 15 minutes. Dilute with water and extract with ethyl acetate three times. Wash combined organic extractions with brine and dry over sodium sulfate. The residue was resuspended in toluene and purified by flash chromatography to afford 50.

Product 50 was dissolved in DCM and TEA. A solution of DMT-Cl in DCM was added portion-wise. The reaction was dried under reduced pressure. The residue was resuspended in toluene and separated from the salts, then purified by flash chromatography to afford 51.

Product 51 dissolved in DCM and TEA. PPA-Cl was added and the reaction was incubated 15 minutes. The reaction was dried down under reduced pressure and resuspended in toluene with 1% TEA, then purified by flash chromatography to afford phosphoramidite 52.

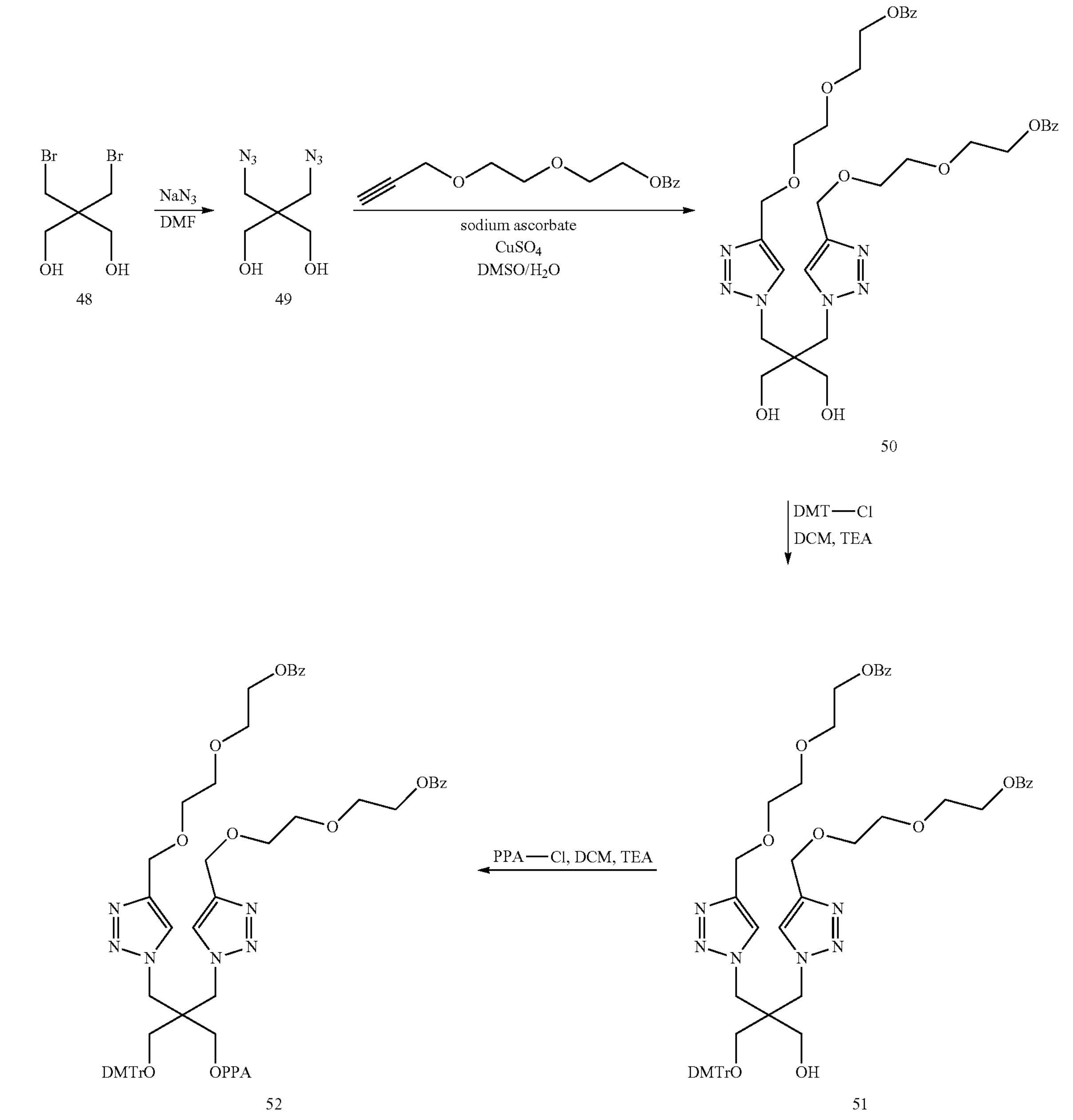

48 49 50 51 52

Example 13

Synthesis and Testing of PEG-Based Reporter Codes (62)

2-(Bromomethyl)-2-(hydroxymethyl)-1,3-propanediol (53, Cat. No. B4057, TCI) was dissolved in DMF and NaN3 was added. The reaction was incubated at 110° C., concentrated, and purified by flash chromatography to afford product 54.

Product 54 was dissolved in DCM and TEA. Benzoyl chloride was added. The solution was incubated overnight at room temperature. The reaction was extracted from water with DCM and purified by flash chromatography to afford product 55, the bis-Bz which was separated from any mono- or tri-protected species and divided.

A portion of product 55 was dissolved in DCM and TEA. A solution of DMT-Cl in DCM was added portion-wise. MeOH was added and the reaction was dried under reduced pressure. The residue was resuspended in toluene and separated from the salts, then purified by flash chromatography to afford the tritylated 56.

41 was dissolved in anhydrous THF. Sodium hydride was added to generate alkoxide. When the bubbling ceased, propargyl bromide was dissolved in THE and added portion-wise. Excess NaH was quenched with 1 mL MeOH, then diluted with water and extracted with DCM. The combined organic layers were dried under reduced pressure. The residue was resuspended in toluene, separated from remaining salts, and purified by flash chromatography to afford 57.

Product 57 was dissolved in MeOH and HCl was added. The reaction was incubated at room temperature overnight, then neutralized with sodium bicarbonate. It was concentrated under reduced pressure and purified by flash chromatography to afford 58.

Product 58 was dissolved in DCM and TEA. Benzoyl chloride was added and the reaction and incubated 60 minutes. The reaction was extracted from water with DCM and purified by flash chromatography to afford product 59.

Products 56 and 59 were dissolved in 9:1 DMSO:H2O. A solution of TBTA, sodium ascorbate and copper sulfate was added and the reaction was incubated 60 minutes. The reaction was extracted from water with DCM and purified by flash chromatography to afford product 60.

Products 60 and 55 were dissolved in 9:1 DMSO:H2O. A solution of TBTA, sodium ascorbate and copper sulfate was added and the reaction was incubated 60 minutes. The reaction was extracted from water with DCM and purified by flash chromatography to afford product 61.

Product 61 was dissolved in DCM and TEA. PPA-Cl was added and the reaction was incubated 15 minutes. The reaction was dried down under reduced pressure and resuspended in toluene with 1% TEA, then purified by flash chromatography. Phosphoramidite 62 was isolated and confirmed by 1H and 31P NMR.

A.

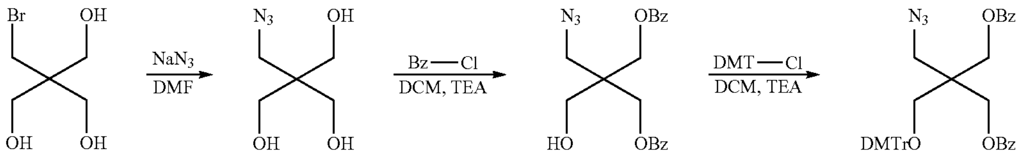

53 54 55 56

B.

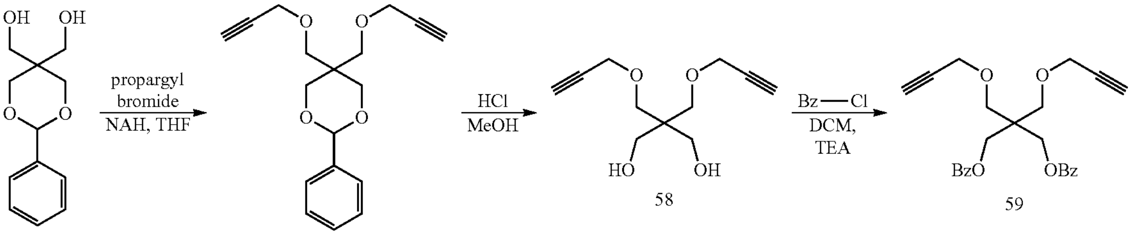

41 57 58 59

C. 56 + 59

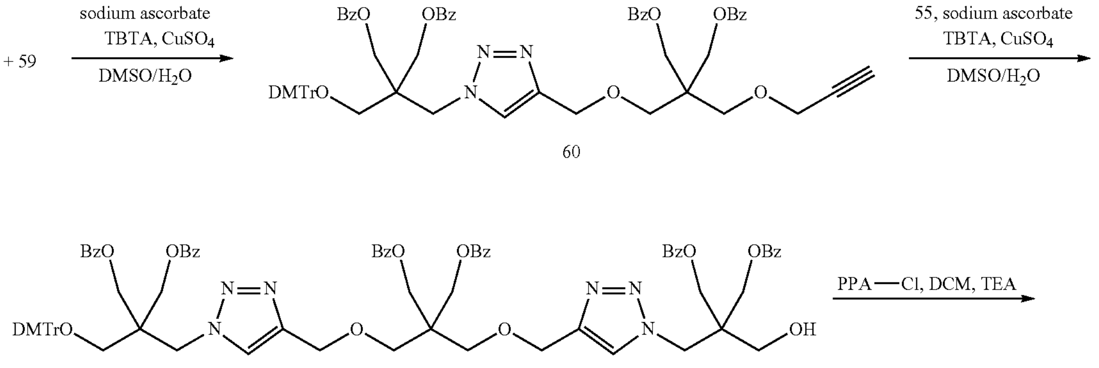

60

61

-continued

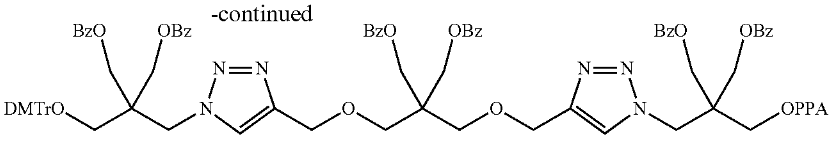

62

Example 14

Synthesis DMT Phosphoramidite of Enantiomer (9S,10S)-2,5,8,11,14,17-hexaoxaoctadecane-9,10-diol (Pendant Code C2 Bis-PEG-2 Phosphoramidite [Enantiomer]) (67)

A solution of (+)-2,3-O-Isopropylidene-L-threitol 63 in anhydrous DMF was slowly added to a mixture of NaH in anhydrous DMF (Note: vigorous evolution of H2 gas). When the bubbling ceased, mPEG2-Tos (Broadpharm Cat. No. BP-20983) was dissolved in DMF and added portion-wise to stir at ambient temperature overnight. The reaction mixture was poured over water, extracted with ethyl acetate and purified by flash chromatography to afford 64.

Product 64 was dissolved in MeOH and HCl was added. The solution was incubated 20 minutes, then neutralized with sodium bicarbonate and dried under reduced pressure. The residue was resuspended in ethyl acetate and purified by flash chromatography to afford 65.

Product 65 was dissolved in DCM and TEA. A solution of DMT-Cl in DCM was added portion-wise. The reaction was dried under reduced pressure. The residue was resuspended in toluene and separated from the salts, then purified by flash chromatography to afford 66.

Product 66 was dissolved in DCM and TEA. PPA-Cl was added and the reaction was incubated 15 minutes. The reaction was dried down under reduced pressure and resuspended in toluene with 1% TEA, then purified by flash chromatography. Phosphoramidite 67 was confirmed by 1H and 31P NMR.

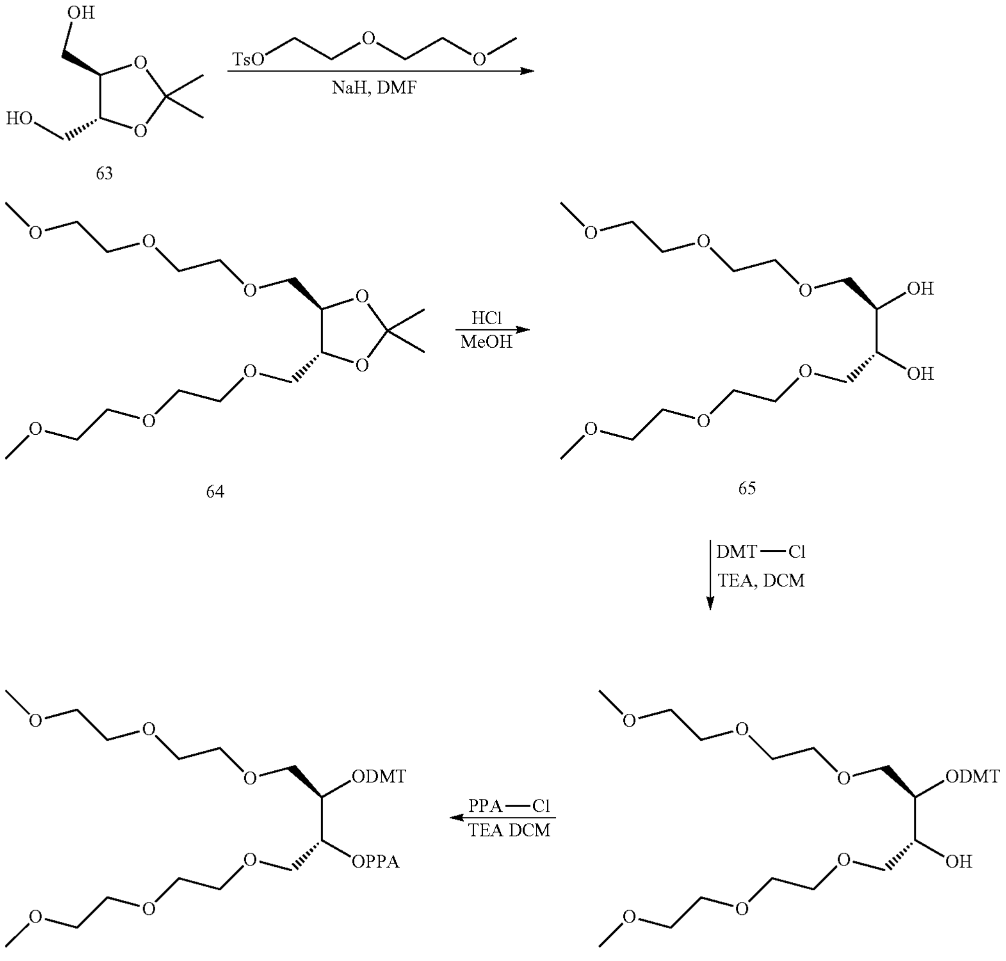

63

64

65

66

67

Example 15

Synthesis of 1-O-DMT-3-O-PPA-2,2-bis(Me-O-mPEG4)-propane (72)

To a solution of pentaerythritol (68, Cat. No. P0039, TCI) in DMF was added p-toluenesulfonic acid. The reaction was neutralized with triethylamine, concentrated and purified by flash chromatography to afford 69.

Product 69 was added to a stirring solution of EDC-HCl, DMAP and levulinic acid in THF and stirred overnight at ambient temperature. The solution was concentrated and purified by flash chromatography to afford 70.

Product 70 was dissolved in DCM and TEA. A solution of DMT-Cl in DCM was added portion-wise. The reaction was dried under reduced pressure. The residue was resuspended in toluene and separated from the salts, then purified by flash chromatography to afford 71.

Product 71 was dissolved in DCM and TEA. PPA-Cl was added and the reaction was incubated 15 minutes. The reaction was dried down under reduced pressure and resuspended in toluene with 1% TEA, then purified by flash chromatography. Phosphoramidite 72 was confirmed by 1H and 31P NMR.

TABLE 5-continued

| Code designator | sequence |
|---|---|
| L3 | DXLL44XXXLLLL |
| L4 | DXXL4444LLXXLL |

Key:
D = PEG6:
X = PEG3;
L = C2;
3 = clicked PEG-2;
4 = pendant PEG-4

The level discrimination (i.e. distinguishable electronic signal) and translocation time of each code was assessed by synthesizing an 100mer Xpandomer copy of a sequence derived from the HIV-2 genome that incorporates XNTPs in which each of the four XNTPs includes a unique code from the group set forth in Table 4. Xpandomer synthesis, processing, and nanopore sequence analysis were carried out as described in Applicants' PCT patent application no. PCT/US18/67763, which is herein incorporated by reference in its entirety. As a control, an Xpandomer copy of the same HIV-2 sequence incorporating different, known codes was sequenced in parallel. A representative trace illustrating the

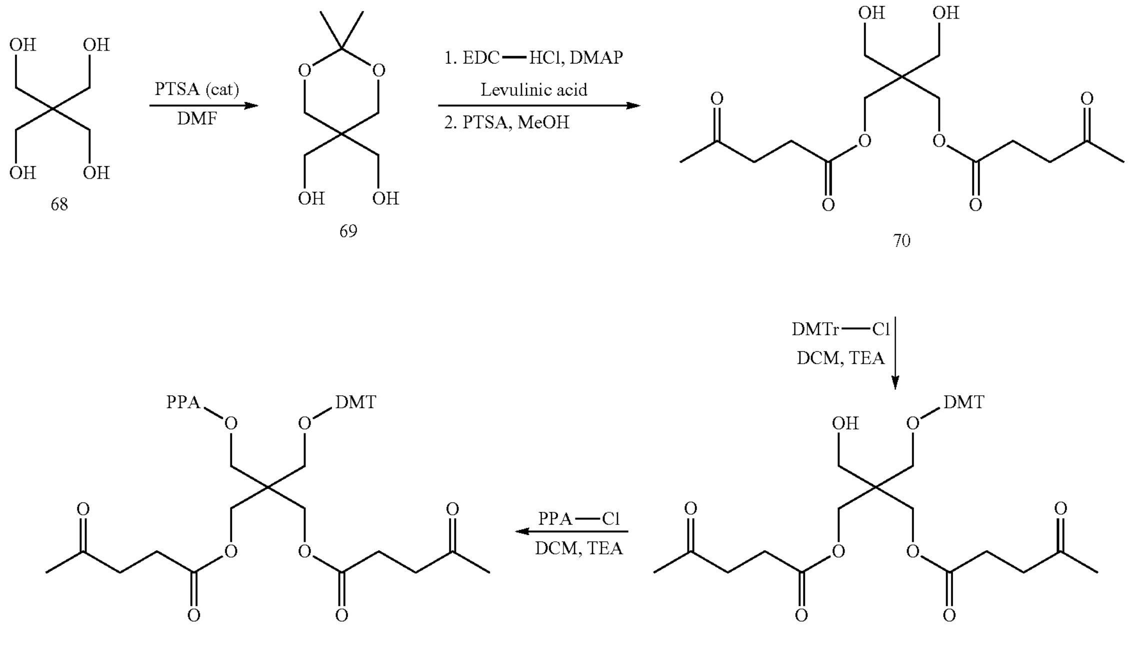

68
69
70
71
72

Example 16

Synthesis and Testing of PEG-Based Reporter Codes

In this Example, reporter codes were synthesized with PEG-based phosphoramidites; notably, these codes do not contain nucleotides. Four exemplary reporter codes are set forth in Table 5.

TABLE 5

Figure 13A:
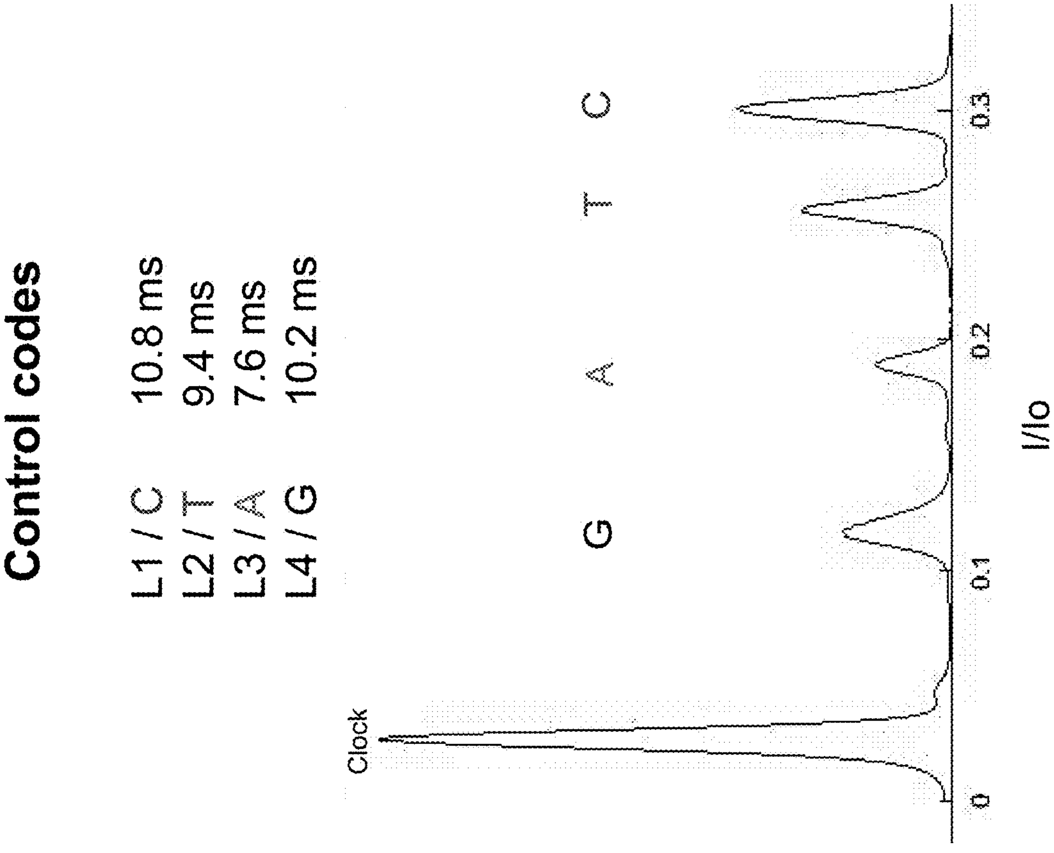
FIGS. 13A and 13B are representative traces depicting properties of reporter codes.
Figure 13B:
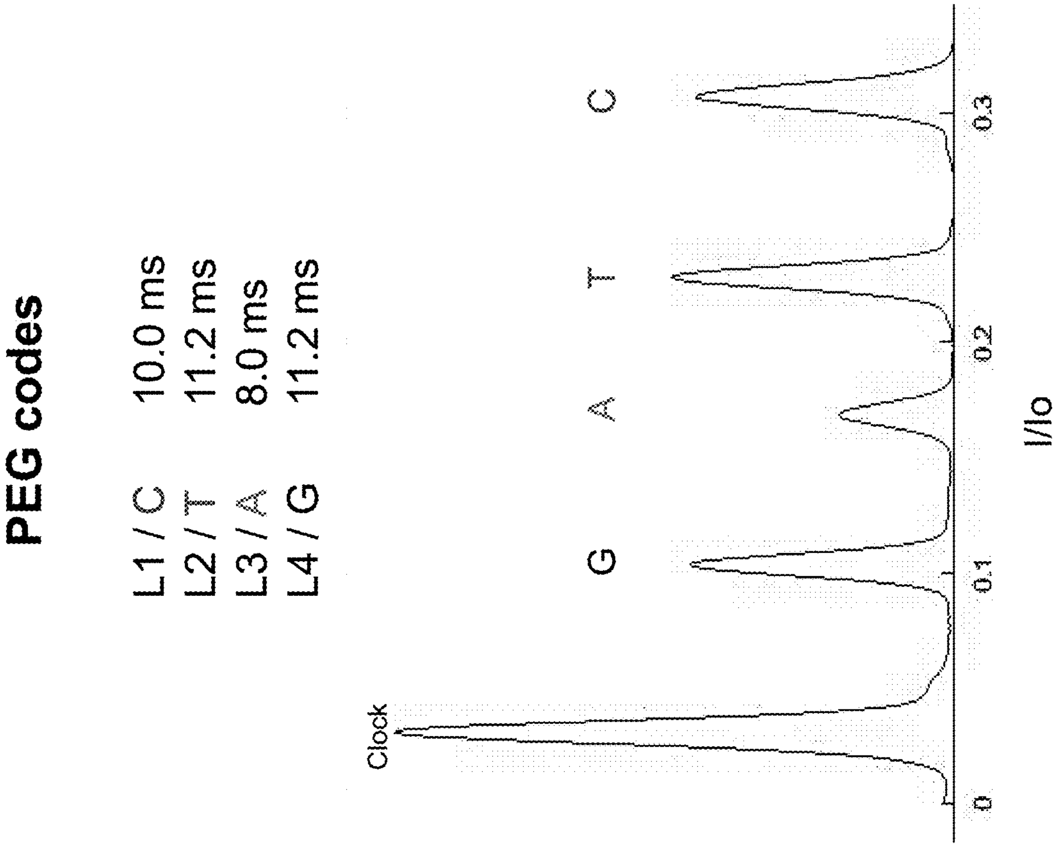

| Code designator | sequence |
|---|---|
| L1 | DDDLLLL |
| L2 | DXXX3LL3XXLL |

level discrimination and translocation time of each code is shown in FIGS. 13A (control—old codes) and 13B (test—new, PEG-based controls).

Figure 14A:
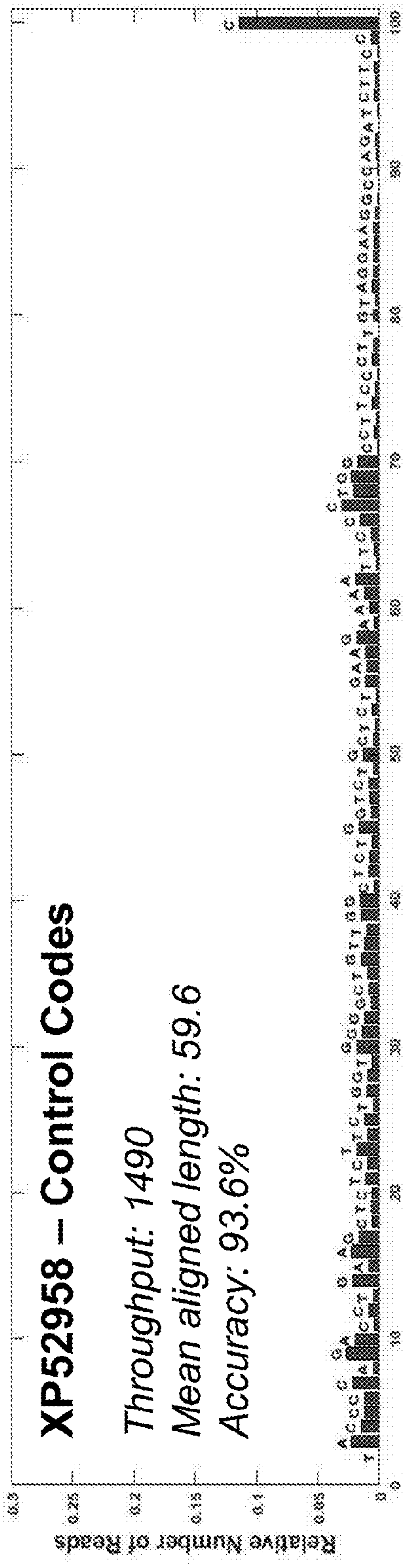
FIGS. 14A and 14B are histogram displays of populations of aligned reads of nanopore-derived sequences (SEQ ID NO:2).
Figure 14B:
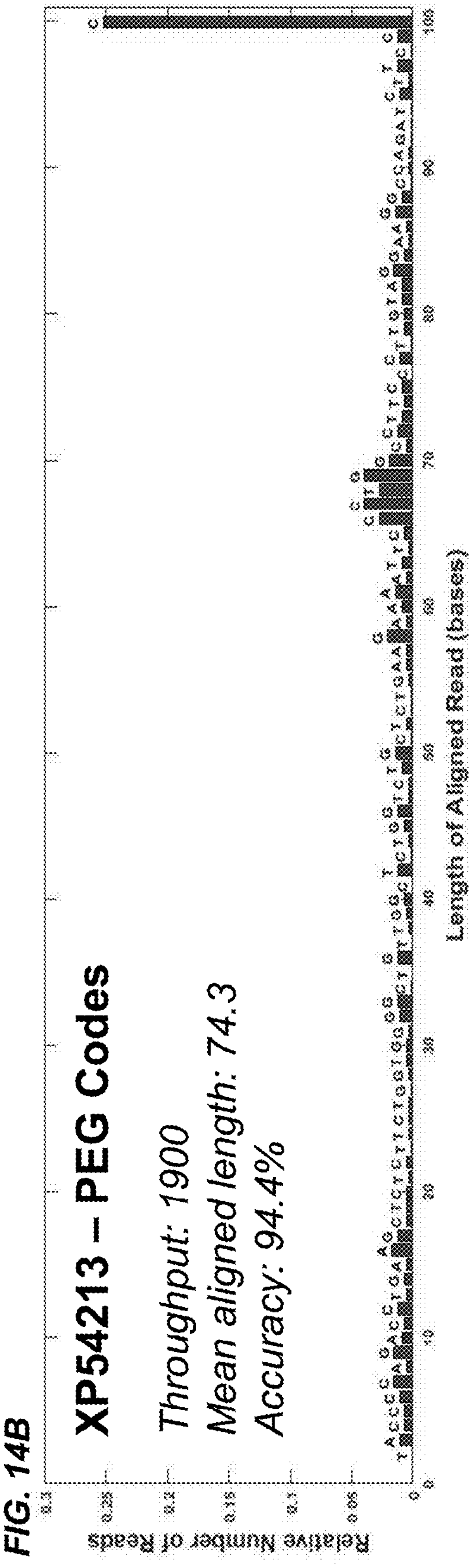

To assess the accuracy of the Xpandomer sequence information, sequence data was analyzed by histogram display of the population of sequence reads from the SBX reactions. The analysis software aligns each sequence read to the sequence of the template and trims the extent of the sequence at the end of the reads that does not align with the correct template sequence. Representative histograms of SBX sequencing of the 100mer template are presented in FIG. 14A (control) and FIG. 14B (new, PEG-based codes).

Notably, Xpandomers incorporating the nucleotide-free PEG-based codes yielded highly accurate sequence reads of this template.

Example 17

Translocation Control with Pendant PEG-Based TCEs—2 Code Levels

In this Example, translocation control with a TCE incorporating a pendant PEG phosphoramidite was assessed by using the SBX protocol to sequence a simple 60mer template consisting of TG dinucleotide repeats. Both XATP and XCTP substrates were designed to incorporate the following TCE: Y22222222222255, in which "Y" represents the symmetric phosphoramidite brancher; "2" represents pendant PEG2; and "5" represents benzofuran. The XATP substrate was designed to incorporate the following reporter code: DDDDDDDLLLL, in which "D" represents PEG6 and "L" represents C2. The XCTP substrate was designed to incorporate the following reporter code: DDDDXX44XXDL, in which "X" represents PEG3 and "4" represents pendant PEG4.

To produce Xpandomer copies of the 60mer template, primer extension reactions were conducted using 4 μm of an extension oligonucleotide and 250 μm of each XNTP. The 10 μL extension reaction included the following reagents: 50 mM TrisCl, pH 8.84, 200 mM $NH_4OAc$, 20% PEG8K, 5% NMS, 0.75 nmol polyphosphate PP-60.20, 2 μg SSB, 0.5M urea, 5 mM PEM additive (suitable Polymerase Enhancing Molecules are disclosed in Applicants' pending PCT patent application no. PCT/US18/67763, which is herein incorporated by reference in its entirety), and 1.2 μg purified recombinant DNA polymerase (suitable engineered variants of DPO4 polymerase are disclosed in Applicants' PCT patent application nos WO2017/087281, PCT/US2018/030972, and PCT/U.S. Pat. No. 1,864,794, which are herein incorporated by reference in their entireties) The extension reaction was run for 30 minutes at 42° C.

Xpandomer products of the extension reactions were next sequenced using the SBX protocol. Briefly, the constrained Xpandomer products were cleaved to generate linearized Xpandomers. This was accomplished by first quenching the extension reaction and subjecting the Xpandomers to amine modification with 2M succinic anhydride. The phosphoramidate bonds of the Xpandomers were then cleaved by treating the sample with 11.7M DCl for 30 minutes at 23° C. Linearized Xpandomers were purified by ethanol precipitation and resuspended in a buffer supplemented with 34% ACN and 15% DMF.

For sequencing, Xpandomers were added to a sample buffer of 2.8M $NH_4Cl$, 1.2M GuanCl, 20 mM NaHex, 10% DMF, 2 mM EDTA, and 20 mM HEPES pH 7.4. Protein nanopores were prepared by inserting a-hemolysin into a DPhPE/hexadecane bilayer member in a buffer containing 2 M $NH_4Cl$ and 100 mM HEPES, pH 7.4. This experiment used buffers of 0.4M $NH_4Cl$, 600 mM GuanCl, and 100 mM HEPES, pH 7.4 in the cis well and 2M NH4Cl and 100 mM HEPES, pH 7.4 in the trans well of the detection system. The Xpandomer sample was heated to 70° C. for 2 minutes, cooled completely, followed by addition of 2 μL of the sample to the cis well. The voltage parameters run were as follows: 60 mV/300 mV/10 μs/2 ms (read voltage/pulse voltage/pulse voltage duration/pulse frequency). Data were acquired via Labview acquisition software. A representative trace from this run is shown in FIG. 15.

Figure 15:
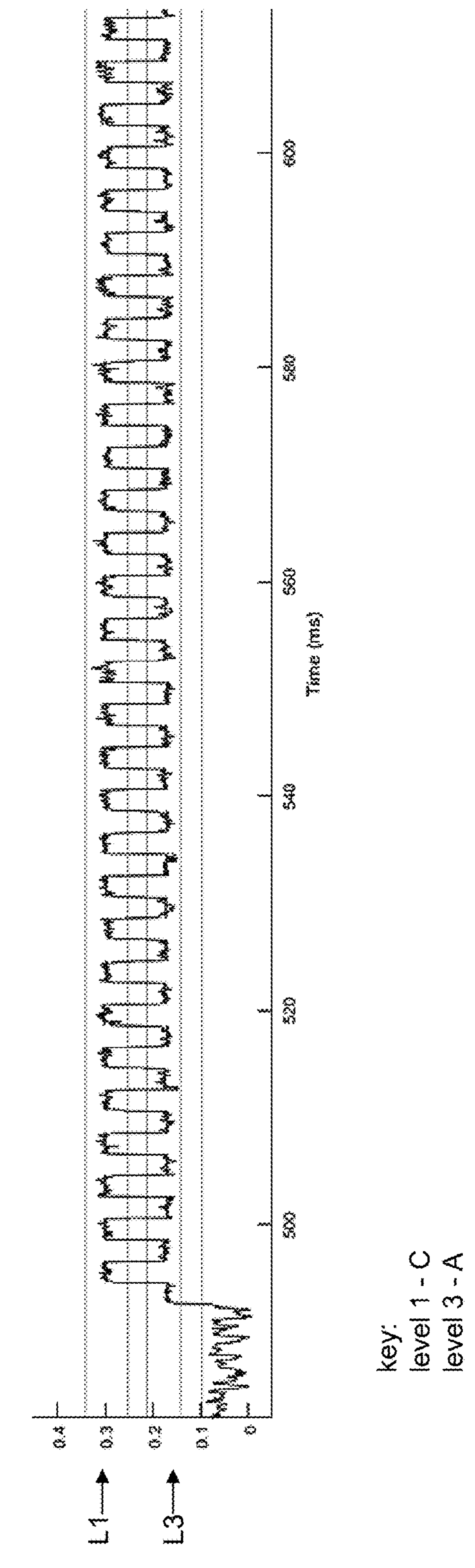
FIG. 15 is a representative trace showing the sequence of a simple DNA template (SEQ ID NO:3).

As shown by the level numbers superimposed above the trace in FIG. 15, all reporter codes were read correctly by the detection system in this experiment, demonstrating 100% accuracy. The absence of deletion or insertion errors validates the efficacy of pendant PEG-based TCEs as structures enabling tight regulation of Xpandomer translocation. Significantly, with the pendant PEG-based TCE used in this experiment, transitions between the two code levels was observed following a single voltage pulse. The ability to transition between sequential reporter codes of the Xpandomer with single voltage pulses is a significant advancement in the art and enables a much higher sequencing throughput.

Example 18

Sequencing by Expansion with Pendant PEG-Based TCEs-4 Code Levels

In this Example, translocation control with a TCE incorporating a pendant PEG phosphoramidite was assessed by using the SBX protocol to sequence a 60mer template consisting of repeats of the sequence, CATG. All XNTP substrates were designed to incorporate the following TCE: Y4444444444444455, in which "Y" represents the symmetric phosphoramidite brancher; "4" represents pendant PEG4; and "5" represents benzofuran. The XATP substrate was designed to incorporate the following reporter code: DDDDDDDLLDX; the XCTP substrate was designed to incorporate the following reporter code: DDDDDDDLLLL; the XTTP substrate was designed to incorporate the following reporter code: DDDDDD44LXXX; and the XGTP substrate was designed to incorporate the following reporter code: DDDDXXL444444XLLLL, in which "D" represents PEG6, "L" represents C2, "X" represents PEG3 and "4" represents pendant PEG4.

To produce Xpandomer copies of the 60mer template, primer extension reactions were conducted using 4 μm of an extension oligonucleotide and 1000 μm of each XNTP and. The 10 μL extension reaction included the following reagents: 50 mM TrisCl, pH 8.84, 200 mM NH4OAc, 20% PEG8K, 10% NMP, 3 nmol polyphosphate PP-60.20, 2 μg SSB, 1M urea, 10 mM PEM additive, and 1.8 μg purified recombinant DNA polymerase. The extension reaction was run for 30 minutes at 37° C.

Xpandomer products of the extension reactions were next sequenced using the SBX protocol. Briefly, the constrained Xpandomer products were cleaved to generate linearized Xpandomers. This was accomplished by first quenching the extension reaction and subjecting the Xpandomers to amine modification with 2M succinic anhydride. The phosphoramidate bonds of the Xpandomers were then cleaved by treating the sample with 11.7M DCl for 30 minutes at 23° C. Linearized Xpandomers were purified by ethanol precipitation and resuspended in a buffer supplemented with 34% ACN and 15% DMF.

For sequencing, Xpandomers were added to a sample buffer of 0.8M NH4Cl, 1.2M GuanCl, and 200 mM HEPES, pH 7.4. Protein nanopores were prepared by inserting α-hemolysin into a DPhPE/hexadecane bilayer member in a buffer containing 2 M NH4Cl and 100 mM HEPES, pH 7.4. This experiment used buffers of 0.4M NH4Cl, 600 mM GuanCl, and 100 mM HEPES, pH 7.4 in the cis well and 2M NH4C1 and 100 mM HEPES, pH 7.4 in the trans well. The Xpandomer sample was heated to 70° C. for 2 minutes, cooled completely, followed by addition of 2 μL of the sample to the cis well. The voltage parameters run were as follows: 70 mV/650 mV/6 μs/1.5 ms (read voltage/pulse voltage/pulse voltage duration/pulse frequency). Data were acquired via Labview acquisition software. A representative trace from this run is shown in FIG. 16

Figure 16:
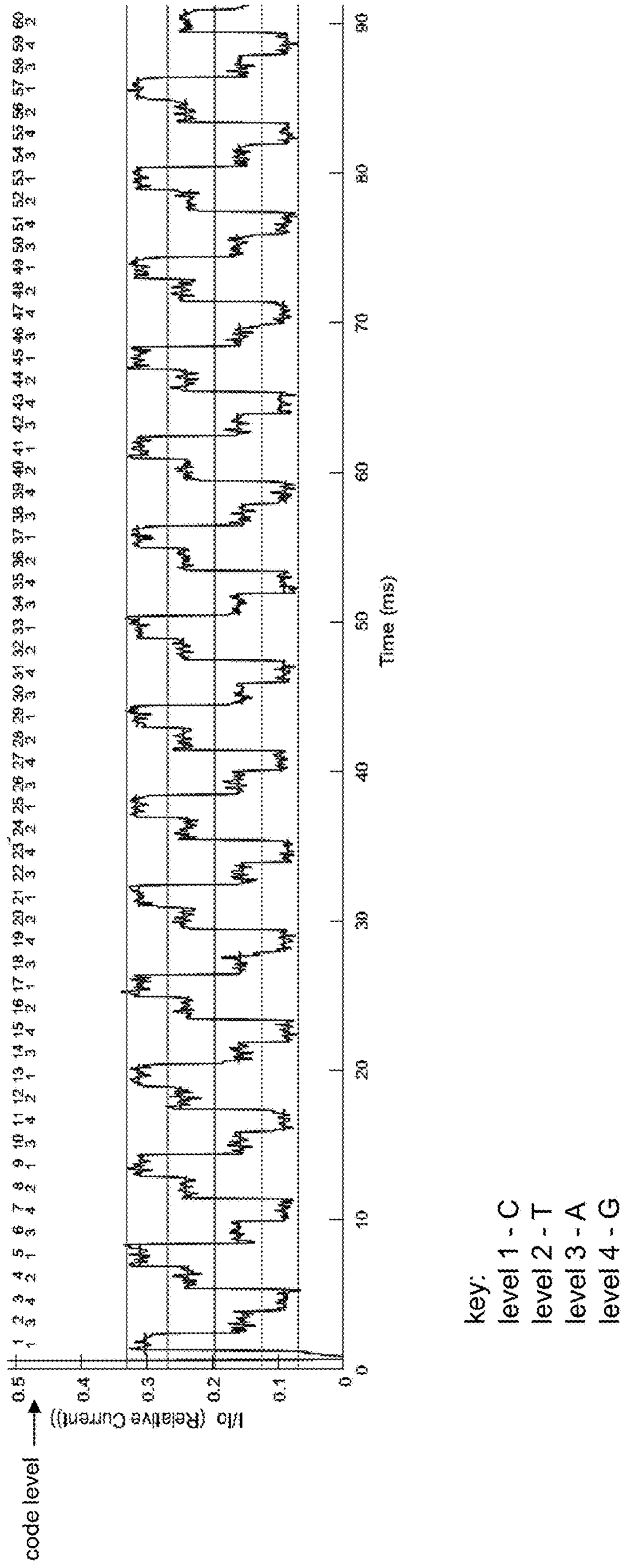
FIG. 16 is a representative trace showing the sequence of a CAGT repeat DNA template (SEQ ID NO:4).

The level numbers superimposed above the trace in FIG. 16 correspond to the signals generated by the XCTP code (L1), the XTTP code (L2), the XATP code (L3) and the XGTP code (L4). In this experiment, all reporter codes were read correctly by the detection system, demonstrating 100% accuracy. The absence of deletion and insertion errors underscores the efficacy of pendant PEG-based TCEs in transiently pausing reporter codes in the pore channel to produce accurate signal reads during the "read voltage" and allowing resumption of translocation during the "pulse voltage". Again, with the pendant PEG-based TCE used in this experiment, transitions between sequential reporter codes was achieved with single voltage pulses. Of note, the same level of accuracy was observed in separate runs of aliquots the of the same Xpandomer sample using the following voltage parameters: 65/700/6/1.5; 65/650/6/1.5; 60/650/6/1.5 and 60/600/6/1.5. It was further observed that the throughput of codes reads can be influenced by various voltage parameters.

Example 19

Sequencing by Expansion of a Complex Template with Pendant PEG-Based TCEs

In this Example, translocation control with a TCE incorporating a pendant PEG phosphoramidite was assessed by using the SBX protocol to sequence a complex 100mer template. Each XNTP substrate was synthesized with the following TCE: Y22222222222255, in which "Y" represents the symmetric phosphoramidite brancher; "2" represents pendant PEG2; and "5" represents benzofuran. The XNTP substrates were synthesized with the following reporter codes: (XC)DDDDDDLLLL, in which "D" represents PEG6 and "L" represents C2; (XT)DDDDDD44LDX, in which "X" represents PEG3 and "4" represents pendant PEG4; (XA)DDDDXX44XXDL; and (XG)DDDDXXL.

To produce Xpandomer copies of the 100mer template solid-state primer extension reactions were conducted using 1 pmol of XATP and XCTP and 1.5 pmol of XGTP and XTTP (solid-state Xpandomer synthesis in which the extension oligo is covalently bound to a chip substrate is described in Applicants' provisional patent application no. 62/826,805, which is herein incorporated by reference in its entirety). The 50 μL extension reaction included the following reagents: 50 mM TrisCl, pH 8.84, 200 mM NH4OAc, 20% PEG8K, 10% NMP, 15 pmol polyphosphate PP-60.20, 10 μg SSB, 1M urea, 10 mM PEM additive and 9 g purified recombinant DNA polymerase. The extension reaction was run for 30 minutes at 37° C.

Xpandomer products were next sequenced using the SBX protocol. Briefly, the constrained Xpandomer products were cleaved to generate linearized Xpandomers. This was accomplished by first quenching the extension reaction and subjecting the Xpandomers to amine modification with succinic anhydride. The phosphoramidate bonds of the Xpandomers were then cleaved by treating the sample with 7.5M DCl for 30 minutes at 23° C. Linearized Xpandomers were released from the chip substrate by photocleavage of the extension oligonucleotide and recovered in elution buffer supplemented with 15% ACN and 5% DMSO (20% final solvent).

For sequencing, Xpandomers were added to a sample buffer of 0.8M $NH_4Cl$, 1.2M GuCl, 200 mM HEPES; pH 7.4. Protein nanopores were prepared by inserting a-hemolysin into a DPhPE/hexadecane bilayer member in a buffer of 2 M $NH_4Cl$ and 100 mM HEPES, pH 7.4. The cis well was perfused with buffer containing 0.4M NH4Cl, 600 mM GuanCl, 100 mM HEPES; pH 7.4 and the trans well was perfused with a buffer containing 2M NH4Cl, 100 mM HEPES; pH 7.4. The Xpandomer sample was heated to 70° C. for 2 minutes, cooled completely and vortexed, then a 2 μL aliquot was added to the cis well. The voltage parameters were run as follows: 60 mV/600 mV/6 μs/1.5 ms (read voltage/pulse voltage/pulse voltage duration/pulse frequency). Data were acquired via Labview acquisition software. A representative trace from this run is shown in FIG. 17.

Figure 17:
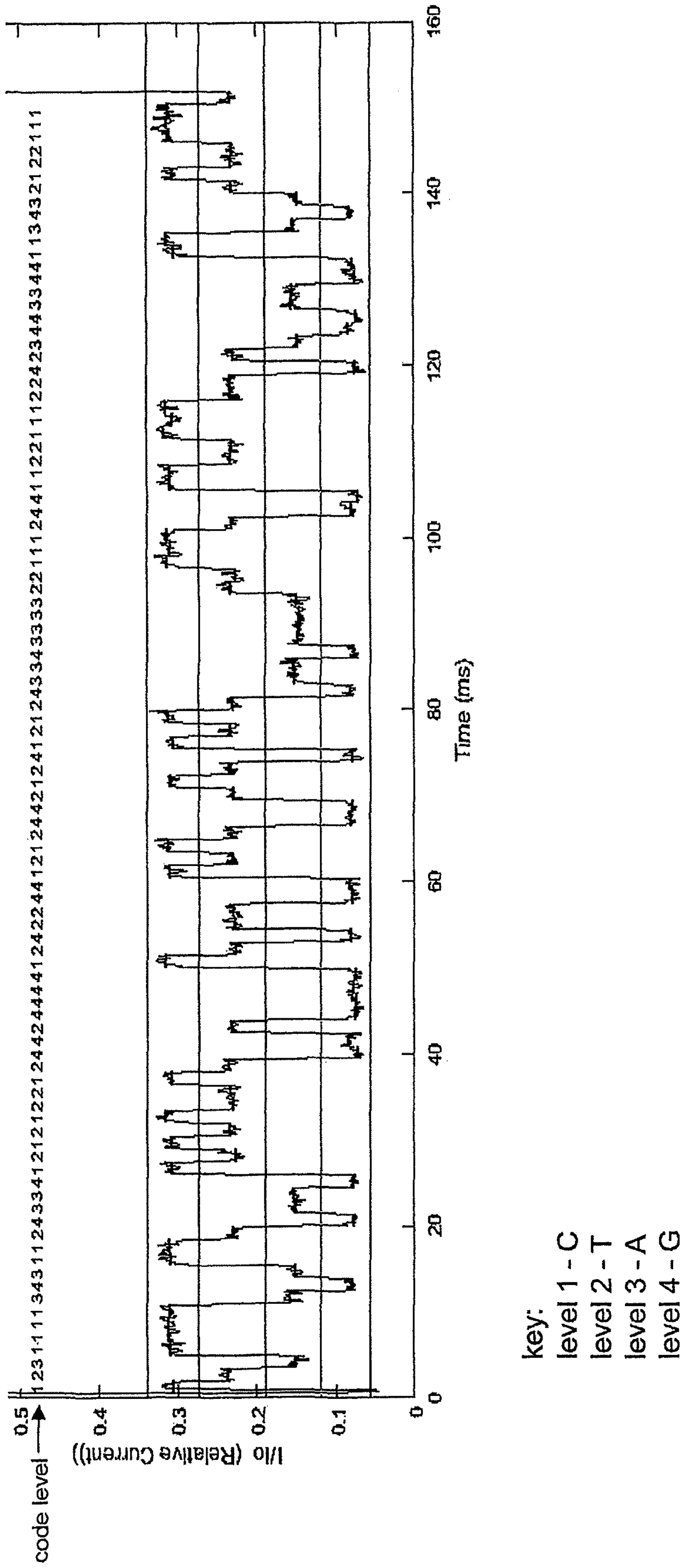
FIG. 17 is a representative trace showing the sequence of a complex DNA template (SEQ ID NO:5).

As shown in FIG. 17, the sequence of all reporter codes was read correctly by the detection system in this experiment, demonstrating 100% accuracy. The absence of deletion or insertion errors again validates the efficacy of pendant PEG-based TCEs as structures enabling highly reliable sequence reads of a polymeric template. Significantly, runs of homopolymers were accurately sequenced under these conditions (see, e.g., the sequence of 4×L1 codes near the start of the trace shown in FIG. 14), thereby highlighting the accuracy of SBX with pendant PEG-based TCEs.

Example 20

Sequencing by Expansion of a Complex 222Mer Template with Pendant PEG-Based TCEs In this Example, translocation control with pendant PEG-based TCEs was assessed by using the SBX protocol to sequence a complex 222mer template. Each XNTP substrate was synthesized to include the following TCE: Y44444444444455, in which "Y" represents the symmetric phosphoramidite brancher; "4" represents pendant PEG-4; and "5" represents benzofuran. The XNTP substrates were synthesized with the following reporter codes: (XC)DDDDDDLLLDX; (XT)DDDDDD44LXXX; (XA)DDDDDD444LLDX; and (XG)DDDDXXL444444XLLLL, in which "D" represents PEG-6, "L" represents C2, "X" represents PEG-3, and "4" represents pendant PEG-4.

To produce Xpandomer copies of the 222mer template, solid-state primer extension reactions were conducted using 1.25 pmol of each XNTP, 10 pmol template and 20 pmol E-oligo primer (solid-state Xpandomer synthesis in which the extension oligo is covalently bound to a chip substrate is described in Applicants' provisional patent application no. 62/826,805, which is herein incorporated by reference in its entirety). The 50 μL extension reaction included the following reagents: 50 mM TrisCl, pH 8.84, 200 mM $NH_4OAc$, 20% PEG8K, 8% NMP, 15 nmol polyphosphate PP-60.20, 10 μg SSB, 1M urea, 5 mM PEM additive and 9 μg purified recombinant DNA polymerase. The extension reaction was run for 30 minutes at 37° C.

Xpandomer products were next sequenced using the SBX protocol. Briefly, the constrained Xpandomer products were washed in buffer B.001 (1% Tween-20/3% SDS/5 mM HEPES, pH 8.0/100 mM $NaPO_4$/15% DMF) and cleaved to generate linearized Xpandomer by adding 200 μl buffer C.001 (7.5M DCl) and incubating for 30 minutes at 23° C. The sample was then neutralized by adding 1000 μl buffer B.001. The Xpandomer sample was then subjected to amine modification by adding 666 mol succinic anhydride and incubating for 5 minutes at 23° C. The sample was then washed in buffer D.094 (50% ACN) and the Xpandomers were released from the substrate by photocleavage and stored in buffer AG497 (0.8M NH4Cl/1.2M GuanCl/200 mM HEPES, pH 7.4)

Protein nanopores were prepared by inserting α-hemolysin into a DPhPE/hexadecane bilayer member in a buffer of 2 M NH4Cl and 100 mM HEPES, pH 7.4. The cis well was perfused with buffer containing 0.4M NH4Cl, 600 mM GuanCl, 100 mM HEPES; pH 7.4 and the trans well was perfused with a buffer containing 2M NH4Cl, 100 mM HEPES; pH 7.4. The Xpandomer sample was heated to 70° C. for 2 minutes, cooled completely and vortexed, then a 2 μL aliquot was added to the cis well. The voltage parameters were run as follows: 60 mV/650 mV/6 μs/1.0 ms (read voltage/pulse voltage/pulse voltage duration/pulse frequency). Data were acquired via Labview acquisition software. A representative trace from this run is shown in FIG. 18.

Figure 18:
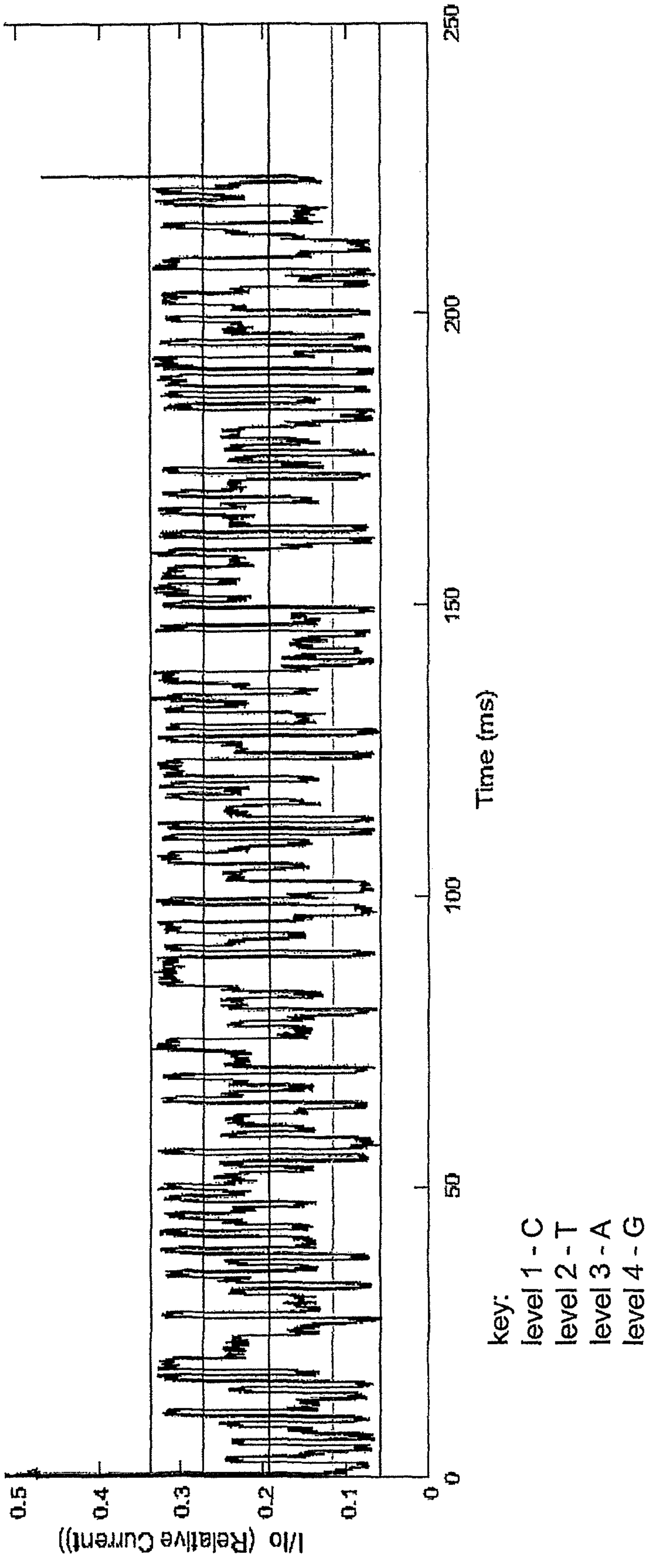
FIG. 18 is a representative trace showing the sequence of a complex DNA 222mer template (SEQ ID NO:6).

As shown in FIG. 18, the sequence of all reporter codes was read correctly by the detection system in this experiment, demonstrating 100% accuracy. The absence of deletion or insertion errors again validates the efficacy of pendant PEG-based TCEs as structures enabling highly reliable sequence reads of a polymeric template. Again, runs of homopolymers were accurately sequenced under these conditions, thus underscoring the accuracy of SBX with pendant PEG-based TCEs.

Example 21

Sequencing by Expansion of a Complex 222Mer Template with Pendant PEG-Based TCEs and D-Cells In this Example, translocation control with pendant PEG-based TCEs and D-cell features was assessed by using the SBX protocol to sequence a complex 222mer template. Each XNTP substrate was synthesized to include the following TCE: Y(32)(32)(32)(32)(32)(32)(61)(61)(61)(61)(61)(61), in which "Y" represents the symmetric phosphoramidite brancher; "32" represents pendant mPEG4 (PPA032); and 61" represents pendant PEG (PPA061). Each XNTP also included the following D-cell feature: D(63)D(63)D(63)DD in which "D" represents PEG6 and "63" represent pendant PEG (PPA063). The XNTP substrates were synthesized with the following reporter codes: (XC)DDLLLX; (XT)LXXX; (XA)DD(32)(32)(32)LLLLLLL; and (XG)XXL(32)(32)(32)(32)(32)(32)LLLLLLL, in which "D" represents PEG-6, "L" represents C2, "X" represents PEG-3, and "32" represents pendant mPEG-4 (PPA032).

To produce Xpandomer copies of the 222mer template, solid-state primer extension reactions were conducted using 5000 pmol of each XNTP, 4 pmol template and 20 pmol E-oligo primer (solid-state Xpandomer synthesis in which the extension oligo is covalently bound to a chip substrate is described in Applicants' provisional patent application no. 62/826,805, which is herein incorporated by reference in its entirety). The 50 μL extension reaction included the following reagents: 50 mM TrisCl, pH 8.84, 200 mM NH4OAc, 50 mM GuCl20% PEG8K, 10% NMP, 15 nmol polyphosphate PP-60.23, 2.5 μg Kod SSB, 0.1M urea, 15 mM PEM additive and 13 μg purified recombinant DNA polymerase (a variant of DPO4 polymerase). The extension reaction was run for 60 minutes at 37° C.

Xpandomer products were next sequenced using the SBX protocol. Briefly, the constrained Xpandomer products were washed in buffer B.064 (1% Tween-20/3% SDS/5 mM HEPES, pH 8.0/100 mM NaPO4/15% DMF) and cleaved to generate linearized Xpandomer by adding 200 μl buffer C.001 (7.5M DCl) and incubating for 30 minutes at 23° C. The sample was then neutralized by adding 2000 μl buffer B.064 and incubating for 2' at RT. The Xpandomer sample was then subjected to amine modification by adding 500 gmol succinate anhydride in buffer B.065 and incubating for 5 minutes at 23° C. The sample was then washed in buffer D.102 (50% ACN) and the Xpandomers were released from the substrate by photocleavage and eluted in 60 μl elution buffer.

Protein nanopores were prepared by inserting α-hemolysin into a DPhPE/hexadecane bilayer member in a buffer of 2 M NH4Cl and 100 mM HEPES, pH 7.4. The cis well was perfused with buffer AG242 containing 0.4M NH4Cl, 600 mM GuanCl, 100 mM HEPES; pH 7.4, and 5% glycerol and the trans well was perfused with buffer AB080 containing 0.4M NH4Cl, 600 mM GuanCl, 5% ethyl acetate, 10 mM HEPES; pH 7.4. The Xpandomer sample was heated to 70° C. for 2 minutes, cooled completely and vortexed, then a 2 μL aliquot was added to the cis well. The voltage parameters were run as follows: 70 mV/625 mV/6 μs/1.0 ms (read voltage/pulse voltage/pulse voltage duration/pulse frequency). Data were acquired via Labview acquisition software.

Figure 19:
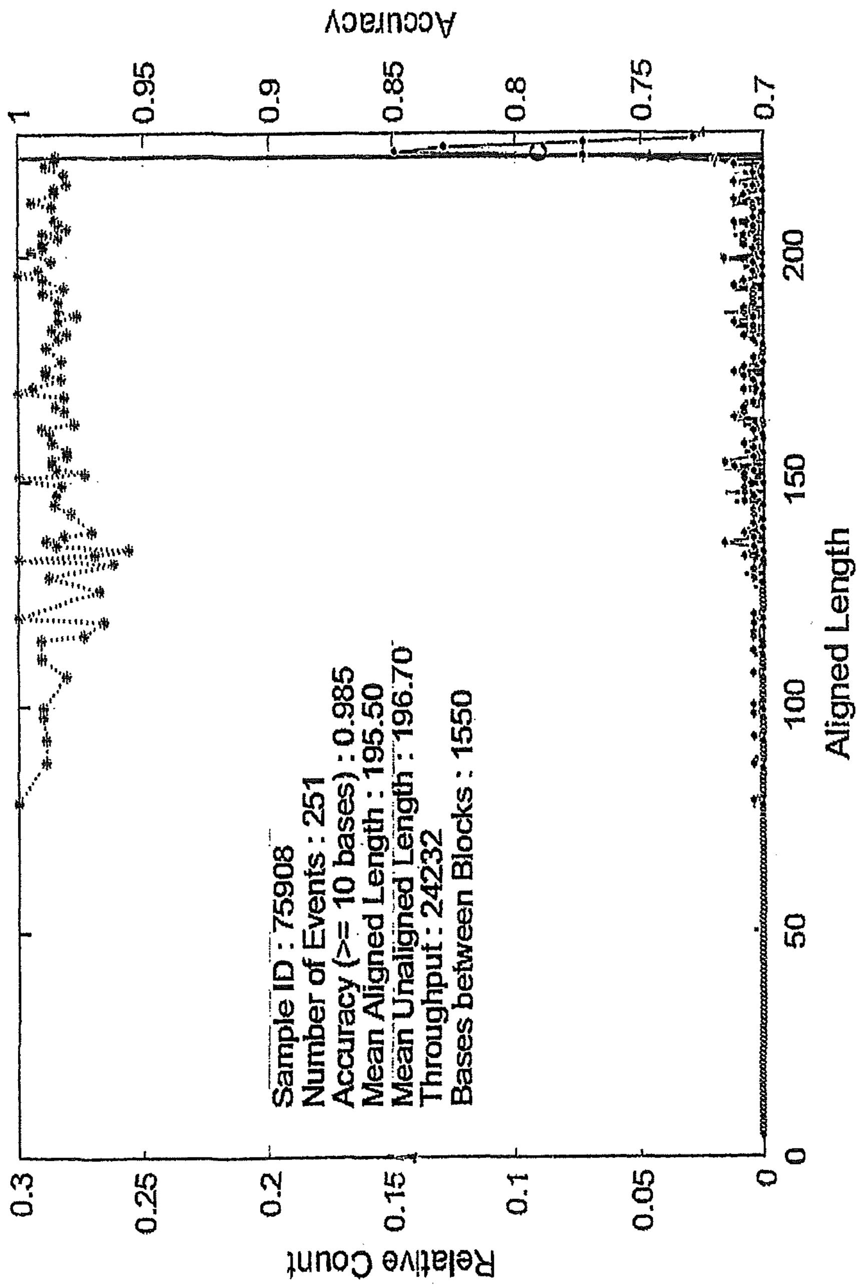
FIG. 19 is a histogram display of a population of aligned reads of nanopore-derived sequences.

To assess the accuracy of the Xpandomer sequence information, sequence data was analyzed by histogram display of the population of sequence reads from the SBX reaction. The analysis software aligns each sequence read to the sequence of the template and trims the extent of the sequence at the end of the reads that does not align with the correct template sequence. A representative histogram of SBX sequencing of the 222mer template is presented in FIG. 19. As can be seen, the SBX experiment generated highly accurate reads of the 222mer template. Notably, the throughput of this experiment was outstanding. These results suggest that SSRTs incorporating pendant PEG-based TCE and D-cell features provide highly accurate and efficient control of Xpandomer translocation through the nanopore.

Example 22

Ratcheting

Figure 20A:
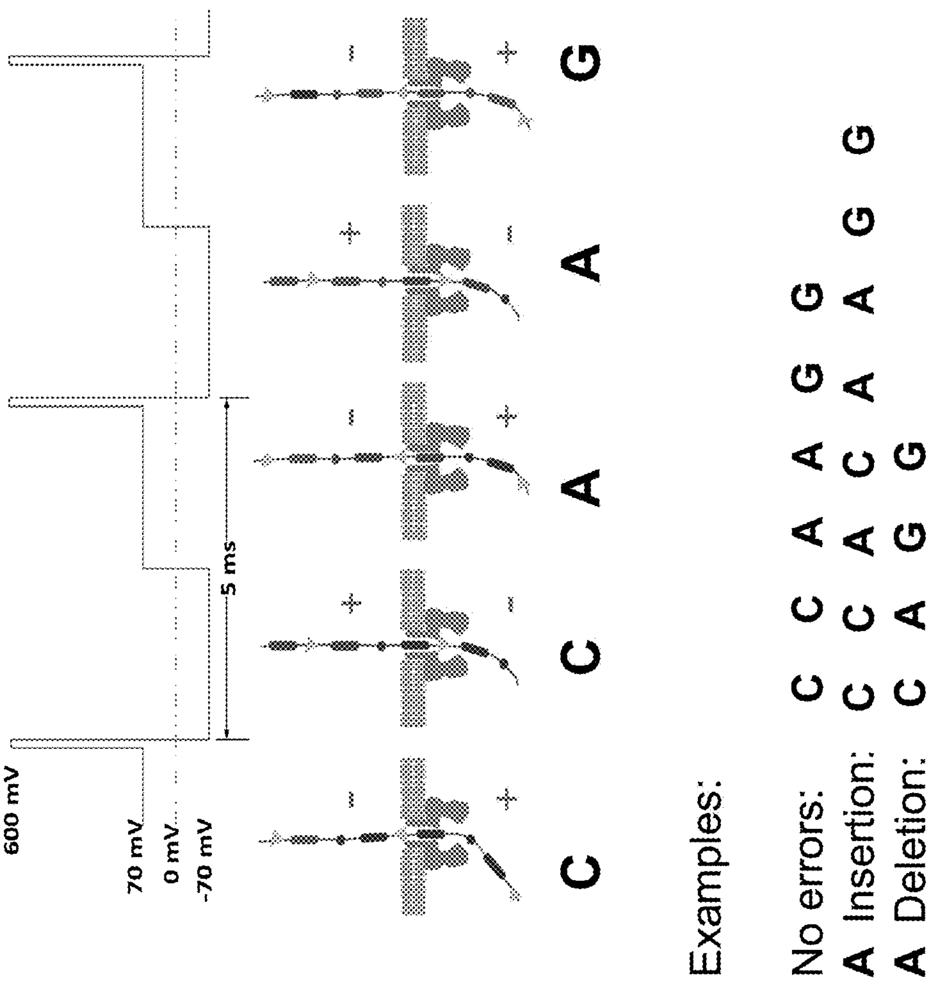
FIG. 20A is a schematic illustrating one embodiment of an Xpandomer subjected to ratcheting through a nanopore.

In this example of ratcheting a single hemolysin nanopore is prepared in a lipid bilayer with vestibule on the trans-side and having reagent mix composed of 0.4M NH4Cl, 600 mM GuanCl, 100 mM HEPES; pH 7.4 in the cis reservoir and 2M NH4Cl, 100 mM HEPES; pH 7.4 in the trans reservoir. Current passing between Ag/AgCl electrodes located in each reservoir is measured by an Axopatch 200B amplifier and digitized at 100k samples/s. To drive the current through the nanopore, a square wave with 50% duty cycle alternating between +70 mV and −50 mV is applied to the trans reservoir along with a 6 μs pulse of +600 mV applied between the transition from positive to negative voltage (all voltages referenced to the cis reservoir potential). With this applied pulse train, assuming ideal translocation with no deletions or insertions, both reporters for each XNTP in incorporated into an Xpandomer are measured, one with +70 mV and the other with −50 mV. Having two measurements for each base provides redundancy that can provide higher confidence in matched results and also help identify deletions and insertions in non-homopolymer sequence. FIG. 20A illustrates how the cycles of +70 mV/600 mV pulse/-50 mV influence Xpandomer translocation through the nanopore and results in two measurements for the C code followed by two measurements for the A code (and the 1 first measurement for the G code). The pattern code shows how in this non-homopolymer sequence (SEQ ID NO:7), the 2 reporter measurements for each base can be used to identify insertions (SEQ ID NO:8) and deletions (SEQ ID NO:9).

Insertions and deletions are caused when the Xpandomer does not advance to the next reporter (in the nanopore) or it skips the next reporter, respectively.

Figure 20B:
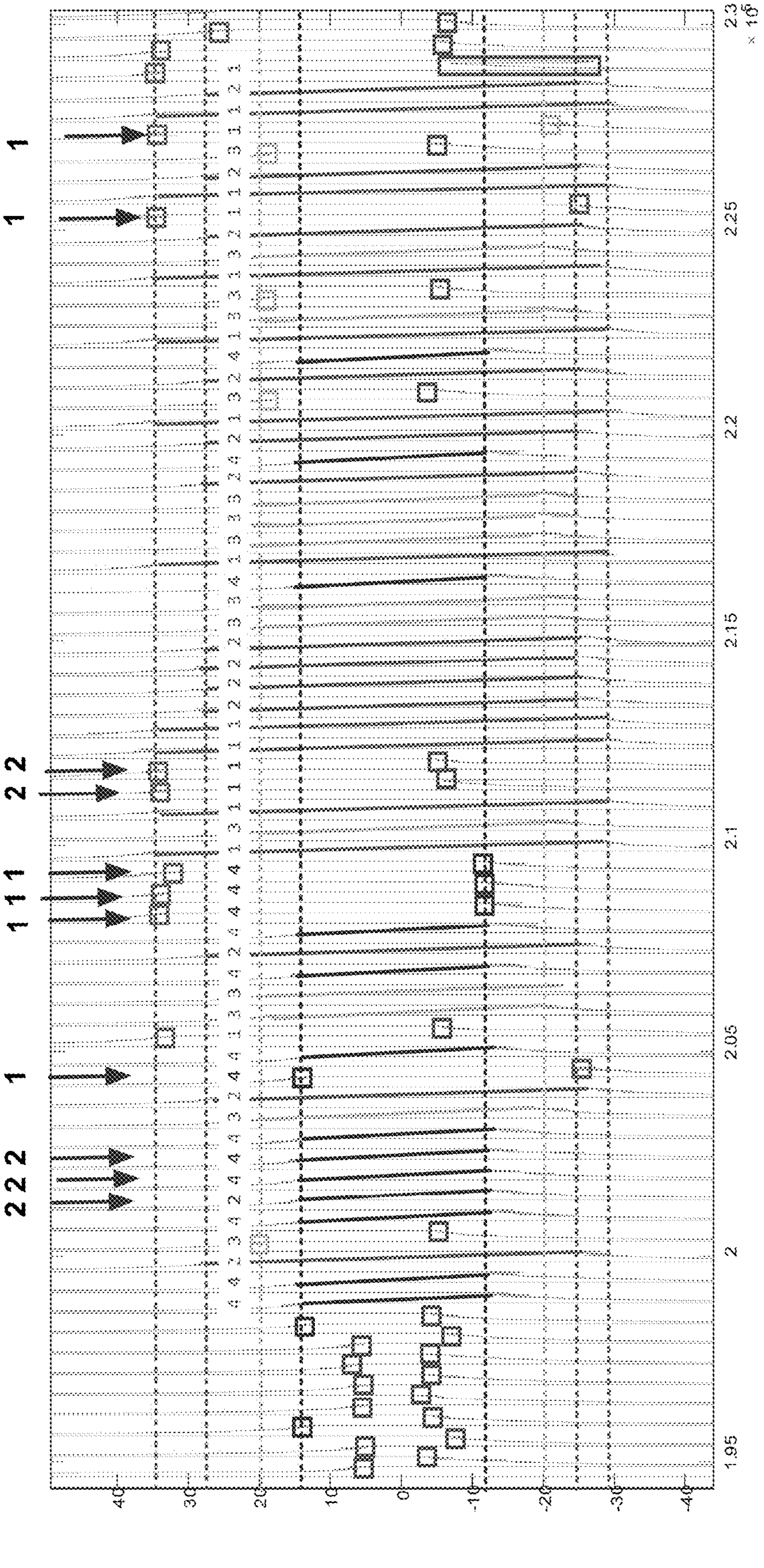
FIG. 20B is an example of the current measurement for a translocating Xpandomer subjected to ratcheting.

Using an SBX synthesis and purification protocol, an Xpandomer sample generated from a synthetic DNA template of known sequence was introduced to the cis reservoir and measurement proceeded. An example of the current measurement for a translocating Xpandomer is shown in FIG. 20B. The graph is scaled so the four reporter current levels from +70 mV measurements (14, 20, 27 and 35 pA) and the 4 four reporter current levels from −50 mV measurements (−12, −20, −25 and −29 pA) are shown as indicated by horizontal dashed lines. The data is aligned to the expected DNA template sequence (SEQ ID NO:10) and indicated by the numeric sequence on the graph. Each of the four numbers refers to a base. The blue sequence number indicates a confirmed base match to the template. The arrows depict errors. The arrows designated with the number 1 are non-homopolymer insertions that can be recognized because of the basecall indicated the Xpandomer did not advance. The arrows designated with the number 2 indicate homopolymer insertions that are not recognized since the basecalls are all the same level.

Example 24

Synthesis of Fluoroarabinosyl XNTP Epimers

This Example describes the synthesis of 2' fluoro (F) epimers of each XNTP (2' FANA XNTPs). These epimers are based on fluorinated nucleosides, referred to as "fluoroarabinosyl nucleic acids" (FANA). It is predicted that the 2' F epimers will demonstrate increased stability during acid treatment, which is a critical step in the synthetic pathway that produces the linearized Xpandomer product. Below are synthetic schemes for generating each 2' FANA XNTP.

A. Process for Making 2'FANA XTTP commercial from TCI-America

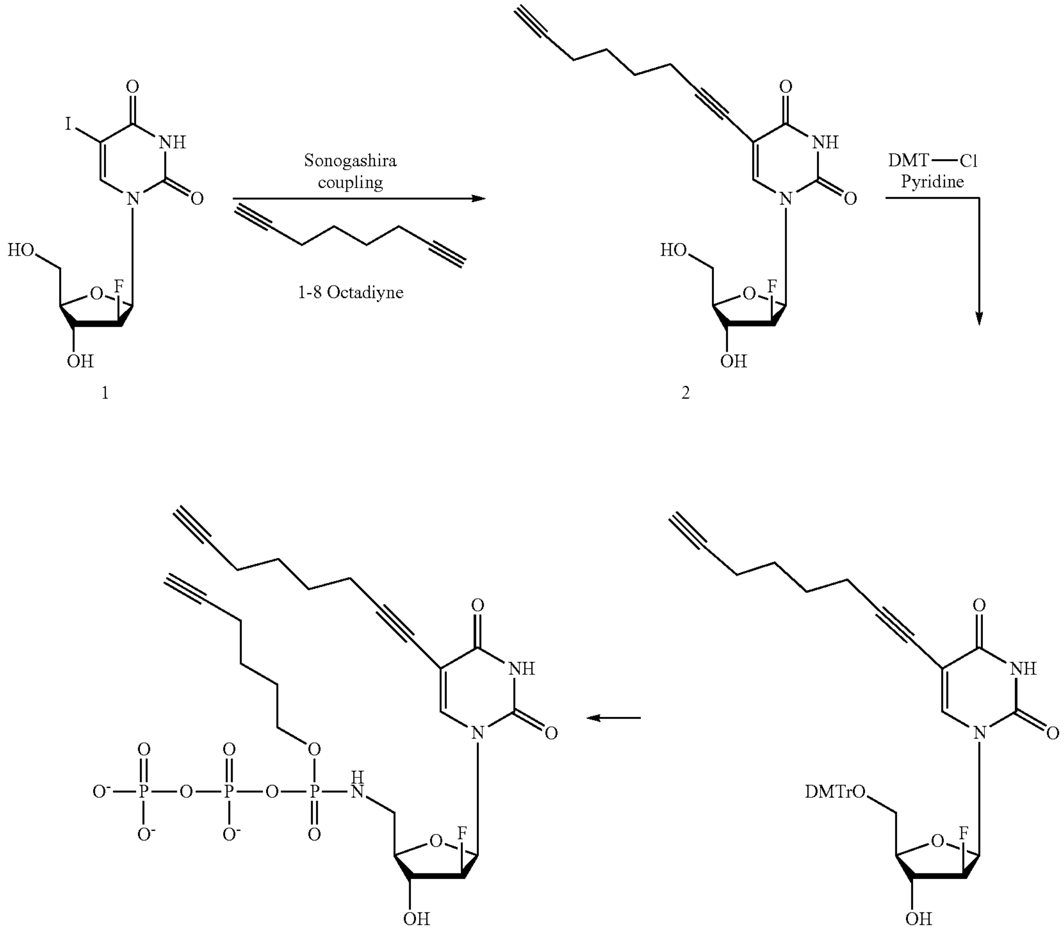

1 2 4 3

In the first step, fialuridine (compound 1, available from TCI America) is coupled to 1-8 octadiyne via a Sonogashira reaction (see, e.g., Bag, S., Jana, S., and Kasula, M. (2018). Sonogashira Cross-Coupling: Alkyne-Modified Nucleosides and Their Applications. In Palladium-Catalyzed Modification of Nucleosides, Nucleosides, and Oligonucleotides (pp. 75-146). Elsevier). In the second step, compound 2 is treated with approximately one equivalent of DMTrCL in pyridine to produce compound 3. In the third step, compound 3 is converted to the amidate triphosphate, following the protocol described in U.S. Pat. No. 10,301,345 to Kokoris et al. entitled, "Phosphoramidate esters and use and synthesis thereof", which is herein incorporated by reference in its entirety.

B. Process for Making 2'FANA XCTP commercial from TRC Canada

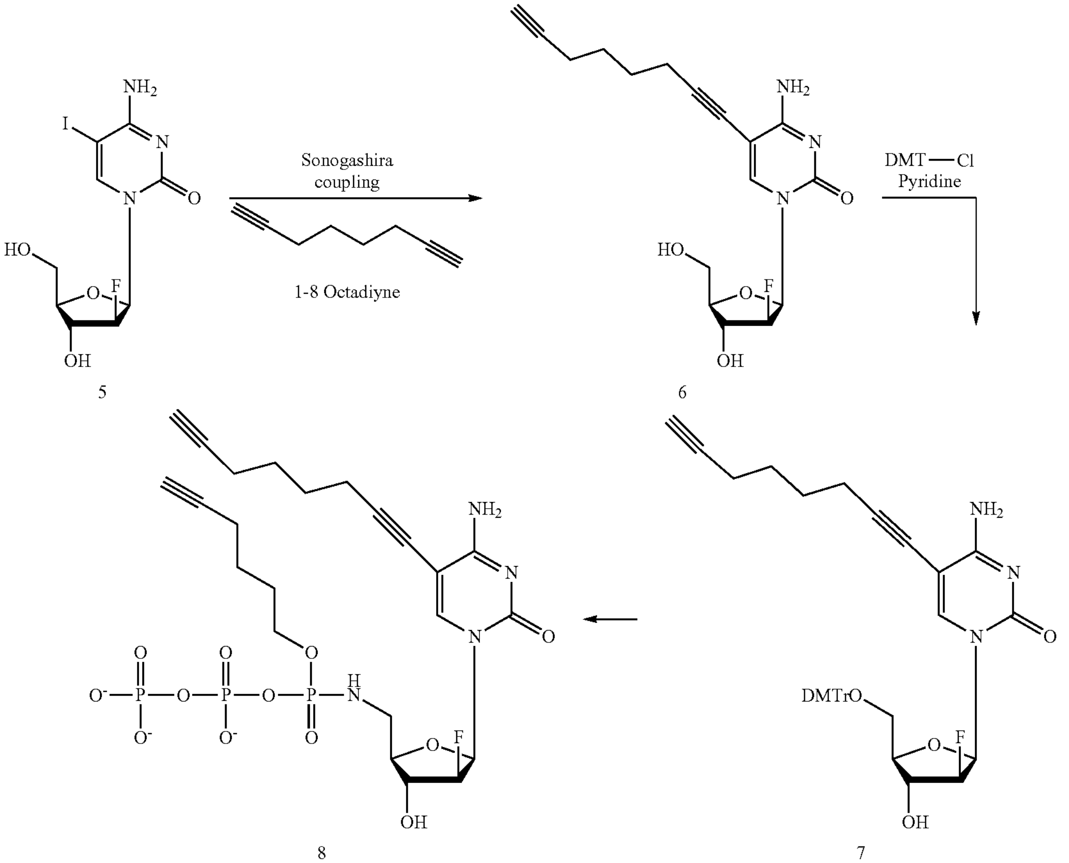

5 6 8 7

In the first step, fialcitabine (compound 5, available from TRC Canada) is coupled to to 1-8 octadiyne via a Sonogashira reaction (as described above) to produce compound 6. In the second step, compound 6 is treated with approximately one equivalent of DMTrCL in pyridine to produce compound 7. In the third step, the exocyclic amine of compound 7 is protected by an acetyl group (see, e.g., Fan, Y., Gaffney, B., and Jones, R. (2004).

C. Process for Making 2'FANA XGTP commercial from Granlen

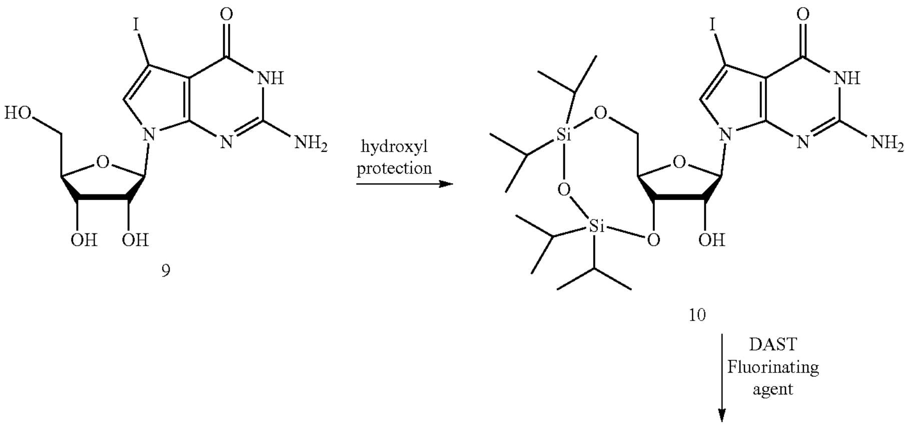

9 10

-continued

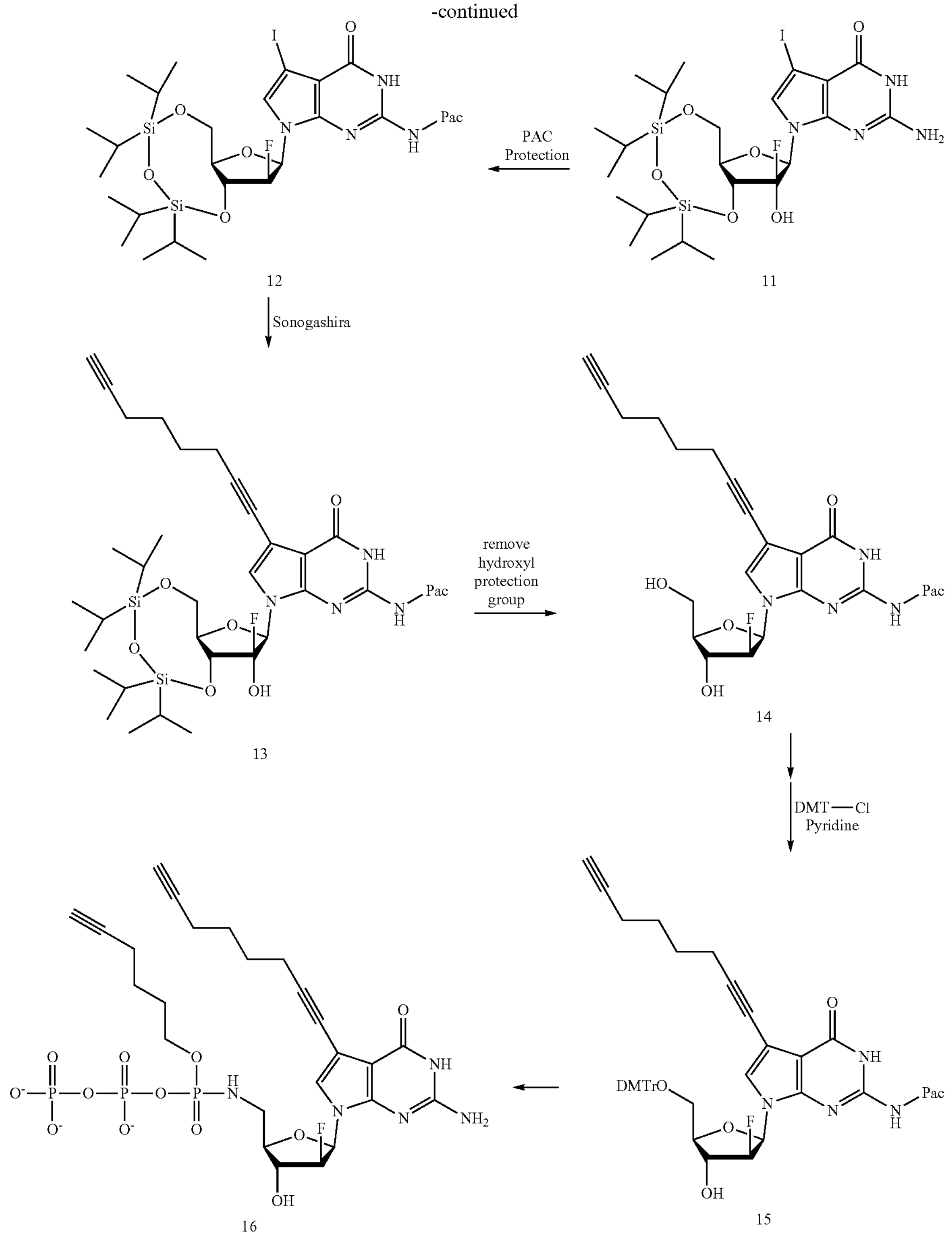

12 11 13 14 15 16

Transient Silylation of the Guanosine O6 and the Amino Groups Faciltates N-Acylation. Organic Letters, 6, 15, 2555-2557.) and subsequently converted to the amidate triphosphate 8, as described in U.S. Pat. No. 10,301,345 to Kokoris et al.

In the first step, 7-Deaza-7-iodoguanosine (Compound 9 available from Granlen; CAS: 444020-71-7) is treated with 1 equivalent of 1,3-Dichloro-1,1,3,3-tetramethyldisiloxane to provide compound 10 (see, e.g., Markiewicz, W. T. and Wiewiorowski, M. (1978) A new type of silyl protecting groups in nucleoside chemistry. Nuc. Acids Res. 5, s185-ss190). In the second step, compound 10 is converted to compound 11 by using fluorinating agent DAST (see, e.g., Pankiewicz, K., Kreminski, J., Ciszewski, L., Ren, W., and Watanabe, K. (1992). A synthesis of 9-(2-deoxy-2-fluoro-B-D-arabinofuranosyl)adenine and -hypoxanthine. An effect of C3'-endo to C2'-endo conformational shift on the reaction course of 2'-hydroxyl group with DAST. J. of Organic Chem. 57, 2, 553-559.) In the third step, the exocyclic amine in compound 11 is protected with a phenoxyacetyl group as described above. In the fourth step, the resulting compound 12 is coupled to 1-8 octadiyne by the Sonogashira reaction described above to afford compound 13. In the fifth step, deprotection of the siloxane group as described above will give compound 14. In the sixth step, treatment of compound 14 with 1 equivalent of DMTrCl in pyridine produces compound 15. In the seventh step, compound 15 is converted to guanosine amidate triphosphate 16 as described in U.S. Pat. No. 10,301,345 to Kokoris et al.

This same scheme can be used to synthesize the following adenosine triphosphoramidate analog:

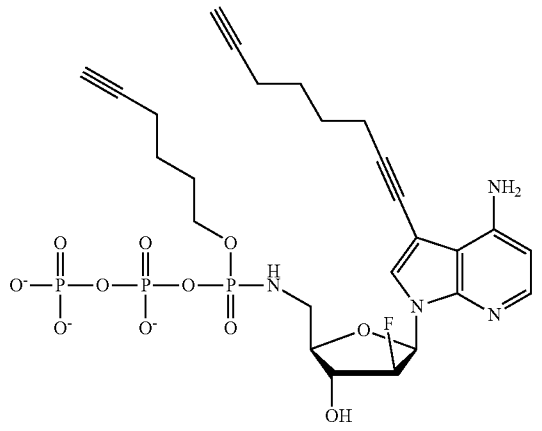

from starting compound 7-Deaza-7-iodoadenosine (available from Granlen, CAS:24386-93-4).

All of the U.S. patents, U.S. patent application publications, U.S. patent applications, foreign patents, foreign patent applications and non-patent publications referred to in this specification and/or listed in the Application Data Sheet, including but not limited to, U.S. Provisional Patent Application No. 62/852,262 filed on May 23, 2019, U.S. Provisional Patent Application No. 62/877,183 filed on Jul. 22, 2019, and U.S. Provisional Patent Application No. 62/885,746 filed on Aug. 12, 2019, are incorporated herein by reference, in their entirety. Such documents may be incorporated by reference for the purpose of describing and disclosing, for example, materials and methodologies described in the publications, which might be used in connection with the presently described invention. The publications discussed above and throughout the text are provided solely for their disclosure prior to the filing date of the present application. Nothing herein is to be construed as an admission that the inventors are not entitled to antedate any referenced publication by virtue of prior invention.

SPECIFICALLY INCLUDED EMBODIMENTS

The following embodiments are specifically contemplated as part of the disclosure. This is not intended to be an exhaustive listing of potentially claimed embodiments included within the scope of the disclosure.

Embodiment 1. A compound having the following structure:

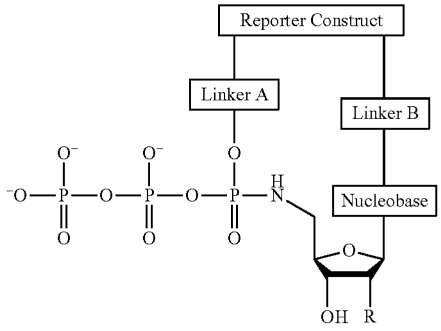

wherein

- R is OH or H;
- nucleobase is adenine, cytosine, guanine, thymine, uracil or a nucleobase analog;
- reporter construct is a polymer having a first end and a second end, and comprising, in series from the first end to the second end, a first reporter code, a symmetrical chemical brancher bearing a translocation control element, and a second reporter code;
- linker A joins the oxygen atom of the alpha phosphoramidate to the first end of the reporter construct;
- linker B joins the nucleobase to the second end of the reporter construct; and wherein
- the translocation control element is a polymer comprising two or more repeat units selected from: 1,3-O-bis(phosphodiester)-2S-O-mPEG4-propane (compound 12b), 1,3-O-bis(phosphodiester)-2-(4-Me-O-PEG3)-1-(Et-O-Ac)-1,2,3-triazole)-propane (compound 35b), 1,3-O-bis(phosphodiester)-2s-O-mPEG6-propane (compound 12c), 1,2-O-bis(phosphodiester)-3-O-mPEG2-propane (compound 16), 2,3-O-bis(phosphodiester)-1-(5-benzofuran)-propane (compound 20i), 1,2-O-bis(phosphodiester)-3-(4-methylpiperazine-1-yl)-propane (compound 20j), 2,3-O-bis(phosphodiester)-1-(N1-(2-Me-5-nitroindole)-propane (compound 20g), 1,8-O-bis(phosphodiester)-N,N-Diethylpiperazine (compound 26h), 1,2-O-bis(phosphodiester)-3-(4-(Me-O-PEG3-O-Bz)-1-(1,2,3-triazole))-propane (compound 31d), 1,3-O-bis(phosphodiester)-2s-O-(4-(Me-O-PEG2)-1-(Et-OBz)-1,2,3-triazole)-propane (compound 35a), 1,3-O-bis(phosphodiester-2-(4-(Me-O-PEG5)-1-(Et-O-Ac)-1,2,3-triazole)-propane (compound 35c), 1,3-O-bis(phosphodiester-2s-O-(4-(Me-O-PEG7)-1-(Et-OBz)-1,2,3-triazole)-propane (compound 35d), 1,3-O-bis(phosphodiester-2s-O-(4-(Me-O-PEG3)-1-(Me-acetate)-1,2,3-triazole)-propane (compound 35e), 1,3-O-bis(phosphodiester-2s-O-(4-(Me-O-PEG3)-1-(Et-2,2,2-Tris-(Me-O-Bz))-1,2,3-triazole)-propane (compound 37a), 1,3-O-bis(phosphodiester-2-(4-(Me-O-PEG5)-1-(Et-2,2,2-Tris-(Me-O-Ac))-1,2,3-triazole)-propane (compound 37b), 1,3-O-bis(phosphodiester-2S-O-(PEG4-O-Bz)-propane (compound 38b), 1,3-O-bis(phosphodiester-2,2-bis(Me-O-mPEG2)-propane (compound 45b), 1,3-O-bis(phosphodiester-2,2-bis(4-(Me-O-PEG2-O-Me)-1-(Et-O-Bz)-1,2,3-triazole)-propane (compound 47f), 1,3-O-bis(phosphodiester-2,2-bis(4-(Me-O-PEG3-O-Me)-1-(Et-O-Bz)-1,2,3-triazole)-propane (compound 47g), 1,3-O-bis (phosphodiester-2,2-bis(4-(Me-O-PEG3-O-Me)-1-(Et-2,2,2-Tris-(Me-O-Bz))-1,2,3-triazole)-propane (compound 47i), or 1,3-O-bis(phosphodiester-2,2-bis (1-Me-4-(Me-O-PEG2-O-Bz)-1,2,3-triazole)-propane (compound 52).

Embodiment 2. The compound of Embodiment 1, wherein R is OH.

Embodiment 3. The compound of Embodiment 1, wherein R is H.

Embodiment 4. The compound of any one of Embodiments 1-3 wherein nucleobase is adenine.

Embodiment 5. The compound of any one of Embodiments 1-3 wherein nucleobase is cytosine.

Embodiment 6. The compound of any one of Embodiments 1-3 wherein nucleobase is guanine.

Embodiment 7. The compound of any one of Embodiments 1-3 wherein nucleobase is thymine.

Embodiment 8. The compound of any one of Embodiments 1-3 wherein nucleobase is uracil.

Embodiment 9. The compound of any one of Embodiments 1-3 wherein nucleobase is a nucleobase analog.

Embodiment 10. The compound of any one of Embodiments 1-9 wherein the symmetrical chemical brancher is selected from 1,2,3-O-tris-(phosphosphodiester)-propane, 1,3-bis-(5-O-phosphodiester-pentylamido)-2-O-phosphodiester-propane, and 1,4,7-O-tris-(phosphodiester)-heptane.

Embodiment 11. The compound of any one of Embodiments 1-9 wherein the symmetrical chemical brancher is 1,2,3-O-tris-(phosphosphodiester)-propane.

Embodiment 12. The compound of any one of Embodiments 1-11, wherein the translocation control element is a polymer comprising two or more repeat units selected from Table 1A.

Embodiment 13. The compound of any one of Embodiments 1-11, wherein the translocation control element is a polymer comprising two or more repeat units selected from 1,3-O-bis(phosphodiester)-2S-O-mPEG4-propane (compound 12b) and 1,3-O-bis(phosphodiester)-2-(4-Me-O-PEG3)-1-(Et-O-Ac)-1,2,3-triazole)-propane (compound 35b).

Embodiment 14. The compound of any one of claims 1-11, wherein the translocation control element is a polymer comprising the following sequence: [(1,3-O-bis(phosphodiester)-2S-O-mPEG4-propane (compound 12b))]n1[(1,3-O-bis(phosphodiester)-2-(4-Me-O-PEG3)-1-(Et-O-Ac)-1,2,3-triazole)-propane (compound 35b))]n2, wherein n1 is from 0 to 6 and n2 is from 6 to 10.

Embodiment 15. The compound of any one Embodiments 1-14, wherein the first and second reporter codes are identical.

Embodiment 16. The compound of any one Embodiments 1-14, wherein the first and second reporter codes are polymers comprising two or more repeat units selected from: hexaethylene glycol (D), ethane (L), triaethylene glycol (X), 1,3-O-bis(phosphodiester)-2S-O-mPEG4-propane (compound 12b), 1,3-O-bis(phosphodiester)-2-(4-Me-O-PEG3)-1-(Et-O-Ac)-1,2,3-triazole)-propane (compound 35b), 1,3-O-bis(phosphodiester-2,2-bis(Me-O-mPEG2)-propane (compound 45b), 1,3-O-bis(phosphodiester-2S-O-(PEG4-O-Bz)-propane (compound 38b), 1,3-O-bis(phosphodiester)-2s-O-mPEG6-propane (compound 12c), 1,3-O-bis (phosphodiester-2s-O-(4-(Me-O-PEG3)-1-(Et-2,2,2-Tris-(Me-O-Bz))-1,2,3-triazole)-propane (compound 37a), 1,3-O-bis(phosphodiester-2s-O-(4-(Me-O-PEG3)-1-(Me-acetate)-1,2,3-triazole)-propane (compound 35e), 1,3-O-bis (phosphodiester)-2s-O-(4-(Me-O-PEG2)-1-(Et-OBz)-1,2,3-triazole)-propane (compound 35a), 1,3-O-bis (phosphodiester)-2-(4-Et-1-(Et-O-mPEG1)-1,2,3-triazole)-propane (compound 31a), 2,3-O-bis(phosphodiester)-1-(1 dimethoxyquinazolinedione)-propane (compound 20c), 2,3-O-bis(phosphodiester)-1-(N9-(3,6-dimethoxycarbazole)-propane (compound 20e), 1,1'-O-bis(phosphodiester)-2,2'-(sulfonylbis(benz-4-yl))-diethanol (compound 26d), 1,1'-O-bis(phosphodiester)-2,2'-bipyridin-4,4'-yl)-dimethanol (compound 26a), 2,3-O-bis(phosphodiester)-1-(N1-(4,6-dimethoxy-3-Me-indole)-propane (compound 20b), 3-(1,2-O-bis(phosphodiester)-propyl)-8,8-dimethylhexahydro-3H-3a, 6-methanobenzo[c]isothiazole 2,2-dioxide (compound 20d), 2,3-O-bis(phosphodiester)-1-(N1-(6-Azathymine))-propane (compound 20f), 1,5-O-bis(phosphodiester)-hexahydrofuro [2,6]furan (compound 23), 1,1'-O-bis(phosphodiester)-octahydro-2,6-dimethyl-3,8:4,7-dimethano-2,6-naphthyridin-4, 8-diyl)-dimethanol (compound 26e), 2,3-O-bis (phosphodiester)-1-(N1-(2-Me-5-nitroindole)-propane (compound 20h), 2,3-O-bis(phosphodiester)-1-(N1-(2-Me-5-nitroindole)-propane (compound 20g), 2,3-O-bis(phosphodiester)-1-(5-benzofuran)-propane (compound 20i), 1,2-O-bis(phosphodiester)-3-O-mPEG2-propane (compound 5b), 1,3-O-bis(phosphodiester)-2-(4-Et-1-(Et-O-mPEG3)-1, 2,3-triazole)-propane (compound 31b), and 1,3-O-bis(phosphodiester)-3-O-mPEG4-propane (compound 5a).

Embodiment 17. The compound of any one of Embodiments 1-14, wherein the first and second reporter codes are polymers comprising two or more repeat units selected from hexaethylene glycol, ethane, triaethylene glycol, and any of the compounds set forth in Table 1A.

Embodiment 18. The reporter code of any one of Embodiments 1-14, wherein the first and second reporter codes are polymers comprising two or more repeat units selected from hexaethylene glycol, ethane, triaethylene glycol, and 1,3-O-bis(phosphodiester)-2S-O-mPEG4-propane (compound 12b).

Embodiment 19. The compound of any one of Embodiments 1-14, wherein the first and second reporter codes are polymers comprising a sequence selected from: (i) [(hexaethylene glycol)2(ethane)3(hexaethylene glycol)(triaethylene glycol)], (ii) [(hexaethyleneglycol)2(1,3-O-bis(phosphodiester)-2S-O-mPEG4-propane (compound 12b))2 (ethane)(triaethylene glycol)3], (iii) [(hexaethylene glycol) 2(1,3-O-bis(phosphodiester)-2S-O-mPEG4-propane (compound 12b))3(ethane)2(hexaethylene glycol)(triaethylene glycol)], and (iv) [(triaethylene glycol)2(ethane)(1,3-O-bis(phosphodiester)-2S-O-mPEG4-propane (compound 12b))6(ethane)7].

Embodiment 20. The compound of any one of Embodiments 1-19, wherein Linker A and Linker B are polymers comprising two or more repeat units selected from: spermine (Q), hexaethylene glycol (D), 2-((4-((3-(benzoyloxy)-2-(((1-(3-(benzoyloxy)-2-((benzoyloxy)methyl)-2-((phosphodiester-oxy)methyl)propyl)-1H-1,2,3-triazol-4-yl) methoxy)methyl)-2-((benzoyloxy)methyl)propoxy)methyl)-1H-1,2,3-triazol-1-yl)methyl)-2-O-phosphodiester-propane-1,3-diyl dibenzoate (compound 62), 1,3-O-bis (phosphodiester-2,2-bis(1-Me-4-(Me-O-PEG2-O-Bz)-1,2, 3-triazole)-propane (compound 52), 1,3-O-bis (phosphodiester-2-(4-(Me-O-PEG5)-1-(Et-O-Ac)-1,2,3-triazole)-propane (compound 35c), 1,3-O-bis (phosphodiester-2s-O-(4-(Me-O-PEG7)-1-(Et-OBz)-1,2,3-triazole)-propane (compound 35d), 1,3-O-bis (phosphodiester-2s-O-(4-(Me-O-PEG3)-1-(Et-2,2,2-Tris-(Me-O-Bz))-1,2,3-triazole)-propane (compound 37a), 1,3-O-bis(phosphodiester-2-(4-(Me-O-PEG5)-1-(Et-2,2,2-Tris-(Me-O-Ac))-1,2,3-triazole)-propane (compound 37b), 1,2-O-bis(phosphodiester)-3-(4-(Me-O-PEG3-O-Bz)-1-(1,2,3-triazole))-propane (compound 31d), 1,3-O-bis(phosphodiester-2,2-bis(4-(Me-O-PEG2-O-Me)-1-(Et-O-Bz)-1,2,3-triazole)-propane (compound 47f), 1,3-O-bis(phosphodiester-2,2-bis(4-(Me-O-PEG3-O-Me)-1-(Et-2,2,2-Tris-(Me-O-Bz))-1,2,3-triazole)-propane (compound 47i), 1,2-O-bis (phosphodiester)-3-(4-methylpiperazine-1-yl)-propane (compound 20j), 1,3-O-bis(phosphodiester-2,2-bis(4-(Me-O-PEG3-O-Me)-1-(Et-O-Bz)-1,2,3-triazole)-propane (compound 47g), and 1,1'-O-bis(phosphodiester)-N(p-tolyl)-diethanolamine (compound 26b).

Embodiment 21. The compound of any one of Embodiments 1-19, wherein Linker A and Linker B are polymers comprising two or more repeat units selected from spermine and any of the compounds set forth in Table 1A.

Embodiment 22. The compound of any one of Embodiments 1-19 wherein Linker A and Linker B comprise a polymerase enhancement region comprising two repeat units of spermine.

Embodiment 23. The compound of any one of Embodiments 1-22 wherein Linker A and Linker B comprise a translocation deceleration region comprising two or more repeat units selected from: 1,3-O-bis(phosphodiester-2-(4-(Me-O-PEG5)-1-(Et-O-Ac)-1,2,3-triazole)-propane (compound 35c), 1,3-O-bis(phosphodiester-2s-O-(4-(Me-O-PEG7)-1-(Et-OBz)-1,2,3-triazole)-propane (compound 35d), 1,3-O-bis(phosphodiester-2s-O-(4-(Me-O-PEG3)-1-(Et-2,2,2-Tris-(Me-O-Bz))-1,2,3-triazole)-propane (compound 37a), and 1,3-O-bis(phosphodiester-2-(4-(Me-O-PEG5)-1-(Et-2,2,2-Tris-(Me-O-Ac))-1,2,3-triazole)-propane (compound 37b).

Embodiment 24. The compound of any one of Embodiments 1-22 wherein Linker A and Linker B comprise a translocation deceleration region comprising a polymer selected from: (i) [((hexaethylene glycol) (1,3-O-bis(phosphodiester-2-(4-(Me-O-PEG5)-1-(Et-O-Ac)-1,2,3-triazole)-propane (compound 35c))3(hexaethylene glycol)2], (ii) [((hexathylene glycol)(1,3-O-bis(phosphodiester-2-(4-(Me-O-PEG5)-1-(Et-O-Ac)-1,2,3-triazole)-propane (compound 35c))4(hexaethylene glycol)2], (iii) [((hexathylene glycol) (1,3-O-bis(phosphodiester-2s-O-(4-(Me-O-PEG7)-1-(Et-OBz)-1,2,3-triazole)-propane (compound 35d))4(hexaethylene glycol)2], and (iv) [((hexathylene glycol)(1,3-O-bis (phosphodiester-2-(4-(Me-O-PEG5)-1-(Et-2,2,2-Tris-(Me-O-Ac))-1,2,3-triazole)-propane (compound 37b))4 (hexaethylene glycol)2].

Embodiment 25. The compound of any one of Embodiments 1-24 wherein Liker A is joined to the oxygen atom of the alpha phosphoramidate by a linkage comprising a triazole.

Embodiment 26. The compound of any one of Embodiments 1-24 wherein Liker B is joined to the nucleobase by a linkage comprising a triazole.

Embodiment 27. A reporter construct comprising a polymer having a first end and a second end, and comprising, in series from the first end to the second end, a first reporter code, a symmetrical chemical brancher bearing a translocation control element, and a second reporter code; and wherein the translocation control element is a polymer comprising two or more repeat units selected from: 1,3-O-bis(phosphodiester)-2S-O-mPEG4-propane (compound 12b), 1,3-O-bis(phosphodiester)-2-(4-Me-O-PEG3)-1-(Et-O-Ac)-1,2,3-triazole)-propane (compound 35b), 1,3-O-bis (phosphodiester)-2s-O-mPEG6-propane (compound 12c), 1,2-O-bis(phosphodiester)-3-O-mPEG2-propane (compound 16), 2,3-O-bis(phosphodiester)-1-(5-benzofuran)-propane (compound 20i), 1,2-O-bis(phosphodiester)-3-(4-methylpiperazine-1-yl)-propane (compound 20j), 2,3-O-bis (phosphodiester)-1-(N1-(2-Me-5-nitroindole)-propane (compound 20g), 1,8-O-bis(phosphodiester)-N,N-Diethylpiperazine (compound 26h), 1,2-O-bis(phosphodiester)-3-(4-(Me-O-PEG3-O-Bz)-1-(1,2,3-triazole))-propane (compound 31d), 1,3-O-bis(phosphodiester)-2s-O-(4-(Me-O-PEG2)-1-(Et-OBz)-1,2,3-triazole)-propane (compound 35a), 1,3-O-bis(phosphodiester-2-(4-(Me-O-PEG5)-1-(Et-O-Ac)-1,2,3-triazole)-propane (compound 35c), 1,3-O-bis (phosphodiester-2s-O-(4-(Me-O-PEG7)-1-(Et-OBz)-1,2,3-triazole)-propane (compound 35d), 1,3-O-bis (phosphodiester-2s-O-(4-(Me-O-PEG3)-1-(Me-acetate)-1,2,3-triazole)-propane (compound 35e), 1,3-O-bis (phosphodiester-2s-O-(4-(Me-O-PEG3)-1-(Et-2,2,2-Tris-(Me-O-Bz))-1,2,3-triazole)-propane (compound 37a), 1,3-O-bis(phosphodiester-2-(4-(Me-O-PEG5)-1-(Et-2,2,2-Tris-(Me-O-Ac))-1,2,3-triazole)-propane (compound 37b), 1,3-O-bis(phosphodiester-2S-O-(PEG4-O-Bz)-propane (compound 38b), 1,3-O-bis(phosphodiester-2,2-bis(Me-O-mPEG2)-propane (compound 45b), 1,3-O-bis(phosphodiester-2,2-bis(4-(Me-O-PEG2-O-Me)-1-(Et-O-Bz)-1,2,3-triazole)-propane (compound 47f), 1,3-O-bis(phosphodiester-2,2-bis(4-(Me-O-PEG3-O-Me)-1-(Et-O-Bz)-1,2,3-triazole)-propane (compound 47Gg, 1,3-O-bis(phosphodiester-2,2-bis(4-(Me-O-PEG3-O-Me)-1-(Et-2,2,2-Tris-(Me-O-Bz))-1,2,3-triazole)-propane (compound 47i), or 1,3-O-bis (phosphodiester-2,2-bis(1-Me-4-(Me-O-PEG2-O-Bz)-1,2,3-triazole)-propane (compound 52).

Embodiment 28. The reporter construct of Embodiment 27, wherein the symmetrical chemical brancher is selected from 1,2,3-O-tris-(phosphosphodiester)-propane, 1,3-bis-(5-O-phosphodiester-pentylamido)-2-O-phosphodiester-propane, and 1,4,7-O-tris-(phosphodiester)-heptane.

Embodiment 29. The reporter construct of Embodiment 27, wherein the symmetrical chemical brancher is 1,2,3-O-tris-(phosphosphodiester)-propane.

Embodiment 30. The reporter construct of any one of Embodiment 27-29, wherein the translocation control element is a polymer comprising two or more repeat units selected from Table 1A.

Embodiment 31. The reporter construct of any one of Embodiments 27-29, wherein the translocation control element is a polymer comprising two or more repeat units selected from 1,3-O-bis(phosphodiester)-2S-O-mPEG4-propane (compound 12b) and 1,3-O-bis(phosphodiester)-2-(4-Me-O-PEG3)-1-(Et-O-Ac)-1,2,3-triazole)-propane (compound 35b).

Embodiment 32. The reporter construct of any one of Embodiments 27-29, wherein the translocation control element is a polymer comprising the following sequence: [(1,3-O-bis(phosphodiester)-2S-O-mPEG4-propane (compound 12b))]n1[(1,3-O-bis(phosphodiester)-2-(4-Me-O-PEG3)-1-(Et-O-Ac)-1,2,3-triazole)-propane (compound 35b))]n2, wherein n1 is from 0 to 6 and n2 is from 6 to 10.

Embodiment 33. The reporter construct of any one of Embodiments 27-32, wherein the wherein the first and second reporter codes are identical.

Embodiment 34. The reporter construct of any one of Embodiments 27-32, wherein the wherein the first and second reporter codes are polymers comprising two or more repeat units selected from: hexaethylene glycol (D), ethane (L), triaethylene glycol (X), 1,3-O-bis(phosphodiester)-2S-O-mPEG4-propane (compound 12b), 1,3-O-bis(phosphodiester)-2-(4-Me-O-PEG3)-1-(Et-O-Ac)-1,2,3-triazole)-propane (compound 35b), 1,3-O-bis(phosphodiester-2,2-bis (Me-O-mPEG2)-propane (compound 45b), 1,3-O-bis (phosphodiester-2S-O-(PEG4-O-Bz)-propane (compound 38b), 1,3-O-bis(phosphodiester)-2s-O-mPEG6-propane (compound 12c), 1,3-O-bis(phosphodiester-2s-O-(4-(Me-O-PEG3)-1-(Et-2,2,2-Tris-(Me-O-Bz))-1,2,3-triazole)-propane (compound 37a), 1,3-O-bis(phosphodiester-2s-O-(4-(Me-O-PEG3)-1-(Me-acetate)-1,2,3-triazole)-propane (compound 35e), 1,3-O-bis(phosphodiester)-2s-O-(4-(Me-O-PEG2)-1-(Et-OBz)-1,2,3-triazole)-propane (compound 35a), 1,3-O-bis(phosphodiester)-2-(4-Et-1-(Et-O-mPEG1)-1,2,3-triazole)-propane (compound 31a), 2,3-O-bis(phosphodiester)-1-(1 dimethoxyquinazolinedione)-propane (compound 20c), 2,3-O-bis(phosphodiester)-1-(N9-(3,6-dimethoxycarbazole)-propane (compound 20e), 1,1'-O-bis(phosphodiester)-2,2'-(sulfonylbis(benz-4-yl))-diethanol (compound 26d), 1,1'-O-bis(phosphodiester)-2,2'-bipyridin-4,4'-yl)-dimethanol (compound 26a), 2,3-O-bis(phosphodiester)-1-(N1-(4,6-dimethoxy-3-Me-indole)-propane (compound 20b), 3-(1,2-O-bis(phosphodiester)-propyl)-8,8-dimethylhexahydro-3H-3a,6-methanobenzo[c]isothiazole 2,2-dioxide (compound 20d), 2,3-O-bis(phosphodiester)-1-(N1-(6-Azathymine))-propane (compound 20f), 1,5-O-bis(phosphodiester)-hexahydrofuro[2,6]furan (compound 23), 1,1'-O-bis(phosphodiester)-octahydro-2,6-dimethyl-3,8:4,7-dimethano-2,6-naphthyridin-4,8-diyl)-dimethanol (compound 26e), 2,3-O-bis(phosphodiester)-1-(N1-(2-Me-5-nitroindole)-propane (compound 20h), 2,3-O-bis(phosphodiester)-1-(N1-(2-Me-5-nitroindole)-propane (compound 20g), 2,3-O-bis(phosphodiester)-1-(5-benzofuran)-propane (compound 20i), 1,2-O-bis(phosphodiester)-3-O-mPEG2-propane (compound 5b), 1,3-O-bis(phosphodiester)-2-(4-Et-1-(Et-O-mPEG3)-1,2,3-triazole)-propane (compound 31b), and 1,3-O-bis(phosphodiester)-3-O-mPEG4-propane (compound 5a).

Embodiment 35. The reporter construct of any one of Embodiments 27-32, wherein the wherein the first and second reporter codes are polymers comprising two or more repeat units selected from hexaethylene glycol, ethane, triaethylene glycol, and any of the compounds set forth in Table 1A.

Embodiment 36. The reporter construct of any one of Embodiments 27-32, wherein the wherein the first and second reporter codes are polymers comprising two or more repeat units selected from hexaethylene glycol, ethane, triaethylene glycol, and 1,3-O-bis(phosphodiester)-2S-O-mPEG4-propane (compound 12b).

Embodiment 37. The reporter construct of any one of Embodiments 27-32, wherein the wherein the first and second reporter codes are polymers comprising a sequence selected from: (i) [(hexaethylene glycol)2(ethane)3(hexaethylene glycol)(triaethylene glycol)], (ii) [(hexaethyleneglycol)2(1,3-O-bis(phosphodiester)-2S-O-mPEG4-propane (compound 12b))2(ethane)(triaethylene glycol)3], (iii) [(hexaethylene glycol)2(1,3-O-bis(phosphodiester)-2S-O-mPEG4-propane (compound 12b))3(ethane)2(hexaethylene glycol)(triaethylene glycol)], and (iv) [(triaethylene glycol) 2(ethane)(1,3-O-bis(phosphodiester)-2S-O-mPEG4-propane (compound 12b))6(ethane)7].

Embodiment 38. A symmetrically synthesized report tether (SSRT), wherein the symmetrically synthesized reporter tether is a polymer having a first end and a second end, and comprising in series from the first end to the second end a first linker, a reporter construct according to any one of embodimentss 27-37, and a second linker, wherein the first and second linkers are identical and are polymers comprising two or more repeat units selected from: spermine (Q), hexaethylene glycol (D), 2-((4-((3-(benzoyloxy)-2-(((1-(3-(benzoyloxy)-2-((benzoyloxy)methyl)-2-((phosphodiester-oxy)methyl)propyl)-1H-1,2,3-triazol-4-yl) methoxy)methyl)-2-((benzoyloxy)methyl)propoxy)methyl)-1H-1,2,3-triazol-1-yl)methyl)-2-O-phosphodiester-propane-1,3-diyl dibenzoate (compound 62), 1,3-O-bis(phosphodiester-2,2-bis(1-Me-4-(Me-O-PEG2-O-Bz)-1,2,3-triazole)-propane (compound 52), 1,3-O-bis(phosphodiester-2-(4-(Me-O-PEG5)-1-(Et-O-Ac)-1,2,3-triazole)-propane (compound 35c), 1,3-O-bis(phosphodiester-2s-O-(4-(Me-O-PEG7)-1-(Et-OBz)-1,2,3-triazole)-propane (compound 35d), 1,3-O-bis(phosphodiester-2s-O-(4-(Me-O-PEG3)-1-(Et-2,2,2-Tris-(Me-O-Bz))-1,2,3-triazole)-propane (compound 37a), 1,3-O-bis(phosphodiester-2-(4-(Me-O-PEG5)-1-(Et-2,2,2-Tris-(Me-O-Ac))-1,2,3-triazole)-propane (compound 37b), 1,2-O-bis(phosphodiester)-3-(4-(Me-O-PEG3-O-Bz)-1-(1,2,3-triazole))-propane (compound 31d), 1,3-O-bis(phosphodiester-2,2-bis(4-(Me-O-PEG2-O-Me)-1-(Et-O-Bz)-1,2,3-triazole)-propane (compound 47f), 1,3-O-bis(phosphodiester-2,2-bis(4-(Me-O-PEG3-O-Me)-1-(Et-2,2,2-Tris-(Me-O-Bz))-1,2,3-triazole)-propane (compound 47i), 1,2-O-bis(phosphodiester)-3-(4-methylpiperazine-1-yl)-propane (compound 20j), 1,3-O-bis(phosphodiester-2,2-bis(4-(Me-O-PEG3-O-Me)-1-(Et-O-Bz)-1,2,3-triazole)-propane (compound 47g), and 1,1'-O-bis(phosphodiester)-N(p-tolyl)-diethanolamine (compound 26b).

Embodiment 39. The symmetrically synthesized reporter tether (SSRT) of Embodiment 38, wherein the first and second linker comprise a polymerase enhancement regions comprising two repeat units of spermine.

Embodiment 40. The symmetrically synthesized reporter tether (SSRT) of Embodiments 38 or 39 comprising a translocation deceleration region comprising two or more repeat units selected from: 1,3-O-bis(phosphodiester-2-(4-(Me-O-PEG5)-1-(Et-O-Ac)-1,2,3-triazole)-propane (compound 35c), 1,3-O-bis(phosphodiester-2s-O-(4-(Me-O-PEG7)-1-(Et-OBz)-1,2,3-triazole)-propane (compound 35d), 1,3-O-bis(phosphodiester-2s-O-(4-(Me-O-PEG3)-1-(Et-2,2,2-Tris-(Me-O-Bz))-1,2,3-triazole)-propane (compound 37a), and 1,3-O-bis(phosphodiester-2-(4-(Me-O-PEG5)-1-(Et-2,2,2-Tris-(Me-O-Ac))-1,2,3-triazole)-propane (compound 37b).

Embodiment 41. The symmetrically synthesized reporter tether (SSRT) of Embodiments 38 or 39 comprising a translocation deceleration region comprising a polymer selected from: (i) [((hexaethylene glycol) (1,3-O-bis(phosphodiester-2-(4-(Me-O-PEG5)-1-(Et-O-Ac)-1,2,3-triazole)-propane (compound 35c))3(hexaethylene glycol)2], (ii) [((hexathylene glycol)(1,3-O-bis(phosphodiester-2-(4-(Me-O-PEG5)-1-(Et-O-Ac)-1,2,3-triazole)-propane (compound 35c))4(hexaethylene glycol)2], (iii) [((hexathylene glycol) (1,3-0-bis(phosphodiester-2s-O-(4-(Me-O-PEG7)-1-(Et-OBz)-1,2,3-triazole)-propane (compound 35d))4(hexaethylene glycol)2], and (iv) [((hexathylene glycol)(1,3-O-bis(phosphodiester-2-(4-(Me-O-PEG5)-1-(Et-2,2,2-Tris-(Me-O-Ac))-1,2,3-triazole)-propane (compound 37b))4 (hexaethylene glycol)2].

Embodiment 42. The symmetrically synthesized reporter tether (SSRT) of any one of Embodiments 38-41 wherein the first end and the second end comprise a linkage moiety.

Embodiment 43. The symmetrically synthesized reporter tether (SSRT) of Embodiment 42 wherein the linkage moieties comprise an azido ($—N_3$) group.

Embodiment 44. A method for sequencing a target nucleic acid, comprising: a) providing a daughter strand produced by a template-directed synthesis, the daughter strand comprising a plurality of XNTP subunits of claim 1 coupled in a sequence corresponding to a contiguous nucleotide sequence of all or a portion of the target nucleic acid, wherein the individual XNTP subunits of the daughter strand comprise a reporter construct, a nucleobase residue, and a selectively cleavable bond, and wherein the reporter construct, upon cleavage of the selectively cleavable bond, permits lengthening of the subunits of the daughter strand; b) cleaving the selectively cleavable bonds to yield an Xpandomer of a length longer than the plurality of the subunits of daughter strand, the Xpandomer comprising the reporter constructs for parsing genetic information in a sequence corresponding to the contiguous nucleotide sequence of all or a portion of the target nucleic acid; and c) detecting the reporter constructs of the Xpandomer.

Embodiment 45. The method of Embodiment 44, wherein the reporter constructs for parsing the genetic information comprise a reporter code and a translocation control element, wherein the translocation control element provides translocation control by steric hindrance and pauses translocation of the Xpandomer when passed through a nanopore subjected to a baseline voltage, wherein the translocation control element engages the reporter code within the aperture of the nanopore, wherein the reporter code is sensed by the nanopore.

Embodiment 46. The method of Embodiment 44, wherein the Xpandomer resumes translocation through the nanopore by application of a pulse voltage, wherein the pulse voltage is sufficient to allow translocation of the translocation control element, while leaving the next reporter construct of the Xpandomer free to engage with the nanopore.

Embodiment 47. The method of Embodiment 45, wherein the translocation control element of the reporter construct engaged with the nanopore by steric hindrance translocates upon each pulse of the pulsed voltage.

Embodiment 48. The method of Embodiment 45, wherein the target construct is sensed by the nanopore during the time period between pulses of the pulsed voltage.

Embodiment 49. The method of Embodiment 44, wherein the baseline voltage is from about 55 mV to about 75 mV.

Embodiment 50. The method of Embodiment 45, wherein the pulse voltage is from about 550 mV to about 700 mV.

Embodiment 51. The method of Embodiment 45, wherein the pulse voltage has a duration from about 5 μs to about 10 μs.

Embodiment 52. The method of Embodiment 45, wherein periodicity of the pulse voltage is from about 0.5 ms to 1.5 ms.

Embodiment 53. The method of Embodiment 44, wherein the nanopore is subjected to an alternating current (AC).

Embodiment 54. The method of any one of Embodiments 44-53, wherein one or more of the plurality of XNTP subunits comprises a 2' fluoroarabinosyl epimer.

Embodiment 55. A buffer for controlling the rate of translocation of a polymer through a nanopore comprising at least one salt selected from the group consisting of NH4Cl, MgCl2, LiCl, KCl, CsCl, NaCl, and CaCl2).

Embodiment 56. The buffer of Embodiment 55, further comprising at least one solvent selected from the group consisting of 3-methyl-2-oxazolidinone (MOA), DMF, ACN, DMSO, and NMP, wherein the solvent is present in the range from about 1% vol/vol to about 35% vol/vol.

Embodiment 57. The buffer of Embodiment 55, further comprising at least one additive selected from the group consisting of sodium hexanoate (NaHex), EDTA, redox reagents, PEG, glycerol, ficoll and the like.

Embodiment 58. A buffer system for controlling the rate of translocation of a polymer through a nanopore detector comprising a cis buffer and a trans buffer, wherein the cis buffer comprises a first salt concentration and the trans buffer comprises a second salt concentration, wherein the first salt concentration is lower than the second salt concentration.

What is claimed is:

1. A compound having the following structure:

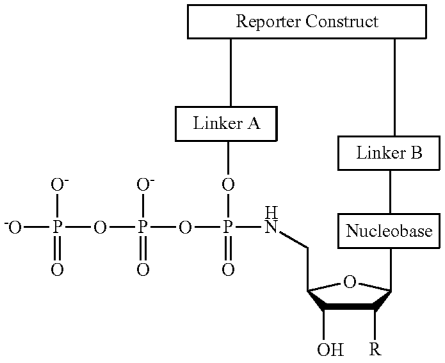

wherein

R is OH or H;

nucleobase is adenine, cytosine, guanine, thymine, uracil or a nucleobase analog;

reporter construct is a polymer having a first end and a second end, and comprising, in series from the first end to the second end, a first reporter code, a symmetrical chemical brancher bearing a translocation control element, and a second reporter code, wherein the chemical brancher is selected from 1,2,3-O-tris-(phosphodiester)-propane, 1,3-bis-(5-O-phosphodiester-pentylamido)-2-O-phosphodiester-propane, and 1,4,7-O-tris-(phosphodiester)-heptane;

linker A joins the oxygen atom of the alpha phosphoramidate to the first end of the reporter construct;

linker B joins the nucleobase to the second end of the reporter construct;

and wherein the translocation control element is a polymer comprising two or more repeat units selected from: 1,3-O-bis(phosphodiester)-2S-O-mPEG4-propane (compound 12b), 1,3-O-bis(phosphodiester)-2-(4-Me-O-PEG3)-1-(Et-O-Ac)-1,2,3-triazole)-propane (compound 35b), 1,3-O-bis(phosphodiester)-2s-O-mPEG6-propane (compound 12c), 1,2-O-bis(phosphodiester)-3-O-mPEG2-propane (compound 16), 2,3-O-bis(phosphodiester)-1-(5-benzofuran)-propane (compound 20i), 1,2-O-bis(phosphodiester)-3-(4-methylpiperazine-1-yl)-propane (compound 20j), 2,3-O-bis(phosphodiester)-1-(N1-(2-Me-5-nitroindole)-propane (compound 20g), 1,8-O-bis(phosphodiester)-N,N-Diethylpiperazine (compound 26h), 1,2-O-bis(phosphodiester)-3-(4-(Me-O-PEG3-O-Bz)-1-(1,2,3-triazole))-propane (compound 31d), 1,3-O-bis(phosphodiester)-2s-O-(4-(Me-O-PEG2)-1-(Et-OBz)-1,2,3-triazole)-propane (compound 35a), 1,3-O-bis(phosphodiester-2-(4-(Me-O-PEG5)-1-(Et-O-Ac)-1,2,3-triazole)-propane (compound 35c), 1,3-O-bis(phosphodiester-2s-O-(4-(Me-O-PEG7)-1-(Et-OBz)-1,2,3-triazole)-propane (compound 35d), 1,3-O-bis(phosphodiester-2s-O-(4-(Me-O-PEG3)-1-(Me-acetate)-1,2,3-triazole)-propane (compound 35e), 1,3-O-bis(phosphodiester-2s-O-(4-(Me-O-PEG3)-1-(Et-2,2,2-Tris-(Me-O-Bz))-1,2,3-triazole)-propane (compound 37a), 1,3-O-bis(phosphodiester-2-(4-(Me-O-PEG5)-1-(Et-2,2,2-Tris-(Me-O-Ac))-1,2,3-triazole)-propane (compound 37b), 1,3-O-bis(phosphodiester-2S-O-(PEG4-O-Bz)-propane (compound 38b), 1,3-O-bis(phosphodiester-2,2-bis(Me-O-mPEG2)-propane (compound 45b), 1,3-O-bis(phosphodiester-2,2-bis(4-(Me-O-PEG2-O-Me)-1-(Et-O-Bz)-1,2,3-triazole)-propane (compound 47f), 1,3-O-bis(phosphodiester-2,2-bis(4-(Me-O-PEG3-O-Me)-1-(Et-O-Bz)-1,2,3-triazole)-propane (compound 47g), 1,3-O-bis(phosphodiester-2,2-bis(4-(Me-O-PEG3-O-Me)-1-(Et-2,2,2-Tris-(Me-O-Bz))-1,2,3-triazole)-propane (compound 47i), or 1,3-O-bis(phosphodiester-2,2-bis(1-Me-4-(Me-O-PEG2-O-Bz)-1,2,3-triazole)-propane (compound 52).

2. The compound of claim 1, wherein the symmetrical chemical brancher is 1,2,3-O-tris-(phosphodiester)-propane.

3. The compound of claim 1, wherein the translocation control element is a polymer comprising two or more repeat units selected from 1,3-O-bis(phosphodiester)-2S-O-mPEG4-propane (compound 12b) and 1,3-O-bis(phosphodiester)-2-(4-Me-O-PEG3)-1-(Et-O-Ac)-1,2,3-triazole)-propane (compound 35b).

4. The compound of claim 1, wherein the translocation control element is a polymer comprising the following sequence: [(1,3-O-bis(phosphodiester)-2S-O-mPEG4-propane (compound 12b))]n1[(1,3-O-bis(phosphodiester)-2-(4-Me-O-PEG3)-1-(Et-O-Ac)-1,2,3-triazole)-propane (compound 35b))]n2, wherein n1 is from 0 to 6 and n2 is from 6 to 10.

5. The compound of claim 1, wherein the first and second reporter codes are identical.

6. The compound of claim 1, wherein the first and second reporter codes are polymers comprising two or more repeat units selected from: hexaethylene glycol (D), ethane (L), triaethylene glycol (X), 1,3-O-bis(phosphodiester)-2S-O-mPEG4-propane (compound 12b), 1,3-O-bis(phosphodiester)-2-(4-Me-O-PEG3)-1-(Et-O-Ac)-1,2,3-triazole)-propane (compound 35b), 1,3-O-bis(phosphodiester-2,2-bis(Me-O-mPEG2)-propane (compound 45b), 1,3-O-bis(phosphodiester-2S-O-(PEG4-O-Bz)-propane (compound 38b), 1,3-O-bis(phosphodiester)-2s-O-mPEG6-propane (compound 12c), 1,3-O-bis(phosphodiester-2s-O-(4-(Me-O-PEG3)-1-(Et-2,2,2-Tris-(Me-O-Bz))-1,2,3-triazole)-propane (compound 37a), 1,3-O-bis(phosphodiester-2s-O-(4-(Me-O-PEG3)-1-(Me-acetate)-1,2,3-triazole)-propane (compound 35e), 1,3-O-bis(phosphodiester)-2s-O-(4-(Me-O-PEG2)-1-(Et-OBz)-1,2,3-triazole)-propane (compound 35a), 1,3-O-bis(phosphodiester)-2-(4-Et-1-(Et-O-mPEG1)-1,2,3-triazole)-propane (compound 31a), 2,3-O-bis(phosphodiester)-1-(1 dimethoxyquinazolinedione)-propane (compound 20c), 2,3-O-bis(phosphodiester)-1-(N9-(3,6-dimethoxycarbazole)-propane (compound 20e), 1,1'-O-bis(phosphodiester)-2,2'-(sulfonylbis(benz-4-yl))-diethanol (compound 26d), 1,1'-O-bis(phosphodiester)-2,2'-bipyridin-4,4'-yl)-dimethanol (compound 26a), 2,3-O-bis(phosphodiester)-1-(N1-(4,6-dimethoxy-3-Me-indole)-propane (compound 20b), 3-(1,2-O-bis(phosphodiester)-propyl)-8,8-dimethylhexahydro-3H-3a,6-methanobenzo[c]isothiazole 2,2-dioxide (compound 20d), 2,3-O-bis(phosphodiester)-1-(N1-(6-Azathymine))-propane (compound 20f), 1,5-O-bis(phosphodiester)-hexahydrofuro[2,6]furan (compound 23), 1,1'-O-bis(phosphodiester)-octahydro-2,6-dimethyl-3, 8:4,7-dimethano-2,6-naphthyridin-4,8-diyl)-dimethanol (compound 26e), 2,3-O-bis(phosphodiester)-1-(N1-(2-Me-5-nitroindole)-propane (compound 20h), 2,3-O-bis(phosphodiester)-1-(N1-(2-Me-5-nitroindole)-propane (compound 20g), 2,3-O-bis(phosphodiester)-1-(5-benzofuran)-propane (compound 20i), 1,2-O-bis(phosphodiester)-3-O-mPEG2-propane (compound 5b), 1,3-O-bis(phosphodiester)-2-(4-Et-1-(Et-O-mPEG3)-1,2,3-triazole)-propane (compound 31b), and 1,3-O-bis(phosphodiester)-3-O-mPEG4-propane (compound 5a).

7. The compound of claim 1, wherein the first and second reporter codes are polymers comprising two or more repeat units selected from hexaethylene glycol, ethane, triaethylene glycol, and 1,3-O-bis(phosphodiester)-2S-O-mPEG4-propane (compound 12b).

8. The compound of claim 1, wherein the first and second reporter codes are polymers comprising a sequence selected from: (i) [(hexaethylene glycol)2(ethane)3(hexaethylene glycol)(triaethylene glycol)], (ii) [(hexaethyleneglycol)2(1,3-O-bis(phosphodiester)-2S-O-mPEG4-propane (compound 12b))2(ethane)(triaethylene glycol)3], (iii) [(hexaethylene glycol)2(1,3-O-bis(phosphodiester)-2S-O-mPEG4-propane (compound 12b))3(ethane)2(hexaethylene glycol)(triaethylene glycol)], and (iv) [(triaethylene glycol)2(ethane)(1,3-O-bis(phosphodiester)-2S-O-mPEG4-propane (compound 12b))6(ethane)7].

9. The compound claim 1, wherein Linker A and Linker B are polymers comprising two or more repeat units selected from: spermine (Q), hexaethylene glycol (D), 2-((4-((3-(benzoyloxy)-2-(((1-(3-(benzoyloxy)-2-((benzoyloxy)methyl)-2-((phosphodiester-oxy)methyl)propyl)-1H-1,2,3-triazol-4-yl)methoxy)methyl)-2-((benzoyloxy)methyl)

propoxy)methyl)-1H-1,2,3-triazol-1-yl)methyl)-2-O-phosphodiester-propane-1,3-diyl dibenzoate (compound 62), 1,3-O-bis(phosphodiester-2,2-bis(1-Me-4-(Me-O-PEG2-O-Bz)-1,2,3-triazole)-propane (compound 52), 1,3-O-bis(phosphodiester-2-(4-(Me-O-PEG5)-1-(Et-O-Ac)-1,2,3-triazole)-propane (compound 35c), 1,3-O-bis(phosphodiester-2s-O-(4-(Me-O-PEG7)-1-(Et-OBz)-1,2,3-triazole)-propane (compound 35d), 1,3-O-bis(phosphodiester-2s-O-(4-(Me-O-PEG3)-1-(Et-2,2,2-Tris-(Me-O-Bz))-1,2,3-triazole)-propane (compound 37a), 1,3-O-bis(phosphodiester-2-(4-(Me-O-PEG5)-1-(Et-2,2,2-Tris-(Me-O-Ac))-1,2,3-triazole)-propane (compound 37b), 1,2-O-bis(phosphodiester)-3-(4-(Me-O-PEG3-O-Bz)-1-(1,2,3-triazole))-propane (compound 31d), 1,3-O-bis(phosphodiester-2,2-bis(4-(Me-O-PEG2-O-Me)-1-(Et-O-Bz)-1,2,3-triazole)-propane (compound 47f), 1,3-O-bis(phosphodiester-2,2-bis(4-(Me-O-PEG3-O-Me)-1-(Et-2,2,2-Tris-(Me-O-Bz))-1,2,3-triazole)-propane (compound 47i), 1,2-O-bis(phosphodiester)-3-(4-methylpiperazine-1-yl)-propane (compound 20j), 1,3-O-bis(phosphodiester-2,2-bis(4-(Me-O-PEG3-O-Me)-1-(Et-O-Bz)-1,2,3-triazole)-propane (compound 47g), and 1,1'-O-bis(phosphodiester)-N(p-tolyl)-diethanolamine (compound 26b).

10. The compound of claim 1, wherein Linker A and Linker B comprise a polymerase enhancement region comprising two repeat units of spermine.

11. The compound of claim 1, wherein Linker A and Linker B comprise a translocation deceleration region comprising two or more repeat units selected from: 1,3-O-bis(phosphodiester-2-(4-(Me-O-PEG5)-1-(Et-O-Ac)-1,2,3-triazole)-propane (compound 35c), 1,3-O-bis(phosphodiester-2s-O-(4-(Me-O-PEG7)-1-(Et-OBz)-1,2,3-triazole)-propane (compound 35d), 1,3-O-bis(phosphodiester-2s-O-(4-(Me-O-PEG3)-1-(Et-2,2,2-Tris-(Me-O-Bz))-1,2,3-triazole)-propane (compound 37a), and 1,3-O-bis(phosphodiester-2-(4-(Me-O-PEG5)-1-(Et-2,2,2-Tris-(Me-O-Ac))-1,2,3-triazole)-propane (compound 37b).

12. The compound of claim 1, wherein Linker A and Linker B comprise a translocation deceleration region, wherein the translocation deceleration region of each of Linker A and Linker B comprises a polymer selected from: (i) [((hexaethylene glycol) (1,3-O-bis(phosphodiester-2-(4-(Me-O-PEG5)-1-(Et-O-Ac)-1,2,3-triazole)-propane (compound 35c))3(hexaethylene glycol)2], (ii) [((hexathylene glycol)(1,3-O-bis(phosphodiester-2-(4-(Me-O-PEG5)-1-(Et-O-Ac)-1,2,3-triazole)-propane (compound 35c))4(hexaethylene glycol)2], (iii) [((hexathylene glycol)(1,3-O-bis(phosphodiester-2s-O-(4-(Me-O-PEG7)-1-(Et-OBz)-1,2,3-triazole)-propane (compound 35d))4(hexaethylene glycol)2], and (iv) [((hexathylene glycol)(1,3-O-bis(phosphodiester-2-(4-(Me-O-PEG5)-1-(Et-2,2,2-Tris-(Me-O-Ac))-1,2,3-triazole)-propane (compound 37b))4(hexaethylene glycol)2].

13. The compound of claim 1, wherein Linker A is joined to the oxygen atom of the alpha phosphoramidate by a linkage comprising a triazole.

14. The compound of claim 1, wherein Linker B is joined to the nucleobase by a linkage comprising a triazole.

* * * * *